US010113159B2

(12) United States Patent
Madec et al.

(10) Patent No.: US 10,113,159 B2
(45) Date of Patent: Oct. 30, 2018

(54) SUPPRESSION OF CANCER

(71) Applicant: IPSEN BIOINNOVATION LIMITED, Abingdon (GB)

(72) Inventors: Frederic Madec, Abingdon (GB); Philip Lecane, Abingdon (GB); Philip Marks, Abingdon (GB); Keith Foster, Abingdon (GB)

(73) Assignee: Ipsen Bioinnovation Limited, Abingdon, Oxfordshire (GB)

( * ) Notice: Subject to any disclaimer, the term of this patent is extended or adjusted under 35 U.S.C. 154(b) by 0 days.

(21) Appl. No.: 14/295,798

(22) Filed: Jun. 4, 2014

(65) Prior Publication Data

US 2014/0286925 A1    Sep. 25, 2014

Related U.S. Application Data

(63) Continuation of application No. 13/125,407, filed as application No. PCT/GB2009/051559 on Nov. 17, 2009, now abandoned.

(30) Foreign Application Priority Data

Nov. 17, 2008 (GB) .................................. 0820970.2

(51) Int. Cl.
| | |
|---|---|
| *A61K 38/16* | (2006.01) |
| *C12N 9/50* | (2006.01) |
| *A61K 38/48* | (2006.01) |
| *C07K 14/33* | (2006.01) |
| *C07K 14/475* | (2006.01) |
| *C07K 14/485* | (2006.01) |
| *C07K 14/495* | (2006.01) |
| *C07K 14/50* | (2006.01) |
| *C07K 14/52* | (2006.01) |
| *C07K 14/54* | (2006.01) |
| *C07K 14/65* | (2006.01) |
| *C07K 14/705* | (2006.01) |
| *C12N 9/52* | (2006.01) |
| *A61K 47/60* | (2017.01) |
| *A61K 47/64* | (2017.01) |

(52) U.S. Cl.
CPC ............ *C12N 9/50* (2013.01); *A61K 38/4893* (2013.01); *A61K 47/60* (2017.08); *A61K 47/6415* (2017.08); *C07K 14/33* (2013.01); *C07K 14/4756* (2013.01); *C07K 14/485* (2013.01); *C07K 14/495* (2013.01); *C07K 14/50* (2013.01); *C07K 14/503* (2013.01); *C07K 14/52* (2013.01); *C07K 14/522* (2013.01); *C07K 14/5412* (2013.01); *C07K 14/65* (2013.01); *C07K 14/705* (2013.01); *C12N 9/52* (2013.01); *C07K 2319/50* (2013.01); *C07K 2319/55* (2013.01); *C07K 2319/74* (2013.01)

(58) Field of Classification Search
CPC ...... A61K 38/16; A61K 38/31; C07K 14/575; C07K 14/655; C07K 2319/31
See application file for complete search history.

(56) References Cited

U.S. PATENT DOCUMENTS

| | | | |
|---|---|---|---|
| 7,838,008 B2 * | 11/2010 | Brin .................... | A61K 38/4893 424/184.1 |
| 8,067,200 B2 | 11/2011 | Foster et al. | |
| 2005/0031648 A1 | 2/2005 | Brin et al. | |
| 2007/0184048 A1 | 8/2007 | Foster et al. | |
| 2008/0161543 A1 | 7/2008 | Steward et al. | |

FOREIGN PATENT DOCUMENTS

| | | |
|---|---|---|
| JP | 2003-509476 A | 3/2003 |
| JP | 2003509476 A | 3/2003 |
| JP | 2007-505094 A | 3/2007 |
| JP | 2007505094 A | 3/2007 |
| JP | 2008-511627 A | 4/2008 |
| JP | 2008511627 A | 4/2008 |
| JP | 2008-521428 A | 6/2008 |
| JP | 2008521428 A | 6/2008 |
| WO | 00/10598 A2 | 3/2000 |
| WO | 01/21213 A2 | 3/2001 |
| WO | 02/09743 A1 | 2/2002 |
| WO | 2004/076634 A2 | 9/2004 |
| WO | 2005/023309 A2 | 3/2005 |
| WO | 2006-025976 A1 | 3/2006 |
| WO | 2006/026780 A1 | 3/2006 |
| WO | 2006/059113 A2 | 6/2006 |
| WO | 2006/094539 A1 | 9/2006 |
| WO | 2007/106799 A2 | 9/2007 |
| WO | 2008/105901 A2 | 9/2008 |

(Continued)

OTHER PUBLICATIONS

Koppan et al. 1998;Targeted cytotoxic analogue of somatostatin AN-238 inhibits growth of androgen-independent Dunning R-3327-At-1 prostate cancer in rats at nontoxic doses. Cancer Research 58: 4132-4137.*
Spier et al. Cortistatin: a member of the somatostatin neuropeptide family with distinct physiological functions. Brain Research Reviews. 33: 228-241.*
Office Action issued in related JP 2011-543822 dated May 27, 2014 (Japanese and English Translation).
Notice of Opposition filed in related EP 09 756 555.0 dated Feb. 17, 2014.
T.C. Umland et al., Structure of the receptor binding fragment Hc of tetanus neurotoxin, Nat. Struct. Biol., Oct. 1997, pp. 788-792, vol. 4—No. 10, Nature Publishing Group.
J. Herreros et al., C-terminal half of tetanus toxin fragment C is sufficient for neuronal binding and interaction with a putative protein receptor, Biochem. J., 2000, pp. 199-204, vol. 347, Molecular Neuropathobiology Laboratory, Imperial Cancer Research Fund, U.K.

(Continued)

*Primary Examiner* — Karen Cochrane Carlson

(57) ABSTRACT

The present invention relates to polypeptides for use in suppressing cancer and cancer disorders. The treatment employs use of a non-cytotoxic protease, which is targeted to the cancer cell, and, when so delivered, the protease is internalized and inhibits secretion from the cancer cell.

22 Claims, 54 Drawing Sheets

Figure 1:
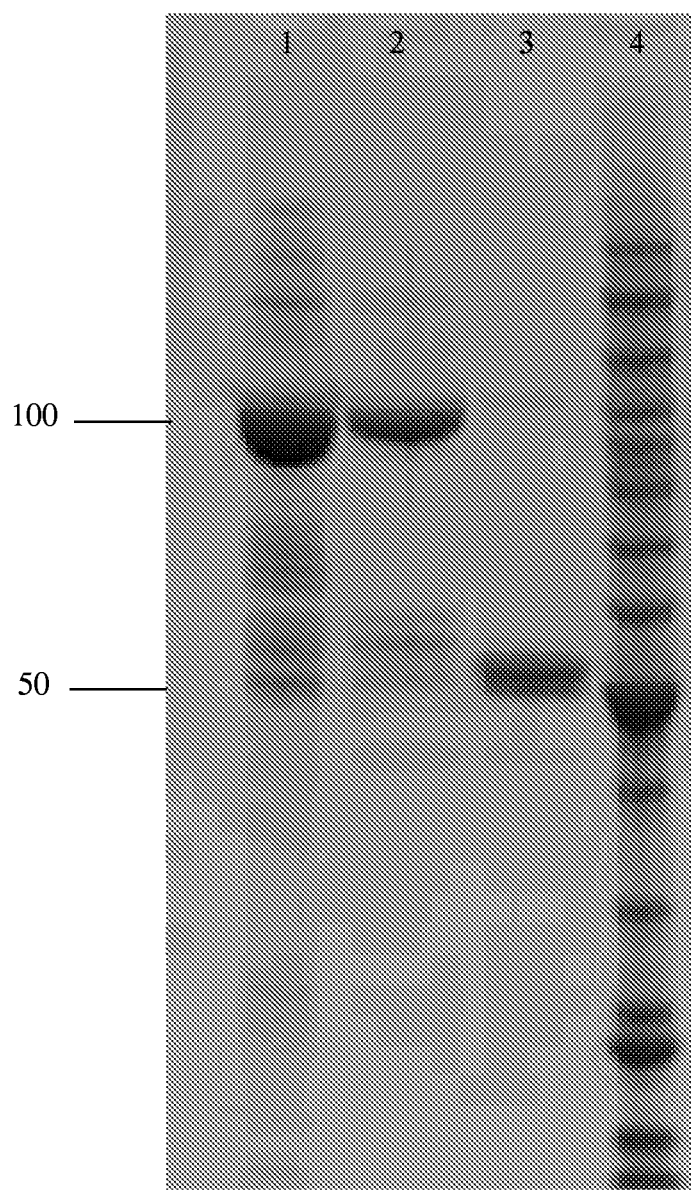

Specification includes a Sequence Listing.

(56) References Cited

FOREIGN PATENT DOCUMENTS

| WO | 2009/150469 A2 | 12/2009 |
|---|---|---|
| WO | 2009/150470 A2 | 12/2009 |
| WO | 2011/020115 A2 | 2/2011 |

OTHER PUBLICATIONS

J.L. Halpern et al., Characterization of the Receptor-binding Domain of Tetanus Toxin, J. Biol. Chem., Jan. 14, 1993, pp. 11188-11192, vol. 268—No. 15, USA.

A. Rummel et al., Identification of the protein receptor binding site of botulinum neurotoxins B and G proves the double-receptor concept, PNAS, Jan. 2, 2007, pp. 359-364, vol. 104—No. 1.

D.B. Lacy et al., Crystal structure of botulinum neurotoxin type A and implications for toxicity, Nat. Struct. Biol., Oct. 1998, pp. 898-902, vol. 5—No. 10.

C. Palma, Tachykinins and their Receptors in Human Malignancies, Current Drug Targets, 2006, pp. 1043-1052, vol. 7, Bentham Science Publishers Ltd.

S. Swaminathan et al., Structural analysis of the catalytic and binding sites of Clostridium botulinum neurotoxin B, Nat. Struct. Biol., Aug. 2000, pp. 693-699, vol. 7—No. 8, Brookhaven National Laboratory, USA.

A. Rummel et al., The Hcc-domain of botulinum neurotoxins A and B exhibits a singular ganglioside binding site displaying serotype specific carbohydrate interaction, Mol. Microbiol., 2004, pp. 631-643, vol. 51—No. 3, Bl

SUPPRESSION OF CANCER

This application is a continuation of U.S. patent application Ser. No. 13/125,407, which is a U.S. National Stage of International Patent Application Serial No. PCT/GB2009/051559, filed Nov. 17, 2009. Each of the above-referenced applications is incorporated herein by reference in its entirety.

Pursuant to the provisions of 37 C.F.R. § 1.52(e)(5), the sequence listing text file named 99336_Seq_Lstng.txt, created on Jun. 4, 2014 and having a size of 357,888 bytes, and which is being submitted herewith, is incorporated by reference herein in its entirety.

The present invention relates to the suppression of cancer.

Cancers are made up of cells that divide, invade and survive in an aberrant manner in the body. Cancers develop when alterations to the DNA within cells affect the control of cell division and other processes relevant to cell survival. As cancerous tumours grow, they invade the body tissues surrounding them. This is harmful to the body as it damages surrounding normal tissues and has a significant effect on physiological responses. In addition, cancers may spread to other parts of the body and develop into secondary tumours. Assessment of cancer can be undertaken using a variety of tests including CT scan, MRI imaging, PET scans, combined PET-CT scan and ultrasound tests. Generally, the earlier a cancer is detected and confirmed, the better the overall prognosis for the patient.

A wide range of treatments are available for patients diagnosed with cancer. These include a variety of surgical interventions, radiotherapy, chemotherapy and hormone therapies. These treatments may be used in isolation but most commonly they are used in combination with each other. The use of a combination of therapies is dependent on the type of cancer diagnosed with certain cancers (such as breast cancer) commonly requiring multiple therapeutic interventions. There are a variety of new therapeutic approaches under development utilising biological products including antibodies, immunotherapies and vaccination techniques to treat cancer. Additional treatment approaches including the use of novel therapeutics designed to block angiogenesis are under development. Novel approaches including the use of gene therapy are also being investigated as potential therapeutics. However, despite the significant scientific efforts and huge financial commitment to developing new cancer therapies, the prognosis for many patients remains extremely poor.

Breast cancer is the most common cancer in the UK and every year more than 44,000 women are diagnosed with this type of cancer. Worldwide, more than a million women are diagnosed with breast cancer every year. In the UK, approximately 80% of patients will survive for 5 years or longer.

Lung cancer is the 2nd commonest cancer in the UK and over 37,000 people were diagnosed with lung cancer in the UK in 2003. For patients diagnosed with lung cancer, only approximately 20% will survive for at least 1 year after diagnosis and only approximately 6% will live for 5 years or longer after diagnosis.

Colorectal cancer is the 3rd commonest cancer type overall and it is the 2nd commonest affecting women (after breast cancer). Just over 35,000 people were diagnosed with colorectal cancer in the UK in 2003. Of those diagnosed with bowel and rectal cancer in England and Wales, 46% will survive for at least 5 years after their diagnosis.

Pancreatic cancer is the fourth most common cause of death from cancer in the Western world and over 7000 cases are diagnosed in the UK each year. Despite therapeutic advances only 3-4% of those diagnosed with pancreatic cancer survive for 5 years or longer and successful therapeutic intervention is limited to surgery that is applicable to only 15% of patients.

Renal cancer is the 9th commonest cancer type overall with over 7000 new cases diagnosed and greater than 3500 deaths in the UK each year. Around 208,500 new cases of renal cancer are diagnosed in the world each year, accounting for just under 2% of all cancers. It is commoner in men than in women, with a male to female ratio of 1.5:1. Thirty percent of renal cancer patients show signs of advanced renal cell carcinoma at initial diagnosis, with metastases detected in 15-25% of patients at this time.

Cancer represents a worldwide problem that is predicted to grow significantly. In the year 2000, malignant tumours were responsible for 12 percent of the nearly 56 million deaths reported worldwide from all causes. In some countries, more than a quarter of deaths could be attributed to cancer. In 2000, 5.3 million men and 4.7 million women developed a malignant tumour and altogether 6.2 million died from the disease. It is predicted that cancer rates could further increase by 50% to 15 million new cases in the year 2020, (WHO World Cancer Report (IARC, Ed B. W. Stewart and P. Kleihues, 2003).

For a large number of cancers, autocrine signalling (defined as a mode of hormone action in which a hormone binds to receptors on and affects the function of the cell type that produced it) and/or paracrine signalling (defined as a mode of hormone action in which hormone released from endocrine or endocrine-like cells binds to receptors on nearby cells and affects their function), are believed to play a significant role in development of the disease state. For a given cancer, multiple autocrine signalling loops may be implicated in development and maintenance of the cancer state. In addition to providing a stimulus for cell division, autocrine signalling can enhance cell survival acting to protect cells from mechanisms of apoptosis and necrosis and increase the metastatic potential of the cancer cell.

There is therefore a need in the art for new therapies/therapeutics capable of specifically addressing cancer. This need is addressed by the present invention, which solves one or more of the above-mentioned problems.

In more detail, a first aspect of the present invention provides a polypeptide for use in suppressing cancer, wherein the polypeptide comprises:
(i) a non-cytotoxic protease, which protease is capable of cleaving a SNARE protein in a cancer cell;
(ii) a Targeting Moiety (TM) that is capable of binding to a Binding Site on a cancer cell, which Binding Site is capable of undergoing endocytosis to be incorporated into an endosome within the cancer cell, and wherein said cancer cell expresses said SNARE protein; and (iii) a translocation domain that is capable of translocating the protease from within an endosome, across the endosomal membrane and into the cytosol of the cancer cell;

and with the proviso that the cancer cell is not a neuroendocrine tumour cell; and with the proviso that the polypeptide is not a clostridial neurotoxin (holotoxin) molecule.

The polypeptide of the present invention is not a naturally-occurring clostridial neurotoxin molecule (also known as clostridial holotoxin). Clostridial holotoxin is one of the most lethal neurotoxins known to man, and, as such, has significant limitations as a therapeutic molecule. Also, in the context of cancer, clostridial holotoxin is associated with undesirable off-site targeting (ie. targeting of non-cancer cells), for example to the neuromuscular junction.

In use, a polypeptide of the invention binds to a cancer cell. Thereafter, the translocation component effects transport of the protease component into the cytosol of the cancer cell. Finally, once inside, the protease inhibits the exocytic fusion process of the cancer cell by cleaving SNARE protein present in the cytosol of the cancer cell. Thus, by inactivating the exocytic fusion apparatus of the cancer cell, the polypeptide of the invention inhibits secretion (eg. of TNF-alpha, acetylcholine, fibroblastic growth factor, gastrin releasing peptide, interleukin-6, VEGF, and/or autocrine mobility factor) therefrom. Accordingly, where said secretion peptides are, for example, involved in autocrine or paracrine signalling, the polypeptide of the invention reduces the signalling drive that the autocrine/paracrine loop would otherwise provide to the cancer cell. Accordingly, the polypeptides of the present invention are capable of suppressing or treating cancer.

The first aspect also embraces a corresponding method for suppressing cancer, said method comprising administering a therapeutically effective amount of a polypeptide of the present invention to a patient. The present invention thereby provides an effective means for treating cancer such as renal, breast, lung, pancreatic, and colorectal (eg. colon).

The polypeptides of the present invention provide a distinct advantage over other therapeutics in that they have the potential to inhibit the secretion of multiple autocrine and paracrine peptides from a targeted cancer cell using a single therapeutic molecule. This reduces significantly the ability of a cancer to adapt to a specific treatment regime by switching to and using alternative autocrine signalling pathways. Thus, the present invention provides a more efficacious therapy by blocking multiple pathways simultaneously.

The principal target cell of the present invention is a cancer cell, for example a cancer cell that secretes one or more hormones (or other bioactive molecules), which, once secreted, bind to a receptor on and affect the function of said cancer cell. Examples of cancer cells targeted by the present invention include: breast, lung, pancreatic, colorectal (eg. colon), adrenal, oesophageal, lymphoma (eg. B-cell; Mantell cell), leukaemia (eg. multiple myeloma), acute leukaemia, bladder, bone, brain tumours, bowel, cervical, chronic lymphocytic leukaemia, Hodgkin's lymphoma, renal, liver, skin (eg. basal, squamous, melanoma), oropharyngeal, myeloma, prostate (eg. soft tissue sarcoma), gastric, testicular, and uterine.

In one embodiment, the target cell of the present invention is a cancer cell in which the level of SNARE protein expression is undesirable.

For example, undesirable SNARE expression may occur when the expression of a SNARE protein is up-regulated when compared with the same (or very similar) cell type when in a non-cancerous state. In one embodiment, the mRNA encoding a SNARE protein is up-regulated in a target cancer cell. In another (or the same) embodiment, the cellular protein concentration of a SNARE protein is (also) increased in the target cancer cell. When measuring SNARE mRNA or protein levels, a value of 'one' may be assigned to the SNARE mRNA or protein concentration in a non-cancerous cell of a normal individual, which cell is otherwise the same (or very similar) to the cell type of the cancer cell in question—this value might be described as a 'basal expression level', and is typically an average of expression level values obtained from several cells (of the same or very similar type) and/or from different normal individuals. For example, a lung cell (e.g. a neuroectodermal lung cell, or a lung epithelium cell) in a normal individual may be used for comparison with a small cell lung cancer cell. Thus, up-regulated in the context of the present invention means that the SNARE mRNA or protein level is 'greater than 1' when compared with the same cell type in a non-cancerous state in a normal individual. In one embodiment, the SNARE protein or mRNA level is up-regulated by greater than 2- or 3-fold, or by greater than 4- or 5-fold, or by greater than 6- or 7-fold. In another embodiment, the SNARE protein or mRNA level is up-regulated by greater than 8- or 9-fold, or by greater than 10- or 12-fold, or by greater than 15- or 20-fold. In another embodiment, the SNARE protein or mRNA level is up-regulated by greater than 40- or 50-fold, or by greater than 60- or 70-fold, or by greater than 90- or 100-fold.

Alternatively, undesirable SNARE expression may occur when the level of SNARE mRNA and/or protein expression in a cancer cell is substantially normal (ie. substantially the same) when compared with that of a corresponding identical or very similar non-cancerous cell type. In this scenario, however, for example when a patient is suffering from a [prostate, bladder or cervical carcinoma], even a low or normal level of SNARE protein expression may support a secretion from the cancer cells of this type that is paracrine or autocrine in function, and so in the context of the cancer, the SNARE protein is supporting an undesirable secretion. In this scenario, the polypeptides of the present invention are capable of suppressing secretion from said cancer cells, and thereby addressing this need in the art.

In this regard, the present inventors have identified undesirable SNARE expression in a range of cancer cell types. These data are presented as Box Plots in FIGS. 3-47. In summary, the present inventors have confirmed that undesirable SNARE expression such as SNAP-25, syntaxin (eg. syntaxin-1a, syntaxin-2), and VAMP (eg. VAMP-1) is observed in small cell lung cancer cells (eg. when compared with normal lung cells); that undesirable SNARE expression such as SNAP-25, syntaxin (eg. syntaxin-2), VAMP (eg. VAMP-1, VAMP-2, VAMP-3) is observed in lung carcinoid cells; that undesirable SNARE expression such as SNAP-25, syntaxin (eg. syntaxin-2), VAMP (eg. VAMP-1, VAMP-2) is observed in lung carcinoid cells (eg. when compared with normal lung cells); that undesirable SNARE expression such as SNAP-25, syntaxin (eg. syntaxin-2, syntaxin-3), and VAMP (eg. VAMP-1, VAMP-3) is observed in bladder carcinoma cells; that undesirable SNARE expression such as SNAP-25, syntaxin (eg. syntaxin-1a), and VAMP (eg. VAMP-2) is observed in breast cancer cells; that undesirable SNARE expression such as SNAP-25, syntaxin (eg. syntaxin-1a, syntaxin-1b, syntaxin-2, syntaxin-3), and VAMP (eg. VAMP-1, VAMP-2, and VAMP-3) is observed in pancreatic adenocarcinoma cells (eg. when compared with normal pancreatic cells); that undesirable SNARE expression such as SNAP-25, syntaxin (eg. syntaxin-1a, syntaxin-1b, syntaxin-3), and VAMP (eg. VAMP-2, VAMP-3) is observed in prostate carcinoma cells (eg. when compared with benign prostate cells); that undesirable SNARE expression such as SNAP-25, syntaxin (eg. syntaxin-2), and VAMP (eg. VAMP-3) is observed in cervix cancer cells (eg. when compared with normal cervix cells); that undesirable SNARE expression such as syntaxin (eg. syntaxin 3) and VAMP (eg. VAMP-1, VAMP-2, VAMP-3) is observed in B-cell leukaemia cells (eg. when compared with normal B-cell lymphocytes); that undesirable SNARE expression such as syntaxin (eg. syntaxin-1a, syntaxin-3) and VAMP (eg. VAMP-1) is observed (eg. up-regulated) in ovarian cancer cells (eg. when compared with normal ovary cells); that undesirable SNARE expression such as SNAP-25 and VAMP (eg. VAMP-1, VAMP-2, VAMP-3) is observed in gastrointestinal (GI) carcinoid cells (eg. when compared with normal GI cells); and that undesirable SNARE expression such as SNAP-25, syntaxin (eg. syntaxin-1a, syntaxin-2) and VAMP (eg. VAMP-3) is observed (eg. up-regulated) in head and neck cancer cells (eg. when compared with normal head and neck cells). In addition, the present inventors have identified that undesirable SNARE expression such as SNAP-25 and VAMP (eg. VAMP-2) is observed in colon cancer cells; that undesirable SNARE expression such as SNAP-25 is observed in adrenal cancer cells; that undesirable SNARE expression such as syntaxin (eg. syntaxin-2) is observed in skin (eg. melanoma) cancer cells; that undesirable SNARE expression such as syntaxin (eg. syntaxin-3) is observed in leukemia (eg. multiple melanoma) cancer cells; that undesirable SNARE expression such as syntaxin (eg. syntaxin-1a) and VAMP (eg. VAMP-1) is observed in lung adenocarcinoma cells; that undesirable SNARE expression such as VAMP (eg. VAMP-1) is observed in liver cancer cells; that undesirable SNARE expression such as VAMP (eg. VAMP-2) is observed in oesophagus cancer cells; and that undesirable SNARE expression such as VAMP (eg. VAMP-3) is observed in lymphoma cancer cells (eg. B-cell lymphoma and Mantell cell).

The 'bioactive' component of the polypeptides of the present invention is provided by a non-cytotoxic protease. This distinct group of proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle formation, and thus to secretion of molecules via vesicle transport from a cell. Accordingly, once delivered to a desired target cell, the non-cytotoxic protease is capable of inhibiting cellular secretion from the target cell.

Non-cytotoxic proteases are a discrete class of molecules that do not kill cells; instead, they act by inhibiting cellular processes other than protein synthesis. Non-cytotoxic proteases are produced as part of a larger toxin molecule by a variety of plants, and by a variety of microorganisms such as *Clostridium* sp. and *Neisseria* sp.

Clostridial neurotoxins represent a major group of non-cytotoxic toxin molecules, and comprise two polypeptide chains joined together by a disulphide bond. The two chains are termed the heavy chain (H-chain), which has a molecular mass of approximately 100 kDa, and the light chain (L-chain), which has a molecular mass of approximately 50 kDa. It is the L-chain, which possesses a protease function and exhibits a high substrate specificity for vesicle and/or plasma membrane associated (SNARE) proteins involved in the exocytic process (eg. synaptobrevin, syntaxin or SNAP-25). These substrates are important components of the neurosecretory machinery.

*Neisseria* sp., most importantly from the species *N. gonorrhoeae*, and *Streptococcus* sp., most importantly from the species *S. pneumoniae*, produce functionally similar non-cytotoxic toxin molecules. An example of such a non-cytotoxic protease is IgA protease (see WO99/58571, which is hereby incorporated in its entirety by reference thereto). Thus, the non-cytotoxic protease of the present invention is preferably a clostridial neurotoxin protease or an IgA protease.

Turning now to the Targeting Moiety (TM) component of the present invention, it is this component that binds the polypeptide of the present invention to a cancer cell. The TM is preferably a peptide.

The TM binds to a Binding Site on the cancer cell, thereby providing selectivity of the polypeptide to this species of target cell over other cells. By way of example, in gastric cancer, the TM preferably binds to gastric cancer cells in preference to other cells of the stomach, such as those that are not cancerous and/or to other non-cancerous (or cancerous) cells in the body. In this regard, preferred TM embodiments of the present invention include antibodies (eg. monoclonal antibodies, antibody fragments such as Fab, F(ab)'$_2$, Fv, ScFv, etc., and antibody domains peptides), as well as binding scaffolds, which bind to the receptors identified below. Accordingly, the polypeptides of present invention may include commercially available antibodies or binding scaffolds, which have been designed to achieve specific binding to the target cell or receptor in question. Alternatively, preferred TMs include peptide ligands, such as cytokines, growth factors, neuropeptides, and lectins.

A TM of the present invention binds to a receptor on a cancer cell. By way of example, a TM of the present invention binds to a receptor on a cancer cell selected from the group comprising: a growth hormone-releasing hormone (GHRH, aka GHRF/GRF) receptor; an insulin-like growth factor receptor (e.g. an IGF-1 receptor); a corticotropin releasing factor receptor (e.g. CRHR-2); a gastrin-releasing peptide (GRP) receptor; a bombesin peptide (BB) receptor such as BRS-1, BRS-2, or BRS-3; a growth hormone (GH) receptor; an interleukin receptor (e.g. IL8RA or IL13RA1); a vascular endothelial growth factor (VEGF) receptor; an acetylcholine (ACH) receptor; a somatostatin (SST) receptor, such as $SST_1$, $SST_2$, $SST_3$, $SST_4$ or $SST_5$; a cortistatin (CST) receptor; a chemokine (C-X-C motif) receptor such as CXCR4; a neuropilin receptor; a gonadotropin-releasing hormone (GnRH) receptor; a VIP-glucagon-GRF-secretin superfamily receptor, such as a PAC (eg. $PAC_1$) receptor or a vasoactive intestinal peptide VPAC receptor (e.g. VPAC-1 or VPAC-2) receptor; or an ErbB family member receptor such as an EGF receptor. All of these receptors are over-expressed in cancer cells.

In one embodiment of the present invention, the TM binds to a receptor on a cancer cell selected from the group comprising: FLT such as FLT1, FLT4, FLT3, BRS such as BRS3; CHRN such as CHRNA1, CHRND or CHRNE; EPHA such as EPHA7, EPHA4, EPHA5, EPHA3, EPHA1, EPHA2; EFN such as EFNB3, EFNA1, EFNB2, EFNA3, EFNB1; ErbB such as ERBB2, ERBB4; DLK1, DLL3, FGF such as FGFR1, FGFR3, FGFR2; GRPR; GNRHR; GRPR; GnRHR; JAG such as JAG1 (CD339) or JAG2, IFGR such as IGF1R; leukaemia inhibitory factor receptor (LIFR); NMBR; NOTCHR such as NOTCH3 or NOTCH4; VIPR such as VIPR1; VEGFR such as VEGFR2; SSTR such as SSTR1; NMBR; or PDGFR such as PDGFRA or PDGFRB. All of these receptors are over-expressed in cancer cells.

In one embodiment, the TM is selected from: an adrenomedullin (ADM) peptide, an AM peptide, an autocrine motility factor (AMF) peptide, an amphiregulin peptide, an APRIL (a proliferation-inducing ligand) peptide, an artemin peptide, a betacellulin peptide, a bombesin peptide, a calcitonin receptor (CTR) binding peptide, an ErbB peptide such as an EGF peptide, an endothelin peptide, an erythropoietin peptide (EPO), a fibroblast growth factor (FGF) peptide such as a FGF-5 peptide, an FGF-18 peptide, a bFGF, a FGF8 or a FGF17 peptide, a follicle-stimulating hormone (FSH) peptide, a gastrin peptide, a gastrin releasing peptide (GRP), a glial cell line-defined neurotrophic factor (GDNF) peptide, a ghrelin (GHRL) peptide, a growth hormone-releasing hormone (GHRH) peptide, a granulocyte colony-stimulating factor (G-CSF) peptide, a growth hormone (GH) peptide, a heparin-binding EGF-like growth factor (HB-EGF) peptide, a hepatocyte growth factor/scatter factor (HGF/SF) peptide, an interleukin (IL) such as an IL-1 alpha peptide, an IL-6 peptide, an IL-8 peptide or an IL-10 peptide, an IGF-1 peptide, a stromal cell-derived factor-1 (SDF-1) peptide, a keratinocyte growth factor (KGF) peptide, a proepithelin/granulin peptide, a leptin (LEP) peptide, a LIF peptide, an alpha-melanotropin peptide, a MGSA/GRO-alpha, beta or gamma peptide, a NRG-1 alpha peptide, an oxytocin peptide, an osteopontin (OPN) peptide, a neuregulin-1 peptide, a PACAP peptide, a PDGF peptide such as a PDGF-alpha peptide, a PDGF-beta peptide, a PDGF-C peptide or a PDGF-D peptide, a prolactin peptide, a SCF peptide, a somatostatin peptide, a tumour necrosis factor (TNF) peptide such as a TNF-alpha peptide, a TGF-beta peptide, a TGF-beta1 peptide, a VEGF peptide such as a VEGF-C peptide or a VEGF-D peptide, a vasopressin peptide, a VIP peptide, an angiopoietin peptide such as an angiopoietin-1 peptide or angiopoietin-2 peptide, a B-CLL peptide, a BCGF-12KD peptide, a BAFF peptide, a galanin peptide, a GDNF peptide, a GnRH peptide, an IGF-II peptide, a LH peptide, a neurotrophin peptide, a substance P peptide, or a TGF-alpha peptide; as well as truncations and peptide analogues thereof.

In one embodiment, a TM of the present invention binds to a leptin receptor. Suitable examples of such TMs include: leptin peptides such as a full-length leptin peptide (eg. leptin$_{1-67}$), and truncations or peptide analogues thereof such as leptin$_{22-167}$, leptin$_{70-95}$, and leptin$_{116-122}$.

In another embodiment, a TM of the present invention binds to a ghrelin receptor. Examples of suitable TMs in this regard include: ghrelin peptides such as full-length ghrelin (eg. ghrelin$_{117}$) and truncations or peptide analogues thereof such as ghrelin$_{24-117}$, and ghrelin$_{52-117}$; [Trp3, Arg5]-ghrelin (1-5), des-Gln-Ghrelin, cortistatin-8, His-D-Trp-Ala-Trp-D-Phe-Lys-NH$_2$, growth hormone releasing peptide (e.g. GHRP-6), or hexarelin.

In one embodiment, a TM of the present invention binds to a somatostatin (SST) receptor. By way of example, suitable TMs include: SST peptides and cortistatin (CST)-peptides, as well as peptide analogues thereof such as D-Phe-Phe-Phe-D-Trp-Lys-Thr-Phe-Thr-NH$_2$ (BIM 23052), D-Phe-Phe-Tyr-D-Trp-Lys-Val-Phe-D-Nal-NH$_2$ (BIM 23056) or c[Cys-Phe-Phe-D-Trp-Lys-Thr-Phe-Cys]-NH$_2$ (BIM-23268). Further examples include the SST peptides SST-14 and SST-28; as well as peptide and peptide analogues such as: octreotide, lanreotide, BIM23027, vapreotide, seglitide, and SOM230. These TMs are preferred TMs for binding to SST receptors, in particular to sst$_1$, sst$_2$, sst$_3$, sst$_4$ and sst$_5$ receptors.

In another embodiment, a TM of the present invention binds to a gonadotropin-releasing hormone (GnRH) receptor. GnRH is also known as Luteinizing-Hormone Releasing Hormone (LHRH). Examples of suitable GnRH receptor TMs include: GnRHI peptides, GnRHII peptides and GnRHIII peptides, for example the full-length 92 amino acid GnRH precursor polypeptide and truncations thereof such as the decapeptide: pyroGlu-His-Trp-Ser-Tyr-Gly-Leu-Arg-Pro-Gly CONH2.

In one embodiment, a TM of the present invention binds to insulin-like growth factor (IGF) receptor. Suitable examples include, for example IGF-1 peptides and IGF-2 peptides.

In one embodiment, a TM of the present invention binds to a VIP-glucagon-GRF-secretin superfamily receptor, such as to a PAC (eg. PAC$_1$) or to a VPAC (e.g. VPAC-1 or VPAC-2) receptor. Suitable examples of such TMs include pituitary adenylate cyclase-activating peptides (PACAP), vasoactive intestinal peptides (VIP), as well as truncations and peptide analogues thereof.

In one embodiment the TM is a VIP peptide including VIP-1 and VIP-2 peptides, for example VIP(1-28), or a truncation or peptide analogue thereof. These TMs demonstrate a selective binding to VPAC-1. Alternatively, a TM demonstrating a selective binding to VPAC2 may be employed, such as, for example mROM (see Yu et al., Peptides 27 (6) p1359-66 (2006), which is hereby incorporated by reference thereto). In another embodiment, the TM may be a PACAP peptide, for example PACAP(1-38) or PACAP(1-27), or a truncation of peptide analogue thereof. These TMs are preferred TMs for binding to PAC (eg. PAC-1) receptors.

In one embodiment, a TM of the present invention binds to an interleukin receptor. Suitable TM examples include: IL-1 peptides (e.g. IL-1α, IL-β, IL-18 peptides) and truncations or peptide analogues thereof, IL-2 peptides (e.g. IL-2, IL-3, IL-12, IL-23 peptides) and truncations or peptide analogues thereof, IL-6 and IL-8 peptides and truncations or peptide analogues thereof, and IL-17 peptides (e.g. Il-17A, IL-17C peptides) and truncations or peptide analogues thereof.

In another embodiment, a TM of the present invention binds to an NGF receptor. Examples of suitable TMs include full-length NGF, and truncations or peptide analogues thereof.

In one embodiment, a TM of the present invention binds to a vasoactive epidermal growth factor (VEGF) receptor. Examples of suitable TMs include: VEGF peptide (e.g. VEGF-A, VEGF-B, VEGF-C, VEGF-D or VEGF-E and associated splice variants) and truncations or peptide analogues thereof, and placental growth factor (PlGF) and truncations or peptide analogues thereof.

In another embodiment, a TM of the present invention binds to an ErbB receptor. By way of example, the TM is selected from EGF peptides, transforming growth factor-α (TGF-α) peptides, chimeras of EGF and TGF-α, amphiregulin peptides, betacellulin peptides, epigen peptides, epiregulin peptides, heparin-binding EGF (HB-EGF) peptides, neuregulin (NRG) peptides such as NRG1α, NRG1β, NRG2α, NRG2β, NRG3, NRG4 and neuroregulin splice variants, tomoregulin 1 and 2 peptides, neuroglycan-C peptides, lin-3 peptides, vein peptides, gurken peptides, spitz peptides, or keren peptides; as well as truncations and peptide analogues thereof. There are 4 classes of ErbB receptor (termed ErbB1, erbB2, erbB3 and erbB4), which are also referred to as HER receptors. A number of variants of these receptors exist, which arise from alternate splicing and/or cleavage of the full-length receptor (eg EGFR v1 translation starts at aa543; EGFR vII deletion of aa521-603; EGFR vIII deletion of aa 6-273; EGFRvIII/Δ12-13 deletion of aa 6-273 and 409-520; EGFR vIV deletion of aa 959-1030; EGFR vV truncation at residue 958; EGFR TDM/2-7 tandem duplication of 6-273; EGFR TDM/18-25 tandem duplication of 664-1030; EGFR-TDM/18-26 tandem duplication of 664-1014). In addition, there are four ErbB4 receptor isoforms called erbB4 JM-a, erbB4 JM-b, erbB4 CYT-1 and erbB4 CYT-1.

Preferred TMs bind to ErbB receptors (eg. ErbB1, ErbB2, ErbB3, ErbB4) and splice variants thereof, in particular the ErbB1 receptor. ErbB TMs may also include proteins which contain EGF motifs with a splice site between the fourth and fifth cysteines within the six cysteine EGF-module, where this module is placed in close proximity to the transmembrane region of the potential ligand. For example, interphotoreceptor matrix proteoglycan-2 (IMP-2), meprin (MEP) 1α, MEP1β, mucin (MUC)3, MUC4, MUC12. and MUC17, as well as proteins with a T-knot scaffold such as potato carboxypeptidase inhibitor, and antibodies to ErbB receptors such as cetuximab, ABX-EGF, trastuzumab, or EMD72000. Further examples include chimeras generated by swapping domains (loop sequences and/or connecting amino acids) of different ErbB ligands, such as a mammalian erbB receptor ligand in which the B-loop sequence has replaced by those present in the insect (*Drosophila*) ErbB ligands, an ErbB ligand in which the C-loop sequence of EGF has been replaced by that of TGFα(44-50), EGF ligands in which one or more domain has been replaced by corresponding sequences in TGFα to create EGF/TGFα chimeras (e.g. E3T, T3E, E4T, T4E, T3E4T, T6E and E3T4E, and EGF chimeras in which the N-terminal TGFα sequence (WSHFND) or the neuregulin sequence (SHLVK) has been used to replace the N-terminal EGF sequence C-terminal of the first cysteine residue (NSDSE), T1E, and Biregulin. Yet further chimeras include EGF in which a domain has been replaced by an EGF-like domain of another protein, such as a blood coagulation, neural development or cell adhesion protein (e.g. Notch 3, Delta 1, EMR1, F4/80, EMR3 and EMR4 receptors).

In another embodiment, a TM of the present invention binds to a growth-hormone-releasing hormone (GHRH) receptor. GHRH is also known as growth-hormone-releasing factor (GRF or GHRF) or somatocrinin. Suitable TM examples of the present invention include the full-length GHRH (1-44) peptide, and truncations or peptide analogues thereof such as GHRH(1-29); GHRH(1-37); hGHRH(1-40)-OH; [MeTyr1,Ala15,22,Nle27]-hGHRH(1-29)-NH2; [Me-Tyr1,Ala8,9,15,22,28,Nle27]-hGHRH(1-29)-NH$_2$; cyclo (25-29)[MeTyr1,Ala15,DAsp25,Nle27,Orn29+++]-hGHRH (1-29)-NH$_2$; (D-Tyr1)-GHRH (1-29)-NH$_2$; (D-Ala2)-GHRH (1-29)-NH2; (D-Asp3)-GHRH (1-29)-NH$_2$ (D-Ala4)-GHRH (1-29)-NH$_2$; (D-Thr7)-GHRH (1-29)-NH$_2$; (D-Asn8)-GHRH (1-29)-NH$_2$; (D-Ser9)-GHRH (1-29)-NH$_2$; (D-Tyr10)-GHRH (1-29)-NH$_2$; (Phe4)-GHRH (1-29)-NH$_2$; (pCI-Phe6)-GHRH (1-29)-NH$_2$; (N-Ac-Tyr1)-GHRH (1-29)-NH$_2$; (N-Ac-Tyr1, D-Ala2)-GHRH (1-29)-NH$_2$; (N-Ac-D-Tyr1, D-Ala2)-GHRH (1-29)-NH$_2$; (N-Ac-D-Tyr1, D-Ala2, D-Asp3)-GHRH (1-29)-NH$_2$; (D-Ala2, NLeu27)-GHRH (1-29)-NH$_2$; (His1, D-Ala2, NLeu27)-GHRH (1-29)-NH$_2$; (N-Ac-His1, D-Ala2, N-Leu27)-GHRH (1-29)-NH$_2$; (His1, D-Ala2, D-Ala4, Nleu27)-GHRH (1-29)-NH$_2$; (D-Ala2, D-Asp3, D-Asn8, NLeu27)-GHRH (1-29)-NH$_2$; (D-Asp3, D-Asn8, NLeu27)-GHRH (1-29)-NH2; [His1, NLeu27]-hGHRH(1-29)-NH$_2$; [NLeu27]-hGHRH(1-29)-NH$_2$; H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu- Ser-Asn-Gln-Glu-Arg-Gly-Ala-Arg-Ala-Arg-Leu-NH2 (SEQ ID NO: 113); H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH2 (SEQ ID NO: 114); H-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH2 (SEQ ID NO: 115); H-Tyr-Ala-Asp-Ala-Ile-Phe-Thr-Asn-Ser-Tyr-Arg-Lys-Val-Leu-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-NH2 (SEQ ID NO: 116); H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-NH2 (SEQ ID NO: 117); His-Val-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Asn-Arg (SEQ ID NO: 118); and His-Val-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Asn-Arg-Gln-Gln-Gly-Glu-Arg-Asn-Gn-Glu-Gn-Gly-Ala (SEQ ID NO: 119).

In a further embodiment, the TM binds to a bombesin receptor (eg. BRS-1, BRS-2, or BRS-3). TMs for use in the present invention that bind to a bombesin receptor include: bombesin-a 14 amino acid peptide originally isolated from the skin of a frog (pGlu-Gln-Arg-Leu-Gly-Asn-Gln-Trp-Ala-Val-Gly-His-Leu-Met-NH2) (SEQ ID NO: 120); and the two known homologs in mammals, namely neuromedin B, and gastrin releasing peptide (GRP) such as porcine GRP-Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-Met-NH2 (SEQ ID NO: 121), and human GRP-Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met-NH2 (SEQ ID NO: 122). Additional TMs include corresponding bombesin, neuromedin B and GRP truncations as well as peptide analogues thereof.

In one embodiment, the cancer cell is a lung cancer cell (e.g. a small cell lung cancer cell, a non-small cell lung cancer cell, or a carcinoid lung cancer cell). The present inventors have confirmed that undesirable SNARE expression is observed in lung cancer cells. In this embodiment, the TM ligand binds to a receptor on the lung cancer cell, such as to a receptor selected from: an erythropoietin (EPO) receptor, a VEGF receptor such as a VEGF-3 receptor, an ErbB receptor such as an EGF receptor, an ErbB2 or 3 receptor, an GRP receptor, an ET(A) receptor, a CCK receptor such as a CCK-A or CCK-B receptor, a FLT receptor such a FLT 3 or FLT4 receptor, a CHRND receptor, an EPHA receptor such as an EPHA7, an EPHA4 or an EPHA5 receptor, an EFNA receptor such as an EFNA3 or EFNB3 receptor, a DLK1 receptor, an FGF receptor such as a FGF1 receptor, or a JAG receptor such as a JAG1 (CD339) or a JAG2 receptor. Preferred TMs in this embodiment include the corresponding natural ligand to said receptors, as well as truncations and peptide analogues thereof. Examples include: erythropoietin (EPO), VEGF such as VEGF-B, VEGF-C, acetylcholine, ephrin peptides such as ephrin-A1, A2, A3, A4 or A5, pro-neuregulin peptides such as pro-neuregulin-2, neuregulin peptides such as neuregulin or NTAK, EGF, TGF such as TGF-beta, GRP, bombesin like peptide, endothelin, PGF, TNF such as TNF-alpha, IL such as IL-6, IL-8, oxytocin, vasopressin, NRG such as NRG-1 alpha, bradykinin, HGF, GHRH, FGF such as bFGF, aFGF, FGF-1, FGF-2, NOTCH peptide ligands, FLT3 cytokine, or gastrin; as well as truncations and peptide analogues thereof.

In another embodiment the cancer cell is a bladder cancer cell. The present inventors have confirmed that undesirable SNARE expression is observed in bladder cancer cells. In this embodiment, the TM ligand binds to a receptor on the bladder cancer cell, such as to a receptor selected from: an IGF receptor such as an IGF1 receptor, a G-CSF receptor, a VEGF receptor such as a VEGF-2 receptor, an ErbB receptor such as an EGF receptor, a HGF receptor, or a FGF receptor such as a high/low affinity bFGF receptor. Preferred TMs in this embodiment include the corresponding natural ligand to said receptors, as well as truncations and peptide analogues thereof. Examples include: G-CSF, VEGF, HB- EGF, IGF such as IGF-1 or IGF-2, amphiregulin, betacellulin, hepatocyte growth factor (HGF), ErbB such as EGF, TGF such as TGF-alpha, IL such as IL-6, granulin peptide such as granulin-4, or FGF such as bFGF; as well as truncations and peptide analogues thereof.

In one embodiment the cancer cell is a breast cancer cell. The present inventors have confirmed that undesirable SNARE expression is observed in breast cancer cells. In this embodiment, the TM ligand binds to a receptor on the breast cancer cell, such as to a receptor selected from: an IGF receptor such as an IGF1 receptor, a VIP receptor such as VIPR-1, a GRP receptor, a NMB receptor, a CXC receptor such as CXCR4, a TNF receptor such as TNF receptor 1 or 2, a VEGF receptor such as VEGFR-2 or VEGFR-3, a neuropilin receptor such as NRP-1 or NRP-2, an integrin receptor such as integrin receptor alpha9beta1, an OB receptor, an ET receptor such as ET-RA or ET-RB, an erythropoietin receptor (EpoR), a TGF-beta receptor, an AMF receptor, or a prolactin receptor. Preferred TMs in this embodiment include the corresponding natural ligand to said receptors, as well as truncations and peptide analogues thereof. Examples include: TNF such as TNF-alpha, VEGF such as VEGF-A, VEGF-B, VEGF-C, IL such as IL-6, amphiregulin, leptin, endothelin such as ET-1, ET-2, ET-3, FGF such as FGF-2, GHRH, granulin peptide such as granulin-4, erythropoietin, neuromedin peptides such as GRP neuromedin C, neuromedin B, autocrine motility factor (AMF), prolactin, growth hormone such as hGH, IGF such as IGF-1 or IGF-2, VIP peptides, or PACAP peptides such as PACAP-27 or PACAP-38; as well as truncations and peptide analogues thereof.

In one embodiment the cancer cell is a pancreatic cancer cell. The present inventors have confirmed that undesirable SNARE expression is observed in pancreatic adenocarcinoma cells. In this embodiment, the TM ligand binds to a receptor on the pancreatic cancer cell, such as to a receptor selected from: a VIP receptor such as a VIP1 receptor, a VEGF receptor such as a VEGF-1 or VEGF2 receptor, a SST receptor such as a SST1 receptor, a CHRN receptor such as CHRNG, CHRNE, CHRNA1 or CHRND, an IGF receptor such as IGF1R, a BRS receptor such as BRS3, a GnRH receptor, a GRP receptor, a NMB receptor, a type-1 growth factor receptor, an ErbB receptor such as EGFR, a CCK receptor such as CCKB or CCKC, a PDGF receptor such as PDGF-alpha, an ADM receptor, a keratinoctye growth factor (KGF) receptor such as FGFR2b, a type I FGF receptor, a GnRH receptor, a GFRalpha3/RET receptor, or a GDNF receptor. Preferred TMs in this embodiment include the corresponding natural ligand to said receptors, as well as truncations and peptide analogues thereof. Examples include: ErbB such as EGF, TGF such as TGF-alpha, gastrin, PDGF, adrenomedullin, VEGF, KGF, FGF such as FGF-5 or FGF (a/b), VIP, SST peptides such as SST-14 or SST-28, acetylcholine, neuromedin peptides such as GRP neuromedin C, neuromedin B, PACAP peptided such as PACAP-27 or PACAP-38, IL such as IL-1a, GnRH, bombesin, artemin, GDNF, or IGF such as IGF-1 or IGF-2; as well as truncations and peptide analogues thereof.

In one embodiment the cancer cell is a prostate cancer cell. The present inventors have confirmed that undesirable SNARE expression is observed in prostate carcinoma cells. In this embodiment, the TM ligand binds to a receptor on the prostate cancer cell, such as to a receptor selected from: a CHRN such as a CHRNG or CHRNE receptor, an IGF receptor such as an IGF1 receptor, a VIP receptor such as a VIP1 receptor, a CT receptor, an ErbB receptor such as an EGFR (MR2), a [p75(NTR)] or TrkA receptor, a CC receptor such as a CCR2, a FGF receptor such as FGFR-1 to -4, a KGF receptor, a FSH receptor, a GHS receptor such as GHS-R 1a, a CXC receptor such as CXCR2, a VPAC or PAC receptor such as VPAC1 or PAC1, a CRL receptor, a c-Met/HGF receptor, or a GH receptor. Preferred TMs in this embodiment include the corresponding natural ligand to said receptors, as well as truncations and peptide analogues thereof. Examples include: calcitonin (CT), TGF such as TGF-alpha, adrenomedullin, acetylcholine, prolactin, IL such as IL-6 or IL-8, NGF, PDF, MCP such as MCP-1, somatostatin, FGF such as FGF1 (acidic FGF), FGF2 (basic FGF), FGF6 or FGF8, EPO, VEGF, KGF, FSH, ghrelin, FGF17, TNF such as TNF-alpha, VIP, PACAP peptides such as PACAP-27 or PACAP-38, AM, HGF, GH, GM-CSF, or IGF such as IGF-1 or IGF-2; as well as truncations and peptide analogues thereof.

In one embodiment the cancer cell is a cervix or uterine cancer cell. The present inventors have confirmed that undesirable SNARE expression is observed in cervix cancer cells. In this embodiment, the TM ligand binds to a receptor on the cervix or uterine cancer cell, such as to a receptor selected from: EPHA receptor such as EPHA5, EPHA7, EPHA4, EPHA3 receptor, a PDGF receptor such as PDGFRA, an EFNA receptor such as EFNA1, an SST receptor such as SSTR1, ab ErbB receptor such as an EGFR, a FLT receptor such as a FLT-1 receptor, a FLK receptor such as a FLK-1 receptor, a VEGF receptor such as VEGFR-3, an ET receptor such as ET(A)R, an IGF receptor such as IGF-1R, or an LIF receptor such as LIFR. Preferred TMs in this embodiment include the corresponding natural ligand to said receptors, as well as truncations and peptide analogues thereof. Examples include: ErbB such as EGF, TGF such as TGF-alpha, G-CSF, PDGF peptides such as PDGFA or PDGFC, SST peptides such as SST-14 or SST-28, IGF such as IGF-1 or IGF-2, ephrin peptides such as ephrin-A1, A2, A3, A5 or A5, VEGF such as VEGF-C or VEGF-D, granulin peptide such as granulin-4, endothelin such as ET-1, or IL such as IL-6 or IL-1; as well as truncations and peptide analogues thereof.

In one embodiment the cancer cell is a leukaemia cancer cell. The present inventors have confirmed that undesirable SNARE expression is observed in leukaemia cells. In this embodiment, the TM ligand binds to a receptor on the leukaemia cell, such as to a receptor selected from: an FLT receptor such as an FLT1 or 3 receptor, an FGF receptor such as FGFR1, 2 or 3, an EFN receptor such as an EFNB1 or EFNB3 receptor, a JAG receptor such as a JAG1 (cd339) receptor, a PDGF receptor such as PDGFRA or B, EPHA1, EPHA2, a NOTCH receptor such as a NOTCH3 or 4 receptor, an EPHA receptor such as an EPHA7 receptor, a LIF receptor, an EFN receptor such as an EFNA1 or 3 receptor, a DLL receptor such as a DLL3 receptor, an ErbB receptor such as an ErbB2 or 3 receptor, a KDR receptor, a GHS receptor such as GHS-R type 1a, an IL receptor such as IL-1 receptor type II, or an IGF receptor such as an IGF1R. Preferred TMs in this embodiment include the corresponding natural ligand to said receptors, as well as truncations and peptide analogues thereof. Examples include: IGF such as IGF-1 or IGF-2, VEGF peptides such as VEGFB, ghrelin, APRIL, pro-neuregulin peptides such as pro-neuregulin-2, neuregulin peptides, NTAK, FGF such as bFGF, aFGF or FGF-1, NOTCH peptides such as NOTCH1, 2 or 3, PGF peptides, PDGF peptides such as PDGFA, PDGFB or PDGFD, ephrin peptides such as ephrin-A (1-5), LIF, GP30 ligand, erythropoietin, JAG peptides such as JAG-1 or JAG-2, Delta-1, IL such as IL1-alpha, or GM-CSF; as well as truncations and peptide analogues thereof.

In one embodiment the cancer cell is an ovary cancer cell. The present inventors have confirmed that undesirable SNARE expression is observed in ovarian cancer cells. In this embodiment, the TM ligand binds to a receptor on the ovary cancer cell, such as to a receptor selected from: an ErbB receptor such as an ErbB2, 3 or 4 receptor, an FGF receptor such as FGFR3, a JAG receptor such as a JAG2 receptor, an EPH receptor such as an EPHA1 or 2 receptor, an IGF receptor such as an IGF1R, a GRP receptor, an EFN receptor such as an EFNB3, A1 or B2 receptor, or a GNRH receptor. Preferred TMs in this embodiment include the corresponding natural ligand to said receptors, as well as truncations and peptide analogues thereof. Examples include: NRG peptides such as NRG-2 or NRG-3, or heparin-binding EGF-like growth factor peptides; neuregulin peptides, GP30 peptide, NOTCH peptides, granulin peptides such as granulin-4, ephrin-A peptides such as ephrin A1-A5, IGF peptides such as IGF-1 or IGF-2, NTAK, GRP, or GnRH; as well as truncations and peptide analogues thereof.

In one embodiment the cancer cell is a bone cancer cell. The present inventors have confirmed that undesirable SNARE expression is observed in bone cancer cells. In this embodiment, the TM ligand binds to a receptor on the bone cancer cell, such as to a receptor selected from: an IGF receptor such as an IGF-IR, a GHRH receptor, or a FGF receptor such as a bFGF receptor. Preferred TMs in this embodiment include the corresponding natural ligand to said receptors, as well as truncations and peptide analogues thereof. Examples include: PDGF such as PDGF-alpha or PDGF-beta, TGF such as TGFbeta1, IGF such as IGF-1, GHRH, FGF such as bFGF, G-CSF, or IL such as IL-6; as well as truncations and peptide analogues thereof.

In one embodiment the cancer cell is a brain cancer cell. The present inventors have confirmed that undesirable SNARE expression is observed in brain cancer cells. In this embodiment, the TM ligand binds to a receptor on the brain cancer cell, such as to a receptor selected from: an EPO receptor, receptor 78 kDa glycoprotein (gp78), an ErbB receptor such as EGFR, as PDGF receptor such as PDGFR-alpha, a CRL receptor such as CRLR/RAMP2 or CRLR/RAMP3, a neuropilin receptor such as NRP-1 or NRP-2, a CXC receptor such as CXCR4, a VEGFR such as VEGFR-1, an IGFR such as IGF1R, a GDNF receptor such as GDNFR-alpha 1, or a MET receptor. Preferred TMs in this embodiment include the corresponding natural ligand to said receptors, as well as truncations and peptide analogues thereof. Examples include: erythropoietin (EPO) peptides, IGF peptides, autocrine motility factor (AMF) peptides, GDNF peptides, HB-EGF peptides, TGF peptides such as TGF-alpha, PDGF peptides such as PDGFA, PDGF-B, PDGF-C or PDGF-D, neuregulin peptides such as neuregulin-1, adrenomedullin, IL peptides such as IL-6, scatter factor/hepatocyte growth factor (SF/HGF) peptides, granulin peptides such as granulin-4, VEGF peptides such as VEGF-A, or TGF peptides such as TGF beta 1 or TGF beta 2; as well as truncations and peptide analogues thereof.

In one embodiment the cancer cell is a colorectal cancer cell. The present inventors have confirmed that undesirable SNARE expression is observed in colorectal cancer cells In this embodiment, the TM ligand binds to a receptor on the colorectal cancer cell, such as to a receptor selected from: an IGF receptor such as IGF-R1, an ErbB receptor such as EGFR, a GRP receptor, an IL receptor such as IL6-R, a CCK receptor such as CCK-B receptor, or a prolactin receptor. Preferred TMs in this embodiment include the corresponding natural ligand to said receptors, as well as truncations and peptide analogues thereof. Examples include: FGF such as FGF18, IGF such as IGF-1, TGF such as TGF-alpha, GRP, IL such as IL6, ErbB such as EGF, gastrin, or prolactin; as well as truncations and peptide analogues thereof.

In one embodiment the cancer cell is a liver cancer cell. The present inventors have confirmed that undesirable SNARE expression is observed in liver cancer cells In this embodiment, the TM ligand binds to a receptor on the liver cancer cell, such as to a receptor selected from: a TrkA (NGF) receptor, an IGF receptor such as IGF-IR, a HGF receptor such as a HGF-Met receptor, a c-met receptor, a gp78 receptor, or an ErbB receptor such as an EGFR. Preferred TMs in this embodiment include the corresponding natural ligand to said receptors, as well as truncations and peptide analogues thereof. Examples include: NGF, IL such as IL-6 or IL-8, IGF such as IGF-1 or IGF-2, HGF, SF/HGF, hepatopoietin (HPO), AMF, TGF such as TGF-beta or TGF-alpha, LIF or PDGF; as well as truncations and peptide analogues thereof.

In one embodiment the cancer cell is a skin cancer cell. The present inventors have confirmed that undesirable SNARE expression is observed in skin cancer cells In this embodiment, the TM ligand binds to a receptor on the skin (eg. basal, melanoma, squamous) cancer cell, such as to a receptor selected from: a FGF receptor such as FGFR-1, a c-kit receptor, a VEGF receptor such as VEGFR-2, a c-Met receptor, or a melanocortin receptor such as a melanocortin-1 receptor. Preferred TMs in this embodiment include the corresponding natural ligand to said receptors, as well as truncations and peptide analogues thereof. Examples include: IL such as IL8 or IL-10, FGF such as bFGF, SCF, VEGF such as VEGF-A, ErbB such as EGF, EPO, osteopontin (OPN), TGF such as TGF-beta, MGSA/GRO such as MGSA/GRO alpha, beta or gamma, HGF/SF, alpha-melanotropin, amphiregulin, or AMF; as well as truncations and peptide analogues thereof.

In one embodiment the cancer cell is a Kaposi sarcoma cancer cell. The present inventors have confirmed that undesirable SNARE expression is observed in Kaposi sarcoma cancer cells In this embodiment, the TM ligand binds to a receptor on the Kaposi sarcoma cell, such as to a receptor selected from: a PDGF receptor such as PDGFRA, a c-kit receptor, a TGF-beta receptor such as TGFR-1, an endothelin receptor such as ETA-R, a chemokine receptor such as CXCR3 or CCRL2, a VEGF receptor such as VEGFR-2, an IGF receptor such as IGF-IR, or an angiopoietin receptor such as TIE2. Preferred TMs in this embodiment include the corresponding natural ligand to said receptors, as well as truncations and peptide analogues thereof. Examples include: PDGFa, IGF-1, Ang2, IL such as IL6, VEGF such as VEGF-A, endothelin-1, TGF such as TGF-beta, CXCL11, CCL8/14; as well as truncations and peptide analogues thereof.

In one embodiment the cancer cell is a renal cancer cell. In this embodiment, the TM ligand binds to a receptor on the renal cancer cell, such as to a receptor selected from: an IGF receptor such as IGF-IR, a VEGF receptor, a CXC receptor, or an ErbB receptor such as an EGFR. Preferred TMs in this embodiment include the corresponding natural ligand to said receptors, as well as truncations and peptide analogues thereof. Examples include: IL such as IL-6 or IL-8, IGF such as IGF-1 or IGF-2, TGF such as TGF-beta or TGF-alpha, VEGF such as VEGF-A, chemokines such as CXCL12; as well as truncations and peptide analogues thereof.

The above embodiments describe particular cancers in which the present inventors have demonstrated undesirable SNARE expression (eg. up-regulated. SNARE expression).

The present invention is not, however, limited to said specific cancer types, and embraces all cancer types in which SNARE expression occurs.

The above-described undesirable SNARE expression (eg. up-regulation) in cancer cells may optionally be linked to an up-regulation of one or more specific receptor types present on the cancer cells in question. In this regard, the present inventors have identified particular receptor types (detailed above), which are up-regulated in the same cells in which undesirable SNARE expression is observed (eg. up-regulated).

Polypeptide Preparation

The polypeptides of the present invention comprise 3 principal components: a 'bioactive' (ie. a non-cytotoxic protease); a TM; and a translocation domain. The general technology associated with the preparation of such fusion proteins is often referred to as re-targeted toxin technology. By way of exemplification, we refer to: WO94/21300; WO96/33273; WO98/07864; WO00/10598; WO01/21213; WO06/059093; WO00/62814; WO00/04926; WO93/15766; WO00/61192; and WO99/58571. All of these publications are herein incorporated by reference thereto.

In more detail, the TM component of the present invention may be fused to either the protease component or the translocation component of the present invention. Said fusion is preferably by way of a covalent bond, for example either a direct covalent bond or via a spacer/linker molecule. The protease component and the translocation component are preferably linked together via a covalent bond, for example either a direct covalent bond or via a spacer/linker molecule. Suitable spacer/linked molecules are well known in the art, and typically comprise an amino acid-based sequence of between 5 and 40, preferably between 10 and 30 amino acid residues in length.

In use, the polypeptides have a di-chain conformation, wherein the protease component and the transocation component are linked together, preferably via a disulphide bond.

The polypeptides of the present invention may be prepared by conventional chemical conjugation techniques, which are well known to a skilled person. By way of example, reference is made to Hermanson, G. T. (1996), Bioconjugate techniques, Academic Press, and to Wong, S. S. (1991), Chemistry of protein conjugation and cross-linking, CRC Press, Nagy et al., PNAS 95 p1794-99 (1998). Further detailed methodologies for attaching synthetic TMs to a polypeptide of the present invention are provided in, for example, EP0257742. The above-mentioned conjugation publications are herein incorporated by reference thereto.

Alternatively, the polypeptides may be prepared by recombinant preparation of a single polypeptide fusion protein (see, for example, WO98/07864). This technique is based on the in vivo bacterial mechanism by which native clostridial neurotoxin (i.e. holotoxin) is prepared, and results in a fusion protein having the following 'simplified' structural arrangement:

NH$_2$-[protease component]-[translocation component]-[TM]-COOH

According to WO98/07864, the TM is placed towards the C-terminal end of the fusion protein. The fusion protein is then activated by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM.

Alternatively, according to WO06/059093, the TM component of the fusion protein is located towards the middle of the linear fusion protein sequence, between the protease cleavage site and the translocation component. This ensures that the TM is attached to the translocation domain (ie. as occurs with native clostridial holotoxin), though in this case the two components are reversed in order vis-à-vis native holotoxin. Subsequent cleavage at the protease cleavage site exposes the N-terminal portion of the TM, and provides the di-chain polypeptide fusion protein.

The above-mentioned protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.). Whilst any protease cleavage site may be employed (ie. clostridial. or non-clostridial), the following are preferred:

```
Enterokinase (DDDDK↓)      (SEQ ID NO: 123)

Factor Xa (IEGR↓/IDGR↓)    (SEQ ID NO: 124/125)

TEV(Tobacco Etch virus)    (SEQ ID NO: 126)
(ENLYFQ↓G)

Thrombin (LVPR↓GS)         (SEQ ID NO: 127)

PreScission (LEVLFQ↓GP).   (SEQ ID NO: 128)
```

Additional protease cleavage sites include recognition sequences that are cleaved by a non-cytotoxic protease, for example by a clostridial neurotoxin. These include the SNARE (eg. SNAP-25, syntaxin, VAMP) protein recognition sequences that are cleaved by non-cytotoxic proteases such as clostridial neurotoxins. Particular examples are provided in US2007/0166332, which is hereby incorporated in its entirety by reference thereto.

Also embraced by the term protease cleavage site is an intein, which is a self-cleaving sequence. The self-splicing reaction is controllable, for example by varying the concentration of reducing agent present. The above-mentioned 'activation' cleavage sites may also be employed as a 'destructive' cleavage site (discussed below) should one be incorporated into a polypeptide of the present invention.

In a preferred embodiment, the fusion protein of the present invention may comprise one or more N-terminal and/or C-terminal located purification tags. Whilst any purification tag may be employed, the following are preferred:

His-tag (e.g. 6× histidine), preferably as a C-terminal and/or N-terminal tag

MBP-tag (maltose binding protein), preferably as an N-terminal tag

GST-tag (glutathione-S-transferase), preferably as an N-terminal tag

His-MBP-tag, preferably as an N-terminal tag

GST-MBP-tag, preferably as an N-terminal tag

Thioredoxin-tag, preferably as an N-terminal tag

CBD-tag (Chitin Binding Domain), preferably as an N-terminal tag.

One or more peptide spacer/linker molecules may be included in the fusion protein. For example, a peptide spacer may be employed between a purification tag and the rest of the fusion protein molecule.

Thus, a third aspect of the present invention provides a nucleic acid (e.g. DNA) sequence encoding a polypeptide as described above (i.e. the second aspect of the present invention).

Said nucleic acid may be included in the form of a vector, such as a plasmid, which may optionally include one or more of an origin of replication, a nucleic acid integration site, a promoter, a terminator, and a ribosome binding site.

The present invention also includes a method for expressing the above-described nucleic acid sequence (i.e. the third aspect of the present invention) in a host cell, in particular in E. coli.

The present invention also includes a method for activating a polypeptide of the present invention, said method comprising contacting the polypeptide with a protease that cleaves the polypeptide at a recognition site (cleavage site) located between the non-cytotoxic protease component and the translocation component, thereby converting the polypeptide into a di-chain polypeptide wherein the non-cytotoxic protease and translocation components are joined together by a disulphide bond. In a preferred embodiment, the recognition site is not native to a naturally-occurring clostridial neurotoxin and/or to a naturally-occurring IgA protease.

The polypeptides of the present invention may be further modified to reduce or prevent unwanted side-effects associated with dispersal into non-targeted areas. According to this embodiment, the polypeptide comprises a destructive cleavage site. The destructive cleavage site is distinct from the 'activation' site (i.e. di-chain formation), and is cleavable by a second protease and not by the non-cytotoxic protease. Moreover, when so cleaved at the destructive cleavage site by the second protease, the polypeptide has reduced potency (e.g. reduced binding ability to the intended target cell, reduced translocation activity and/or reduced non-cytotoxic protease activity). For completeness, any of the 'destructive' cleavage sites of the present invention may be separately employed as an 'activation' site in a polypeptide of the present invention.

Thus, according to this embodiment, the present invention provides a polypeptide that can be controllably inactivated and/or destroyed at an off-site location.

In a preferred embodiment, the destructive cleavage site is recognised and cleaved by a second protease (i.e. a destructive protease) selected from a circulating protease (e.g. an extracellular protease, such as a serum protease or a protease of the blood clotting cascade), a tissue-associated protease (e.g. a matrix metalloprotease (MMP), such as an MMP of muscle), and an intracellular protease (preferably a protease that is absent from the target cell).

Thus, in use, should a polypeptide of the present invention become dispersed away from its intended target cell and/or be taken up by a non-target cell, the polypeptide will become inactivated by cleavage of the destructive cleavage site (by the second protease).

In one embodiment, the destructive cleavage site is recognised and cleaved by a second protease that is present within an off-site cell-type. In this embodiment, the off-site cell and the target cell are preferably different cell types. Alternatively (or in addition), the destructive cleavage site is recognised and cleaved by a second protease that is present at an off-site location (e.g. distal to the target cell). Accordingly, when destructive cleavage occurs extracellularly, the target cell and the off-site cell may be either the same or different cell-types. In this regard, the target cell and the off-site cell may each possess a receptor to which the same polypeptide of the invention binds.

The destructive cleavage site of the present invention provides for inactivation/destruction of the polypeptide when the polypeptide is in or at an off-site location. In this regard, cleavage at the destructive cleavage site minimises the potency of the polypeptide (when compared with an identical polypeptide lacking the same destructive cleavage site, or possessing the same destructive site but in an uncleaved form). By way of example, reduced potency includes: reduced binding (to a mammalian cell receptor) and/or reduced translocation (across the endosomal membrane of a mammalian cell in the direction of the cytosol), and/or reduced SNARE protein cleavage.

When selecting destructive cleavage site(s) in the context of the present invention, it is preferred that the destructive cleavage site(s) are not substrates for any proteases that may be separately used for post-translational modification of the polypeptide of the present invention as part of its manufacturing process. In this regard, the non-cytotoxic proteases of the present invention typically employ a protease activation event (via a separate 'activation' protease cleavage site, which is structurally distinct from the destructive cleavage site of the present invention). The purpose of the activation cleavage site is to cleave a peptide bond between the non-cytotoxic protease and the translocation or the binding components of the polypeptide of the present invention, thereby providing an 'activated' di-chain polypeptide wherein said two components are linked together via a di-sulfide bond.

Thus, to help ensure that the destructive cleavage site(s) of the polypeptides of the present invention do not adversely affect the 'activation' cleavage site and subsequent di-sulfide bond formation, the former are preferably introduced into polypeptide of the present invention at a position of at least 20, at least 30, at least 40, at least 50, and more preferably at least 60, at least 70, at least 80 (contiguous) amino acid residues away from the 'activation' cleavage site.

The destructive cleavage site(s) and the activation cleavage site are preferably exogenous (i.e. engineered/artificial) with regard to the native components of the polypeptide. In other words, said cleavage sites are preferably not inherent to the corresponding native components of the polypeptide. By way of example, a protease or translocation component based on BoNT/A L-chain or H-chain (respectively) may be engineered according to the present invention to include a cleavage site. Said cleavage site would not, however, be present in the corresponding BoNT native L-chain or H-chain. Similarly, when the Targeting Moiety component of the polypeptide is engineered to include a protease cleavage site, said cleavage site would not be present in the corresponding native sequence of the corresponding Targeting Moiety.

In a preferred embodiment of the present invention, the destructive cleavage site(s) and the 'activation' cleavage site are not cleaved by the same protease. In one embodiment, the two cleavage sites differ from one another in that at least one, more preferably at least two, particularly preferably at least three, and most preferably at least four of the tolerated amino acids within the respective recognition sequences is/are different.

By way of example, in the case of a polypeptide chimera containing a Factor Xa 'activation' site between clostridial L-chain and $H_N$ components, it is preferred to employ a destructive cleavage site that is a site other than a Factor Xa site, which may be inserted elsewhere in the L-chain and/or $H_N$ and/or TM component(s). In this scenario, the polypeptide may be modified to accommodate an alternative 'activation' site between the L-chain and $H_N$ components (for example, an enterokinase cleavage site), in which case a separate Factor Xa cleavage site may be incorporated elsewhere into the polypeptide as the destructive cleavage site. Alternatively, the existing Factor Xa 'activation' site between the L-chain and $H_N$ components may be retained, and an alternative cleavage site such as a thrombin cleavage site incorporated as the destructive cleavage site.

When identifying suitable sites within the primary sequence of any of the components of the present invention for inclusion of cleavage site(s), it is preferable to select a primary sequence that closely matches with the proposed cleavage site that is to be inserted. By doing so, minimal structural changes are introduced into the polypeptide. By way of example, cleavage sites typically comprise at least 3 contiguous amino acid residues. Thus, in a preferred embodiment, a cleavage site is selected that already possesses (in the correct position(s)) at least one, preferably at least two of the amino acid residues that are required in order to introduce the new cleavage site. By way of example, in one embodiment, the Caspase 3 cleavage site (DMQD) SEQ ID NO: 129 may be introduced. In this regard, a preferred insertion position is identified that already includes a primary sequence selected from, for example, Dxxx, xMxx, xxQx, xxxD, DMxx, DxQx, DxxD, xMQx, xMxD, xxQD, DMQx, xMQD, DxQD, and DMxD.

Similarly, it is preferred to introduce the cleavage sites into surface exposed regions. Within surface exposed regions, existing loop regions are preferred.

In a preferred embodiment of the present invention, the destructive cleavage site(s) are introduced at one or more of the following position(s), which are based on the primary amino acid sequence of BoNT/A. Whilst the insertion positions are identified (for convenience) by reference to BoNT/A, the primary amino acid sequences of alternative protease domains and/or translocation domains may be readily aligned with said BoNT/A positions.

For the protease component, one or more of the following positions is preferred: 27-31, 56-63, 73-75, 78-81, 99-105, 120-124, 137-144, 161-165, 169-173, 187-194, 202-214, 237-241, 243-250, 300-304, 323-335, 375-382, 391-400, and 413-423. The above numbering preferably starts from the N-terminus of the protease component of the present invention.

In a preferred embodiment, the destructive cleavage site(s) are located at a position greater than 8 amino acid residues, preferably greater than 10 amino acid residues, more preferably greater than 25 amino acid residues, particularly preferably greater than 50 amino acid residues from the N-terminus of the protease component. Similarly, in a preferred embodiment, the destructive cleavage site(s) are located at a position greater than 20 amino acid residues, preferably greater than 30 amino acid residues, more preferably greater than 40 amino acid residues, particularly preferably greater than 50 amino acid residues from the C-terminus of the protease component.

For the translocation component, one or more of the following positions is preferred: 474-479, 483-495, 507-543, 557-567, 576-580, 618-631, 643-650, 669-677, 751-767, 823-834, 845-859. The above numbering preferably acknowledges a starting position of 449 for the N-terminus of the translocation domain component of the present invention, and an ending position of 871 for the C-terminus of the translocation domain component.

In a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the N-terminus of the translocation component. Similarly, in a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the C-terminus of the translocation component.

In a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the N-terminus of the TM component. Similarly, in a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the C-terminus of the TM component.

The polypeptide of the present invention may include one or more (e.g. two, three, four, five or more) destructive protease cleavage sites. Where more than one destructive cleavage site is included, each cleavage site may be the same or different. In this regard, use of more than one destructive cleavage site provides improved off-site inactivation. Similarly, use of two or more different destructive cleavage sites provides additional design flexibility.

The destructive cleavage site(s) may be engineered into any of the following component(s) of the polypeptide: the non-cytotoxic protease component; the translocation component; the Targeting Moiety; or the spacer peptide (if present). In this regard, the destructive cleavage site(s) are chosen to ensure minimal adverse effect on the potency of the polypeptide (for example by having minimal effect on the targeting/binding regions and/or translocation domain, and/or on the non-cytotoxic protease domain) whilst ensuring that the polypeptide is labile away from its target site/target cell.

Preferred destructive cleavage sites (plus the corresponding second proteases) are listed in the Table immediately below. The listed cleavage sites are purely illustrative and are not intended to be limiting to the present invention.

| Second protease | Destructive cleavage site recognition sequence | Tolerated recognition sequence variance P4-P3-P2-P1-▼-P1'-P2'-P3' | | | | | | |
|---|---|---|---|---|---|---|---|---|
| | | P4 | P3 | P2 | P1 | P1' | P2' | P3' |
| Thrombin | LVPR▼GS (SEQ ID NO: 127) | A,F,G, I,L,T, V or M | A,F, G,I,L, T,V, W or A | P | R | Not D or E | Not D or E | — |

-continued

| Second protease | Destructive cleavage site recognition sequence | Tolerated recognition sequence variance P4-P3-P2-P1-▼-P1'-P2'-P3' | | | | | | |
|---|---|---|---|---|---|---|---|---|
| | | P4 | P3 | P2 | P1 | P1' | P2' | P3' |
| Thrombin | GR▼G | | | | G | R | G | |
| Factor Xa | IEGR▼ (SEQ ID NO: 124) | A,F,G, I,L,T, V or M | D or E | | G | R | — | — | — |
| ADAM17 | PLAQA▼VRSSS (SEQ ID NO: 130) | | | | | | | |
| Human airway trypsin-like protease (HAT) | SKGR▼SLIGRV (SEQ ID NO: 131) | | | | | | | |
| ACE (peptidyl-dipeptidase A) | | — | — | — | — | Not P | Not D or E | N/A |
| Elastase (leukocyte) | MEA▼VTY (SEQ ID NO: 132) | M,R | E | A, H | V, T | V,T,H | Y | — |
| Furin | RXR/KR▼ (SEQ ID NO: 133) | R | X | R or K | R | | | |
| Granzyme | IEPD▼ (SEQ ID NO: 134) | I | E | P | D | — | — | — |
| Caspase 1 | | F,W,Y, L | — | H, A, T | D | Not P,E.D. Q.K or R | — | — |
| Caspase 2 | DVAD▼ (SEQ ID NO: 135) | D | V | A | D | Not P,E.D. Q.K or R | — | — |
| Caspase 3 | DMQD▼ (SEQ ID NO: 136) | D | M | Q | D | Not P,E.D. Q.K or R | — | — |
| Caspase 4 | LEVD▼ (SEQ ID NO: 137) | L | E | V | D | Not P,E.D. Q.K or R | — | — |
| Caspase 5 | | L or W | E | H | D | — | — | — |
| Caspase 6 | | V | E | H or I | D | Not P,E.D. Q.K or R | — | — |
| Caspase 7 | DEVD▼ (SEQ ID NO: 138) | D | E | V | D | Not P,E.D. Q.K or R | — | — |
| Caspase 8 | | I or L | E | T | D | Not P,E.D. Q.K or R | — | — |
| Caspase 9 | LEHD▼ (SEQ ID NO: 139) | L | E | H | D | — | — | — |
| Caspase 10 | IEHD▼ (SEQ ID NO: 140) | I | E | H | D | — | — | — |

Matrix metalloproteases (MMPs) are a preferred group of destructive proteases in the context of the present invention. Within this group, ADAM17 (EC 3.4.24.86, also known as TACE), is preferred and cleaves a variety of membrane-anchored, cell-surface proteins to "shed" the extracellular domains. Additional, preferred MMPs include adamalysins, serralysins, and astacins.

Another group of preferred destructive proteases is a mammalian blood protease, such as Thrombin, Coagulation Factor VIIa, Coagulation Factor IXa, Coagulation Factor Xa, Coagulation Factor XIa, Coagulation Factor XIIa, Kallikrein, Protein C, and MBP-associated serine protease.

In one embodiment of the present invention, said destructive cleavage site comprises a recognition sequence having at least 3 or 4, preferably 5 or 6, more preferably 6 or 7, and particularly preferably at least 8 contiguous amino acid residues. In this regard, the longer (in terms of contiguous amino acid residues) the recognition sequence, the less likely non-specific cleavage of the destructive site will occur via an unintended second protease.

It is preferred that the destructive cleavage site of the present invention is introduced into the protease component and/or the Targeting Moiety and/or into the translocation component and/or into the spacer peptide. Of these four components, the protease component is preferred. Accordingly, the polypeptide may be rapidly inactivated by direct destruction of the non-cytotoxic protease and/or binding and/or translocation components.

Polypeptide Delivery

In use, the present invention employs a pharmaceutical composition, comprising a polypeptide, together with at least one component selected from a pharmaceutically acceptable carrier, excipient, adjuvant, propellant and/or salt.

The polypeptides of the present invention may be formulated for oral, parenteral, continuous infusion, implant, inhalation or topical application. Compositions suitable for injection may be in the form of solutions, suspensions or emulsions, or dry powders which are dissolved or suspended in a suitable vehicle prior to use.

Local delivery means may include an aerosol, or other spray (eg. a nebuliser). In this regard, an aerosol formulation of a polypeptide enables delivery to the lungs and/or other nasal and/or bronchial or airway passages.

The preferred route of administration is selected from: systemic, laparoscopic and/or localised injection (e.g. injection directly into the tumour).

In the case of formulations for injection, it is optional to include a pharmaceutically active substance to assist retention at or reduce removal of the polypeptide from the site of administration. One example of such a pharmaceutically active substance is a vasoconstrictor such as adrenaline. Such a formulation confers the advantage of increasing the residence time of polypeptide following administration and thus increasing and/or enhancing its effect.

The dosage ranges for administration of the polypeptides of the present invention are those to produce the desired therapeutic effect. It will be appreciated that the dosage range required depends on the precise nature of the polypeptide or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of polypeptide as the 1× dose. In this regard, preferred dosages are in the range 1×-100× (i.e. 2.5-250 ng).

Fluid dosage forms are typically prepared utilising the polypeptide and a pyrogen-free sterile vehicle. The polypeptide, depending on the vehicle and concentration used, can be either dissolved or suspended in the vehicle. In preparing solutions the polypeptide can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

Administration in accordance with the present invention may take advantage of a variety of delivery technologies including microparticle encapsulation, viral delivery systems or high-pressure aerosol impingement.

DEFINITIONS SECTION

Targeting Moiety (TM) means any chemical structure that functionally interacts with a Binding Site to cause a physical association between the polypeptide of the invention and the surface of a target cell. In the context of the present invention, the target cell is a cancerous cell, for example one in which autocrine stimulation is driving proliferation, survival, metastatic potential or angiogenesis. The term TM embraces any molecule (ie. a naturally occurring molecule, or a chemically/physically modified variant thereof) that is capable of binding to a Binding Site on the target cell, which Binding Site is capable of internalisation (eg. endosome formation)—also referred to as receptor-mediated endocytosis. The TM may possess an endosomal membrane translocation function, in which case separate TM and Translocation Domain components need not be present in an agent of the present invention. Throughout the preceding description, specific TMs have been described. Reference to said TMs is merely exemplary, and the present invention embraces all variants and derivatives thereof, which retain the basic binding (i.e. targeting) ability of the exemplified TMs.

In one embodiment, the cancer cell target of the present invention may be a cancer cell that does not secrete growth hormone (ie. no significant or detectable growth hormone is secreted therefrom).

As mentioned previously, preferred TMs include antibodies (eg. antibody fragments) and binding scaffolds; especially commercially available antibodies/fragments and scaffolds designed for the purpose of binding (eg. specifically) to cancer cells.

Protein scaffolds represent a new generation of universal binding frameworks to complement the expanding repertoire of therapeutic monoclonal antibodies and derivatives such as scFvs, Fab molecules, dAbs (single-domain antibodies), diabodies and minibodies, each of which may be employed as a TM of the present invention. Scaffold systems create or modify known protein recognition domains either through creation of novel scaffolds or modification of known protein binding domains. Such scaffolds include but are not limited to:

(i) protein A based scaffolds—affibodies (Nord, K. et al 1997 "Binding proteins selected from combinatorial libraries of an alpha-helical bacterial receptor domain". Nat Biotechnol 15, 772-777);
(ii) lipocalin based scaffolds—anticalins (Skerra 2008 "Alternative binding proteins: anticalins—harnessing the structural plasticity of the lipocalin ligand pocket to engineer novel binding activities". FEBS J. 275:2677-83);
(iii) fibronectin based scaffolds—adnectin (Dineen et al 2008 "The Adnectin CT-322 is a novel VEGF receptor 2 inhibitor that decreases tumor burden in an orthotopic mouse model of pancreatic cancer". BMC Cancer 8:352);
(iv) avimers (Silverman et al 2005 "Multivalent avimer proteins evolved by exon shuffling of a family of human receptor domains". Nat Biotechnol 23:1556-61);
(v) ankyrin based scaffolds—darpins (Zahnd et al 2006 "Selection and characterization of Her2 binding-designed ankyrin repeat proteins". J Biol Chem. 281:35167-75); and
(vi) centyrin scaffolds—based on a protein fold that has significant structural homology to Ig domains with loops that are analogous to CDRs. Ig domains are a common module in human proteins and have been widely applied as alternative scaffold proteins. Each of the above 'scaffold' publications is hereby incorporated (in its entirety) by reference thereto.

Binding scaffolds can be used to target particular cell types via interaction with specific cell surface proteins, receptors or other cell surface epitopes such as sugar groups. Such modified scaffolds can be engineered onto recombinant non-cytotoxic protease based polypeptides of the present invention to target specific cancer cell types of interest.

The TM of the present invention binds (preferably specifically binds) to the target cell in question. The term "specifically binds" preferably means that a given TM binds to the target cell with a binding affinity (Ka) of $10^6$ $M^{-1}$ or greater, preferably $10^7$ $M^{-1}$ or greater, more preferably $10^8$ $M^{-1}$ or greater, and most preferably, $10^9$ $M^{-1}$ or greater.

Reference to TM in the present specification embraces fragments and variants thereof, which retain the ability to bind to the target cell in question. By way of example, a variant may have at least 80%, preferably at least 90%, more preferably at least 95%, and most preferably at least 97 or at least 99% amino acid sequence homology with the reference TM. Thus, a variant may include one or more analogues of an amino acid (e.g. an unnatural amino acid), or a substituted linkage. Also, by way of example, the term fragment, when used in relation to a TM, means a peptide having at least ten, preferably at least twenty, more preferably at least thirty, and most preferably at least forty amino acid residues of the reference TM. The term fragment also relates to the above-mentioned variants. Thus, by way of example, a fragment of the present invention may comprise a peptide sequence having at least 10, 20, 30 or 40 amino acids, wherein the peptide sequence has at least 80% sequence homology over a corresponding peptide sequence (of contiguous) amino acids of the reference peptide.

By way of example, ErbB peptide TMs may be modified to generate mutein ErbB ligands with altered properties such as increased stability. By way of example, ErbB TM muteins include ErbB peptides having amino acid modifications such as a valine residue at position 46 or 47 (EGFVal46 or 47), which confers stability to cellular proteases. ErbB TMs may also have amino acids deleted or additional amino acids inserted. This includes but is not limited to EGF having a deletion of the two C-terminal amino acids and a neutral amino acid substitution at position 51 (particularly EGF51Gln51; see US20020098178A1), and EGF with amino acids deleted (e.g. rEGF2-48; rEGF3-48 and rEGF4-48). Fragments of ErbB TMs may include fragments of TGFα which contain predicted β-turn regions (e.g. a peptide of the sequence Ac-C-H-S-G-Y-V-G-A-R-C-O-OMe) (SEQ ID NO: 141), fragments of EGF such as [Ala20]EGF(14-31), and the peptide YHWYGYTPQNVI (SEQ ID NO: 142) or GE11. All of the above patent specifications are incorporated herein by reference thereto.

By way of further example, somatostatin (SST) and cortistatin (CST) have high structural homology, and bind to all known SST receptors. Full-length SST has the amino acid sequence:

```
                                        (SEQ ID NO: 143)
MLSCRLQCALAALSIVLALGCVTGAPSDPRLRQFLQKSLAAAAGKQELAK

YFLAELLSEPNQTENDALEPEDLSQAAEQDEMRLELQRSANSNPAMAPRE

RKAGCKNFFWKTFTSC)
```

Full-length CST has the amino acid sequence:

```
                                        (SEQ ID NO: 144)
MYRHKNSWRLGLKYPPSSKEETQVPKTLISGLPGRKSSSRVGEKLQSAHK

MPLSPGLLLLLLSGATATAALPLEGGPTGRDSEHMQEAAGIRKSSLLTFL

AWWFEWTSQASAGPLIGEEAREVARRQEGAPPQQSARRDRMPCRNFFWKT

FSSCK
```

Reference to these TMs includes the following fragments (and corresponding variants) thereof:

```
                                        (SEQ ID NO: 145)
            NFFWKTF;
                                        (SEQ ID NO: 146)
      (R or K)NFFWKTF;
                                        (SEQ ID NO: 147)
     C(R or K)NFFWKTF;
                                        (SEQ ID NO: 148)
(P or G)C(R or K)NFFWKTF;
                                        (SEQ ID NO: 149)
            NFFWKTF(S or T);
                                        (SEQ ID NO: 150)
            NFFWKTF(S or T)S;
                                        (SEQ ID NO: 151)
            NFFWKTF(S or T)SC;
                                        (SEQ ID NO: 152)
      (R or K)NFFWKTF(S or T);
                                        (SEQ ID NO: 153)
      (R or K)NFFWKTF(S or T)S;
                                        (SEQ ID NO: 154)
      (R or K)NFFWKTF(S or T)SC;
                                        (SEQ ID NO: 155)
     C(R or K)NFFWKTF(S or T);
                                        (SEQ ID NO: 156)
     C(R or K)NFFWKTF(S or T)S;
                                        (SEQ ID NO: 157)
     C(R or K)NFFWKTF(S or T)SC;
```

```
                                          (SEQ ID NO: 158)
(P or G)C(R or K)NFFWKTF(S or T);

(SEQ ID NO: 159)
(P or G)C(R or K)NFFWKTF(S or T)S;
or (SEQ ID NO: 160)
(P or G)C(R or K)NFFWKTF(S or T)SC.
```

With regard to the above sequences, where a (P or G) alternative is given, a P is preferred in the case of a CST TM, whereas a G is preferred in the case of an SST TM. Where an (R or K) alternative is given, an R is preferred in the case of a CST TM, whereas a K is preferred in the case of an SST TM. Where an (S or T) alternative is given, an S is preferred in the case of a CST TM, whereas a T is preferred in the case of an SST TM.

Preferred fragments comprise at least 7 or at least 10 amino acid residues, preferably at least 14 or at least 17 amino acid residues, and more preferably at least 28 or 29 amino acid residues. By way of example, preferred sequences include:

```
                                          (SEQ ID NO: 161)
SANSNPAMAPRERKAGCKNFFWKTFTSC (SST-28);

(SEQ ID NO: 162)
             AGCKNFFWKTFTSC (SST-14);

(SEQ ID NO: 163)
QEGAPPQQSARRDRMPCRNFFWKTFSSCK (CST-29);

(SEQ ID NO: 164)
QERPPLQQPPHRDKKPCKNFFWKTFSSCK (CST-29);

(SEQ ID NO: 165)
QERPPPQQPPHLDKKPCKNFFWKTFSSCK (CST-29)

(SEQ ID NO: 166)
             DRMPCRNFFWKTFSSCK (CST-17);

(SEQ ID NO: 167)
                 PCRNFFWKTFSSCK (CST-14);
and
                                          (SEQ ID NO: 168)
                 PCKNFFWKTFSSCK (CST-14).
```

The TM may comprise a longer amino acid sequence, for example, at least 30 or 35 amino acid residues, or at least 40 or 45 amino acid residues, so long as the TM is able to bind to a normal GH-secreting cell, preferably to an SST or to a CST receptor on a normal GH-secreting cell. In this regard, the TM is preferably a fragment of full-length SST or CST, though including at least the core sequence "NFFWKTF" or one of the above-defined primary amino acid sequences.

It is routine to confirm that a TM binds to the selected target cell. For example, a simple radioactive displacement experiment may be employed in which tissue or cells representative of a growth hormone-secreting cell are exposed to labelled (eg. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

In the context of the present invention, reference to a peptide TM (e.g. GHRH peptide, or leptin peptide) embraces peptide analogues thereof, so long as the analogue binds to the same receptor as the corresponding 'reference' TM. Said analogues may include synthetic residues such as:

ß-Nal=ß-naphthylalanine
ß-Pal=ß-pyridylalanine
hArg(Bu)=N-guanidino-(butyl)-homoarginine
hArg(Et)$_2$=N,N'-guanidino-(dimethyl)-homoarginine
hArg(CH$_2$CF$_3$)$_2$=N,N'-guanidino-bis-(2,2,2,-trifluoroethyl)-homoarginine
hArg(CH$_3$, hexyl)=N,N'-guanidino-(methyl, hexyl)-homoarginine
Lys(Me)=N$^e$-methyllysine
Lys(iPr)=N$^e$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle—norleucine
Nva=norvaline
Trp(Br)=5-bromo-tryptophan
Trp(F)=5-fluoro-tryptophan
Trp(N0$_2$)=5-nitro-tryptophan
Gaba=γ-aminobutyric acid
Bmp=J-mercaptopropionyl
Ac=acetyl
Pen—pencillamine By way of example, the above peptide analogue aspect is described in more detail with reference to specific peptide TMs, such as SST peptides, GHRH peptides, bombesin peptides, GnRH peptides, and ghrelin peptides, though the same principle applies to all TMs of the present invention.

Somatostatin analogues, which can be used to practice the present invention include, but are not limited to, those described in the following publications, which are hereby incorporated by reference: Van Binst, G. et al. Peptide Research 5: 8 (1992); Horvath, A. et al. Abstract, "Conformations of Somatostatin Analogs Having Antitumor Activity", 22nd European peptide Symposium, Sep. 13-19, 1992, Interlaken, Switzerland; U.S. Pat. No. 5,506,339; EP0363589; U.S. Pat. No. 4,904,642; U.S. Pat. No. 4,871,717; U.S. Pat. No. 4,725,577; U.S. Pat. No. 4,684,620; U.S. Pat. No. 4,650,787; U.S. Pat. No. 4,585,755; U.S. Pat. No. 4,725,577; U.S. Pat. No. 4,522,813; U.S. Pat. No. 4,369,179; U.S. Pat. No. 4,360,516; U.S. Pat. No. 4,328,214; U.S. Pat. No. 4,316,890; U.S. Pat. No. 4,310,518; U.S. Pat. No. 4,291,022; U.S. Pat. No. 4,238,481; U.S. Pat. No. 4,235,886; U.S. Pat. No. 4,211,693; U.S. Pat. No. 4,190,648; U.S. Pat. No. 4,146,612; U.S. Pat. No. 4,133,782; U.S. Pat. No. 5,506,339; U.S. Pat. No. 4,261,885; U.S. Pat. No. 4,282,143; U.S. Pat. No. 4,190,575; U.S. Pat. No. 5,552,520; EP0389180; EP0505680; U.S. Pat. No. 4,603,120; EP0030920; U.S. Pat. No. 4,853,371; WO90/12811; WO97/01579; WO91/18016; WO98/08529 and WO98/08528; WO/0075186 and WO00/06185; WO99/56769; and FR 2,522,655. Each of these publications is incorporated in its entirety by reference thereto.

Methods for synthesizing analogues are well documented, as illustrated, for example, by the patents cited above. For example, synthesis of H-D-Phe-Phe-Phe-D-Trp-Lys-Thr-Phe-Thr-NH2, can be achieved by following the protocol set forth in Example 1 of EP0395417A1. Similarly, synthesis analogues with a substituted N-terminus can be achieved, for example, by following the protocol set forth in WO88/02756, EP0329295, and U.S. Pat. No. 5,240,561.

The use of linear SST analogues are also included within the scope of this invention, for example: H-D-Phe-p-chloro-Phe-Tyr-D-Trp-Lys-Thr-Phe-Thr-NH2; H-D-Phe-p-N02-Phe-Tyr-D-Trp-Lys-Val-Phe-Thr-NH2; H-D-*Nal-p-chloro-Phe-Tyr-D-Trp-Lys-Val-Phe-Phe-Thr-NH2; H-D-Phe-Phe-Phe-D-Trp-Lys-Thr-Phe-Thr-NH2; H-D-Phe-Phe-Tyr-D-Trp-Lys-Val-Phe-Thr-NH2; H-D-Phe-p-chloro-Phe-Tyr-D-Trp-Lys-Val-Phe-Thr-NH2; and H-D-Phe-Ala-Tyr-D-Trp-Lys-Val-Ala-D-beta-Nal-NH2.

One or more chemical moieties, eg. a sugar derivative, mono or poly-hydroxy (C2-12) alkyl, mono or poly-hydroxy (C2-12) acyl groups, or a piperazine derivative, can be attached to a SST analogue, e g. to the N-terminus amino acid—see WO88/02756, EP0329295, and U.S. Pat. No. 5,240,561. GHRH peptide analogues date back to the 1990s, and include the 'standard antagonist' [Ac-Tyr, D-Arg2jhGH-RH (1-29) Nha. U.S. Pat. No. 4,659,693 discloses GH-RH antagonistic analogs which contain certain N,N'-dialkyl-omega-guanidino alpha-amino acyl residues in position 2 of the GH-RH (1-29) sequence. Additional examples are provided in WO91/16923, U.S. Pat. No. 5,550,212, U.S. Pat. No. 5,942,489, U.S. Pat. No. 6,057,422 U.S. Pat. No. 5,942,489, U.S. Pat. No. 6,057,422, WO96/032126, WO96/022782, WO96/016707, WO94/011397, WO94/011396, each of which is herein incorporated by reference thereto.

Examples of bombesin analogues suitable for use in the present invention include TMs comprising: D-Phe-Gln-Trp-Ala-Val-Gly-His-Leu-Met-NH$_2$ (code named BIM-26218), D-Phe-Gln-Trp-Ala-Val-Gly-His-Leu-Leu-NH$_2$ (code named BIM-26187); D-Cpa-Gln-Trp-Ala-Val-Gly-His-Leu-φ [CH$_2$NH]-Phe-NH$_2$ (code named BIM-26159), and D-Phe-Gln-Trp-Ala-Val-Gly-His-Leu-φ [CH$_2$NH]-Cpa-NH$_2$ (code named BIM-26189); D-Phe-Gln-Trp-Ala-Val-N-methyl-D-Ala-His-Leu-methylester, and D-F$_g$-Phe-Gln-Trp-Ala-Val-D-Ala-His-Leu-methylester.

Bombesin analogues include peptides derived from the naturally-occurring, structurally-related peptides, namely, bombesin, neuromedin B, neuromedin C, litorin, and GRP. The relevant amino acid sequences of these naturally occurring TM peptides are listed below:

```
Bombesin (last 10 aa's):
                                    (SEQ ID NO: 169)
Gly-Asn-Gln-Trp-Ala-Val-Gly-His-Leu-Met-NH2

Neuromedin B:
                                    (SEQ ID NO: 170)
Gly-Asn-Leu-Trp-Ala-Thr-Gly-His-Phe-Met-NH2

Neuromedin C:
                                    (SEQ ID NO: 171)
Gly-Asn-His-Trp-Ala-Val-Gly-His-Leu-Met-NH2

Litorin:
                                    (SEQ ID NO: 172)
Glu-Gln-Trp-Ala-Val-Gly-His-Phe-Met-NH2

Human GRP (last 10 aa's):
                                    (SEQ ID NO: 173)
Gly-Asn-His-Trp-Ala-Val-Gly-His-Leu-Met-NH2
```

Analogs suitable for use in the present invention are described in U.S. Serial Number 502,438, filed Mar. 30, 1990, U.S. Ser. No. 397,169, filed Aug. 21, 1989, U.S. Ser. No. 376,555, filed Jul. 7, 1989, U.S. Ser. No. 394,727, filed Aug. 16, 1989, U.S. Ser. No. 317,941, filed Mar. 2, 1989, U.S. Ser. No. 282,328, filed Dec. 9, 1988, U.S. Ser. No. 257,998, filed Oct. 14, 1988, U.S. Ser. No. 248,771, filed Sep. 23, 1988, U.S. Ser. No. 207,759, filed Jun. 16, 1988, U.S. Ser. No. 204,171, filed Jun. 8, 1988, U.S. Ser. No. 173,311, filed Mar. 25, 1988, U.S. Ser. No. 100,571, filed Sep. 24, 1987; and U.S. Ser. No. 520,225, filed May 9, 1990, U.S. Ser. No. 440,039, filed Nov. 21, 1989. All these applications are hereby incorporated by reference. Bombesin analogs are also described in Zachary et al., Proc. Nat. Aca. Sci. 82:7616 (1985); Heimbrook et al., "Synthetic Peptides: Approaches to Biological Problems", UCLA Symposium on Mol. and Cell. Biol. New Series, Vol. 86, ed. Tam and Kaiser; Heinz-Erian et al., Am. J. Physiol. G439 (1986); Martinez et al., J. Med. Chem. 28:1874 (1985); Gargosky et al., Biochem. J. 247:427 (1987); Dubreuil et al., Drug Design and Delivery, Vol 2:49, Harwood Academic Publishers, GB (1987); Heikkila et al., J. Biol. Chem. 262:16456 (1987); Caranikas et al., J. Med. Chem. 25:1313 (1982); Saeed et al., Peptides 10:597 (1989); Rosell et al., Trends in Pharmacological Sciences 3:211 (1982); Lundberg et al., Proc. Nat. Aca. Sci. 80:1120, (1983); Engberg et al., Nature 293:222 (1984); Mizrahi et al., Euro. J. Pharma. 82:101 (1982); Leander et al., Nature 294:467 (1981); Woll et al., Biochem. Biophys. Res. Comm. 155:359 (1988); Rivier et al., Biochem. 17:1766 (1978); Cuttitta et al., Cancer Surveys 4:707 (1985); Aumelas et al., Int. J. Peptide Res. 30:596 (1987); all of which are also hereby incorporated by reference.

The analogs can be prepared by conventional techniques, such as those described in WO92/20363 and EP0737691. Additional bombesin analogues are described in, for example, WO89/02897, WO91/17181, WO90/03980 and WO91/02746, all of which are herein incorporated by reference thereto.

Examples of ghrelin analogues suitable for use as a TM of the present invention comprise: Tyr-DTrp-DLys-Trp-DPhe-NH$_2$, Tyr-DTrp-Lys-Trp-DPhe-NH$_2$, His-DTrp-DLys-Trp-DPhe-NH$_2$, His-DTrp-DLys-Phe-DTrp-NH$_2$, His-DTrp-DArg-Trp-DPhe-NH$_2$, His-DTrp-DLys-Trp-DPhe-Lys-NH$_2$, DesaminoTyr-DTrp-Ala-Trp-DPhe-NH$_2$, DesaminoTyr-DTrp-DLys-Trp-DPhe-NH$_2$, DeaminoTyr-DTrp-Ser-Trp-DPhe-Lys-NH$_2$, DesaminoTyr-DTrp-Ser-Trp-DPhe-NH$_2$, His-DTrp-DTrp-Phe-Met-NH$_2$, Tyr-DTrp-DTrp-Phe-Phe-NH$_2$, Glyψ[CH$_2$NH]-Dβal-Ala-Trp-DPhe-Lys-NH$_2$, Glyψ[CH$_2$NH]-DbetaNal-DLyS-TrP-DPhe-Lys-NH$_2$, DAla-DbetaNal-DLys-DTrp-Phe-Lys-NH$_2$, His-DbetaNal-DLys-Trp-DPhe-Lys-NH$_2$, Ala-His-DTrp-DLys-Trp-DPhe-Lys-NH$_2$, Alaφ[CH$_2$NH]-DbetaNal-Ala-Trp-DPhe-Lys-NH$_2$, DbetaNal-Ala-Trp-DPhe-Ala-NH$_2$, DAla-DcyclohexylAla-Ala-Phe-DPhe-Nle-NH$_2$, DcyclohexylAla-Ala-Phe-DTrp-Lys-N H$_2$, DAla-DbetaAla-Thr-DThr-Lys-NH$_2$, DcyclohexylAla-Ala-Trp-DPhe-NH2, DAla-DbetaNal-Ala-Ala-DAla-Lys-NH$_2$, DbetaNal-Ala-Trp-DPhe-Leu-NH$_2$, His-DTrp-Phe-Trp-DPhe-Lys-NH$_2$, DAla-DbetaNal-DAla-DTrp-Phe-Lys-NH$_2$, pAla-Trp-DAla-DTrp-Phe-NH$_2$, His-Trp-DAla-DTrp-Phe-LysNH$_2$, DLys-DβNal-Ala-Trp-DPhe-Lys-NH$_2$, DAla-DbetaNal-DLys-DTrp-Phe-Lys-NH$_2$, Tyr-DAla-Phe-Aib-NH$_2$, Tyr-DAla-Sar-NMePhe-NH$_2$, αγAbu-DTrp-DTrp-Ser-N H$_2$, αγAbu-DTrp-DTrp-Lys-N H$_2$, αγAbu-DTrp-DTrp-Orn-N H$_2$, αAbu-DTrp-DTrp-Orn-NH$_2$, DThr-DαNal-DTrp-DPro-Arg-NH$_2$, DAla-Ala-DAla-DTrp-Phe-Lys-NH$_2$, Alaψ[CH$_2$NH]His-DTrp-Ala-Trp-DPhe-Lys-NH$_2$, Lys-DHis-DTrp-Phe-NH$_2$, γAbu-DTrp-DTrp-Orn-NH$_2$, inip-Trp-Trp-Phe-NH$_2$, Ac-DTrp-Phe-DTrp-Leu-NH$_2$, Ac-DTrp-Phe-DTrp-Lys-NH$_2$, Ac-DTrp-DTrp-Lys-NH$_2$, DLys-Tyr-DTrp-DTrp-Phe-Lys-NH$_2$, Ac-DbetaNal-Leu-Pro-NH$_2$, pAla-Trp-DTrp-DTrp-Orn-NH$_2$, DVal-DαNal-DTrp-Phe-Arg-NH$_2$, DLeu-DαNal- DTrp-Phe-Arg-NH$_2$, CyclohexylAla-DαNal-DTrp-Phe-Arg-NH$_2$, DTp-DαNal-DTrp-Phe-Arg-NH$_2$, DAla-DβNal-DPro-Phe-Arg-NH$_2$, Ac-DαNal-DTrp-Phe-Arg-NH$_2$, DαNal-DTrp-Phe-Arg-N H$_2$, His-DTrp-DTrp-Lys-N H$_2$, Ac-DpNal-DTrp-N H$_2$, αAib-DTrp-DcyclohexylAla-N H$_2$, αAib-DTrp-DAla-cyclohexylAla-N H$_2$, DAla-Dcyclohexy-lAla-Ala-Ala-Phe-DPhe-N Ie-NH$_2$, DPhe-Ala-Phe-DPal-NH$_2$, DPhe-Ala-Phe-DPhe-Lys-NH$_2$, DLys-Tyr-DTrp-DTrp-Phe-NH$_2$, Ac-DLys-Tyr-DTrp-DTrp-Phe-NH$_2$, Arg-DTrp-Leu-Tyr-Trp-Pro(cyclic Arg-Pro), Ac-DβNal-PicLys-ILys-DPhe-NH2, DPal-Phe-DTrp-Phe-Met-NH$_2$, DPhe-Trp-DPhe-Phe-Met-NH$_2$, DPal-Trp-DPhe-Phe-Met-NH$_2$, pAla-Pal-DTrp-DTrp-Orn-NH$_2$, αγAbu-Trp-DTrp-DTrp-Orn-NH$_2$, βAla-Trp-DTrp-DTrp-Lys-NH$_2$, γAbu-Trp-DTrp-DTrp-Orn-NH$_2$, Ava-Trp-DTrp-DTrp-Orn-NH$_2$, DLys-Tyr-DTrp-Ala-Trp-DPhe-NH$_2$, His-DTrp-DArg-Trp-DPhe-NH$_2$, <Glu-His-Trp-DSer-DArg-NH$_2$, DPhe-DPhe-DTrp-Met-DLys-NH$_2$, 0-(2-methylallyl) benzophonone oxime, (R)-2-amino-3-(IH-indol-3-yl)-1-(4-phenylpiperidin-1-yl)propan-1-one, N—((R)-1-((R)-1-((S)-3-(IH-indol-3-yl)-1-oxo-1-(4-phenylpiperidin-1-yl)propan-2-ylamino)-6-amino-1-oxohexan-2-ylamino)-3-hydroxy-1-oxopropan-2-yl) benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide, (S)—N—((R)-3-(1H-indol-3-yl)-1-oxo-1-(4-phenylpiperidin-1-yl)propan-2-yl)-2-((S)-2-acetamido-3-(benzyloxy) propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S)-2,4-diamino-N—((R)-3-(naphthalen-2-ylmethoxy)-1-oxo-1-(4-phenylpiperidin-1-yl)propan-2-yl) butanamide, naphthalene-2,3-diylbis((4-(2-methoxyphenyl) piperazin-1-yl)methanone), (R)-2-amino-N-(3-(benzyloxy)-1-oxo-1-(4-phenylpiperazin-1-yl)propan-2-yl)-2-methylpropanamide, or (R)-2-amino-3-(benzyloxy)-1-(4-phenylpiperazin-1-yl)propan-1-one.

Examples of GnRH analogues suitable for use as a TM in the present invention include those known from, for example, EP171477, WO96/033729, WO92/022322, WO92/013883, and WO91/05563, each of which is herein incorporated by reference thereto. Specific examples comprise:
(NAcDQal$^1$,DPtf$^2$,DPAl$^3$,cjsPzACAla$^5$,DPicLys$^6$,DAla$^{10}$) LHRH;
(NAcDNal$^1$,DpClPhe$^2$,DPal$^3$, cjsPzACAla$^5$,DNicLys$^6$, ILys$^8$,DAla$^{10}$)LHRH;
(NAcDNal$^1$, DpClPhe$^2$,DPal$^3$,Thr$^4$, PicLys$^5$, DPicLys$^6$, ILys$^8$, DAla$^{10}$)LHRH;
(NAcDNal$^1$,DpClPhe$^2$,DPal$^3$, PicLys$^5$, DPicLys$^6$,Thr$^7$, ILys$^8$,DAla$^{10}$)LHRH;
(NapDThr$^1$,DpClPhe$^2$,DPal$^3$,PicLys$^5$,DPicLys$^6$,ILys$^8$, DAla$^{10}$)LHRH;
(NAcDNal$^1$,DpClPhe$^2$,DPal$^3$,NicLys$^5$,DNicLys$^6$,Thr$^7$, ILys$^8$,DAla$^{10}$)LHRH;
(NAcDNal$^1$,DpClPhe$^2$,DPal$^3$,Thr$^4$,NicLys$^5$,DNicLys$^6$,Thr$^7$, ILys$^8$, DAla$^{10}$)LHRH;
(NAcDNal$^1$,DpClPhe$^2$,DPal$^3$,PicLys$^5$,D(PicSar)Lys$^6$,ILys$^8$, DAla$^{10}$)LHRH'
(NAcDNal$^1$,DpClPhe$^2$,DPal$^3$,D(PicSar)Lys$^6$,IlLys$^8$, DAla$^{10}$)LHRH;
(NAcDNal$^1$,DpClPhe$^2$,DPal$^3$,PicLys$^5$,D(6ANic)Lys$^6$,ILys$^8$, DAla$^{10}$)LHRH;
(NAcDNal$^1$,DpClPhe$^2$,DPal$^3$,PicLys$^5$,D(6ANic)0rn$^6$,ILys$^8$, DAla$^{10}$)LHRH;
(NAcDQal$^1$,DCpa$^2$,DPal$^3$,cisPzACAla$^5$,DPicLys$^6$,NLeu$^7$, ILys$^8$,DAla$^{10}$)LHRH;
(NAcDNal$^1$,DCpa$^2$,DPal$^3$,DPicLys$^5$,DAPhe(PicSar)$^β$, ILys$^8$,DAla$^{10}$)LHRH;
(NAcDQal$^1$,DCpa$^2$,DPal$^3$,PicLys$^5$,DPal$^6$,ILys$^8$,DAla$^{10}$) LHRH;
(NAcDNal$^1$,DCpa$^2$,DPal$^3$,PicLys$^5$,DOrn(ACyp)$^6$,ILys$^8$, DAla$^{10}$)LHRH; N-acetyl-D-beta-Nal-D-Phe-D-Phe-Ser-Tyr-D-Lys(cyclo-pentyl)-Phe-Arg-Pro-D-Ala-NH$_2$;
N-acetyl-D-ø-Nal-D-Phe-D-Phe-Ser-Tyr-D-Lys(cyclopentyl)-Phe-Lys(cyclopentyl)-Pro-D-Ala-N H$_2$; N-acetyl-D-beta-Nal-D-Phe-D-Phe-Ser-Tyr-D-Arg-Phe-(isopropyl)D-Lys-Pro-D-Ala-NH$_2$;
N-acetyl-D-beta-Nal-D-Phe-D-Phe-Ser-Tyr-D-Lys(benzyl)-Phe-Arg-Pro-D-Ala-NH$_2$; N-acetyl-D-beta-Nal-D-Phe-D-Phe-Ser-Tyr-D-Lys(Cl-benzyl)-Phe-Arg-Pro-D-Ala-NH$_2$;
N-acetyl-D-beta-Nal-D-Phe-D-Phe-Ser-Tyr-D-Lys(heptyl)-Phe-Arg-Pro-D-Ala-NH$_2$; N-acetyl-D-beta-Nal-D-Phe-D-Phe-Ser-Tyr-D-Arg-Phe-Lys-(t-butylmethyl)-Pro-D-Ala-NH$_2$; N-acetyl-D-beta-Nal-D-Phe-D-Phe-Ser-Tyr-D-Arg-Phe-Lys-(4-methyl-benzyl)-Pro-D-Ala-N H$_2$; N-acetyl-D-beta-Nal-D-Phe-D-Phe-Ser-Tyr-D-Arg-Phe-Lys-(benzyl)-Pro-D-Ala-NH$_2$; N-acetyl-D-beta-Nal-D-p-Cl-Phe-D-Trp-Ser-Tyr-D-p-NH$_2$-Phe-Phe-(isopropyl)Lys-Pro-D-Ala-NH$_2$; N-acetyl-D-beta-Nal-D-Phe-D-Phe-Ser-Tyr-D-Lys(heptyl)-Phe-Lys-(heptyl)-Pro-D-Ala-NH$_2$; N-acetyl-D-3-Nal-D-Phe-D-Phe-Ser-Tyr-D-Lys(1-butylpentyl)-Phe-Lys(1-butyl-pentyl)-Arg-Pro-D-Ala-NH$_2$.

The polypeptides of the present invention lack a functional H$_C$ domain of a clostridial neurotoxin. Accordingly, said polypeptides are not able to bind rat synaptosomal membranes (via a clostridial H$_C$ component) in binding assays as described in Shone et al. (1985) Eur. J. Biochem. 151, 75-82. In a preferred embodiment, the polypeptides preferably lack the last 50 C-terminal amino acids of a clostridial neurotoxin holotoxin. In another embodiment, the polypeptides preferably lack the last 100, preferably the last 150, more preferably the last 200, particularly preferably the last 250, and most preferably the last 300 C-terminal amino acid residues of a clostridial neurotoxin holotoxin. Alternatively, the H$_C$ binding activity may be negated/reduced by mutagenesis—by way of example, referring to BoNT/A for convenience, modification of one or two amino acid residue mutations (W1266 to L and Y1267 to F) in the ganglioside binding pocket causes the H$_C$ region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of H$_C$ receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

In another embodiment, the polypeptides of the present invention lack a functional H$_C$ domain of a clostridial neurotoxin and also lack any functionally equivalent TM. Accordingly, said polypeptides lack the natural binding function of a clostridial neurotoxin and are not able to bind rat synaptosomal membranes (via a clostridial H$_C$ component, or via any functionally equivalent TM) in binding assays as described in Shone et al. (1985) Eur. J. Biochem. 151, 75-82.

The $H_C$ peptide of a native clostridial neurotoxin comprises approximately 400-440 amino acid residues, and consists of two functionally distinct domains of approximately 25 kDa each, namely the N-terminal region (commonly referred to as the $H_{CN}$ peptide or domain) and the C-terminal region (commonly referred to as the $H_{CC}$ peptide or domain). This fact is confirmed by the following publications, each of which is herein incorporated in its entirety by reference thereto: Umland T C (1997) Nat. Struct. Biol. 4: 788-792; Herreros J (2000) Biochem. J. 347: 199-204; Halpem J (1993) J. Biol. Chem. 268: 15, pp. 11188-11192; Rummel A (2007) PNAS 104: 359-364; Lacey DB (1998) Nat. Struct. Biol. 5: 898-902; Knapp (1998) Am. Cryst. Assoc. Abstract Papers 25: 90; Swaminathan and Eswaramoorthy (2000) Nat. Struct. Biol. 7: 1751-1759; and Rummel A (2004) Mol. Microbiol. 51(3), 631-643. Moreover, it has been well documented that the C-terminal region ($H_{CC}$), which constitutes the C-terminal 160-200 amino acid residues, is responsible for binding of a clostridial neurotoxin to its natural cell receptors, namely to nerve terminals at the neuromuscular junction—this fact is also confirmed by the above publications. Thus, reference throughout this specification to a clostridial heavy-chain lacking a functional heavy chain $H_C$ peptide (or domain) such that the heavy-chain is incapable of binding to cell surface receptors to which a native clostridial neurotoxin binds means that the clostridial heavy-chain simply lacks a functional $H_{CC}$ peptide. In other words, the $H_{CC}$ peptide region is either partially or wholly deleted, or otherwise modified (e.g. through conventional chemical or proteolytic treatment) to inactivate its native binding ability for nerve terminals at the neuromuscular junction.

Thus, in one embodiment, a clostridial $H_N$ peptide of the present invention lacks part of a C-terminal peptide portion ($H_{CC}$) of a clostridial neurotoxin and thus lacks the $H_C$ binding function of native clostridial neurotoxin. By way of example, in one embodiment, the C-terminally extended clostridial $H_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial $H_N$ peptide of the present invention lacks the entire C-terminal peptide portion ($H_{CC}$) of a clostridial neurotoxin and thus lacks the $H_C$ binding function of native clostridial neurotoxin. By way of example, in one embodiment, the clostridial $H_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial $H_N$ peptide of the present invention lacks a clostridial $H_{CC}$ reference sequence selected from the group consisting of:

Botulinum type A neurotoxin—amino acid residues (Y1111-L1296)
Botulinum type B neurotoxin—amino acid residues (Y1098-E1291)
Botulinum type C neurotoxin—amino acid residues (Y1112-E1291)
Botulinum type D neurotoxin—amino acid residues (Y1099-E1276)
Botulinum type E neurotoxin—amino acid residues (Y1086-K1252)
Botulinum type F neurotoxin—amino acid residues (Y1106-E1274)
Botulinum type G neurotoxin—amino acid residues (Y1106-E1297)
Tetanus neurotoxin—amino acid residues (Y1128-D1315).

The above-identified reference sequences should be considered a guide as slight variations may occur according to sub-serotypes.

The protease of the present invention embraces all non-cytotoxic proteases that are capable of cleaving one or more proteins of the exocytic fusion apparatus in eukaryotic cells.

The protease of the present invention is preferably a bacterial protease (or fragment thereof). More preferably the bacterial protease is selected from the genera *Clostridium* or *Neisseria/Streptococcus* (e.g. a clostridial L-chain, or a neisserial IgA protease preferably from *N. gonorrhoeae* or *S. pneumoniae*).

The present invention also embraces variant non-cytotoxic proteases (ie. variants of naturally-occurring protease molecules), so long as the variant proteases still demonstrate the requisite protease activity. By way of example, a variant may have at least 70%, preferably at least 80%, more preferably at least 90%, and most preferably at least 95 or at least 98% amino acid sequence homology with a reference protease sequence. Thus, the term variant includes non-cytotic proteases having enhanced (or decreased) endopeptidase activity—particular mention here is made to the increased $K_{cat}/K_m$ of BoNT/A mutants Q161A, E54A, and K165L see Ahmed, S. A. (2008) Protein J. DOI 10.1007/s10930-007-9118-8, which is incorporated by reference thereto. The term fragment, when used in relation to a protease, typically means a peptide having at least 150, preferably at least 200, more preferably at least 250, and most preferably at least 300 amino acid residues of the reference protease. As with the TM 'fragment' component (discussed above), protease 'fragments' of the present invention embrace fragments of variant proteases based on a reference sequence.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

BoNTs are the most potent toxins known, with median lethal dose (LD50) values for mice ranging from 0.5 to 5 ng/kg depending on the serotype. BoNTs are adsorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/C, BoNT/A and BoNT/E cleave the synaptosomal-associated protein of 25 kDa (SNAP-25); and BoNT/C cleaves syntaxin.

BoNTs share a common structure, being di-chain proteins of ~150 kDa, consisting of a heavy chain (H-chain) of ~100 kDa covalently joined by a single disulphide bond to a light chain (L-chain) of ~50 kDa. The H-chain consists of two domains, each of ~50 kDa. The C-terminal domain ($H_C$) is required for the high-affinity neuronal binding, whereas the N-terminal domain ($H_N$) is proposed to be involved in membrane translocation. The L-chain is a zinc-dependent metalloprotease responsible for the cleavage of the substrate SNARE protein.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

Examples of suitable protease (reference) sequences include:
  Botulinum type A neurotoxin—amino acid residues (1-448)
  Botulinum type B neurotoxin—amino acid residues (1-440)
  Botulinum type C neurotoxin—amino acid residues (1-441)
  Botulinum type D neurotoxin—amino acid residues (1-445)
  Botulinum type E neurotoxin—amino acid residues (1-422)
  Botulinum type F neurotoxin—amino acid residues (1-439)
  Botulinum type G neurotoxin—amino acid residues (1-441)
  Tetanus neurotoxin—amino acid residues (1-457)
  IgA protease—amino acid residues (1-959)*
    *Pohlner, J. et al. (1987). Nature 325, pp. 458-462, which is hereby incorporated by reference thereto.

The above-identified reference sequence should be considered a guide as slight variations may occur according to sub-serotypes. By way of example, US 2007/0166332 (hereby incorporated by reference thereto) cites slightly different clostridial sequences:
  Botulinum type A neurotoxin—amino acid residues (M1-K448)
  Botulinum type B neurotoxin—amino acid residues (M1-K441)
  Botulinum type C neurotoxin—amino acid residues (M1-K449)
  Botulinum type D neurotoxin—amino acid residues (M1-R445)
  Botulinum type E neurotoxin—amino acid residues (M1-R422)
  Botulinum type F neurotoxin—amino acid residues (M1-K439)
  Botulinum type G neurotoxin—amino acid residues (M1-K446)
  Tetanus neurotoxin—amino acid residues (M1-A457)

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain (residues 417-448) are not required for enzymatic activity. As another non-limiting example, the last 31 amino acids of the TeNT light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

The polypeptides of the present invention, especially the protease component thereof, may be PEGylated—this may help to increase stability, for example duration of action of the protease component. PEGylation is particularly preferred when the protease comprises a BoNT/A, B or $C_1$ protease. PEGylation preferably includes the addition of PEG to the N-terminus of the protease component. By way of example, the N-terminus of a protease may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is incorporated in its entirety by reference thereto.

A Translocation Domain is a molecule that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (eg. $H_N$ domain). As with the TM 'fragment'component (discussed above), translocation 'fragments' of the present invention embrace fragments of variant translocation domains based on the reference sequences.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. The H-chain lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is incapable of binding to the Binding Site on a target cell to which native clostridial neurotoxin (i.e. holotoxin) binds.

Examples of suitable (reference) Translocation Domains include:
Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)
Botulinum type E neurotoxin—amino acid residues (423-845)
Botulinum type F neurotoxin—amino acid residues (440-864)
Botulinum type G neurotoxin—amino acid residues (442-863)
Tetanus neurotoxin—amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:
Botulinum type A neurotoxin—amino acid residues (A449-K871)
Botulinum type B neurotoxin—amino acid residues (A442-S858)
Botulinum type C neurotoxin—amino acid residues (T450-N866)
Botulinum type D neurotoxin—amino acid residues (D446-N862)
Botulinum type E neurotoxin—amino acid residues (K423-K845)
Botulinum type F neurotoxin—amino acid residues (A440-K864)
Botulinum type G neurotoxin—amino acid residues (S447-S863)
Tetanus neurotoxin—amino acid residues (S458-V879)

In the context of the present invention, a variety of Clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of Clostridial toxins are approximately 410-430 amino acids in length and comprise a translocation domain. Research has shown that the entire length of a $H_N$ region from a Clostridial toxin heavy chain is not necessary for the translocating activity of the translocation domain. Thus, aspects of this embodiment can include clostridial toxin $H_N$ regions comprising a translocation domain having a length of, for example, at least 350 amino acids, at least 375 amino acids, at least 400 amino acids and at least 425 amino acids. Other aspects of this embodiment can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in *The Clostridia: Molecular Biology and Pathogenesis, Academic press*.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of *diphtheria* toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the (reference) Translocation Domains listed in Table (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGW EGMIDGWYG (SEQ ID NO: 174), and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

The polypeptides of the present invention may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of amino acids) or spumavirus fusogenic peptide domain such as simian foamy virus fusogenic peptide domain; or fragments or variants thereof.

By way of further example, a translocation facilitating domain may comprise a Clostridial toxin $H_{CN}$ domain or a fragment or variant thereof. In more detail, a Clostridial toxin $H_{CN}$ translocation facilitating domain may have a length of at least 200 amino acids, at least 225 amino acids, at least 250 amino acids, at least 275 amino acids. In this regard, a Clostridial toxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)
Botulinum type B neurotoxin—amino acid residues (859-1097)
Botulinum type C neurotoxin—amino acid residues (867-1111)
Botulinum type D neurotoxin—amino acid residues (863-1098)
Botulinum type E neurotoxin—amino acid residues (846-1085)
Botulinum type F neurotoxin—amino acid residues (865-1105)
Botulinum type G neurotoxin—amino acid residues (864-1105)
Tetanus neurotoxin—amino acid residues (880-1127)

The above sequence positions may vary a little according to serotype/subtype, and further examples of suitable (reference) Clostridial toxin $H_{CN}$ domains include:

Botulinum type A neurotoxin—amino acid residues (874-1110)
Botulinum type B neurotoxin—amino acid residues (861-1097)
Botulinum type C neurotoxin—amino acid residues (869-1111)
Botulinum type D neurotoxin—amino acid residues (865-1098)
Botulinum type E neurotoxin—amino acid residues (848-1085)
Botulinum type F neurotoxin—amino acid residues (867-1105)
Botulinum type G neurotoxin—amino acid residues (866-1105)
Tetanus neurotoxin—amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_{CN}$ translocation facilitating domain may be combined with a non-clostridal translocation domain peptide. Alternatively, a Clostridial toxin $H_{CN}$ facilitating domain may be combined or with a clostridial translocation domain peptide, examples of which include:

Botulinum type A neurotoxin—amino acid residues (449-1110)
Botulinum type B neurotoxin—amino acid residues (442-1097)
Botulinum type C neurotoxin—amino acid residues (450-1111)
Botulinum type D neurotoxin—amino acid residues (446-1098)
Botulinum type E neurotoxin—amino acid residues (423-1085)
Botulinum type F neurotoxin—amino acid residues (440-1105)
Botulinum type G neurotoxin—amino acid residues (447-1105)
Tetanus neurotoxin—amino acid residues (458-1127)

Sequence Homology:

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |

```
W  -3  -3  -4  -4  -2  -2  -3  -2  -2  -3  -2  -3  -1   1  -4  -3  -2  11

Y  -2  -2  -2  -3  -2  -1  -2  -3   2  -1  -1  -2  -1   3  -3  -2  -2   2   7

V   0  -3  -3  -3  -1  -2  -2  -3  -3   3   1  -2   1  -1  -2  -2   0  -3  -1   4
```

The percent identity is then calculated as:

$$\frac{\text{Total number of identical matches}}{[\text{length of the longer sequence plus the number of gaps introduced into the longer sequence in order to align the sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine lysine histidine
Acidic: glutamic acid aspartic acid
Polar: glutamine asparagine
Hydrophobic: leucine isoleucine valine
Aromatic: phenylalanine tryptophan tyrosine
Small: glycine alanine serine threonine methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxyproline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 2:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 3:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

There now follows a brief description of the Figures, which illustrate aspects and/or embodiments of the present invention.

FIG. 1—Purification of LHN/D-CT-CST29 fusion protein

Using the methodology outlined in Example 3, a LHN/D-CT-CST29 fusion protein was purified from *E. coli* BL21 (DE3) cells. Briefly, the soluble products obtained following cell disruption were applied to a nickel-charged affinity capture column. Bound proteins were eluted with 200 mM imidazole, treated with enterokinase to activate the fusion protein and then re-applied to a second nickel-charged affinity capture column. Samples from the purification procedure were assessed by SDS-PAGE. Lane 1: First nickel chelating Sepharose column eluant, Lane 2: Second nickel chelating Sepharose column eluant under non-reducing conditions, Lane 3: Second nickel chelating Sepharose column eluant under reducing conditions, lane 4: Molecular mass markers (kDa).

Figure 2:
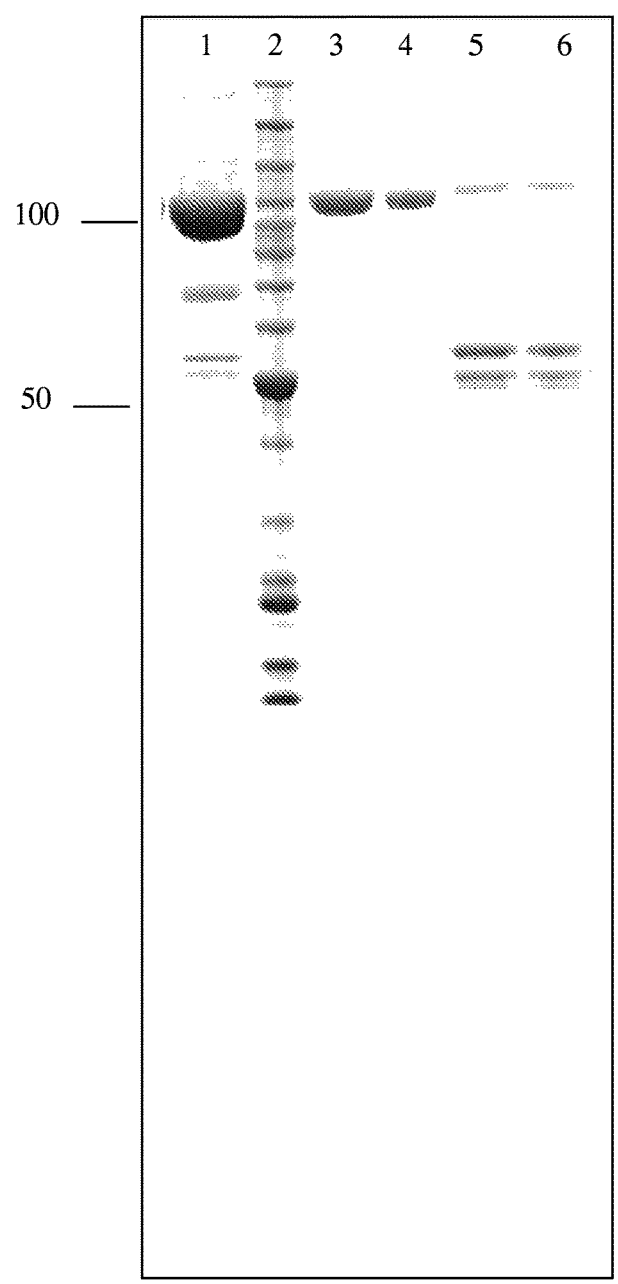
Figure 3:
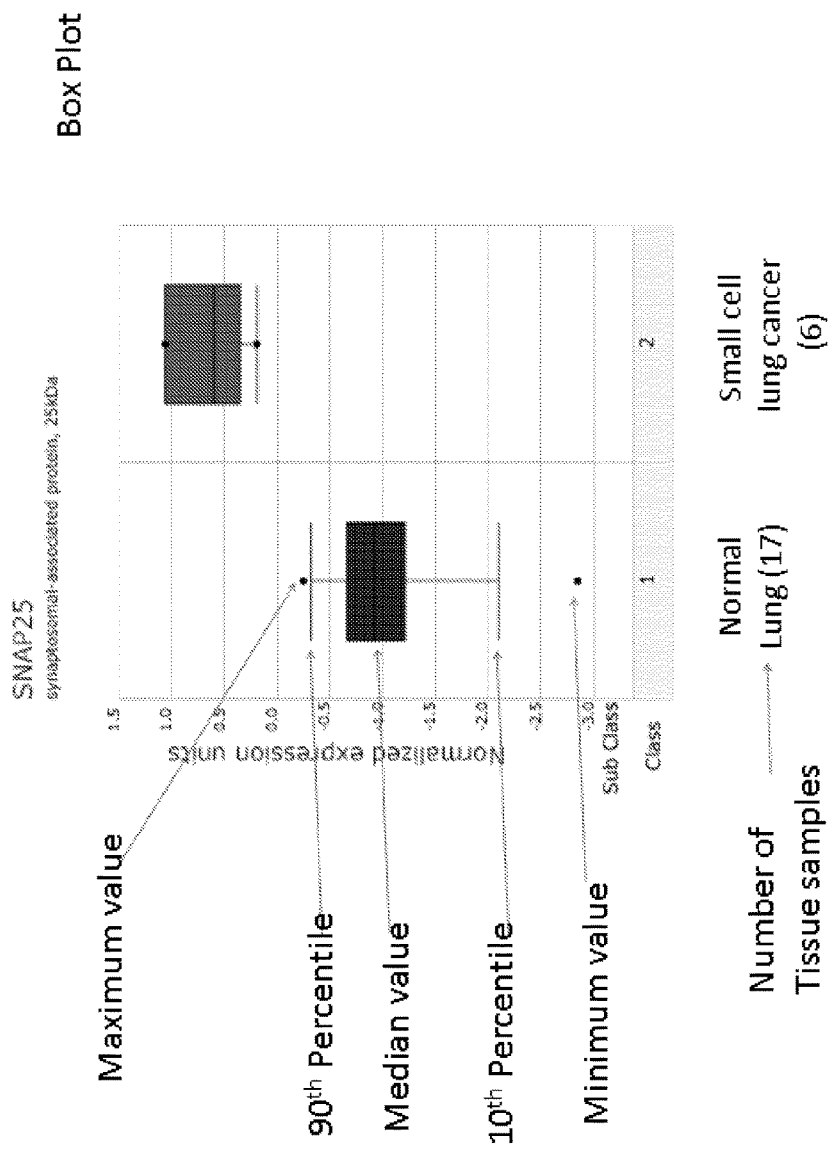
Figure 4:
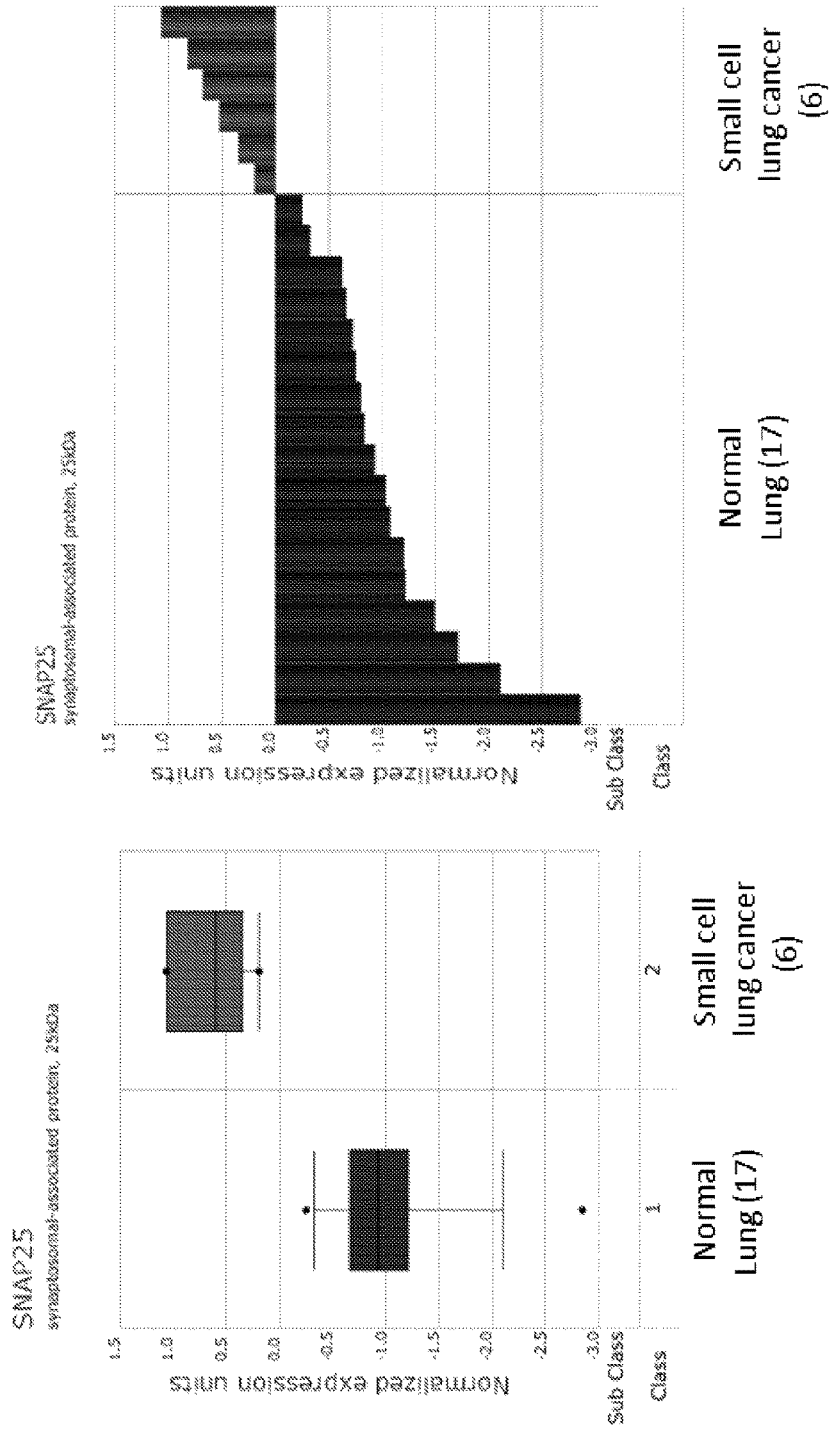
Figure 5:
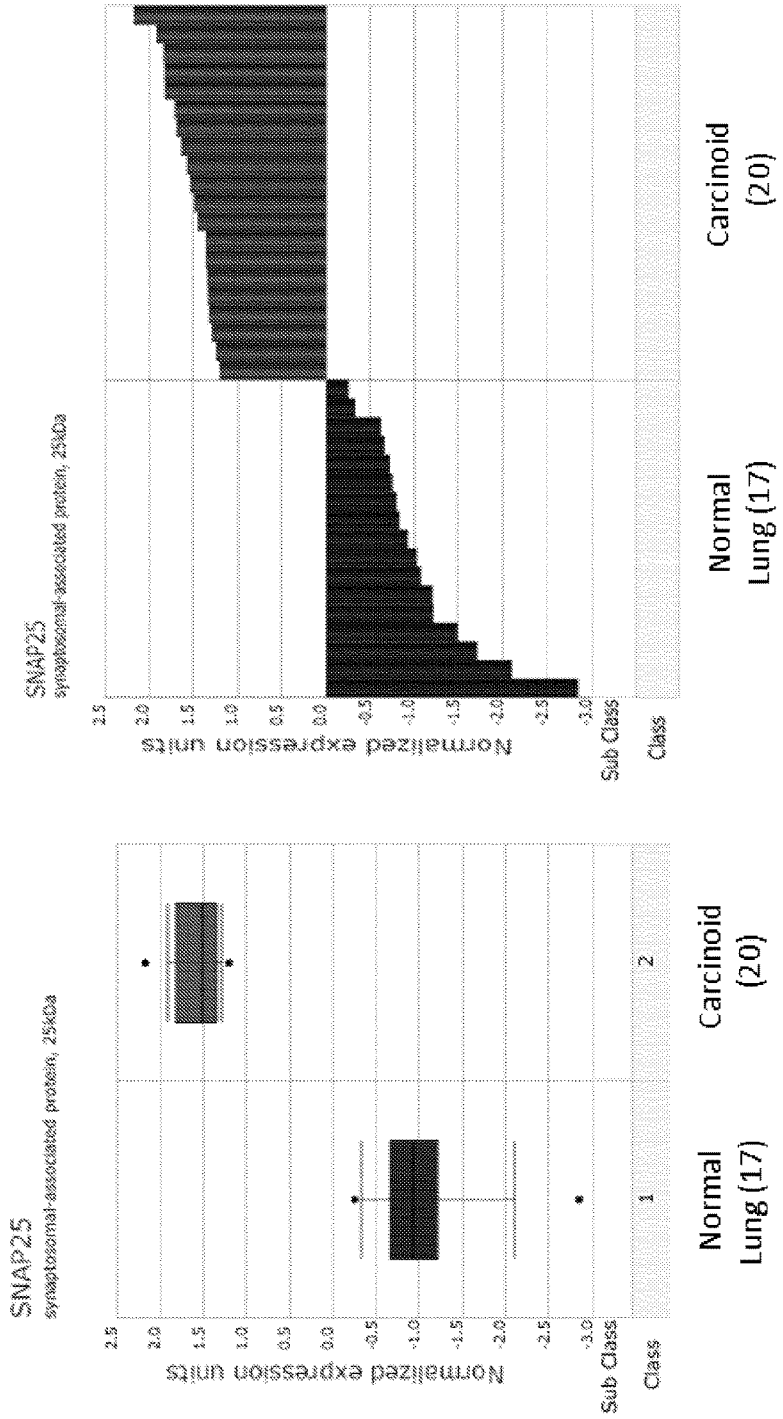
Figure 6:
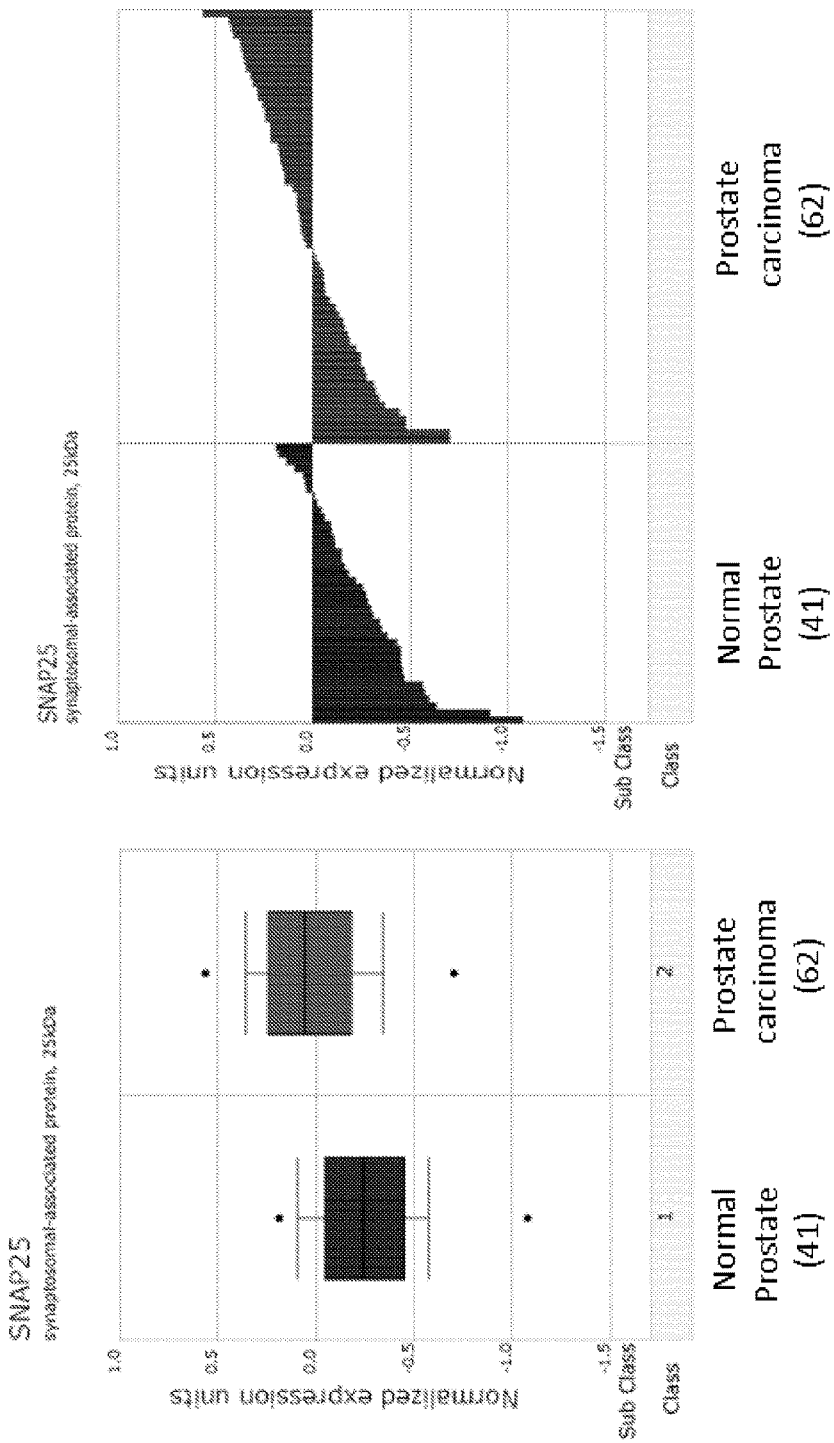
Figure 7:
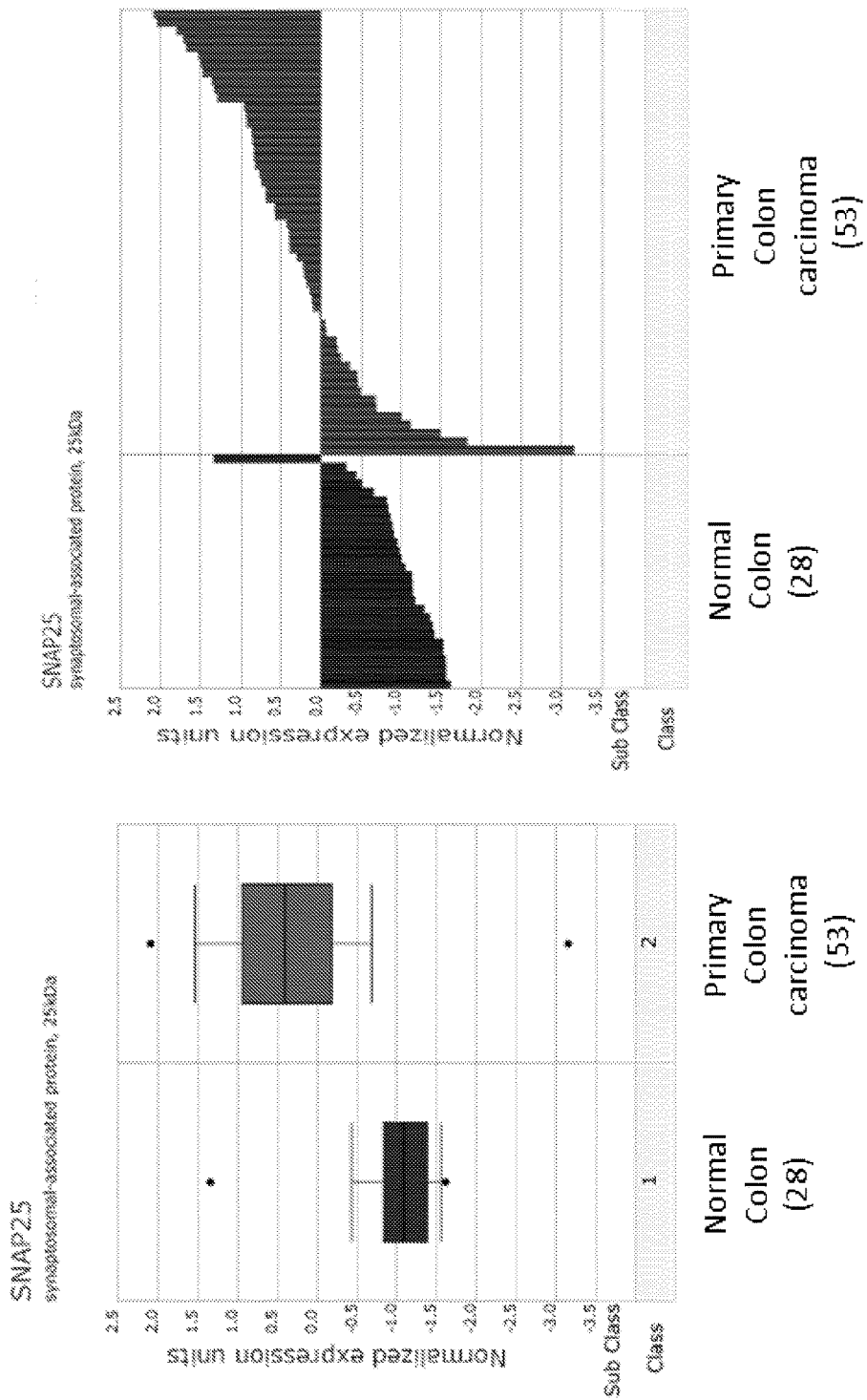
Figure 8:
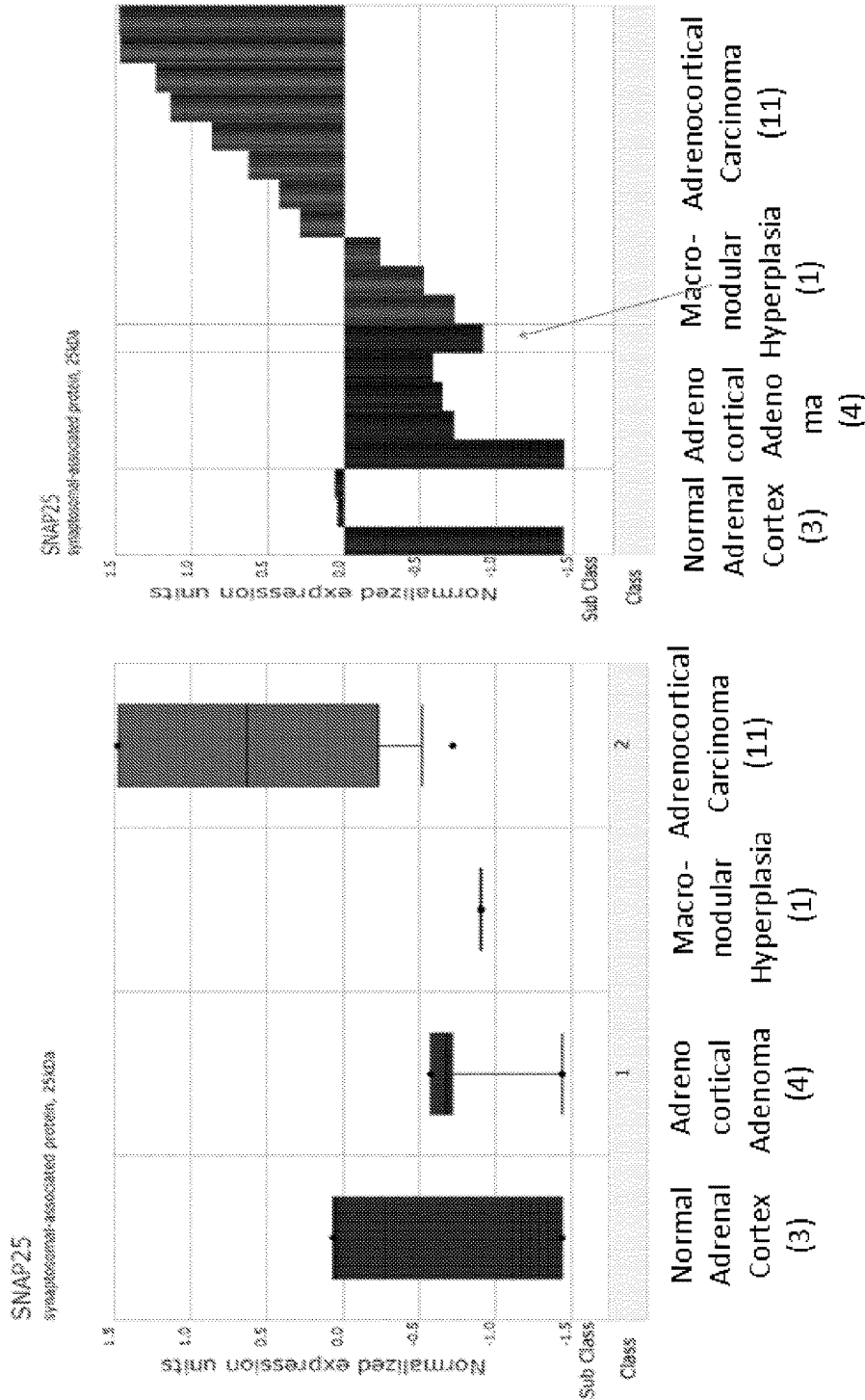
Figure 9:
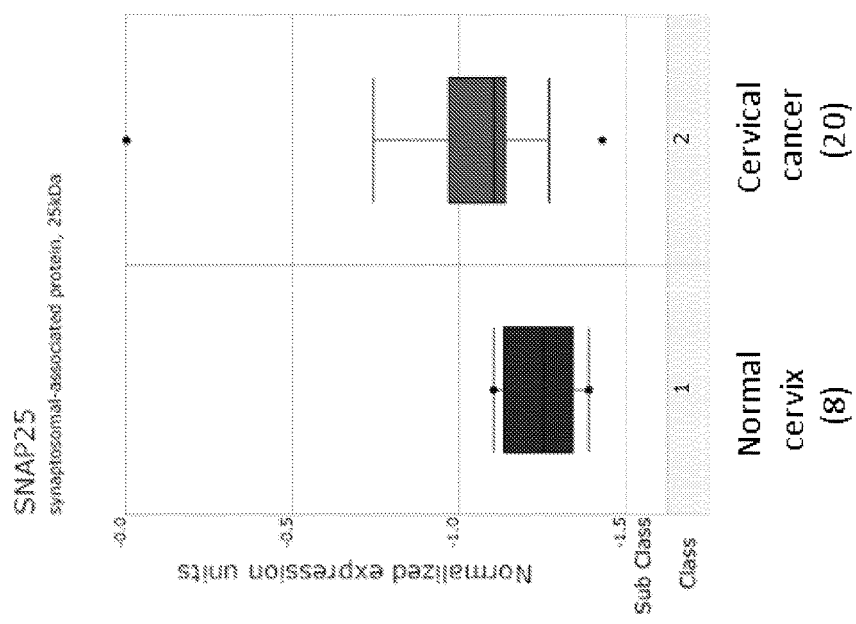
Figure 10:
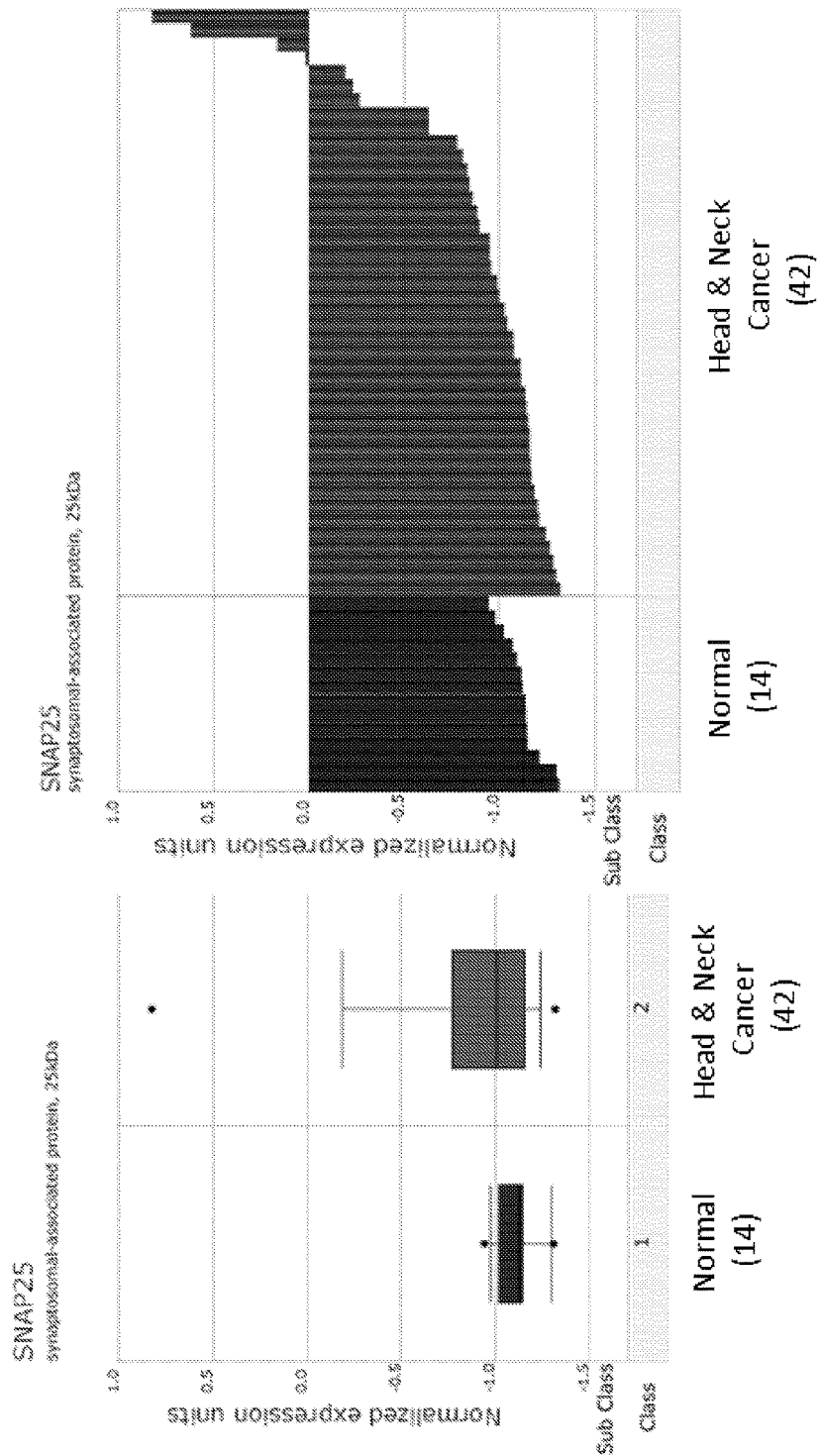
Figure 11:
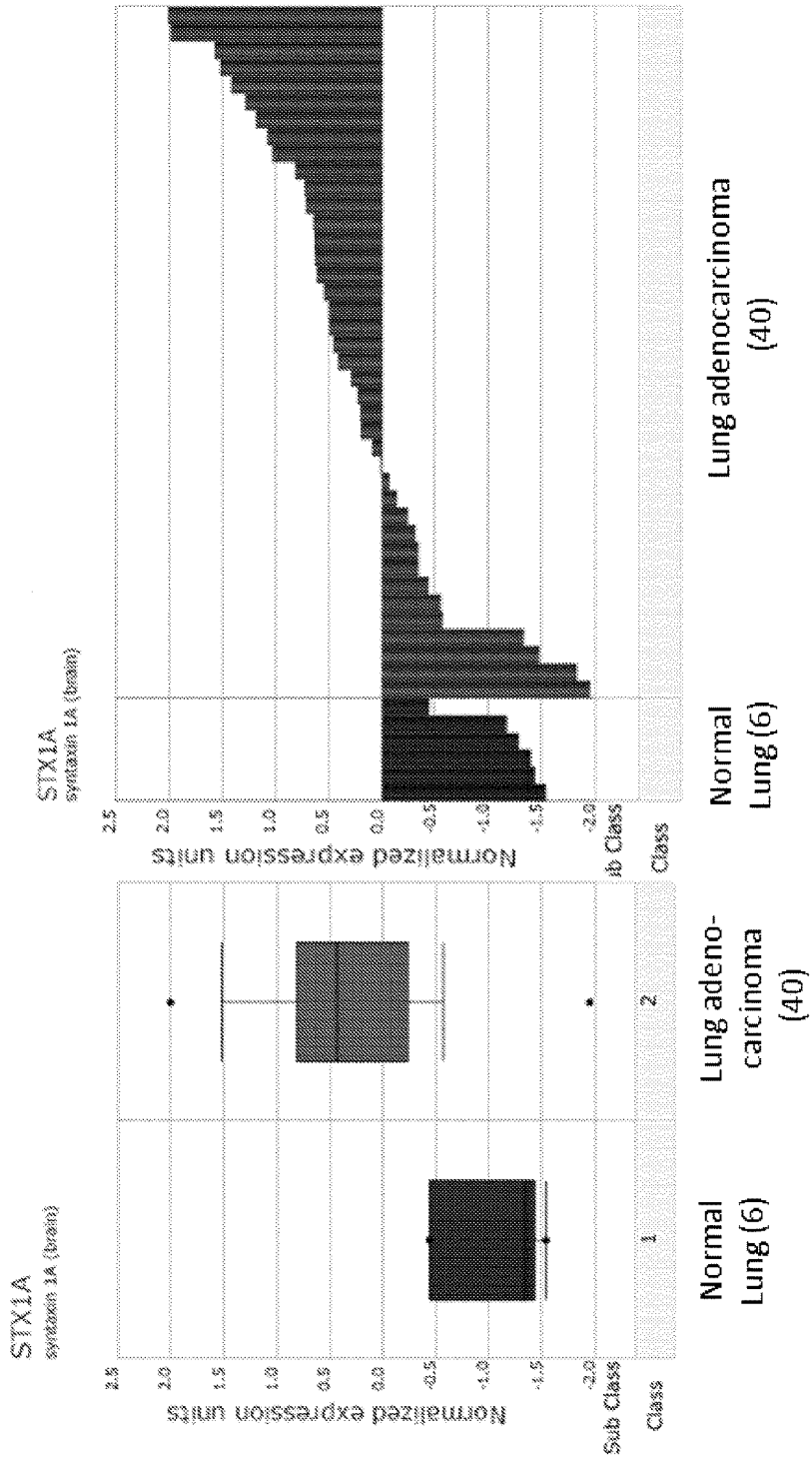
Figure 12:
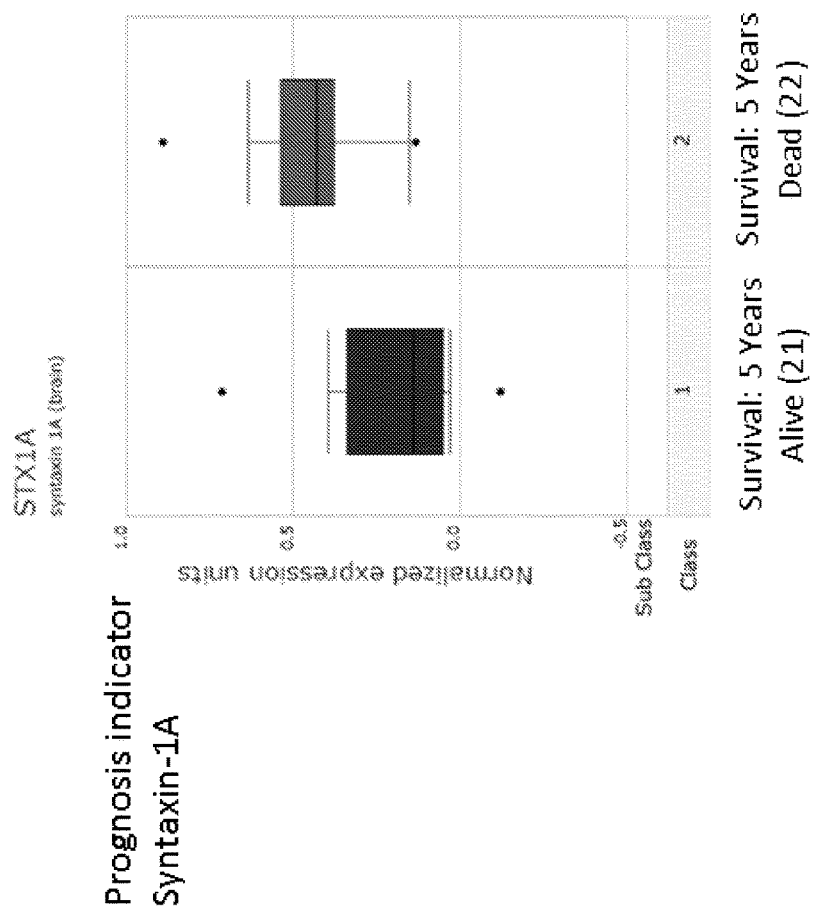
Figure 13:
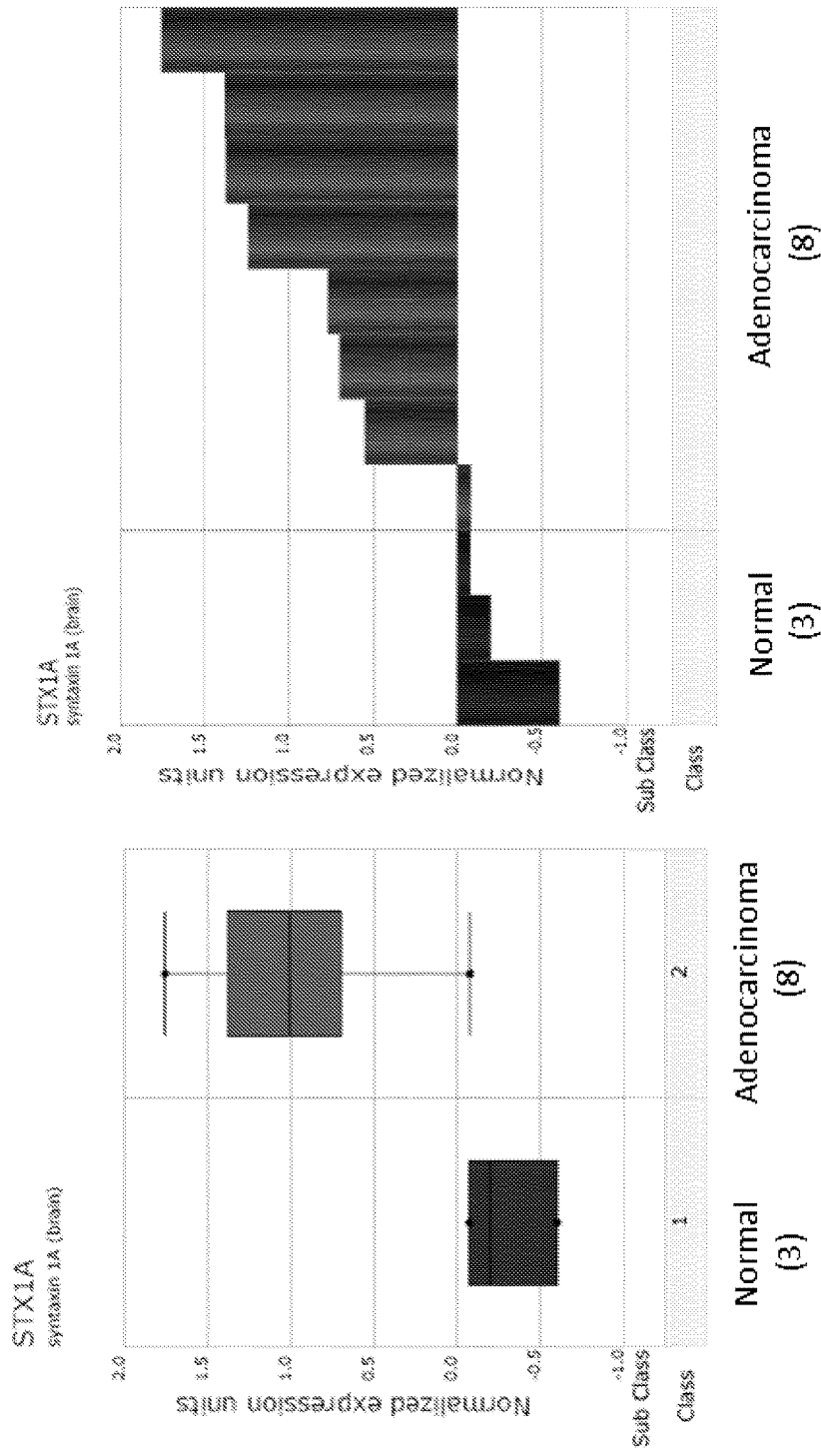
Figure 14:
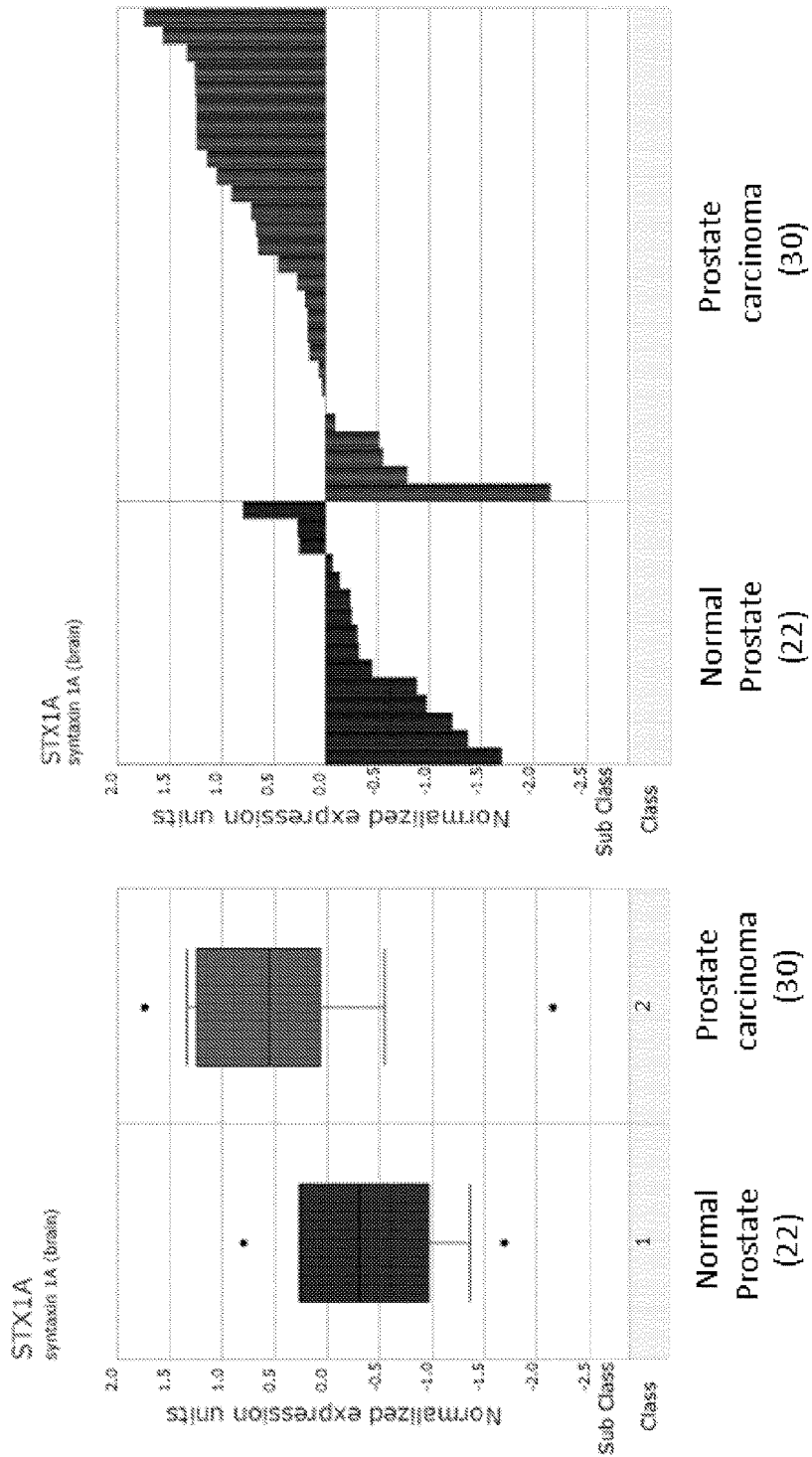
Figure 15:
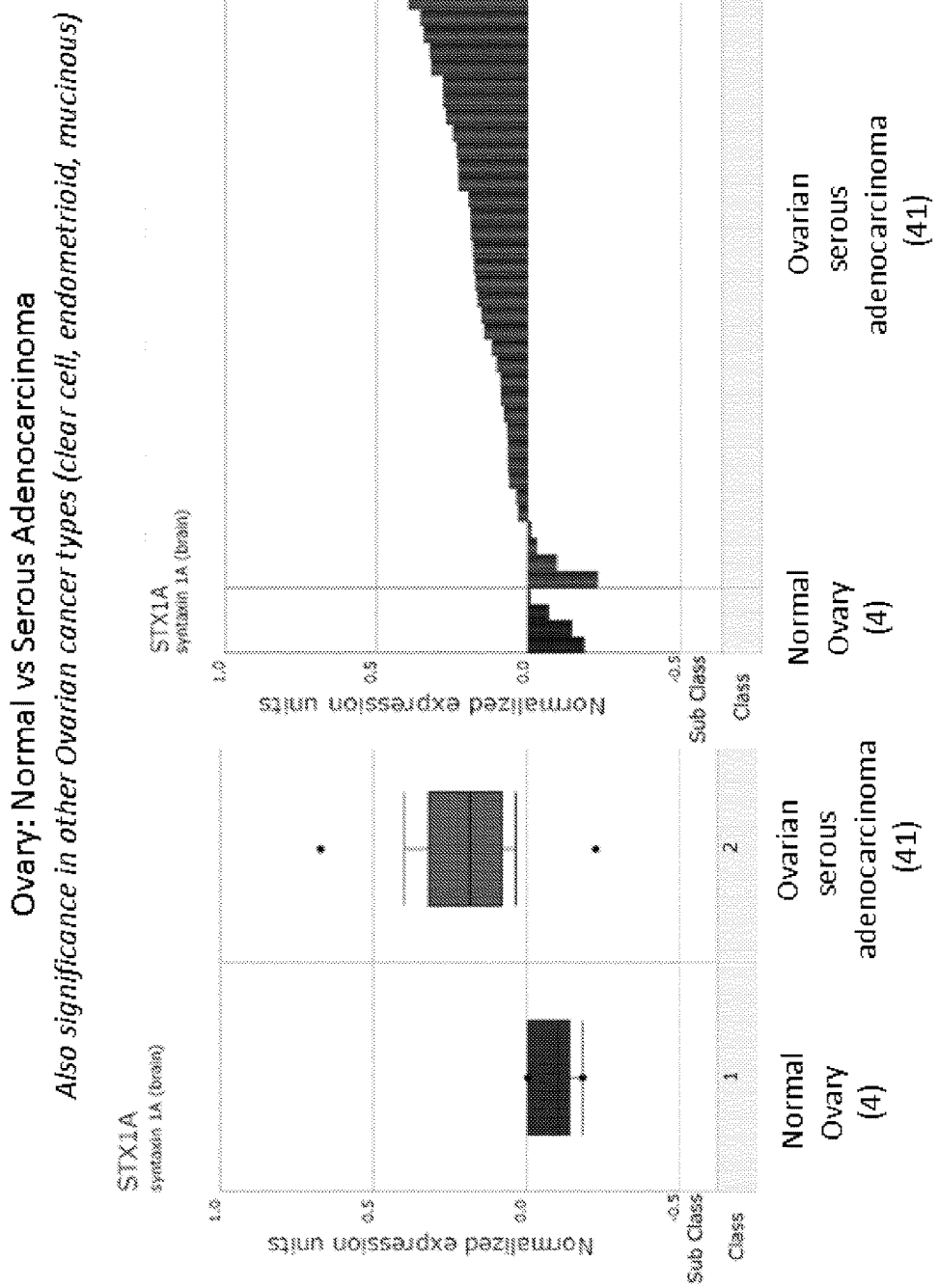
Figure 16:
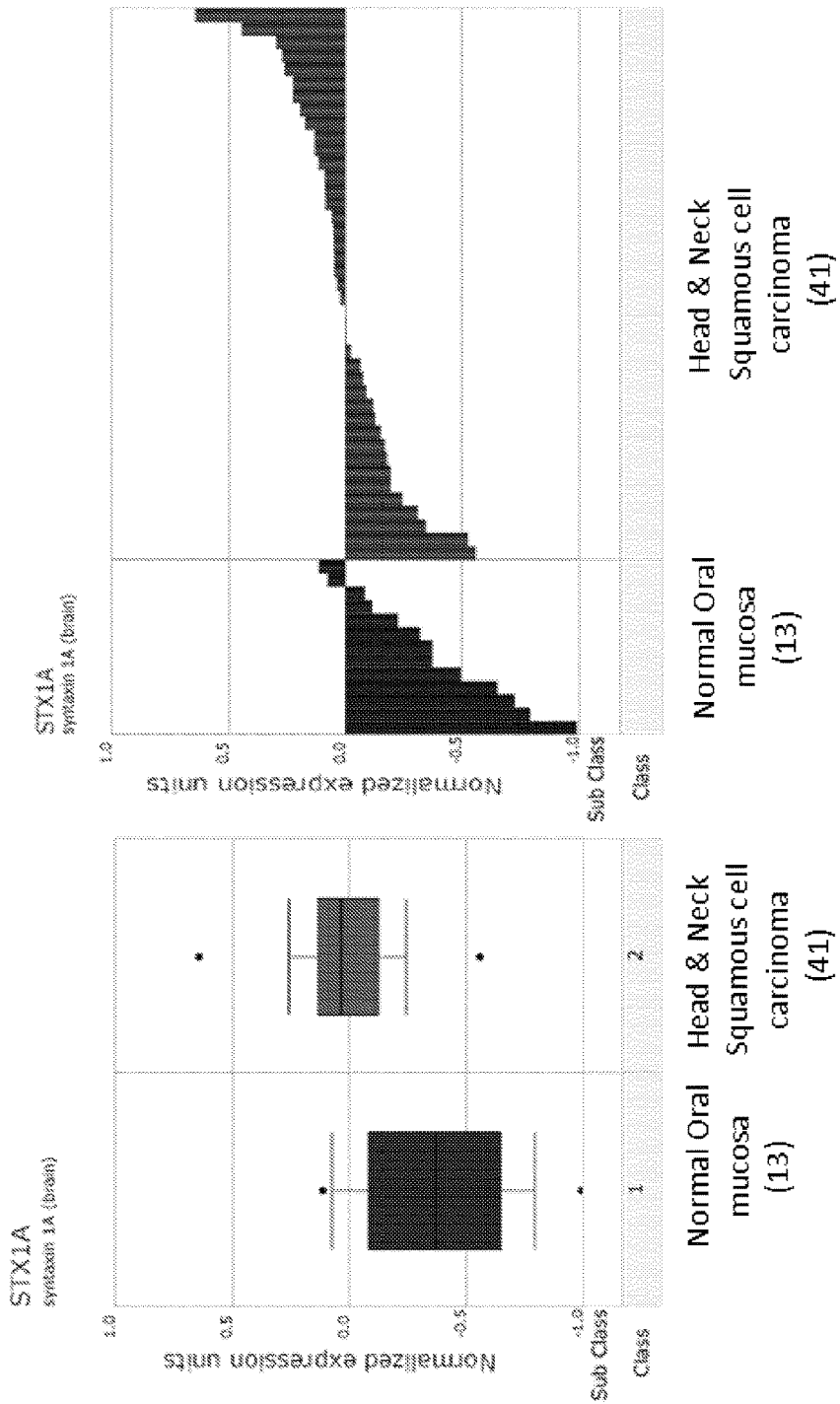
Figure 17:
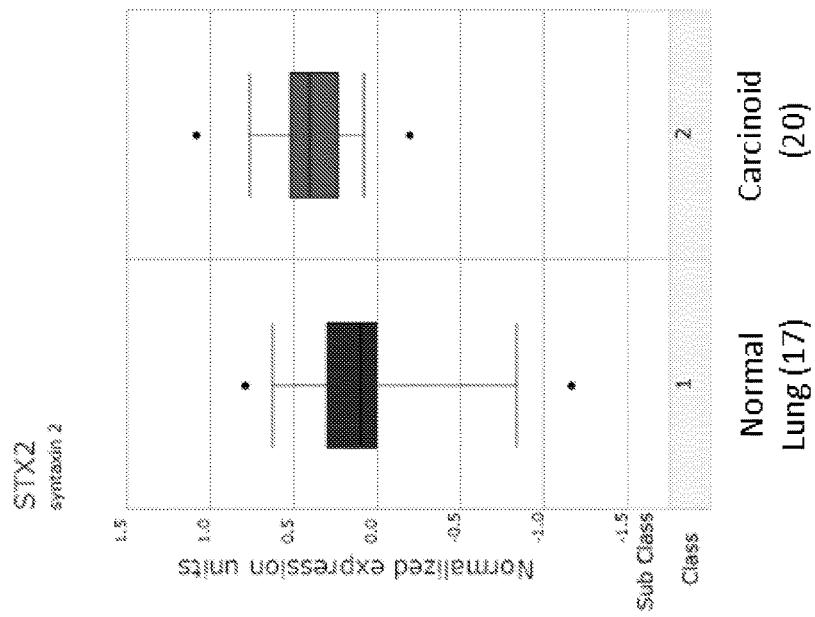
Figure 18:
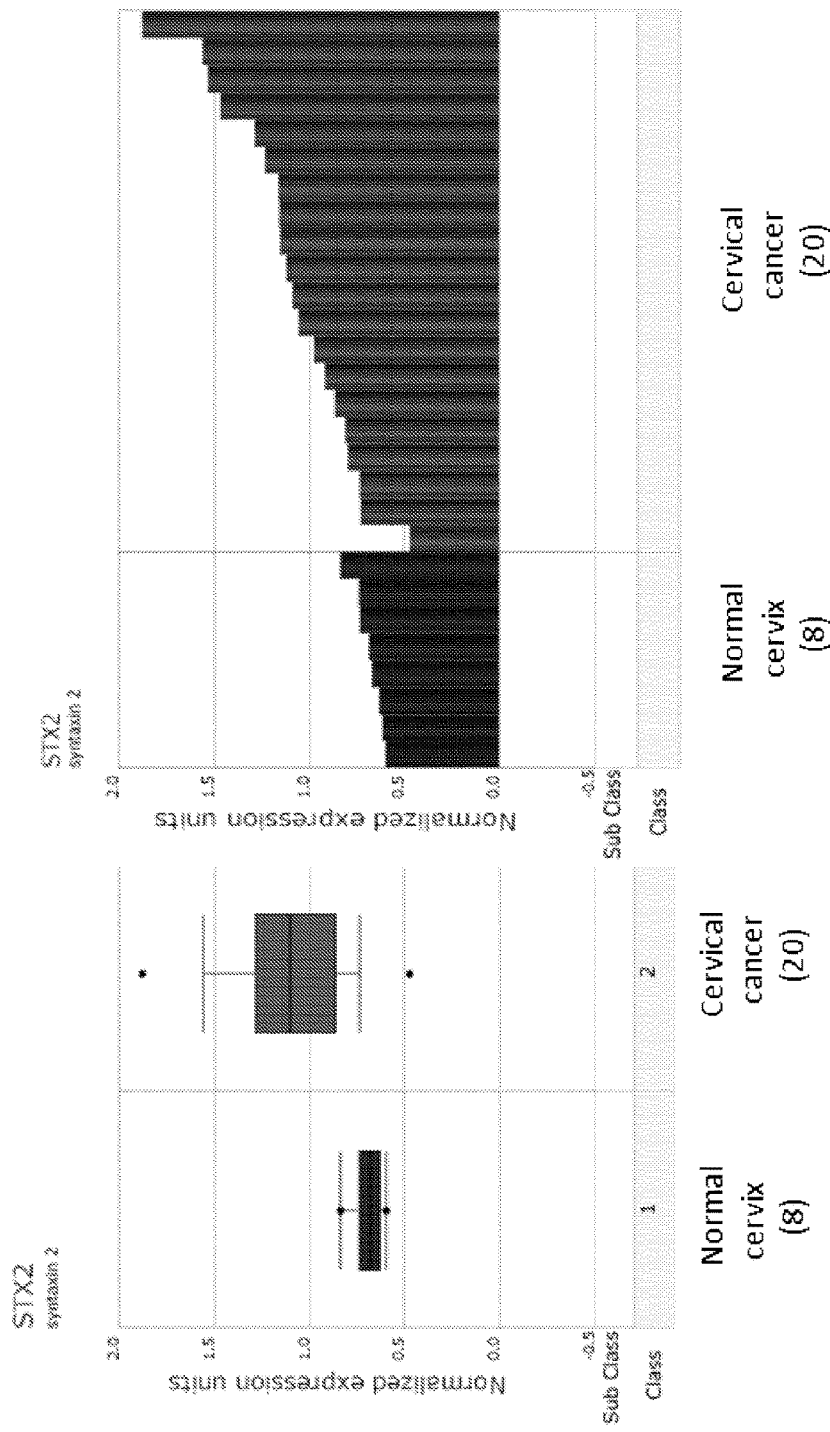
Figure 19:
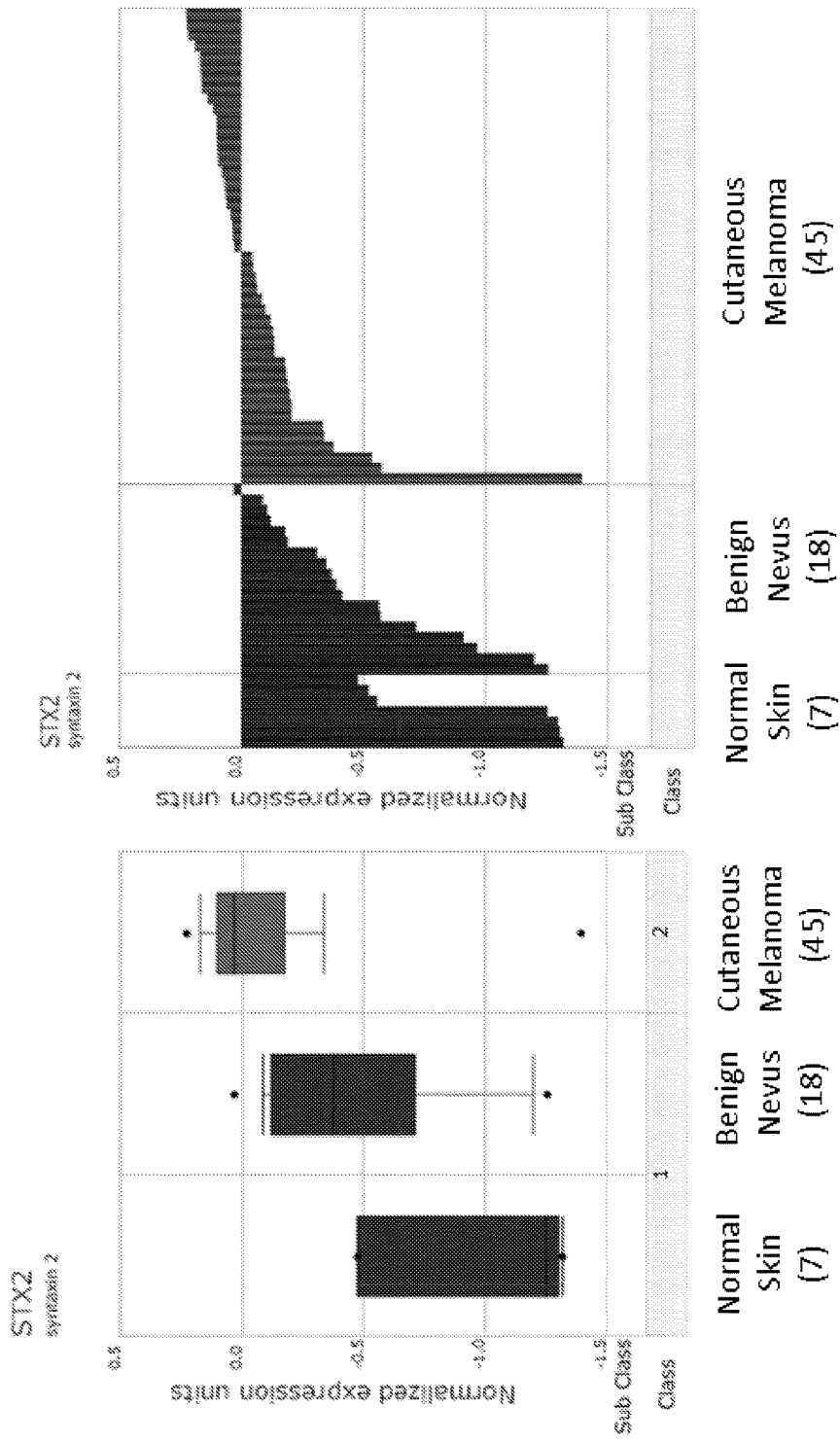
Figure 20:
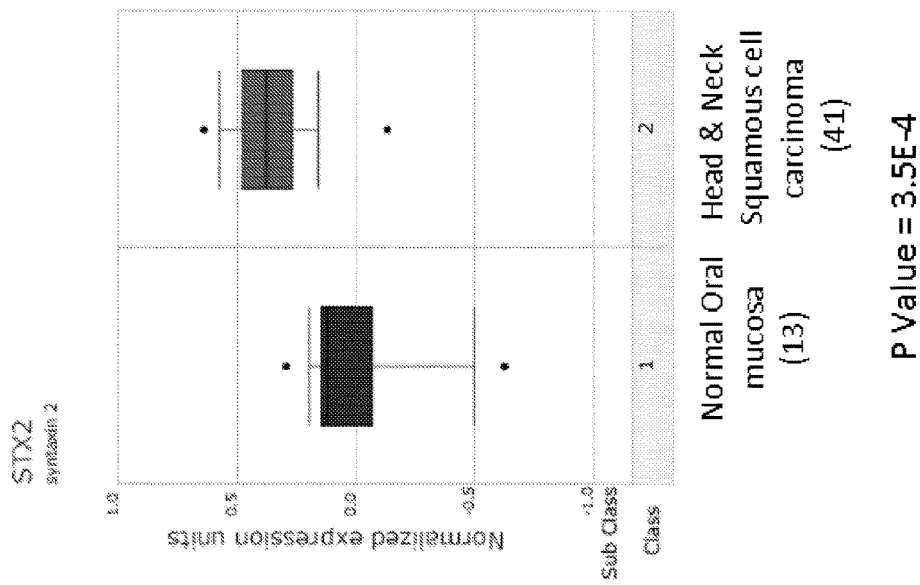
Figure 21:
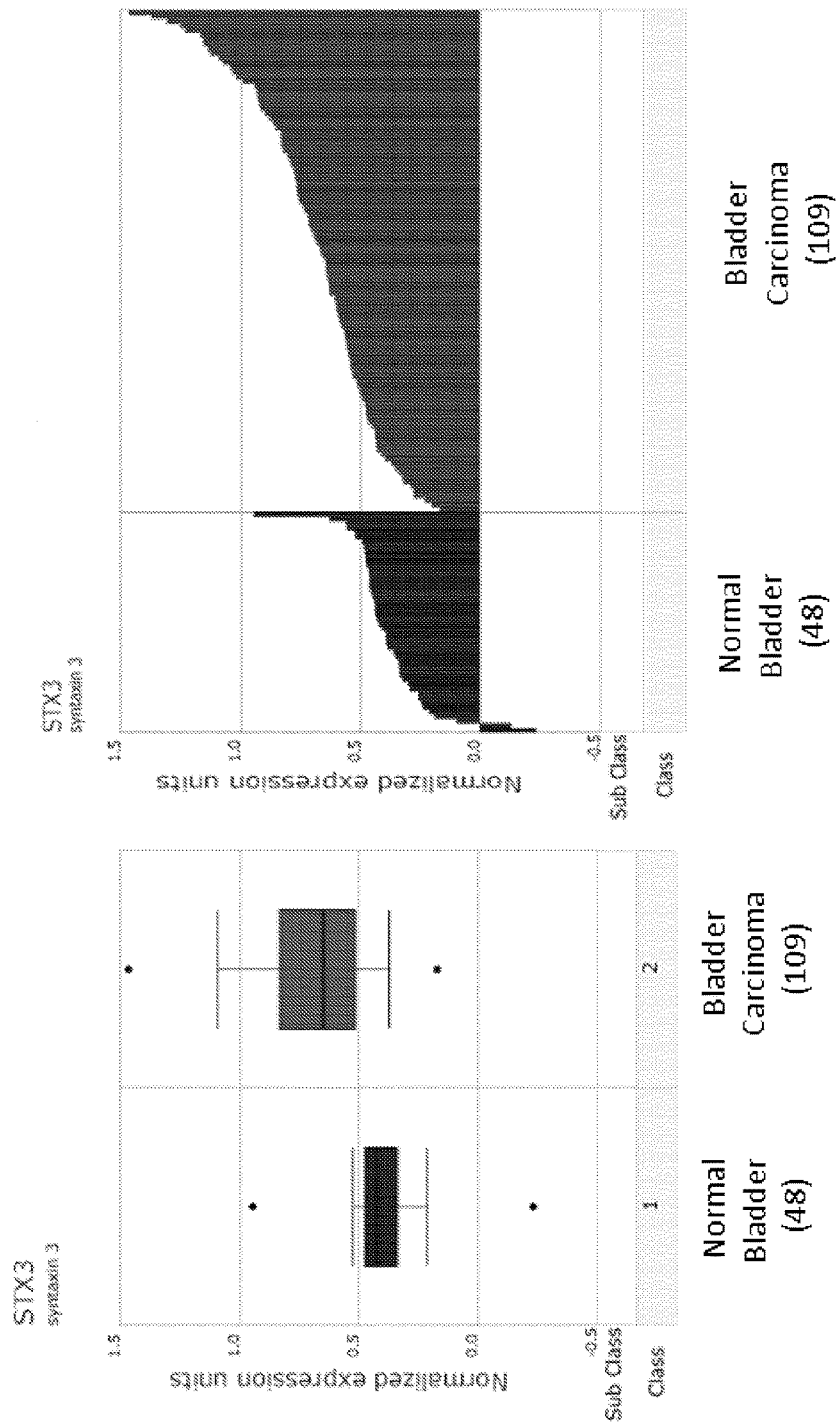
Figure 22:
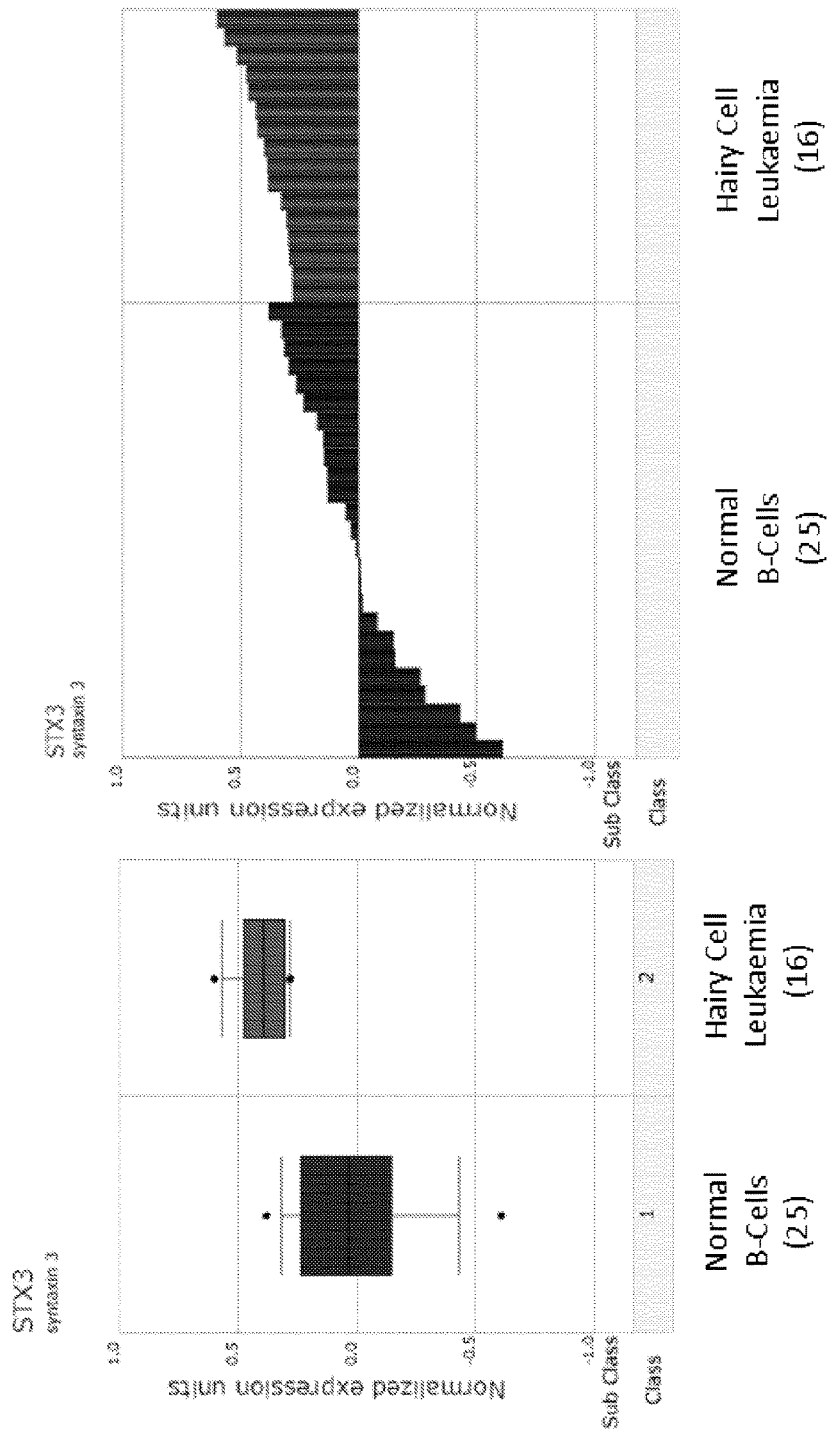
Figure 23:
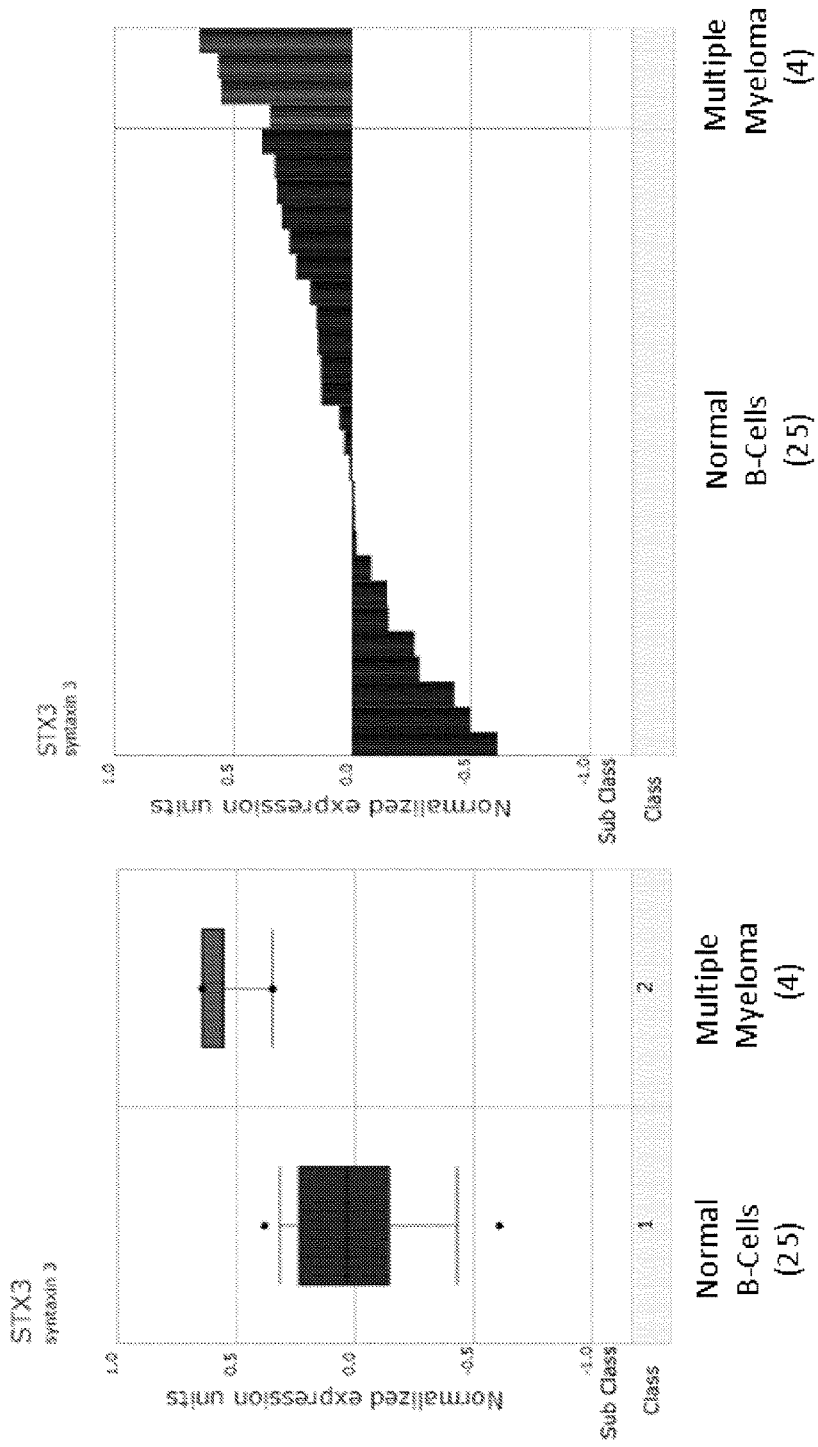
Figure 24:
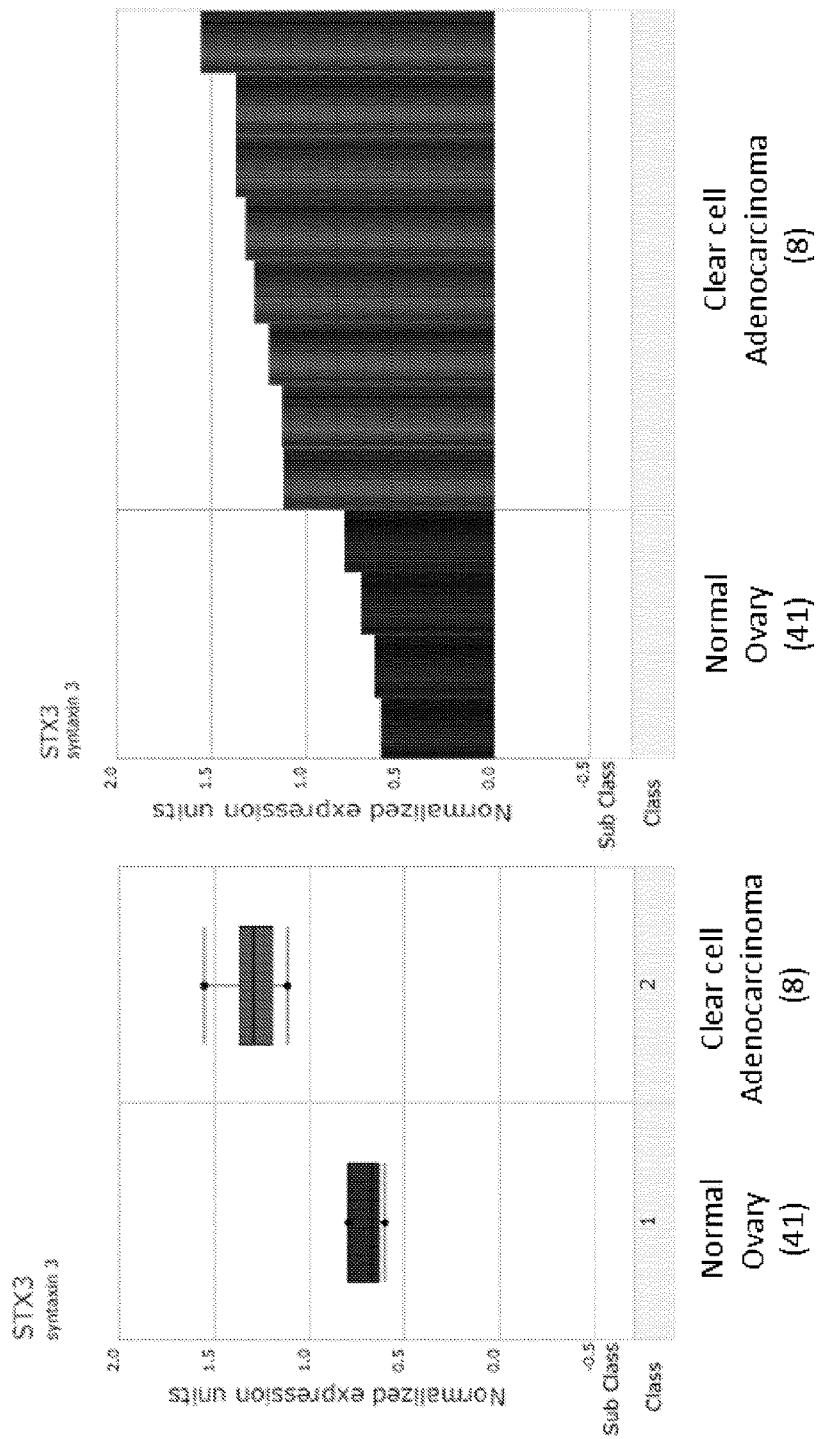
Figure 25:
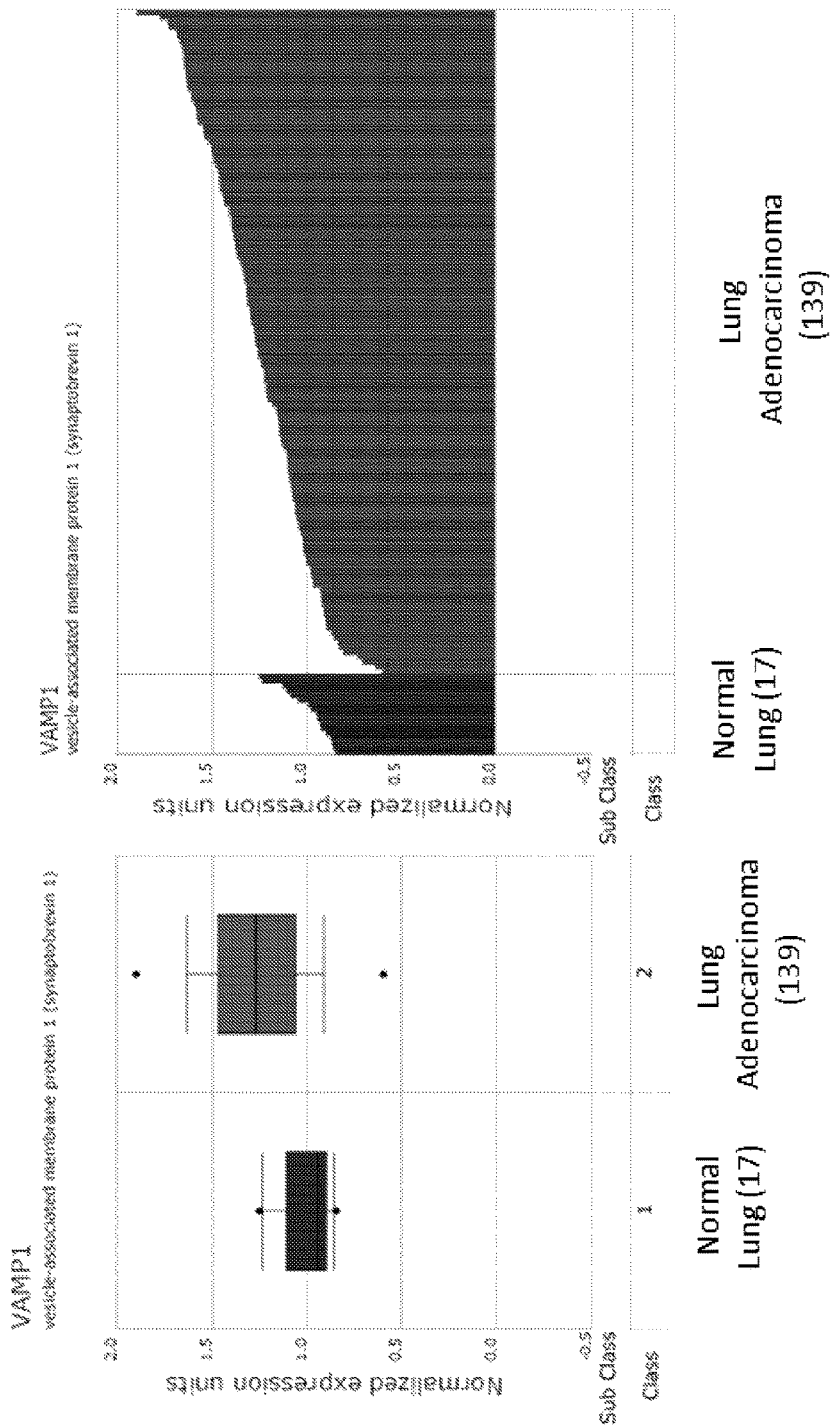
Figure 26:
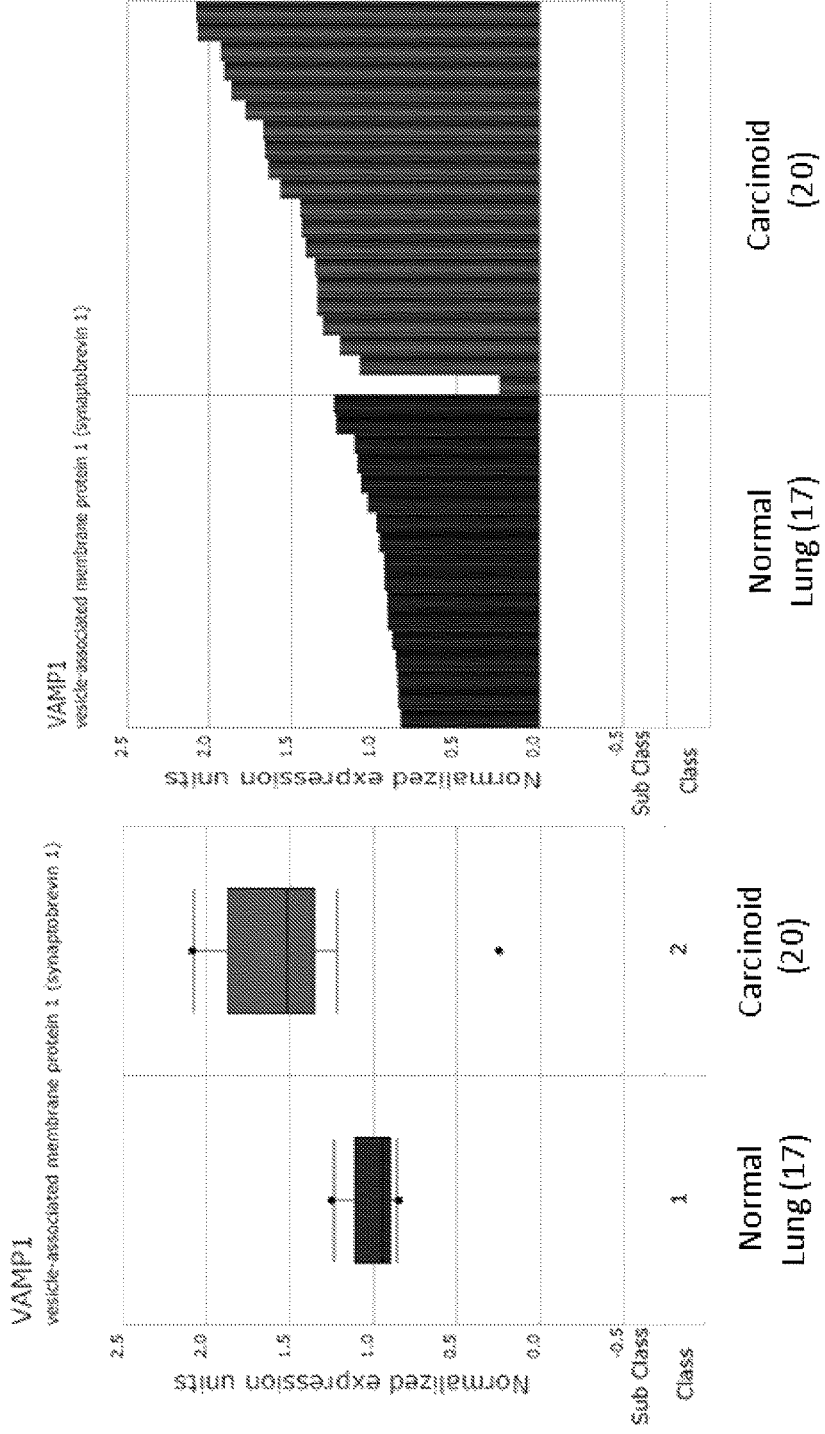
Figure 27:
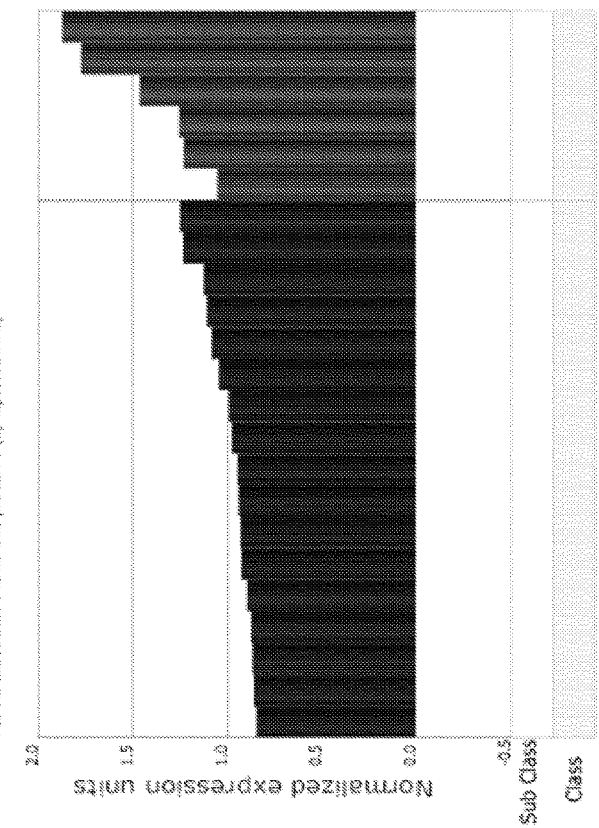
Figure 27:
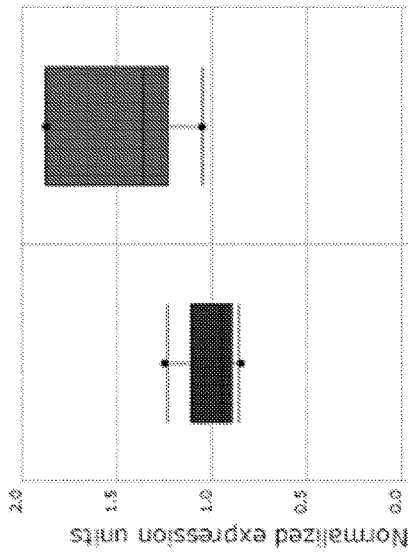
Figure 28:
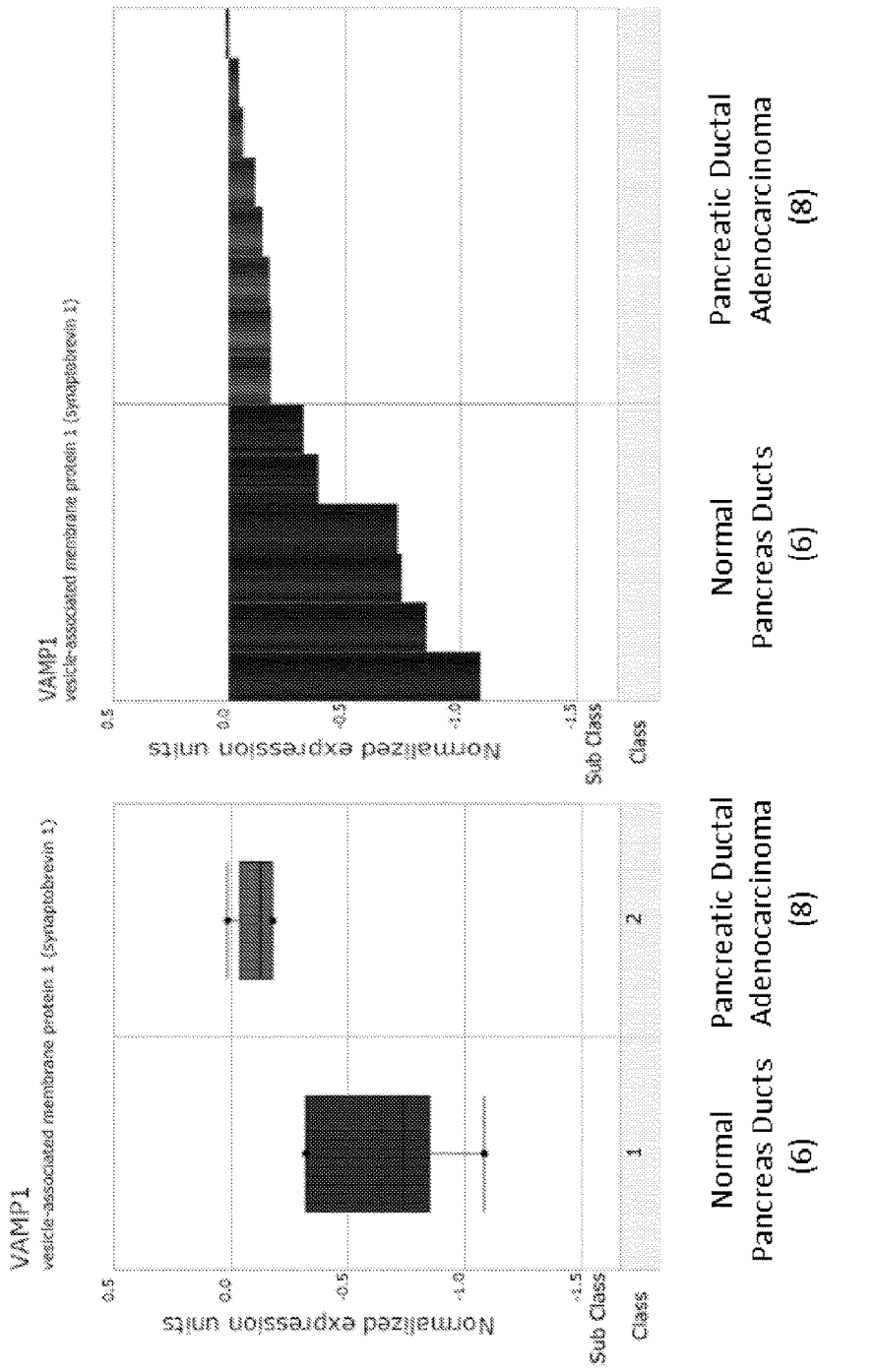
Figure 29:
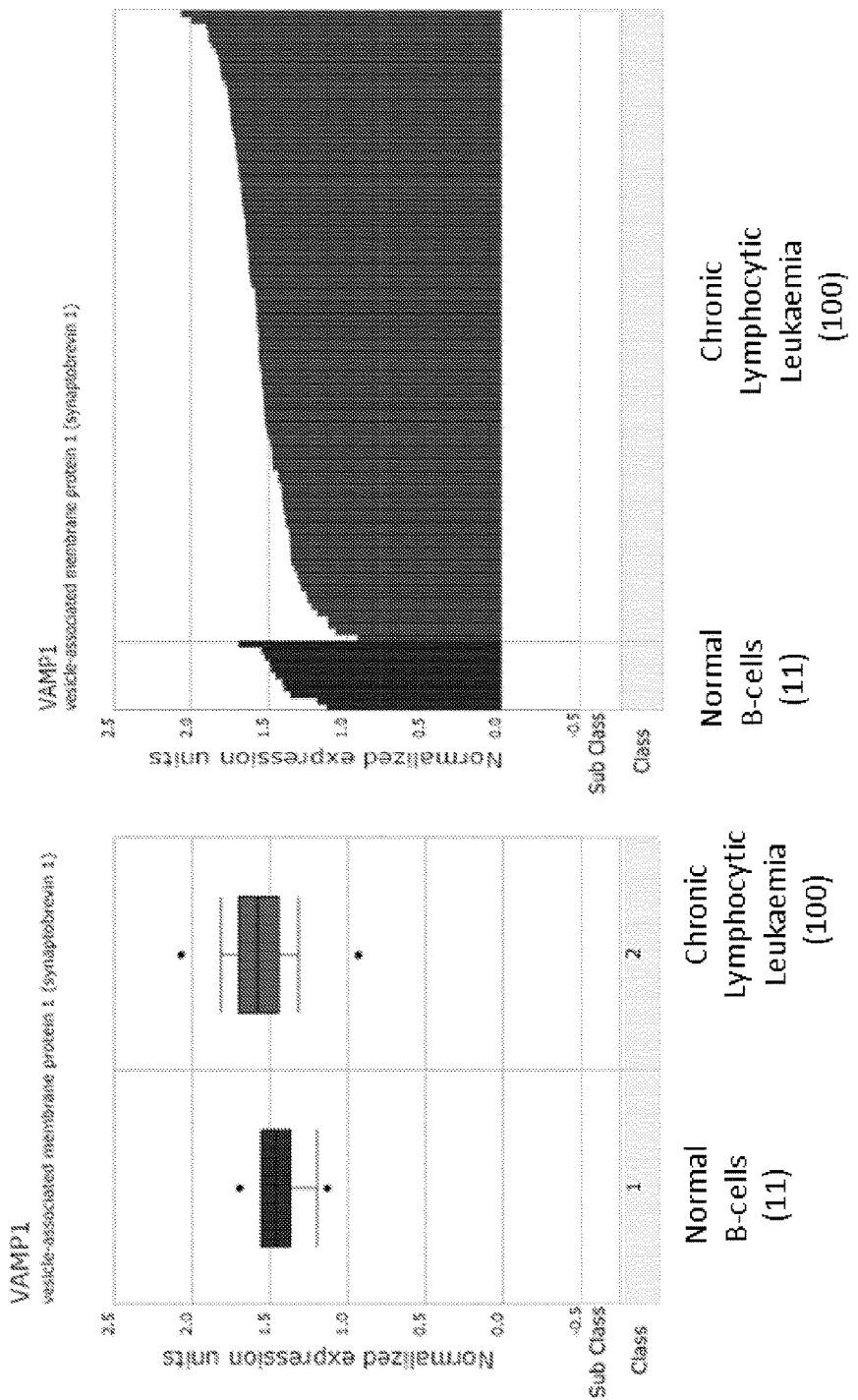
Figure 30:
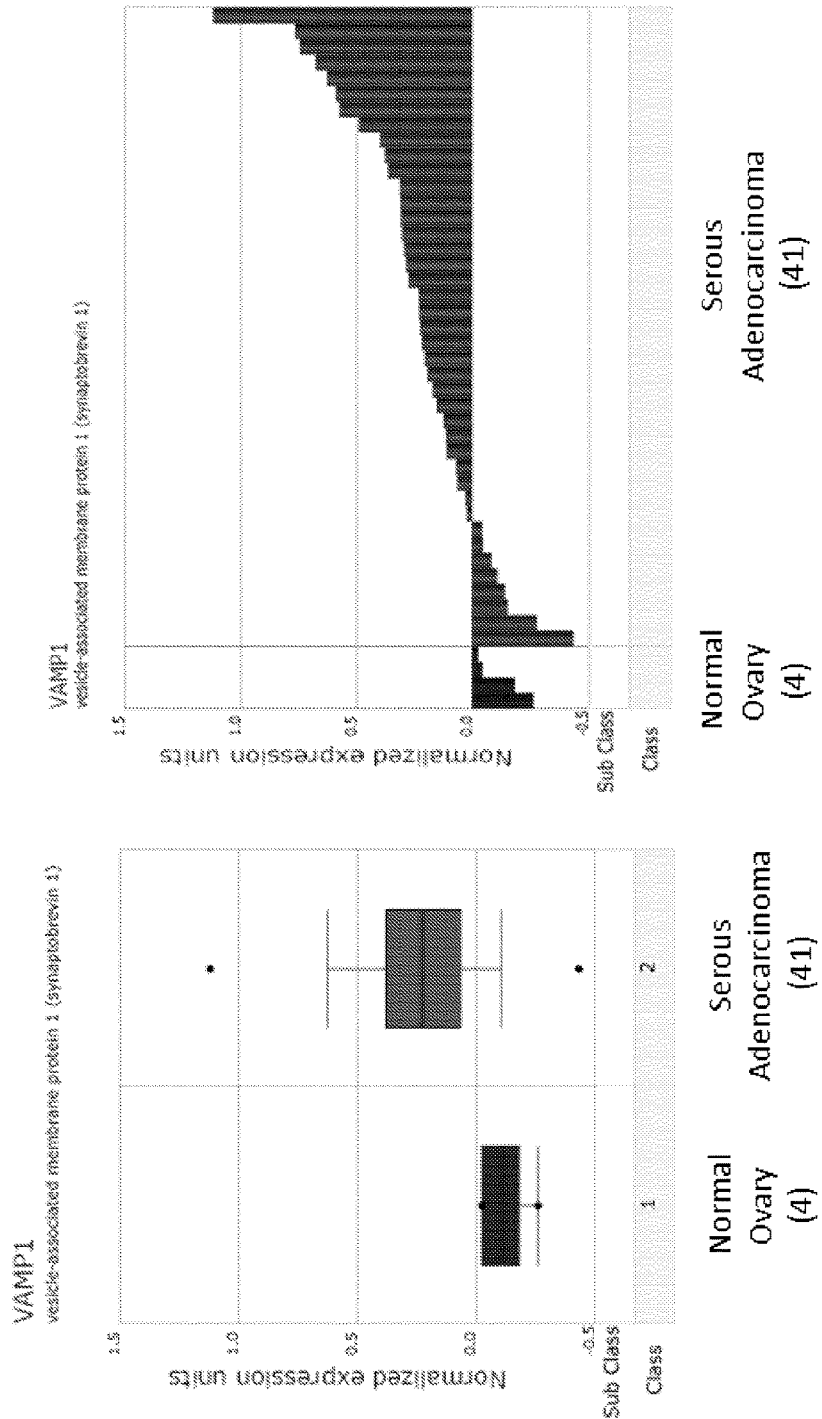
Figure 31:
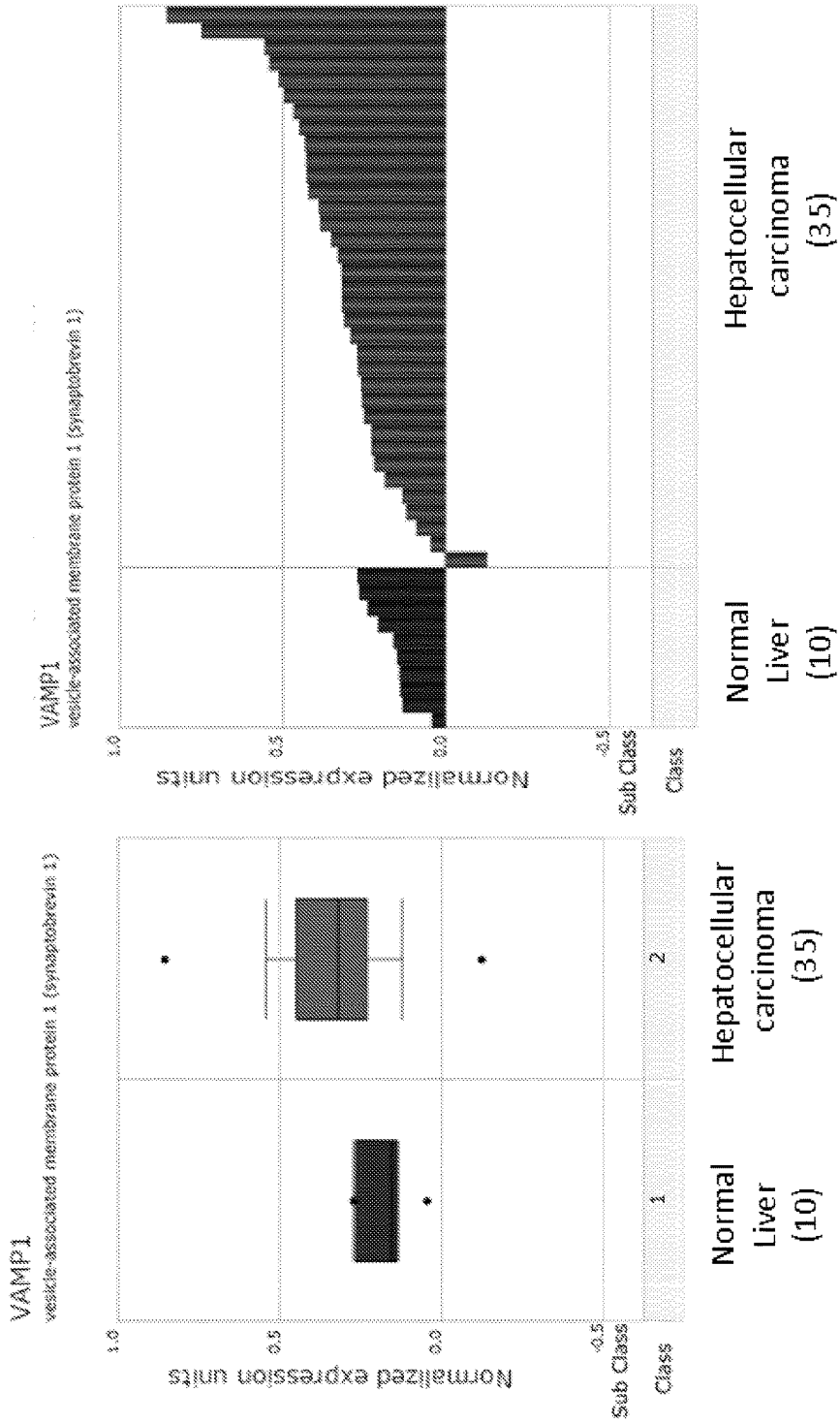
Figure 32:
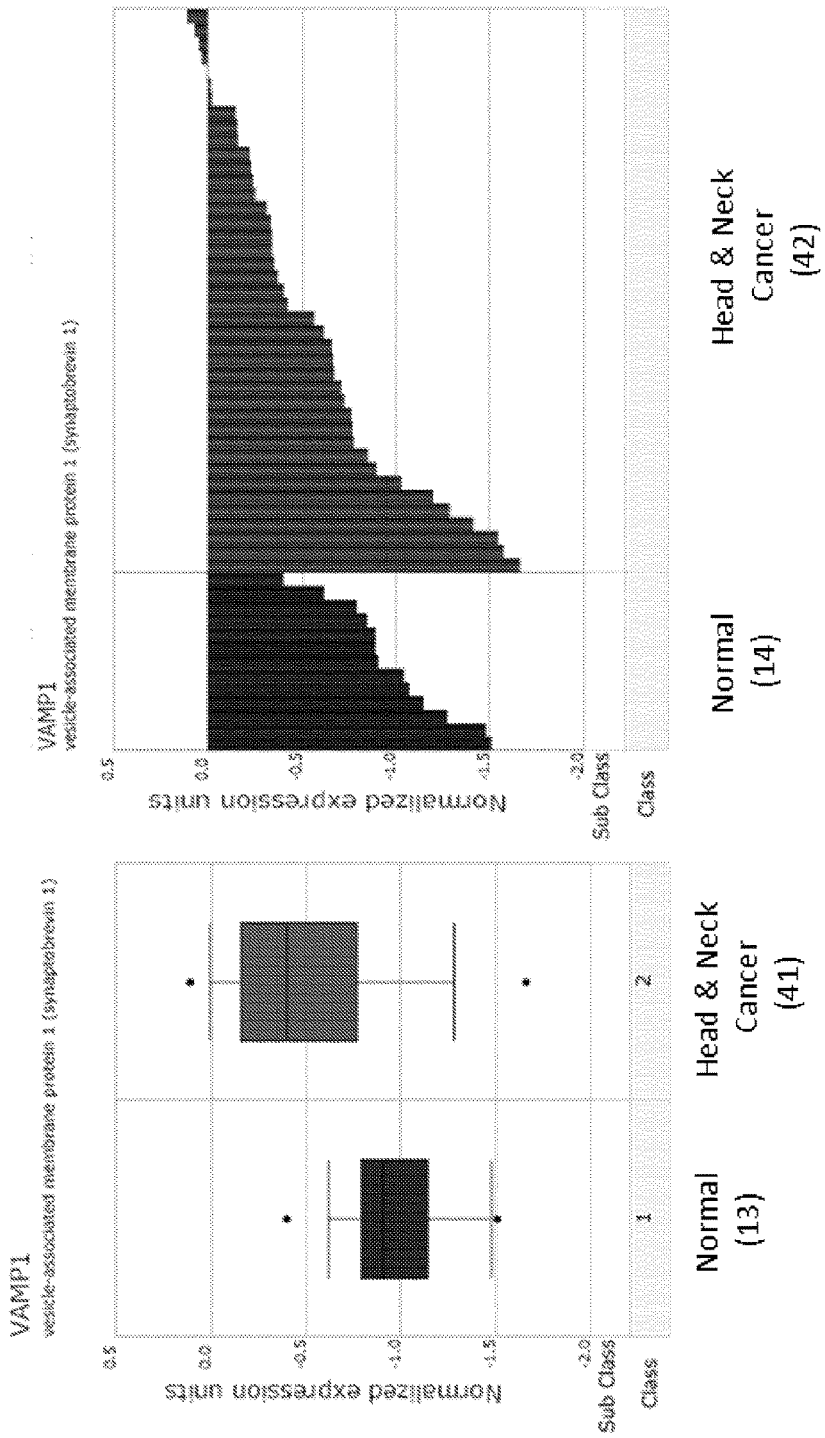
Figure 33:
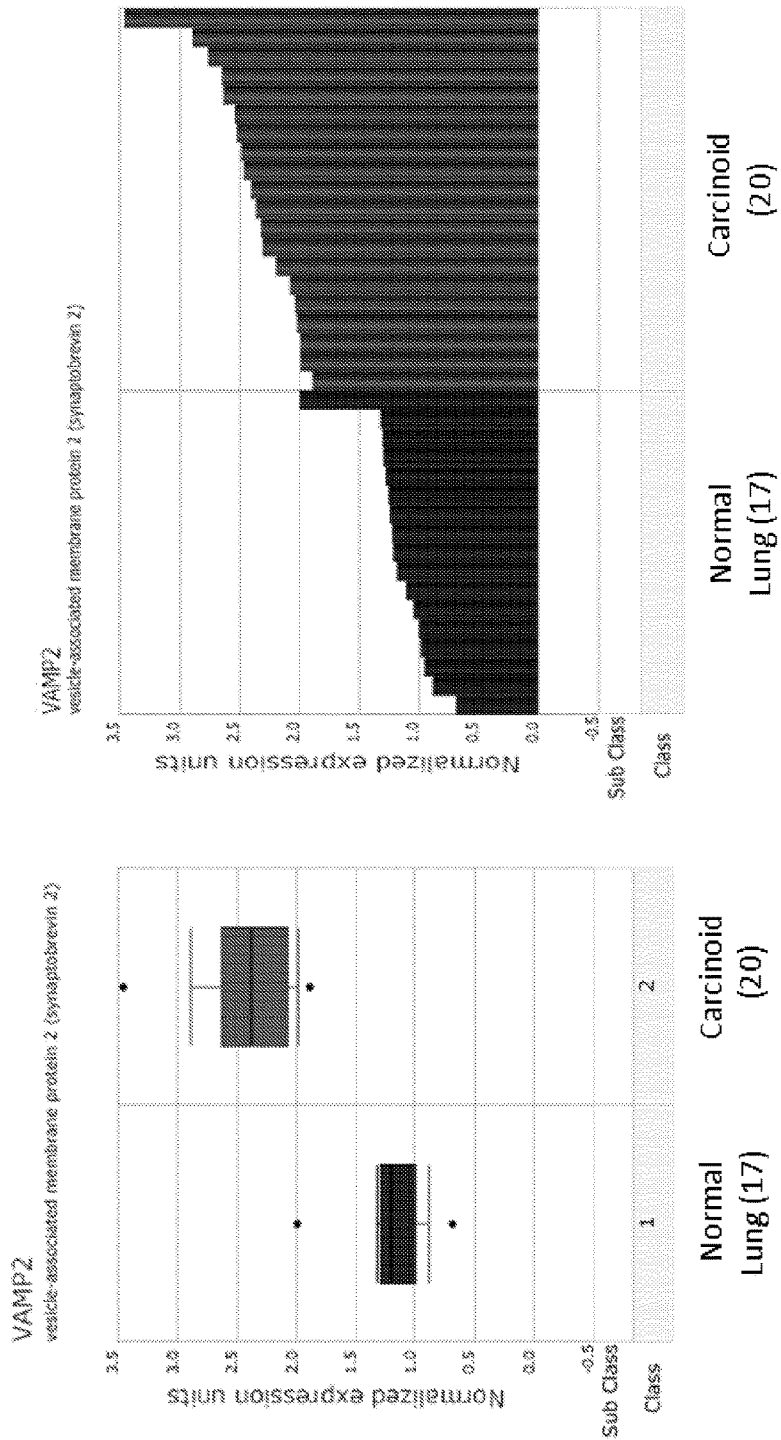
Figure 34:
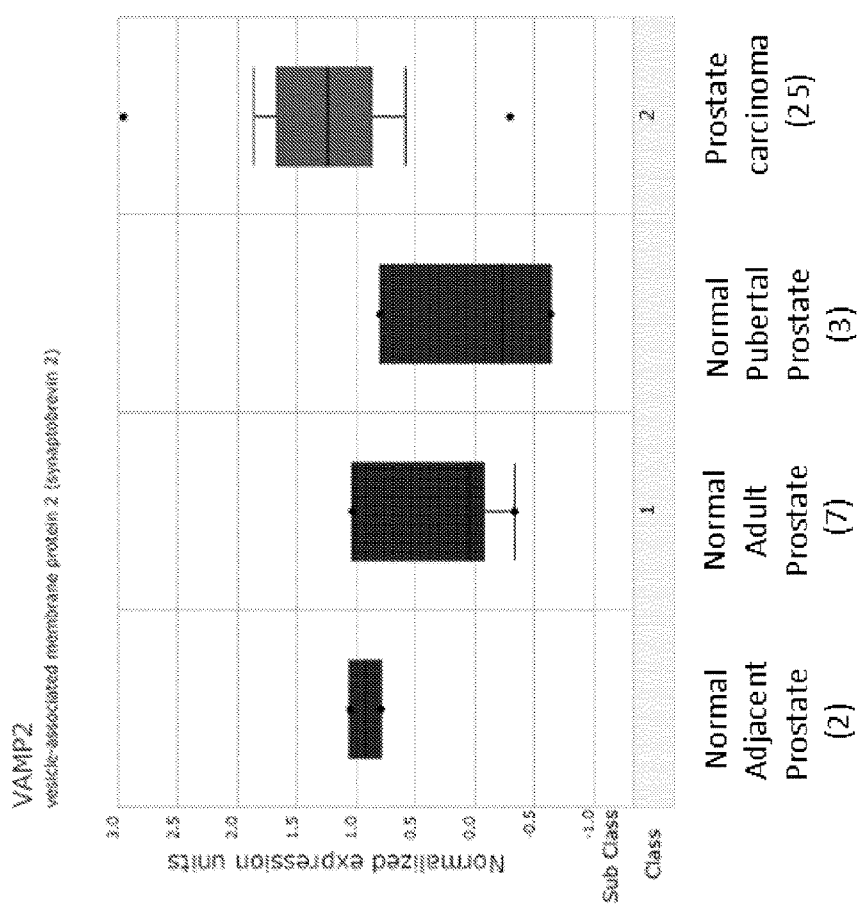
Figure 35:
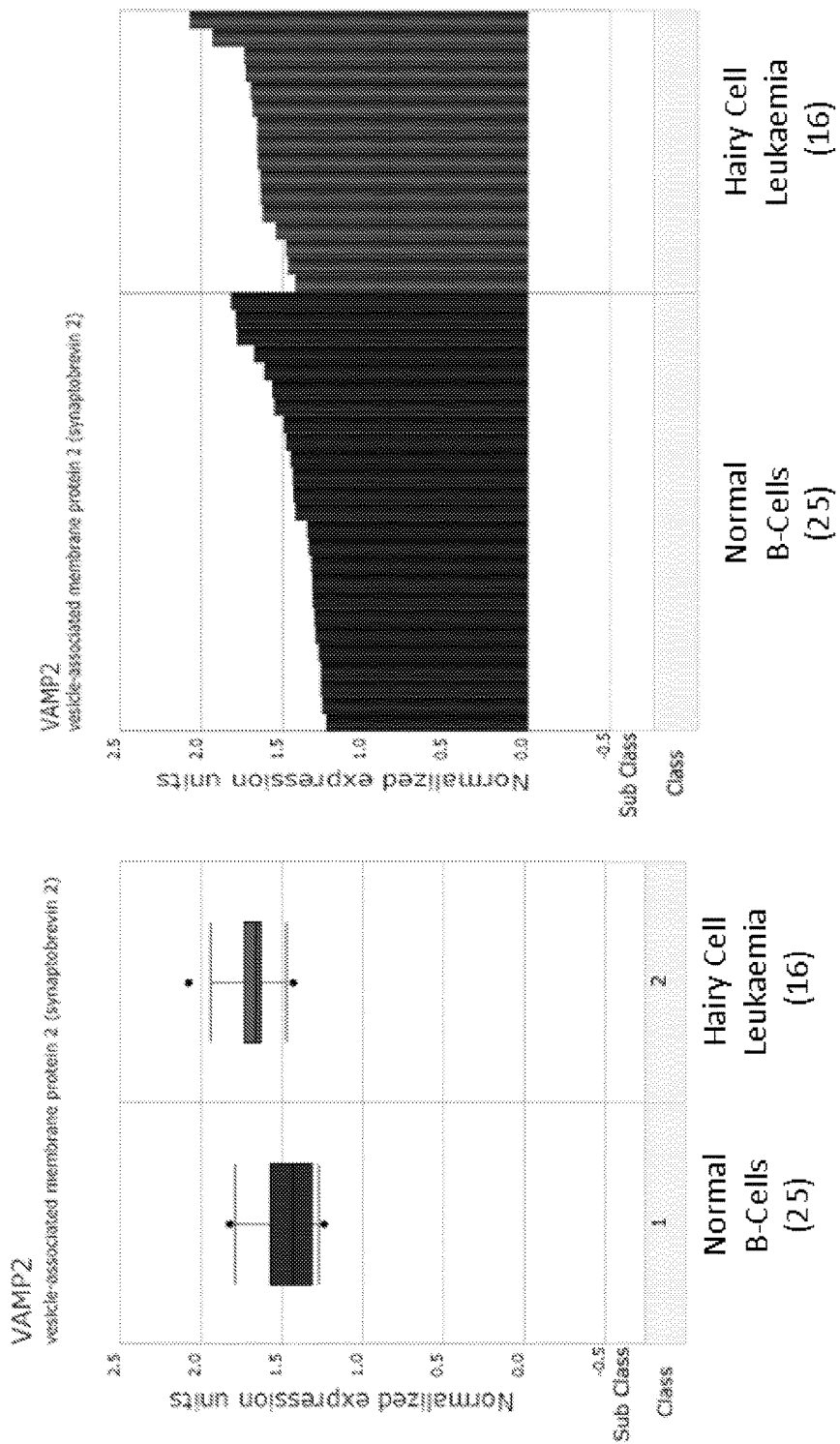
Figure 36:
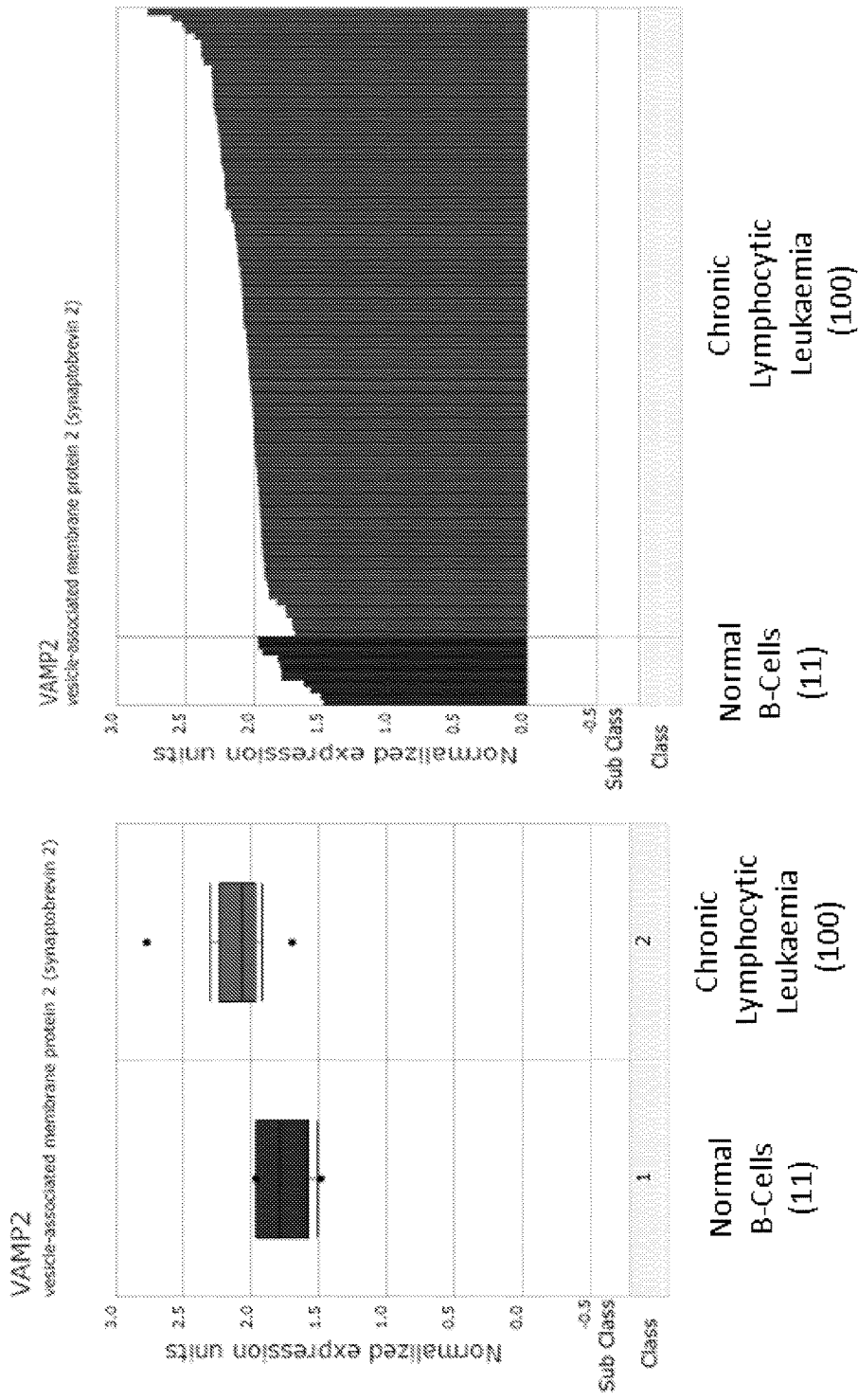
Figure 37:
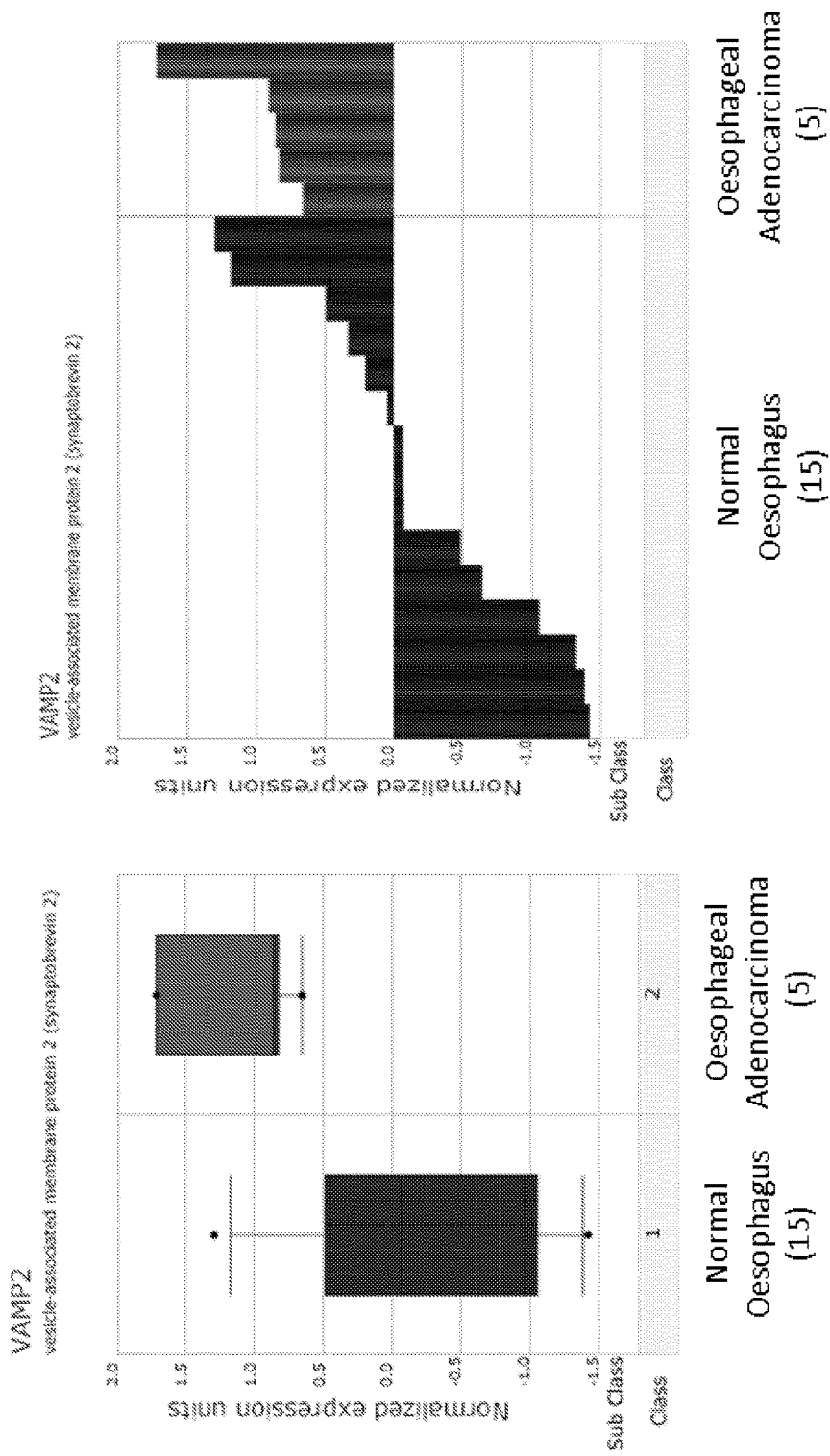
Figure 38:
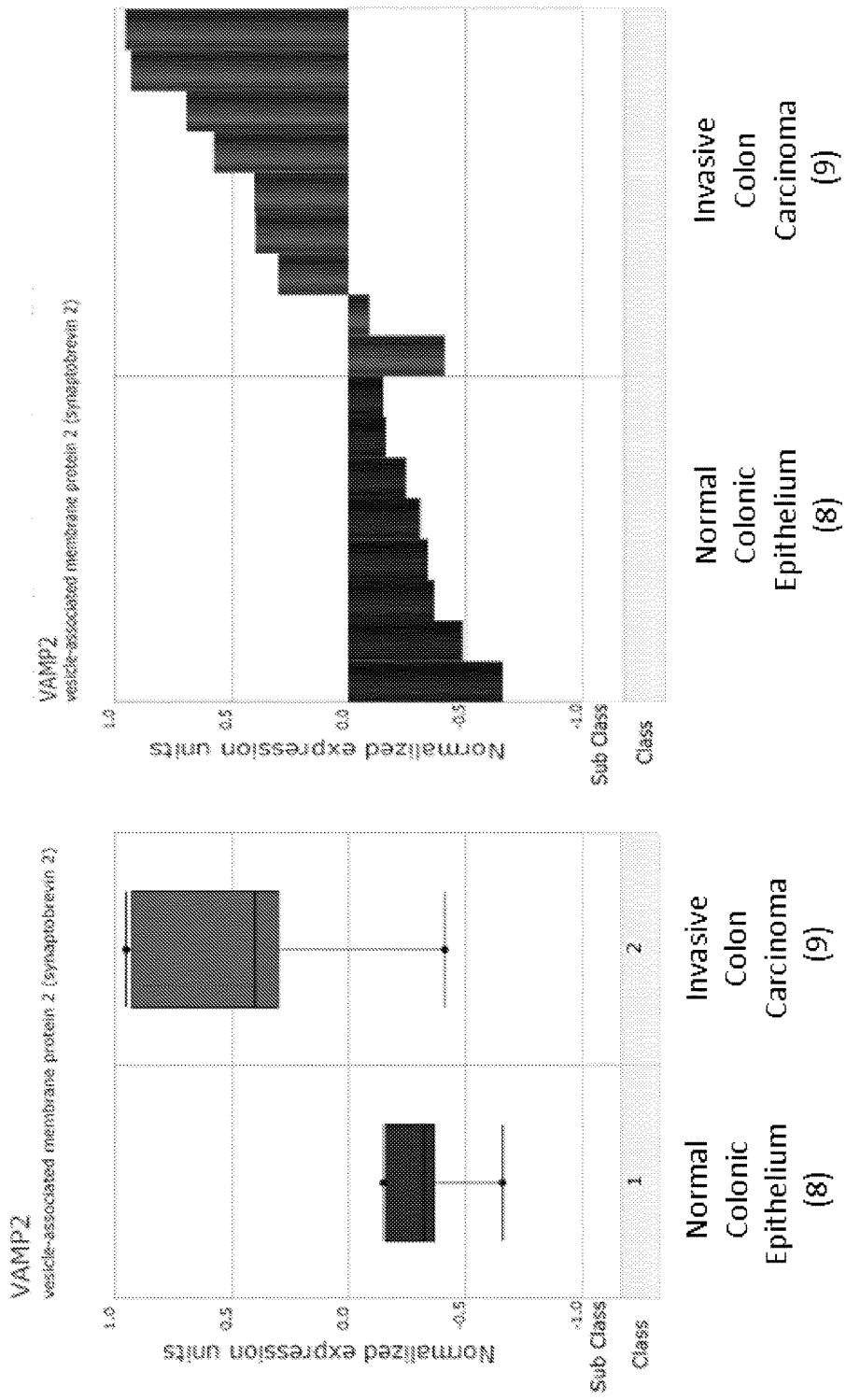
Figure 39:
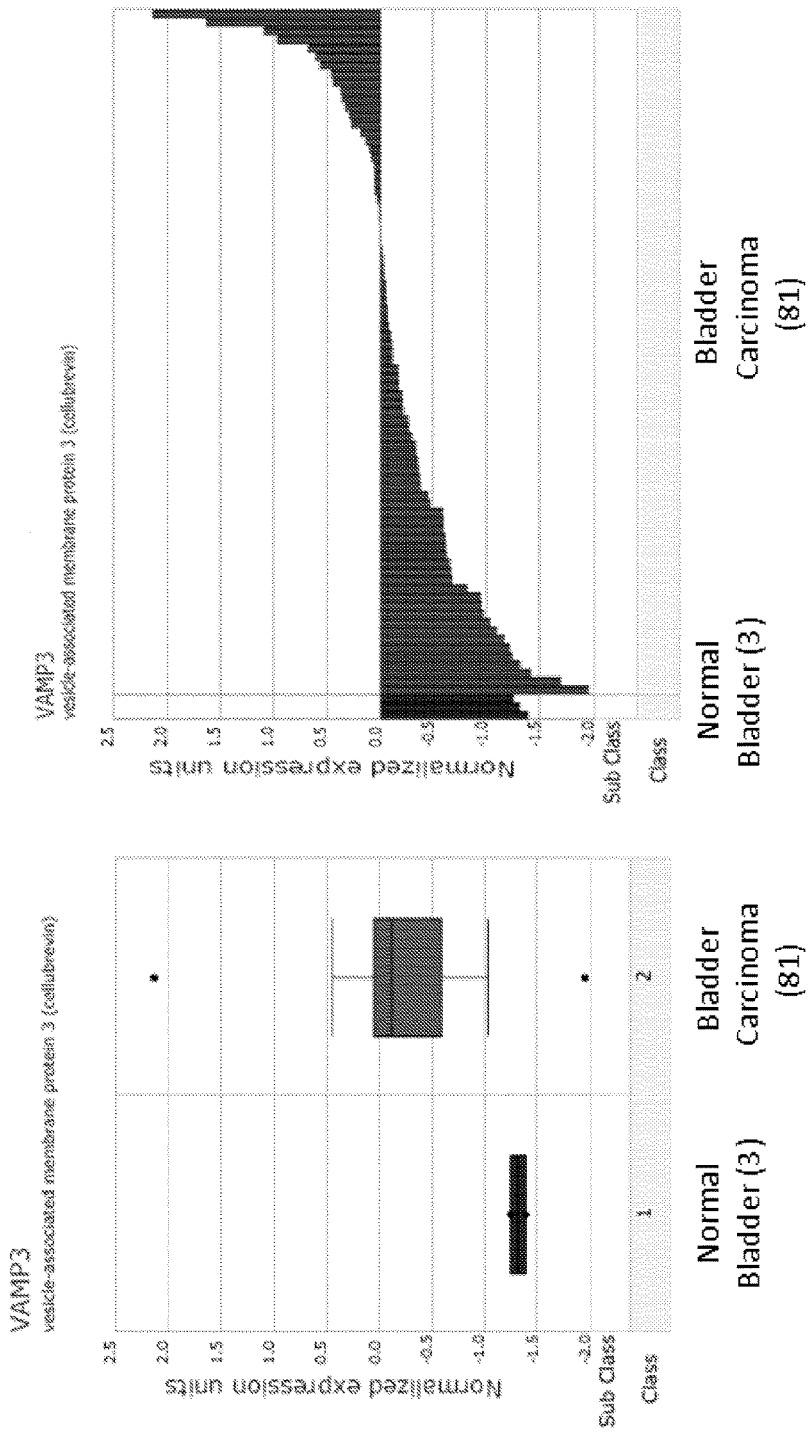
Figure 40:
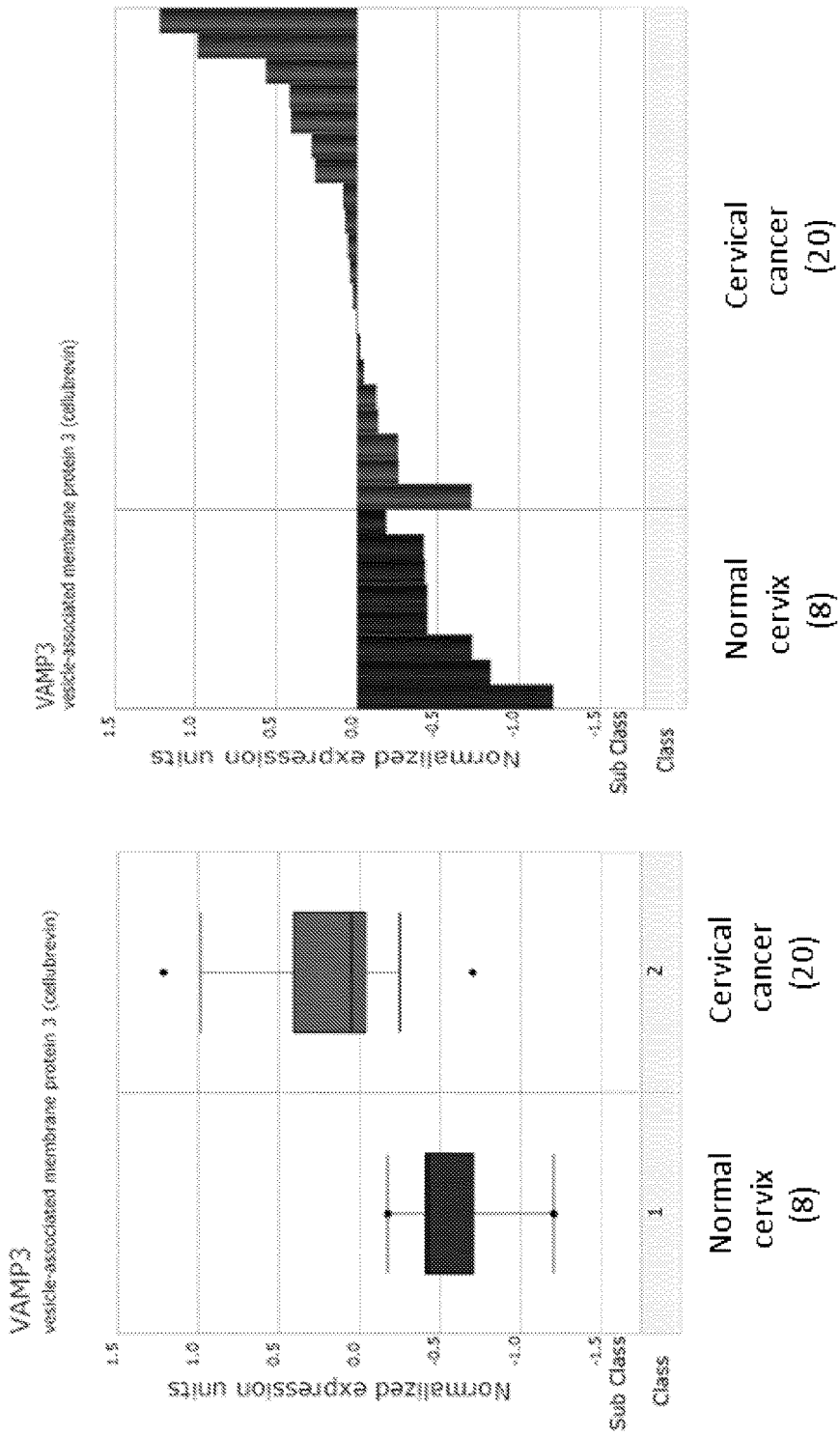
Figure 41:
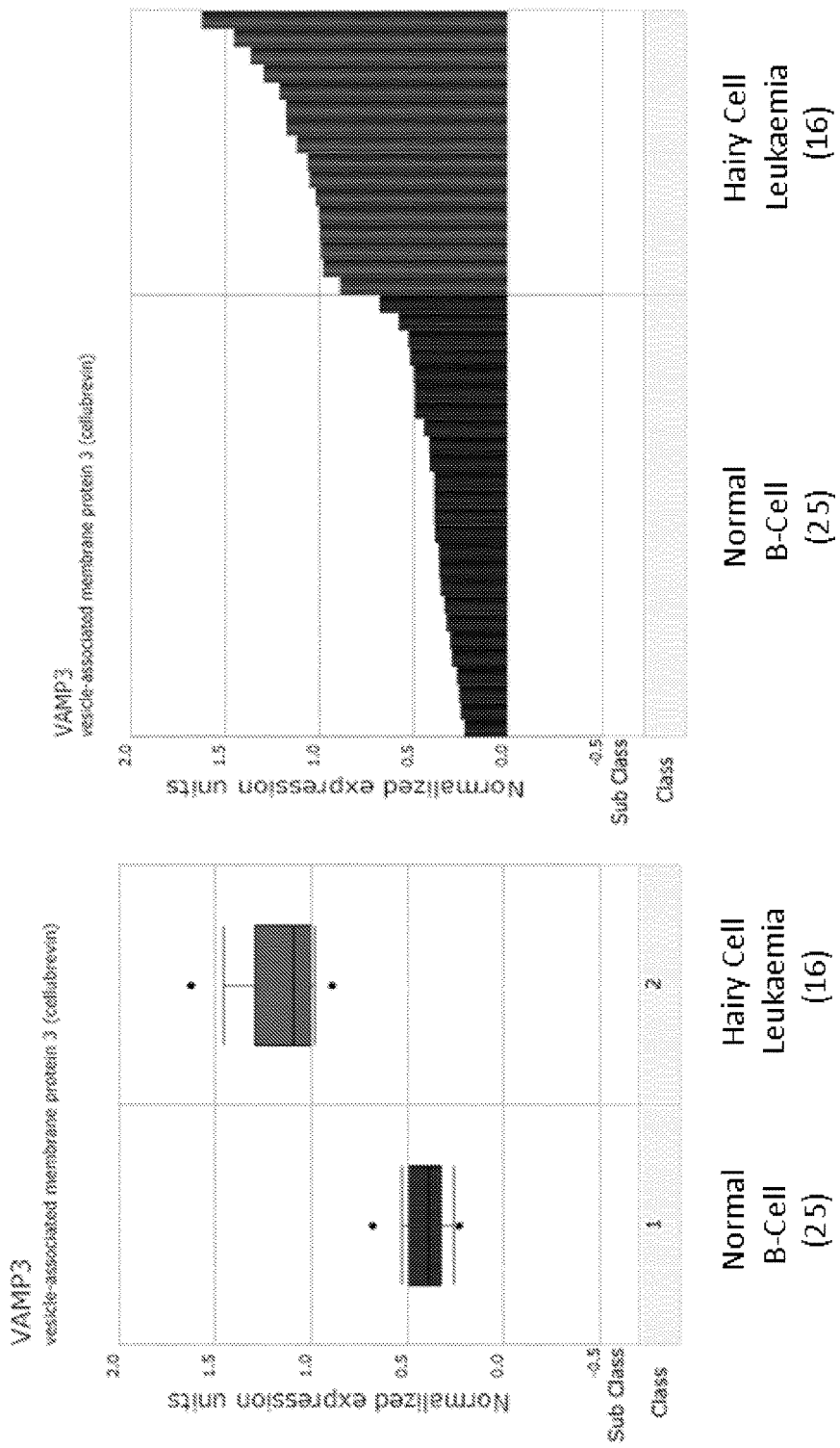
Figure 42:
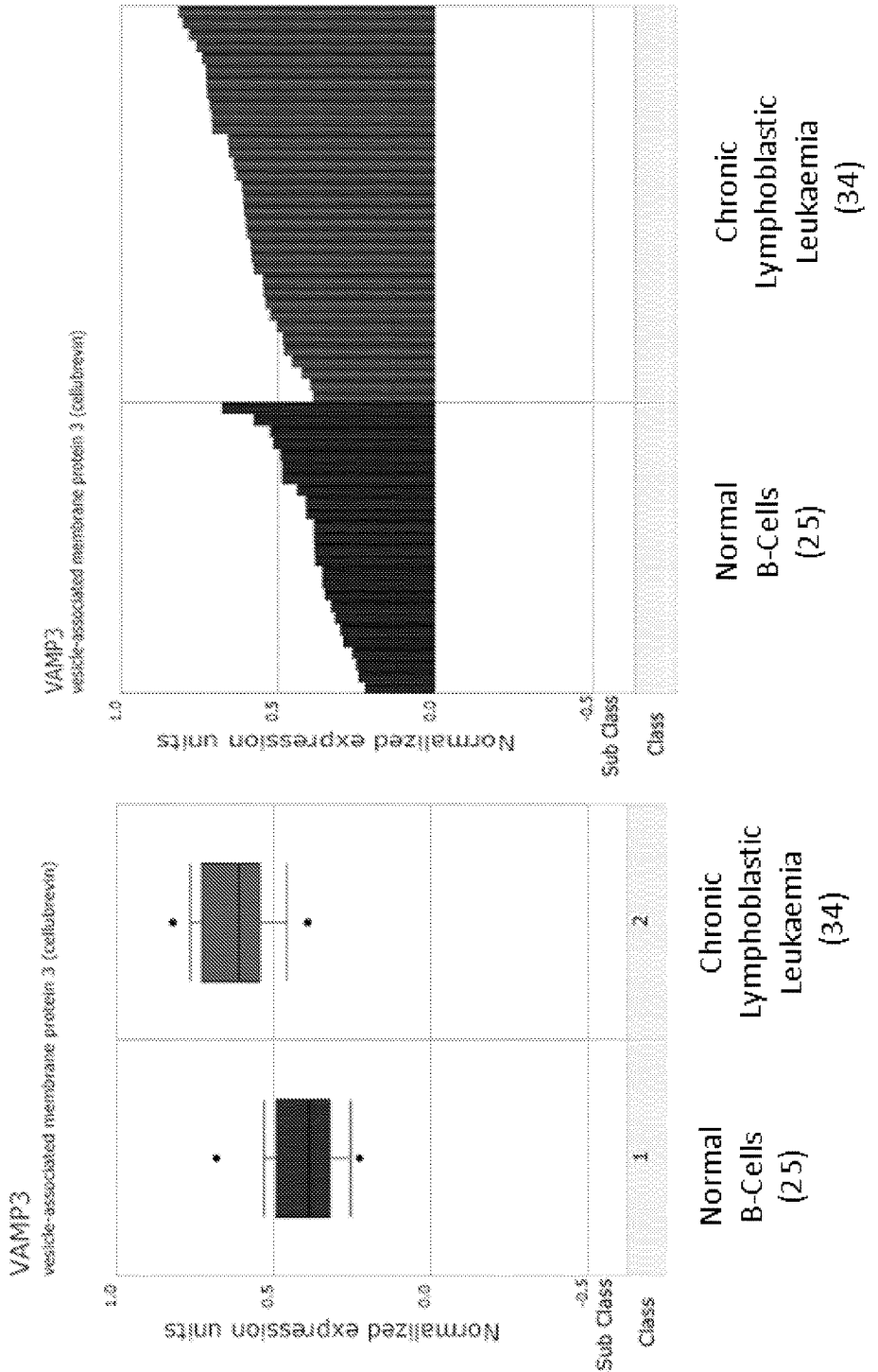
Figure 43:
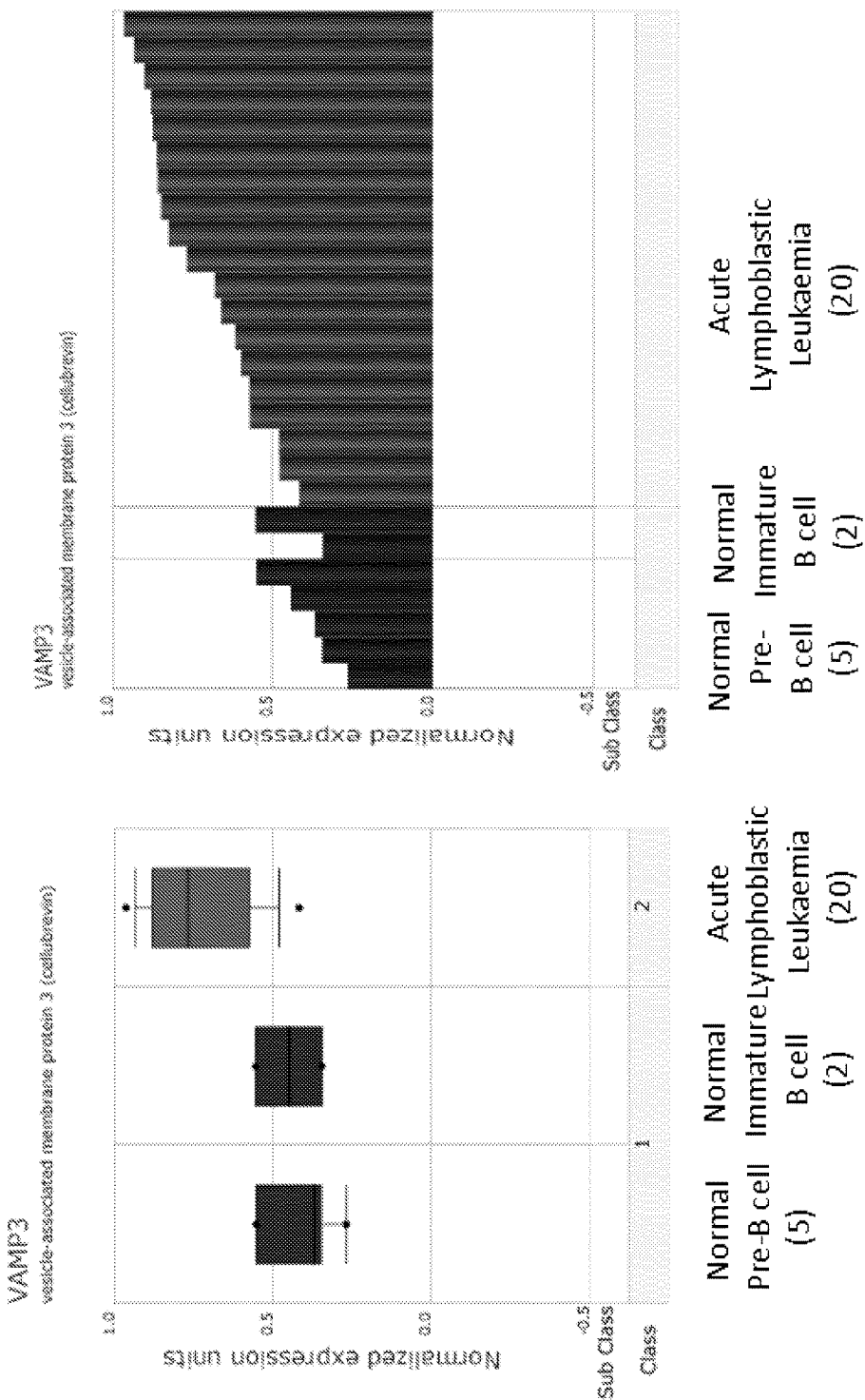
Figure 44:
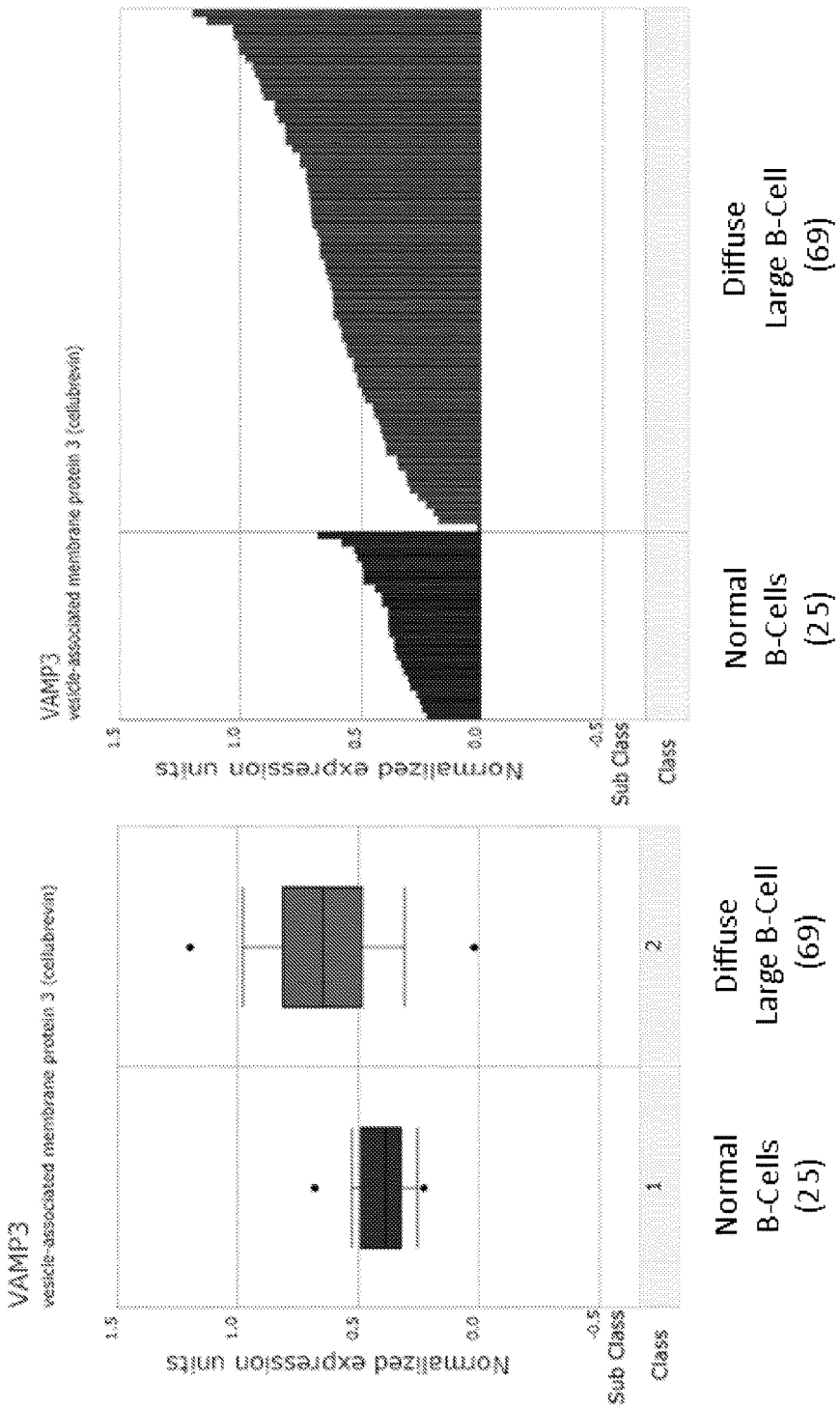
Figure 45:
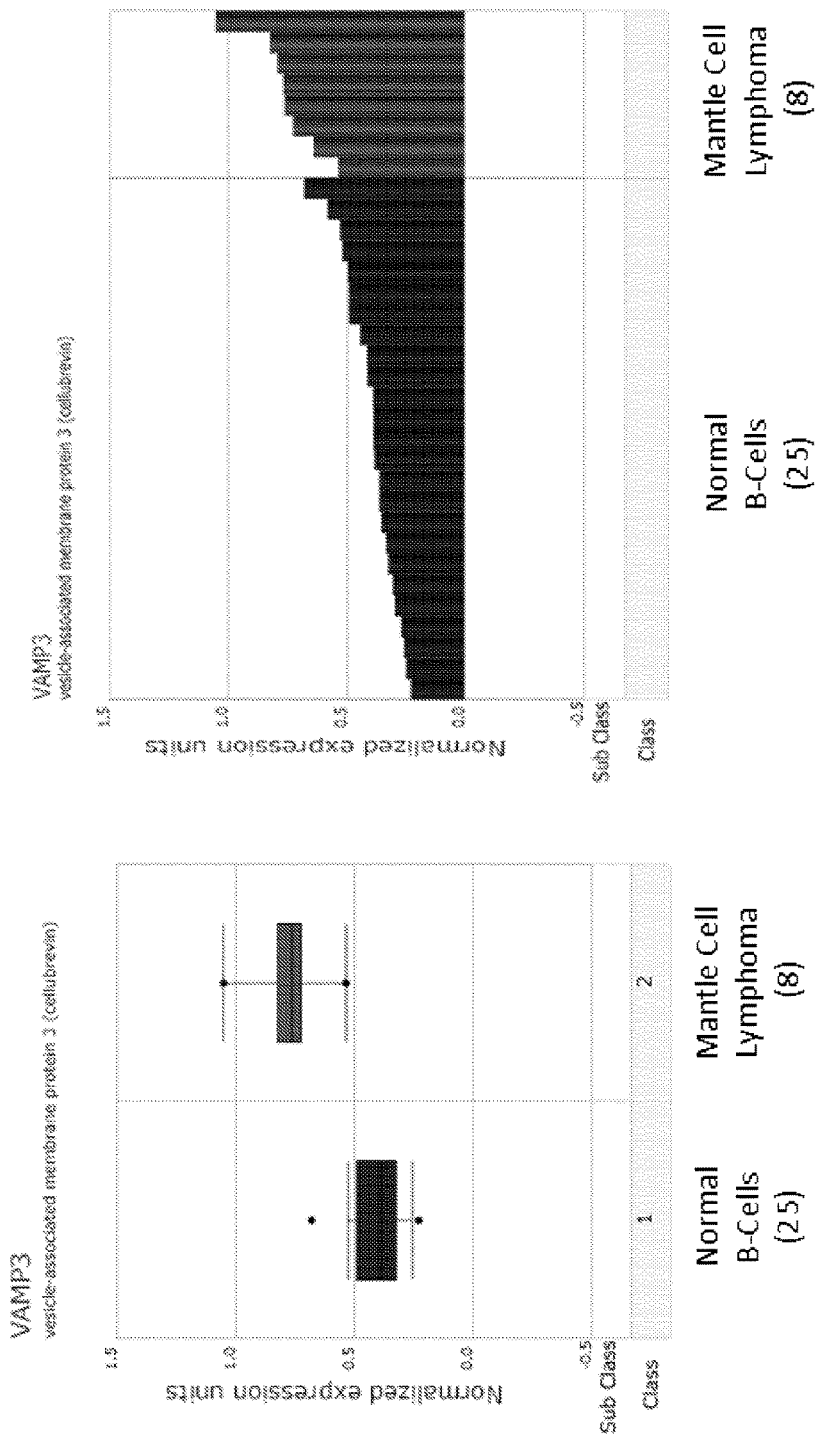

FIG. 2—Purification of $LH_N$/A-CT-SST14 fusion protein

Using the methodology outlined in Example 3, an $LH_N$/A-CT-SST14 fusion protein was purified from *E. coli* BL21 (DE3) cells. Briefly, the soluble products obtained following cell disruption were applied to a nickel-charged affinity capture column. Bound proteins were eluted with 200 mM imidazole, treated with Factor Xa to activate the fusion protein and then re-applied to a second nickel-charged affinity capture column. Samples from the purification procedure were assessed by SDS-PAGE. Lane 1: First nickel chelating Sepharose column eluant, Lane 2: Molecular mass markers (kDa), Lanes 3-4: Second nickel chelating Sepharose column eluant under non-reducing conditions, Lanes 5-6: Second nickel chelating Sepharose column eluant under reducing conditions.

Figure 46:
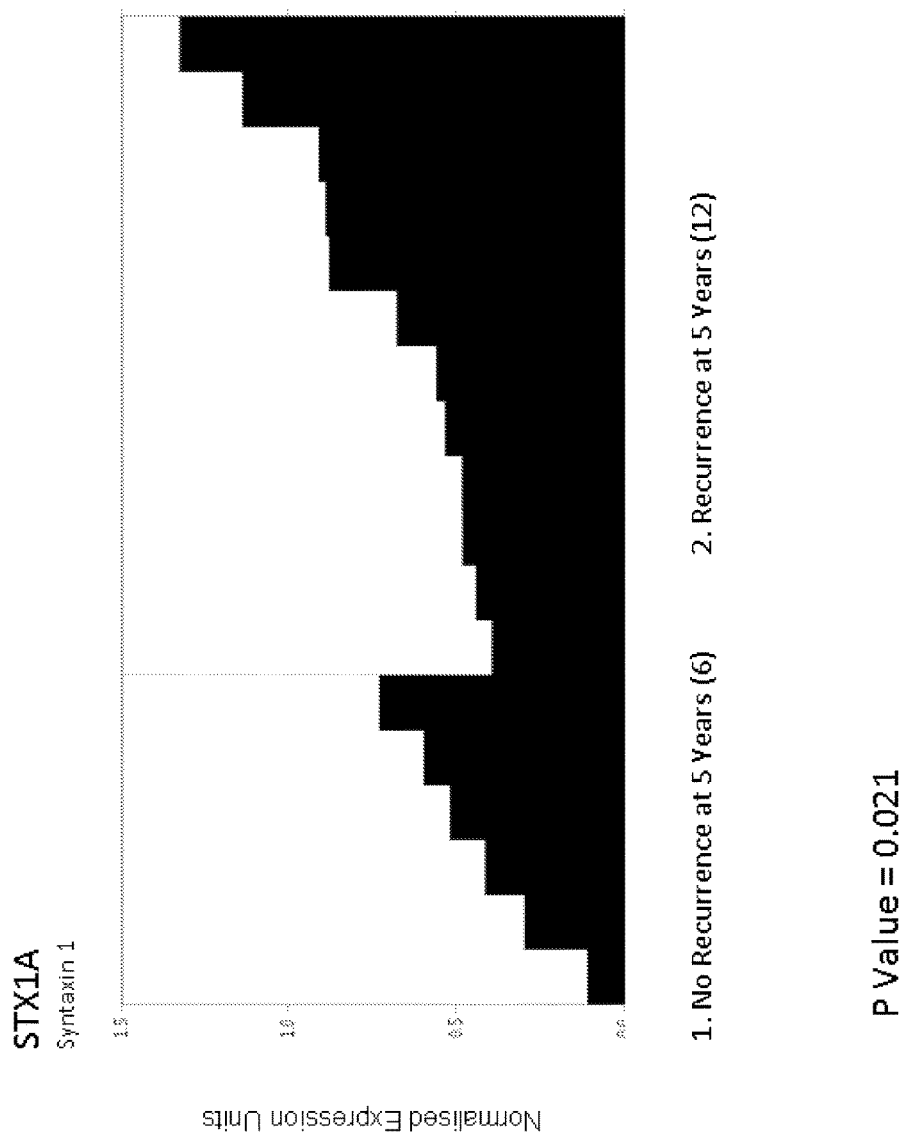
Figure 47:
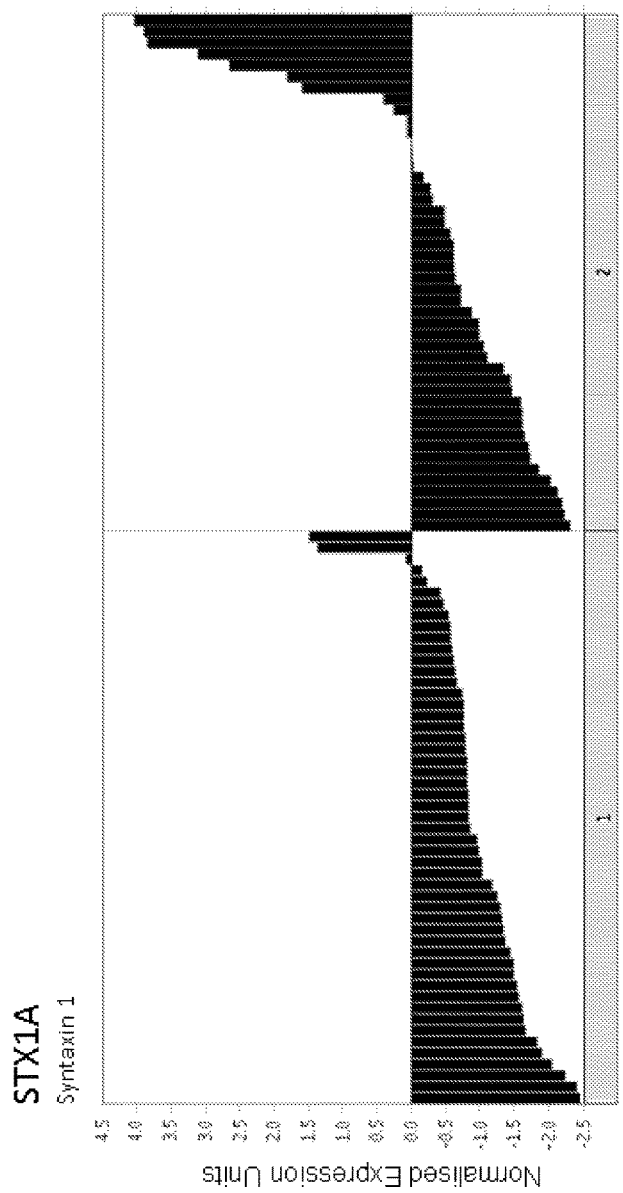

FIGS. 3-47—Box Plots showing up-regulation of SNARE protein mRNA in cancer cells Statistical analysis of the differences in SNARE expression between normal and primary cancer tissues was completed through use of Oncomine algorithms (Compendia Bioscience, Ann Arbor, Mich., USA) and gene microarray analysis tool. SNARE mRNA expression was compared to the median expression of all other genes in the respective study, for which a Normalised expression value was generated. Only studies with analysis results with $P<0.05$ are illustrated. In more detail, FIGS. 3-10 illustrate SNAP-25 expression profiles in different cancer versus non-cancer cells. FIGS. 11-16 illustrate syntaxin-1 expression profiles in different cancer versus non-cancer cells. FIGS. 17-20 illustrate syntaxin-2 expression profiles in different cancer versus non-cancer cells. FIGS. 21-24 illustrate syntaxin-3 expression profiles in different cancer versus non-cancer cells. FIGS. 25-32 illustrate VAMP-1 expression profiles in different cancer versus non-cancer cells. FIGS. 33-38 illustrate VAMP-2 expression profiles in different cancer versus non-cancer cells. FIGS. 39-45 illustrate VAMP-3 expression profiles in different cancer versus non-cancer cells. In all cases, the data illustrate up-regulation of SNARE proteins in cancer cells. FIG. 46 illustrates a statistically significant difference in syntaxin-1 mRNA expression level between patients with recurrent invasive ductal breast cancer at 5 years post diagnosis and those patients without recurrence. FIG. 47 illustrates a statistically significant difference in syntaxin-1mRNA expression level in breast cancer patients in whom a metastatic event has occurred at 5 years post diagnosis versus those without metastases. Data is presented in box-plot form (see FIG. 3 for explanation) and/or as a histogram, where each bar represents the normalised gene expression level in each patient tissue sample.

Figure 48:
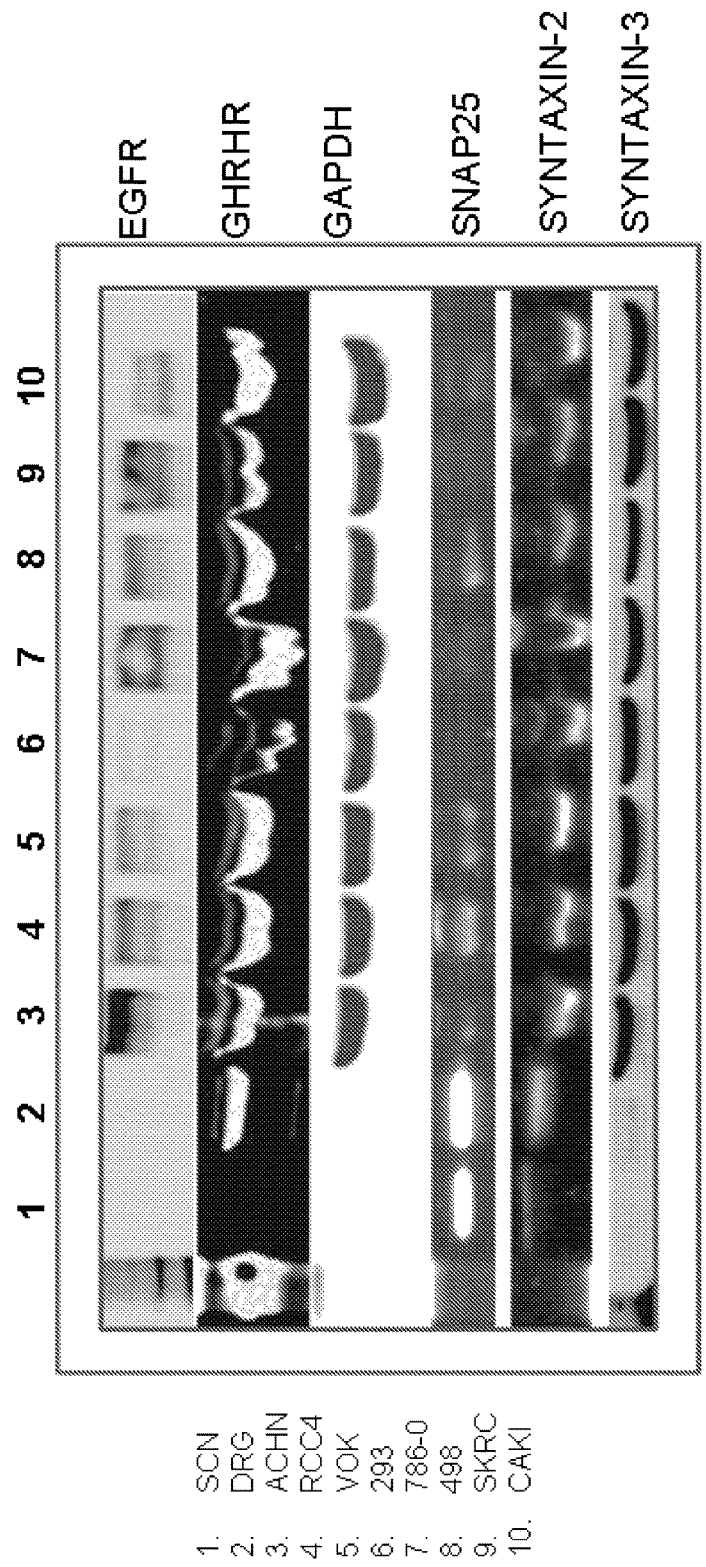

FIG. 48—Profiling cell surface receptor and SNARE protein expression in Renal Cell carcinoma lines by Western blot analysis.

Protein extracts from eight human renal cell carcinoma (RCC) lines grown in vitro were prepared in standard Laemmli sample buffer (lanes 3-10). Protein extracts prepared from primary cultures of rat spinal cord neurons and dorsal root ganglia were included as controls. Proteins were separated on 10% SDS-polyacrylamide gels and electrophoretically transferred to a nitrocellulose membrane. After blocking of the membrane, primary antisera were used to probe for each specific protein and detection was enabled by a peroxidise-conjugated anti-species IgG. The receptor proteins detected were ErbB receptor (epidermal growth factor receptor, EGF) and growth hormone releasing hormone receptor (GHRHR). The SNARE proteins tested were SNAP-25, syntaxin-2 and syntaxin-3. Glyceraldehyde-3-phosphate dehydrogenase (GAPDH) was used as a protein loading control.

Figure 49:
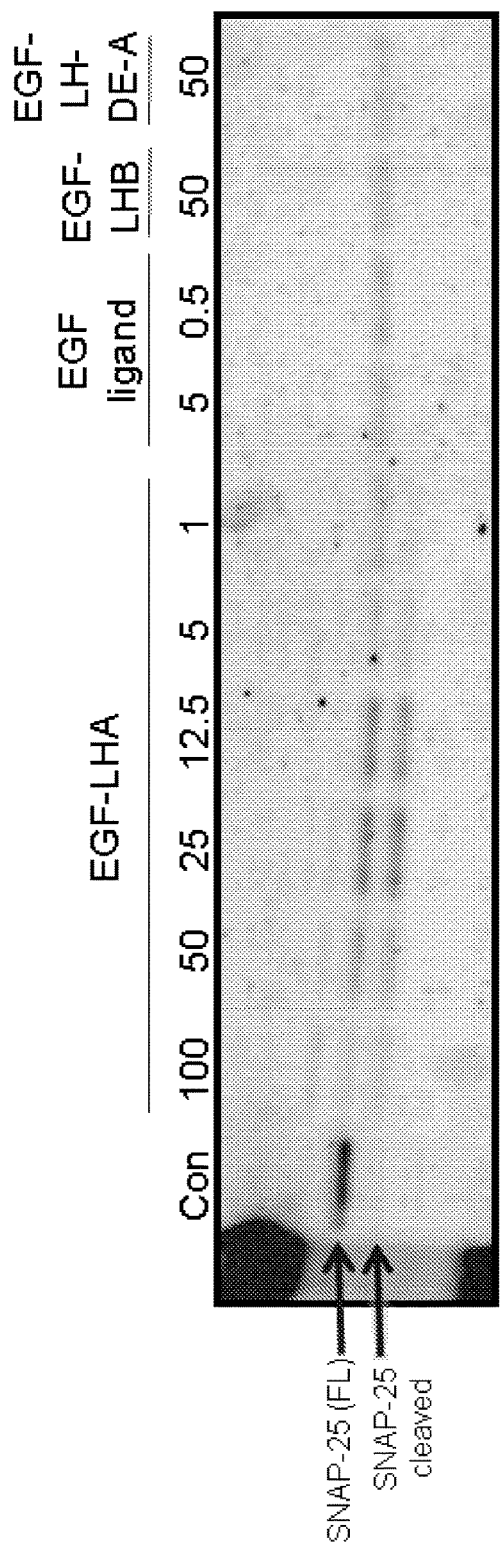

FIG. 49—Detection of SNAP-25 protein cleavage in a Renal Cell carcinoma line by Western blot analysis after 24 hr treatment with an EGF-LHA fusion.

FIG. 49 shows the effect of 24 hour treatment of 786-0 human RCC cells with a number of EGF-liganded fusion protein molecules. In more detail, EGF-LHA, at doses between 1 and 100 nM, generated cleaved SNAP-25 species whereas control molecules, specifically EGF-LHB (non-SNAP-25 targeting), a catalytically inactive form of EGF-LHA, EGF-LH-DE-A (referred to as 'EGF-0' from hereon in) and the 'free' EGF ligand, did not. Indicated concentrations are in nM.

Figure 50:
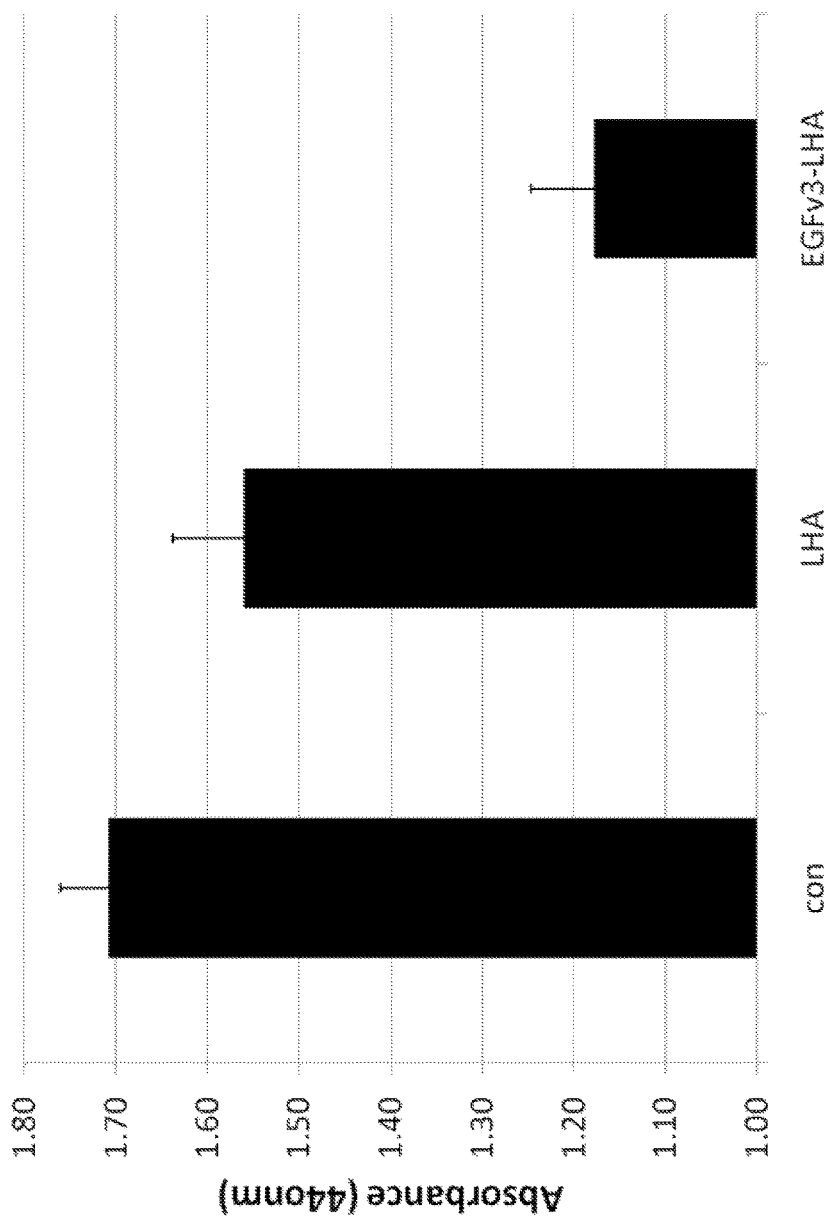

FIG. 50—Inhibition of in vitro proliferation of a Renal Cell carcinoma line by an EGF-LHA fusion.

786-0 cells seeded into a cell culture vessel were counted in a pre-define region at 24 and 48 hours after treatment with 25 nM of EGF-liganded fusion proteins.

Figure 51:
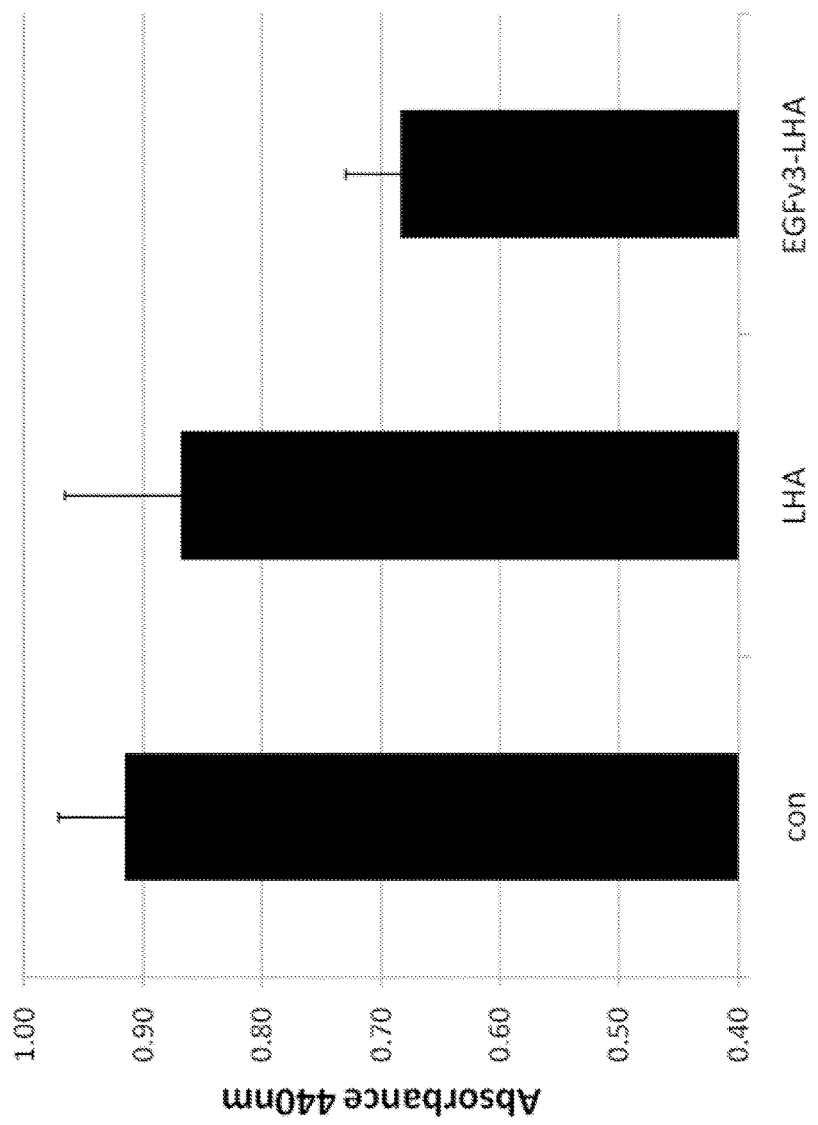

FIG. 51—Inhibition of FGF-2 secretion from a Renal Cell carcinoma line by an EGF-LHA fusion.

Culture media from 786-0 cells treated for 24 hours with EGF-liganded fusion proteins were analysed for Fibroblast Growth Factor-2 by standard methods. In more detail, EGF-LHA, at doses between 1 and 50 nM, demonstrated a dose-dependent decrease in FGF-2 levels present in the culture medium whereas control molecules, specifically the catalytically inactive form of EGF-LHA, EGF-0, and 'free' EGF ligand, did not. Indicated concentrations are in nM.

Figure 52:
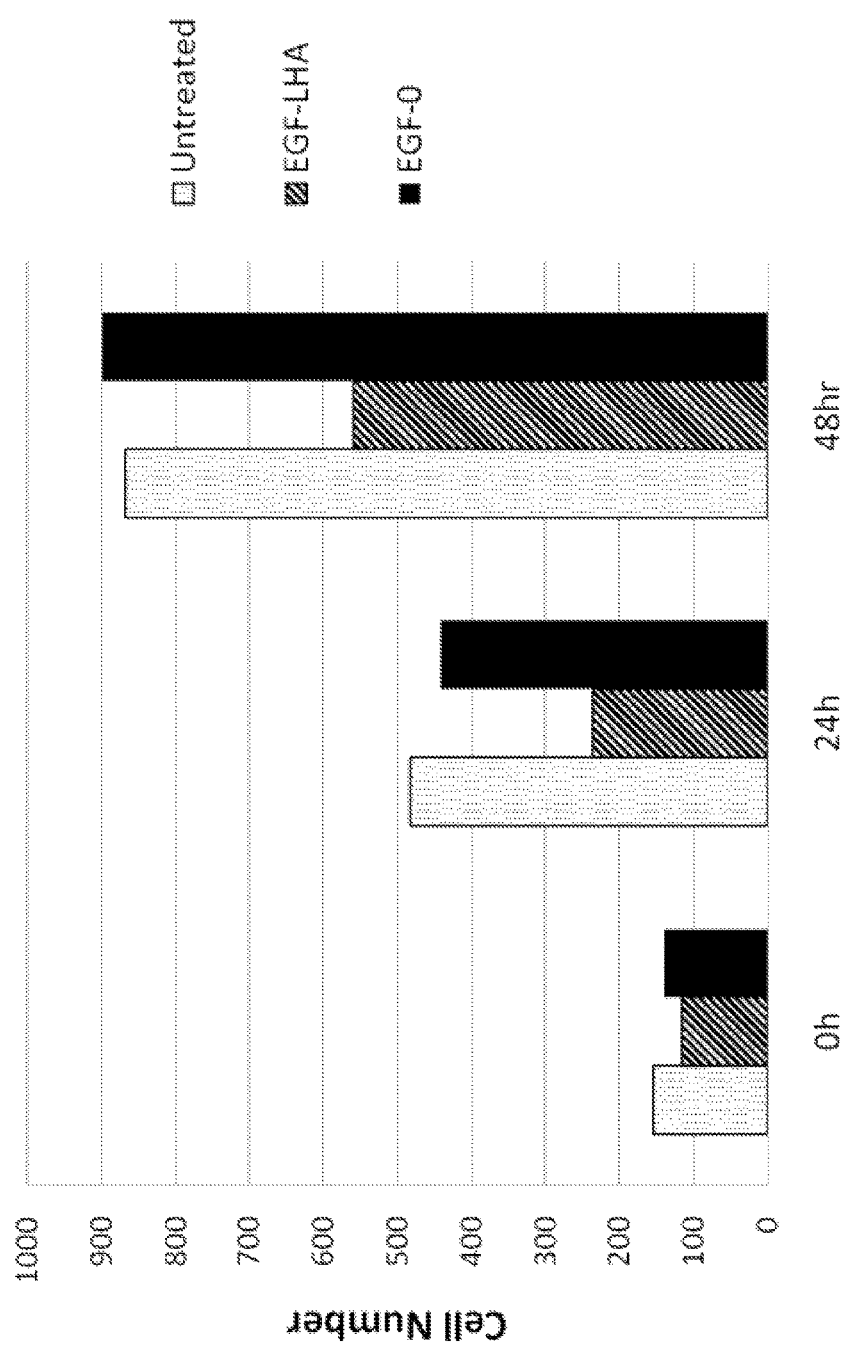

FIG. 52—Inhibition of in vitro proliferation of the A498 Renal Cell carcinoma line by an EGF-LHA fusion.

FIG. 52 shows the effect of an EGF-liganded fusion protein (EGFv3-LHA, 300 nM) on cellular proliferation of A498 cell line after 48 hours. Cells were stained using the tetrazolium salt WST as per standard protocols. The unliganded molecule LHA was included as a control.

Figure 53:
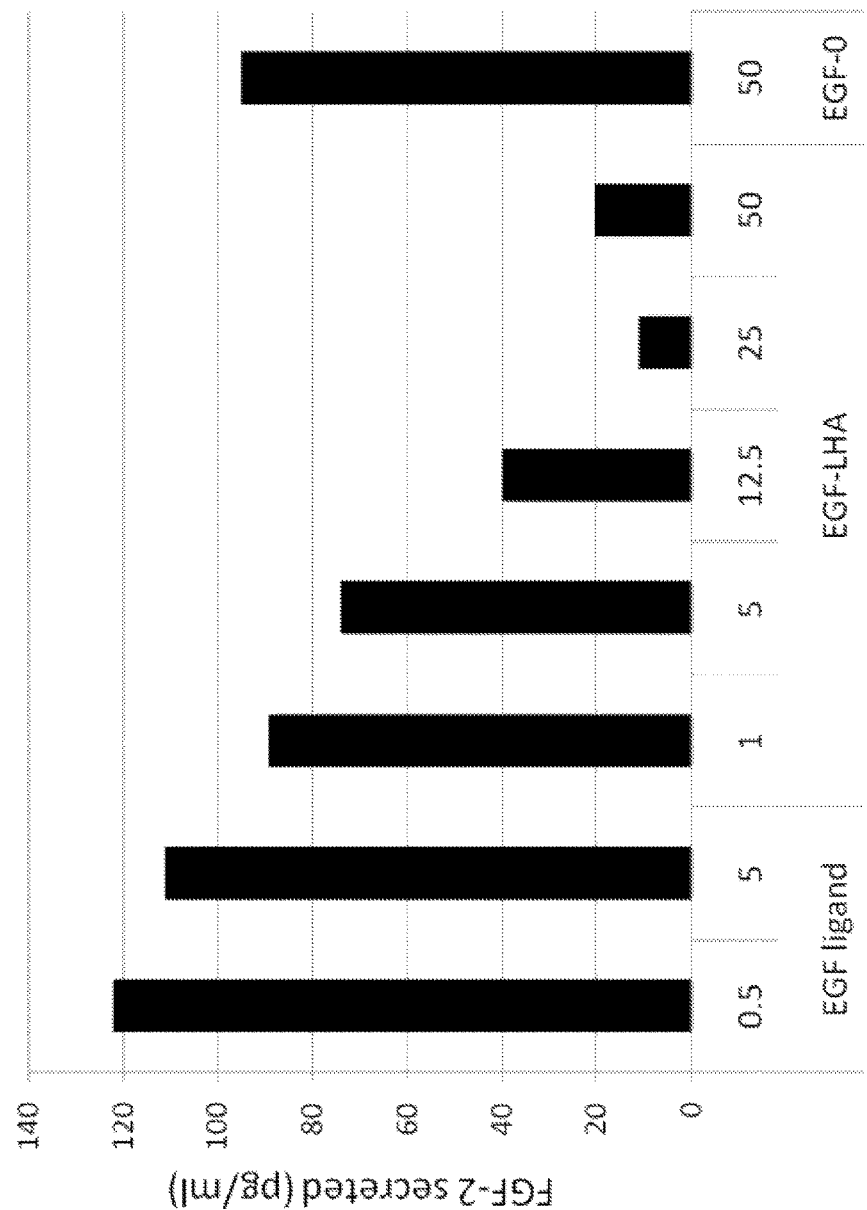

FIG. 53—Inhibition of in vitro proliferation of the ACHN Renal Cell carcinoma line by an EGF-LHA fusion.

FIG. 53 shows the effect of an EGF-liganded fusion protein (EGFv3-LHA, at 300 nM) on cellular proliferation of ACHN cell line after 48 hours. Cells were stained using the tetrazolium salt WST as per standard protocols. The unliganded molecule LHA was included as a control.

Figure 54:
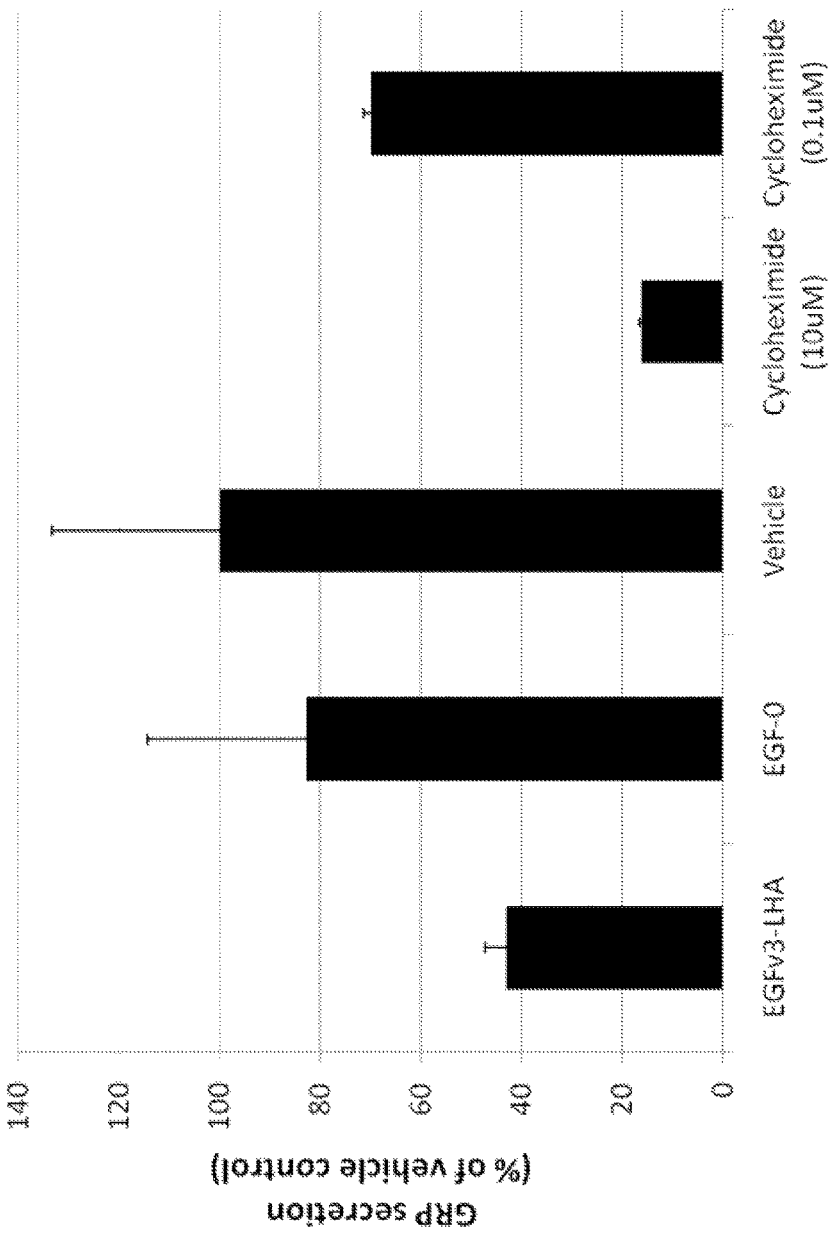

FIG. 54—Inhibition of in vitro secretion of gastrin releasing peptide (GRP) from the small cell lung cancer cell line DMS-53 by an EGF-LHA fusion.

FIG. 54 shows the effect of an EGF-liganded fusion protein (EGFv3-LHA, at 150 nM) on GRP secretion from the DMS-53 cell line after treatment for 24 hr. Medium removed from the cells were analysed 48 hours after removal of fusion proteins. The catalytically inactive form of EGF-LHA, EGF-0, was included as a control, as was cycloheximide, a general protein synthesis inhibitor.

NOMENCLATURE

SST somatostatin
TGF(A) transforming growth factor (alpha)
GHRL ghrelin
LEP leptin
ET(A) endothelin-1
FLT vascular endothelial growth factor receptor
CHRN(D) acetylcholine receptor (subunit delta)
EPHA ephrin type-A receptor
EFNA ephrin-A
DLK1 delta-like protein 1
JAG jagged protein
NRG neuregulin
G-CSF granulocyte colony-stimulating factor
AMF autocrine motility factor
NMB neuromedin-B
CCK cholecystokinin
PDGF platelet-derived growth factor
ADM adrenomedullin
GDNF glial cell line-derived neurotrophic factor
TrkA high affinity nerve growth factor
FSH follicle-stimulating hormone
CXCR C-X-C chemokine receptor
CRLR calcitonin-receptor-like receptor
PDF prostate differentiation factor
MCP monocyte chemotactic protein
KGF keratinocyte growth factor
FLK1 vascular endothelial growth factor receptor 2
PDGFR platelet-derived growth factor receptor
NOTCH neurogenic locus notch homolog protein
DLL delta-like protein
GHS growth hormone secretagogue
c-MET hepatocyte growth factor
c-kit mast/stem cell growth factor
MGSA/GRO melanoma growth stimulatory activity/growth related gene
BCGF B-cell growth factor
GnRH gonadotropin-releasing hormone receptor
Ang-2 angiopoietin-2
FGF fibroblast growth factor
ErbB epidermal growth factor receptor family member
VIPR vasoactive intestinal polypeptide receptor
BRS bombesin receptor subtype
GRP gastrin releasing peptide
LIF leukaemia inhibitory factor
GHRH growth hormone-releasing hormone
IGF insulin-like growth factor
CRHR-2 corticotropin releasing factor receptor-2
BB bombesin
GH growth hormone
IL interleukin
VEGF vascular endothelial growth factor
ACH acetylcholine
CST cortistatin
VPAC vasoactive intestinal peptide receptor
GRPR gastrin releasing peptide receptor
CTR calcitonin binding receptor
EPO erythropoietin
HB-EGF heparin-binding EGF-like growth factor
HGF/SF hepatocyte growth factor/scatter factor
SDF-1 stromal cell-derived factor 1
CXCL12 chemokine (C-X-C motif) ligand 12 (SDF-1)
TNF tumour necrosis factor
PGF placental growth factor
Gran4 granulin-4
TIE2 angiopoietin receptor-2
LH luteinising hormone
CCL CC chemokine ligand
NT neurotrophin
NTAK neuregulin-2
BAFF B-cell activating factor
GM-CSF granulocyte-macrophage colony stimulating factor
NGF nerve growth factor
PACAP pituitary adenylate cyclase-activating peptide
OB leptin
NRP neuropilin receptor Summary of Examples Example 1 Preparation of a LHA backbone construct
Example 2 Construction of LHD-CT-CST29
Example 3 Expression and purification of a LHD-CT-CST29 fusion protein
Example 4 Construction of LHA-CP-EGF
Example 5 Expression and purification of a LHA-CP-EGF fusion protein
Example 6 Chemical conjugation of LHN/A to GnRH TM
Example 7 Method for treating colorectal cancer
Example 8 Method for treating breast cancer
Example 9 Method for treating prostate cancer
Example 10 Method for treating lung carcinoid tumours
Example 11 Method for treating bladder cancer
Example 12 Method for treating small cell lung cancer
Example 13 Method for treating prostate cancer
Example 14 Method for treating cervical cancer
Example 15 Method for treating leukaemia
Example 16 Method for treating small cell lung cancer
Example 17 Method for treating pancreatic cancer
Example 18 Method for treating metastatic bone cancer
Example 19 Method for treating metastatic small cell lung cancer in the brain
Example 20 Method for treating bowel cancer
Example 21 Method for treating chronic lymphocytic leukaemia
Example 22 Method for treating liver cancer
Example 23 Method for treating Hodgkin's lymphoma
Example 24 Method for treating renal cancer
Example 25 Method for treating skin cancer
Example 26 Method for treating oropharyngeal cancer
Example 27 Method for treating myeloma cancer
Example 28 Method for treating soft tissue sarcoma cancer
Example 29 Method for treating gastric cancer
Example 30 Method for treating testicular cancer
Example 31 Method for treating uterine cancer
Example 32 Method for treating Karposi sarcoma
Example 33 Method for treating primary brain cancer
Example 34 Method for treating rectal cancer
Example 35 Assessment of proliferation changes, inhibition of cellular secretion and concomitant SNARE cleavage after treatment of in vitro cultured renal cancer cell lines with a polypeptide of the present invention.

Summary of SEQ ID NOs

Where an initial Met amino acid residue or a corresponding initial codon is indicated in any of the following SEQ ID NOs, said residue/codon is optional.
1. DNA sequence of LHN/A
2. DNA sequence of LHN/B
3. DNA sequence of LHN/C
4. DNA sequence of LHN/D
5. DNA sequence of the CT-CST29 linker
6. DNA sequence of the LHD-CT-CST29 fusion
7. Protein sequence of the LHD-CT-CST29. fusion
8. DNA sequence of the CP-EGF linker
9. DNA sequence of the LHA-CP-EGF fusion
10. Protein sequence of the LHA-CP-EGF fusion
11. Protein sequence of LHN/A
12. Protein sequence of LHN/B
13. Protein sequence of LHN/C
14. Protein sequence of LHN/D
15. Synthesised GnRH peptide
16. Protein sequence of the LHB-CT-SST28 fusion
17. Protein sequence of the LHA-CP-SST28 fusion
18. Protein sequence of the LHD-CT-EGF fusion
19. Protein sequence of the LHD-CT-VIP fusion
20. Protein sequence of the LHC-CT-IGF1 fusion
21. Protein sequence of the LHD-CT-IGF1 fusion
22. Protein sequence of the LHC-CT-VIP fusion
23. Protein sequence of the LHC-CT-GnRH fusion
24. Protein sequence of the LHD-CT-GnRH fusion
25. Protein sequence of the LHD-CT-GRP fusion
26. Protein sequence of the LHB-CT-GRP fusion
27. Protein sequence of the LHC-CT-LIF fusion
28. Protein sequence of the LHB-CP-LIF fusion
29. Protein sequence of the LHC-CT-FGF1 fusion
30. Protein sequence of the LHA-CP-FGF1 fusion
31. Protein sequence of the LHA-CT-FGF9 fusion
32. Protein sequence of the LHC-CP-FGF9 fusion
33. Protein sequence of the IgA-HNtet-CT-SST14 fusion
34. Protein sequence of the IgA-HNtet-CP-SST14 fusion
35. Protein sequence of the LHA-CT-SST14 fusion
36. Protein sequence of the LHA-CT-EGFv3 fusion
37. Protein sequence of the LHE-CT-IL6 fusion
38. Protein sequence of the LHB-CT-IL8 fusion
39. Protein sequence of the LHF-CP-GRAN4 fusion
40. Protein sequence of the LHD-CP-TGFa fusion
41. Protein sequence of the LHD-CP-TGFb fusion
42. Protein sequence of the LHB-CT-TNFa fusion
43. Protein sequence of the LHD-CT-SDF1 fusion
44. Protein sequence of the LHC-CT-VEGF fusion

EXAMPLES

Example 1 Preparation of a $LH_N/A$ Backbone Construct

The following procedure creates a clone for use as an expression backbone for multidomain protein expression. This example is based on preparation of a serotype A based clone (SEQ ID1), though the procedures and methods are equally applicable to all $LH_N$ serotypes such as serotype B (SEQ ID2), serotype C (SEQ ID3) and serotype D (SEQ ID4) and other protease or translocation domains by using the appropriate published sequence for synthesis.

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pET (Novagen) expression vector which has been modified to contain the multiple cloning site NdeI-BamHI-SalI-PstI-XbaI-HindIII for construct insertion, a fragment of the expression vector has been removed to create a non-mobilisable plasmid, a variety of different fusion tags have been inserted to increase purification options and an existing XbaI site in the vector backbone has been removed to simplify sub-cloning.

Preparation of LC/A

The DNA sequence is designed by back translation of the LC/A amino acid sequence (obtained from freely available database sources such as GenBank (accession number P10845) using one of a variety of reverse translation software tools (for example Backtranslation tool v2.0 (Entelechon)). BamHI/SalI recognition sequences are incorporated at the 5' and 3' ends respectively of the sequence maintaining the correct reading frame. The DNA sequence is screened (using software such as SeqBuilder, DNASTAR Inc.) for restriction enzyme cleavage sequences incorporated during the back translation. Any cleavage sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (GeneArt), and the % GC content and codon usage ratio assessed by reference to published codon usage tables (for example GenBank Release 143, Sep. 13 2004). This optimised DNA sequence containing the LC/A open reading frame (ORF) is then commercially synthesized (for example by Entelechon, GeneArt or Sigma-Genosys) and is provided in the pCR 4 vector.

Preparation of $H_N/a$ Insert

The DNA sequence is designed by back translation of the $H_N/A$ amino acid sequence (obtained from freely available database sources such as GenBank (accession number P10845) using one of a variety of reverse translation software tools (for example Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as SeqBuilder, DNASTAR Inc.) for restriction enzyme cleavage sequences incorporated during the back translation. Any sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (GeneArt), and the % GC content and codon usage ratio assessed by reference to published codon usage tables (for example GenBank Release 143, Sep. 13 2004). This optimised DNA sequence is then commercially synthesized (for example by Entelechon, GeneArt or Sigma-Genosys) and is provided in the pCR 4 vector.

Preparation of the Interdomain (LC-$H_N$ Linker)

The LC-HN linker can be designed from first principle, using the existing sequence information for the linker as the template. For example, the serotype A linker (in this case defined as the inter-domain polypeptide region that exists between the cysteines of the disulphide bridge between LC and HN) has the sequence VRGIIPFKTKSLDEGY-NKALNDL (SEQ ID NO: 175). This sequence information is freely available from available database sources such as GenBank (accession number P10845). For generation of a specific protease cleavage site, the native recognition sequence for Factor Xa can be used in the modified sequence VDGIITSKTKSLIEGRNKALNLQ (SEQ ID NO: 176) or an enterokinase recognition sequence is inserted into the activation loop to generate the sequence VDGIITSK-TKSDDDDKNKALNLQ (SEQ ID NO: 177). Using one of a variety of reverse translation software tools (for example Backtranslation tool v2.0 (Entelechon), the DNA sequence encoding the linker region is determined. BamHI/SalI and PstI/XbaI/stop codon/HindIII restriction enzyme sequences are incorporated at either end, in the correct reading frames. The DNA sequence is screened (using software such as Seqbuilder, DNASTAR Inc.) for restriction enzyme cleavage sequences incorporated during the back translation. Any sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (GeneArt), and the % GC content and codon usage ratio assessed by reference to published codon usage tables (for example GenBank Release 143, Sep. 13 2004). This optimised DNA sequence is then commercially synthesized (for example by Entelechon, GeneArt or Sigma-Genosys) and is provided in the pCR 4 vector.

Assembly and Confirmation of the Backbone Clone

Due to the small size, the activation linker must be transferred using a two step process. The pCR-4 linker vector is cleaved with BamHI+SalI combination restriction enzymes and the cleaved linker vector then serves as the recipient for BamHI+SalII restriction enzyme cleaved LC DNA. Once the LC encoding DNA is inserted upstream of the linker DNA, the entire LC-linker DNA fragment can then be isolated and transferred to the pET expression vector MCS. The LC-linker is cut out from the pCR 4 cloning vector using BamHI/PstI restriction enzymes digests. The pET expression vector is digested with the same enzymes but is also treated with antarctic phosphatase as an extra precaution to prevent re-circularisation. The LC-linker and the pET vector backbone are gel purified and the purified insert and vector backbone are ligated together using T4 DNA ligase. The product is transformed with TOP10 cells which are then screened for LC-linker using BamHI/PstI restriction digestion. The process is then repeated for the $H_N$ insertion into the PstI/HindIII restriction sites of the pET-LC-linker construct.

Screening with restriction enzymes is sufficient to ensure the final backbone is correct as all components are already sequenced confirmed during synthesis. However, during the sub-cloning of some components into the backbone, where similar size fragments are being removed and inserted, sequencing of a small region to confirm correct insertion is required.

Example 2 Construction of LHN/D-CT-CST29

The following procedure creates a clone for use as an expression construct for multidomain fusion expression where the targeting moiety (TM) is presented C-terminally to the translocation domain. This example is based on preparation of the LHN/D-CT-CST29 fusion (SEQ ID6), though the procedures and methods are equally applicable to create other protease, translocation and TM fusions, where the TM of C-terminal to the translocation domain. In this example, a flanking 15 amino acid glycine-serine spacer is engineered into the interdomain sequence to ensure accessibility of the ligand to its receptor, but other spacers are applicable.

Preparation of Spacer-CST29 Insert

For presentation of a CST29 sequence at the C-terminus of the HN domain, a DNA sequence is designed to flank the spacer and targeting moiety (TM) regions allowing incorporation into the backbone clone (SEQ ID4). The DNA sequence can be arranged as BamHI-SalI-PstI-XbaI-spacer-CST29 stop codon-HindIII (SEQ ID5). The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is preferred to ensure the correct reading frame is maintained for the spacer, TM and restriction sequences and that the XbaI sequence is not preceded by the bases TC, which would result in DAM methylation. The DNA sequence is screened for restriction sequences incorporated and any additional sequences are removed manually from the remaining sequence ensuring common *E. coli* codon usage is maintained. *E. coli* codon usage is assessed by reference to software programs such as Graphical Codon Usage Analyser (GeneArt), and the % GC content and codon usage ratio assessed by reference to published codon usage tables (for example GenBank Release 143, Sep. 13 2004). This optimised DNA sequence is then commercially synthesized (for example by Entelechon, GeneArt or Sigma-Genosys) and is provided in the pCR 4 vector.

Assembly and Confirmation of the Backbone Clone

In order to create a LHN/D-CT-CST29 construct (SEQ ID6) using the backbone construct (SEQ ID4) and the newly synthesised pCR 4-spacer-TM vector encoding the CST29 TM (SEQ ID5), a one or two step method can be used; typically the two step method is used when the TM DNA is less than 100 base pairs. Using the one step method the TM can be inserted directly into the backbone construct buy cutting the pCR 4-spacer-TM vector with XbaI and HindIII restriction enzymes and inserting the TM encoding DNA fragment into a similarly cut pET backbone construct. Using the two-step method the LHN domain is excised from the backbone clone using restriction enzymes BamHI and XbaI and ligated into similarly digested pCR 4-spacer-TM vector. This creates an LHN-spacer-TM ORF in pCR 4 that can be excised from the vector using restriction enzymes BamHI and HindIII for subsequent ligation into the similarly cleaved pET expression construct. The final construct contains the LC-linker-HN-spacer-CST29 DNA (SEQ ID6) which will result in a fusion protein containing the sequence illustrated in SEQ ID7.

Example 3 Expression and Purification of a LHN/D-CT-CST29 Fusion Protein

This example is based on preparation of an LHN/D protein that incorporates a CST29. TM polypeptide at the carboxyl terminus of the HN domain (SEQ ID7), where the pET expression vector ORF also encodes a histidine purification tag. These procedures and methods are equally applicable to fusion protein sequences shown in SEQ ID 16, 18, 19, 20, 21, 22, 23, 24, 25, 26, 27, 29, 31, 33, 35, 36, 37, 38, 42, 43 or 44. Where appropriate, the activation enzyme should be selected to be compatible with the protease activation site within each sequence.

Expression of LHD-CT-CST29

Expression of the LHN/D-CT-CST29 protein is achieved using the following protocol. Inoculate 100 ml of modified TB containing 0.2% glucosamine and 30 μg/ml kanamycin in a 250 ml flask with a single colony from the LHN/D-CT-CST29 expression strain. Grow the culture at 37° C., 225 rpm for 16 hours. Inoculate 1 L of modified TB containing 0.2% glucosamine and 30 μg/ml kanamycin in a 2 L flask with 10 ml of overnight culture. Grow cultures at 37° C. until an approximate OD600 nm of 0.5 is reached at which point reduce the temperature to 16° C. After 1 hour induce the cultures with 1 mM IPTG and grow at 16° C. for a further 16 hours.

Purification of LHN/D-CT-CST29 Protein

Defrost falcon tube containing 35 ml 50 mM HEPES pH 7.2 200 mM NaCl and approximately 10 g of E. coli BL21 (DE3) cell paste. Homogenise the cell paste (20 psi) ensuring the sample remains cool. Spin the lysed cells at 18 000 rpm, 4° C. for 30 minutes. Load the supernatant onto a 0.1 M NiSO4 charged Chelating column (20-30 ml column is sufficient) equilibrated with 50 mM HEPES pH 7.2 200 mM NaCl. Using a step gradient of 10, 40 and 100 mM imidazole, wash away the non-specific bound protein and elute the fusion protein with 200 mM imidazole. The eluted fusion protein is dialysed against 5 L of 50 mM HEPES pH 7.2 200 mM NaCl at 4° C. overnight and the OD280 nm measured to establish the protein concentration. Add 3.2 μl enterokinase (New England Biolabs) per mg fusion protein and incubate static overnight at 25 C. Load onto a 0.1 M NiSO4 charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10, 40 and 100 mM imidazole, wash away the non-specific bound protein and elute the fusion protein with 200 mM imidazole. Dialyse the eluted fusion protein against 5 L of 50 mM HEPES pH 7.2 150 mM NaCl at 4° C. overnight and concentrate the fusion to about 2 mg/ml, aliquot sample and freeze at −20° C. Test purified protein using OD280, BCA and purity analysis. FIGS. 1 and 2 demonstrate purification of fusion proteins following this method as analysed by SDS-PAGE.

Example 4 Construction of $LH_N/A$-CP-EGF

The following procedure creates a clone for use as an expression construct for multidomain fusion expression where the targeting moiety (TM) is presented centrally between the protease and translocation domain. This example is based on preparation of the $LH_N/A$-CP-EGF fusion (SEQ ID9), though the procedures and methods are equally applicable to create other protease, translocation and TM fusions, where the TM is N-terminal to the translocation domain. In this example, a flanking helical spacer is engineered into the interdomain sequence to ensure accessibility of the ligand to its receptor, but other spacers are applicable.

Preparation of Spacer-Human EGF Insert

The LC-$H_N$ inter-domain polypeptide linker region exists between the cysteines of the disulphide bridge between LC and $H_N$. For insertion of a protease cleavage site, spacer and a targeting moiety (TM) region into the activation loop, one of a variety of reverse translation software tools (for example Backtranslation tool v2.0 (Entelechon) are used to determine the DNA sequence encoding the linker region. For central presentation of a TM sequence at the N-terminus of the $H_N$ domain, a DNA sequence is designed for the spacer and targeting moiety (TM) regions allowing incorporation into the backbone clone (SEQ ID1). The DNA sequence can be arranged as BamHI-SalI-spacer-protease activation site-EGF-spacer-PstI-XbaI-stop codon-HindIII (SEQ ID8). Once the TM DNA is designed, the additional DNA required to encode the preferred spacer is created in silico. It is preferred to ensure the correct reading frame is maintained for the spacer, TM and restriction sequences and that the XbaI sequence is not preceded by the bases TC, which would result in DAM methylation. The DNA sequence is screened for restriction sequence incorporated and any additional sites are removed manually from the remaining sequence ensuring common *E. coli codon usage is maintained. E. coli* codon usage is assessed by reference to software programs such as Graphical Codon Usage Analyser (GeneArt), and the % GC content and codon usage ratio assessed by reference to published codon usage tables (for example GenBank Release 143, Sep. 13 2004). This optimised DNA sequence is then commercially synthesized (for example by Entelechon, GeneArt or Sigma-Genosys) and is provided in the pCR 4 vector.

Assembly and Confirmation of the Backbone Clone

In order to create a LC-spacer-activation site-EGF-spacer-$H_N$ construct (SEQ ID9) using the backbone construct (SEQ ID1) and the newly synthesised pCR 4-spacer-activation site-TM-spacer vector encoding the EGF TM (SEQ ID8), a one or two step method can be used; typically the two step method is used when the TM DNA is less than 100 base pairs. Using the one step method the TM linker region can be inserted directly into the backbone construct buy cutting the pCR 4-spacer-activation site-TM-spacer vector with SalI and PstI restriction enzymes and inserting the TM encoding DNA fragment into a similarly cut pET backbone construct. Using the two-step method the LC domain is excised from the backbone clone using restriction enzymes BamHI and SalI and ligated into similarly digested pCR 4-spacer-activation site-TM-spacer vector. This creates a LC-spacer-activation site-TM-spacer ORF in pCR 4 that can be excised from the vector using restriction enzymes BamHI and PstI for subsequent ligation into similarly pET expression construct. The final construct contains the LC-spacer-activation site-EGF-spacer-$H_N$ DNA (SEQ ID9) which will result in a fusion protein containing the sequence illustrated in SEQ ID10.

Example 5 Expression and Purification of a $LH_N$/A-CP-EGF Fusion Protein

This example is based on preparation of an $LH_N$/A protein that incorporates a EGF TM polypeptide into the interdomain linker region (SEQ ID10), where the pET expression vector ORF also encodes a histidine purification tag. These procedures and methods are equally applicable to the other fusion protein shown in SEQ ID 17, 28, 30, 32, 34, 39, 40 or 41. Where appropriate, the activation enzyme should be selected to be compatible with the protease activation site within each sequence.

Expression of $LH_N$A-CP-EGF

Expression of the $LH_N$/A-CP-EGF protein is achieved using the following protocol. Inoculate 100 ml of modified TB containing 0.2% glucosamine and μg/ml kanamycin in a 250 ml flask with a single colony from the LHA-CP-EGF expression strain. Grow the culture at 37° C., 225 rpm for 16 hours. Inoculate 1 L of modified TB containing 0.2% glucosamine and 30 μg/ml kanamycin in a 2 L flask with 10 ml of overnight culture. Grow cultures at 37° C. until an approximate $OD_{600}$ nm of 0.5 is reached at which point reduce the temperature to 16° C. After 1 hour induce the cultures with 1 mM IPTG and grow at 16° C. for a further 16 hours.

Purification of LH/A-CP-EGF Protein

Defrost falcon tube containing 35 ml 50 mM HEPES pH 7.2 200 mM NaCl and approximately 10 g of *E. coli* BL21 (DE3) cell paste. Homogenise the cell paste (20 psi) ensuring the sample remains cool. Spin the lysed cells at 18 000 rpm, 4° C. for 30 minutes. Load the supernatant onto a 0.1 M NiSO4 charged Chelating column (20-30 ml column is sufficient) equilibrated with 50 mM HEPES pH 7.2 200 mM NaCl. Using a step gradient of 10, 40 and 100 mM imidazole, wash away the non-specific bound protein and elute the fusion protein with 200 mM imidazole. The eluted fusion protein is dialysed against 5 L of 50 mM HEPES pH 7.2 200 mM NaCl at 4° C. overnight and the $OD_{280}$ nm measured to establish the protein concentration. Add 3.2 µl enterokinase (New England Biolabs) per mg fusion protein and incubate static overnight at 25 C. Load onto a 0.1 M NiSO4 charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10, 40 and 100 mM imidazole, wash away the non-specific bound protein and elute the fusion protein with 200 mM imidazole. Dialyse the eluted fusion protein against 5 L of 50 mM HEPES pH 7.2 150 mM NaCl at 4° C. overnight and concentrate the fusion to about 2 mg/ml, aliquot sample and freeze at −20° C. Test purified protein using $OD_{280}$, BCA and purity analysis.

Example 6 Chemical Conjugation of $LH_N/A$ to GnRH TM

The following procedure creates a chemically conjugated molecule containing the $LH_N/A$ amino acid sequence (SEQ ID11), prepared from SEQ ID1 using the production method outlined in example 3, and a GnRH peptide which has been chemically synthesised (SEQ ID15). However, the procedures and methods are equally applicable for the conjugation of other peptides to other protease/translocation domain proteins such as those containing the amino acid sequences SEQ ID12, 13 and 14.

The $LH_N/A$ protein was buffer exchanged from 50 mM Hepes 150 mM salt into PBSE (100 mM 14.2 g NA2HPO4, 100 mM 5.85 g NaCl, 1 mM $EDTANa_2$ pH 7.5 with 1M HCl) using the Bio-rad PD10 column. This was done by washing one column volume of PBSE through the PD10 column, the protein was then added to the column until no more drops exit the end of the PD10 column. 8 mls of PBSE was then added and 0.5 ml fractions are collected. The collected fractions are the measured using the $A_{280}$ reading and fractions containing protein are pooled. A concentration of 1.55 mg/ml of $LH_N/A$ was obtained from the buffer exchange step and this was used to set up the following reactions:

| $LH_N/A$ 1.55 mg/ml | 20 mM SPDP or Sulfo-LC-SPDP |
|---|---|
| A 200 µl | 0 |
| B 200 µl | 4 fold increase 0.62 µl |
| C 200 µl | 8 fold increase 1.24 µl |

Sample were left to tumble at RT for 3 hours before being passed down another PD10 column to buffer exchange into PBSE and the protein containing fractions pooled. A final concentration of 25 mM DTT was then added to derivatised protein and then the samples left at room temperature for 10 minutes. $A_{280}$ and $A_{343}$ readings were then taken to work out the ratio of SPDP:$LH_N/A$ interaction and the reaction which resulted in a derivatisation ration of between 1 and 3 was used for the peptide conjugation. The SPDP reagent binds to the primary amines of the $LH_N/A$ via an N-hydroxysuccinimide (NHS) ester, leaving the sulphydryl-reactive portion to form a disulphide bond to the free SH group on the free cysteine on the synthesised peptide. In this case the peptide sequence is GnRH which has been synthesised with a cysteine contained within the peptide to allow conjugation whilst leaving the N-terminus and C-terminus of the GnRH to interact with its receptor (SEQ ID15). The SPDP-derivatised $LH_N/A$ was mixed with a 4-fold excess of the GnRH ligand and the reaction was then left at RT for 90 minutes whilst tumbling. The excess GnRH was then removed using either a PD10 column leaving $LH_N/A$-GnRH conjugated molecule.

Example 7—Method for Treating Colorectal Cancer

A 62 year old man presents with a stage II colorectal cancer. To reduce and/or to prevent metastasis he receives a direct injection of a polypeptide of the present invention (eg. botulinum type A neurotoxin protease and translocation domain and a VIP peptide). Within 4 weeks a significant shrinkage of the tumour is observed without appearance of metastasis elsewhere. The treatment is optionally performed in combination with chemotherapy, and is repeated 2 months later and 4 weeks later no tumour is observable anymore with the usual detection tools (colonoscopy, CT scan, PET scan, etc.) and the level of carcinoembryonic antigen (CEA) returned to the normal.

Example 8—Method for Treating Breast Cancer

A 61 year old woman presents with a stage II breast cancer. To treat and/or prevent metastasis she receives an IV injection of a polypeptide of the present invention (eg. a botulinum type C neurotoxin protease, a botulinum type C neurotoxin translocation domain and a GnRH peptide), optionally in combination with chemotherapy. Within 4 weeks a significant shrinkage of the tumour is observed without appearance of metastasis elsewhere. The treatment is repeated 2 months later and 6 weeks later no tumour is observable anymore with the usual detection tools (MRI, ultrasound, breast-specific positron emission tomography, mammography, Scintigraphy, etc).

Example 9—Method for Treating Prostate Cancer

A 77 year old man presents with a stage II prostate cancer. To treatment and/or to prevent metastasis he receives a intravenous injection of a polypeptide of the present invention (eg. a botulinum type C neurotoxin protease, a botulinum type C neurotoxin translocation domain and an IGF-1 peptide), optionally in combination with hormone therapy. Within 4 weeks a significant shrinkage of the tumour is observed without appearance of metastasis elsewhere. The treatment is repeated 2 months later and 8 weeks later no tumour is observable anymore with the usual detection tools (X-ray, ProstaScint scan, MRI, transrectal ultrasonography, CT scan, etc.) and the levels of PSA came back to normal.

Example 10—Method for Treating Lung Carcinoid Tumours

A 66 year old woman presents with lung carcinoid tumours. To treat and/or prevent metastasis she receives an IV injection of a polypeptide of the present invention (eg. a botulinum type A neurotoxin protease, a botulinum type A neurotoxin translocation domain and a bFGF-1 peptide), optionally in combination with chemotherapy. Within 4 weeks a significant decrease in the size of the tumour is observed without appearance of metastasis elsewhere. The treatment is repeated 1 month later and 4 weeks later no tumour is observable anymore with the usual detection tools (X-rays, CT scan, bronchoscopy, etc.) or using the usual blood tests recommended for this cancer.

Example 11—Method for Treating Bladder Cancer

A 56 year old man presents with a stage II bladder cancer. To treat and/or to prevent metastasis he receives a direct injection of a polypeptide of the present invention (eg. an IgA protease, a tetanus neurotoxin translocation domain and an IGF-1 peptide), optionally in combination with chemotherapy. Within 2 weeks a significant shrinkage of the tumour is observed without appearance of metastasis elsewhere. The treatment is repeated 2 months later and 4 weeks later no tumour is observable anymore with the usual detection tools (colonoscopy, CT scan, PET scan, etc.).

Example 12—Method for Treating Small Cell Lung Cancer

A 79 year old man is diagnosed with a stage I small cell lung cancer. To treat and/or to prevent metastasis he receives a injection of a polypeptide of the present invention (eg. a botulinum type A neurotoxin protease, a botulinum type A neurotoxin translocation domain and a neuregulin ERBB3 peptide), optionally in combination with chemotherapy. Within 3 weeks a significant decrease in size of the tumour is observed without appearance of metastasis elsewhere. The treatment is repeated 2 months later and 5 weeks later no tumour is observable anymore with the usual detection tools (X-rays, CT scan, MRI, PET scanning, Radionuclide imaging, bronchoscopy, etc.) or using the usual blood tests recommended for this cancer.

Example 13—Method for Treating Prostate Cancer

A 72 year old man is diagnosed with a stage II prostate cancer. To treat and/or to prevent metastasis he receives a intravenous injection of a polypeptide of the present invention (eg. a botulinum type D neurotoxin protease, a botulinum type C neurotoxin translocation domain, a GS20 linker, and an IGF-1 peptide), optionally in combination with androgen deprivative treatment. Within 10 days a significant shrinkage of the tumour is observed without appearance of metastasis elsewhere. The treatment is repeated 2 months later and 5 weeks later no tumour is observable anymore with the usual detection tools (X-ray, ProstaScint scan, MRI, transrectal ultrasonography, CT scan, etc.) and the levels of PSA came back to normal.

Example 14—Method for Treating Cervical Cancer

A 60 year old woman diagnosed with cervical cancer at a limited stage is treated with surgery. To improve the effects of the treatment and to prevent metastasis she receives an intravenous injection of a polypeptide of the present invention (eg. botulinum type D neurotoxin protease, a botulinum type D neurotoxin translocation domain, a GS20 linker, and a somatostatin-14 peptide). Within 6 weeks no re-appearance of the tumour is observed. The treatment is repeated 3 months later and 8 weeks later no tumour is observable anymore with the usual detection tools (X-rays, CT scan, MRI, PET scanning, Radionuclide imaging, bronchoscopy, etc.) or using the usual blood tests recommended for this cancer.

Example 15—Method for Treating Leukaemia

A 42 year old man is diagnosed with a stage II Hairy cell leukaemia cancer. To treat and/or to prevent metastasis he receives an intravenous injection of a polypeptide of the present invention (eg. a botulinum type D neurotoxin protease, a botulinum type D neurotoxin translocation domain, a GS20 linker, and a FGF-1 peptide), optionally in combination with chemotherapy. Within 10 days significant reduction in tumour burden is observed without appearance of metastasis. The treatment is repeated 1 month later and 3 weeks later no tumour is observable anymore with the usual detection tools (MRI, complete blood count, etc).

Example 16—Method for Treating Small Cell Lung Cancer

A 56 year old man is diagnosed with a small cell lung cancer at an extensive stage. To treat and/or to prevent metastasis elsewhere he receives an intravenous injection of a polypeptide of the present invention (eg. a botulinum type D neurotoxin protease, a botulinum type C neurotoxin translocation domain and an EGF peptide), optionally in combination with chemotherapy and radiation therapy. Within 3 weeks a significant shrinkage of the tumour and a diminution in size of the metastasis is observed without appearance of new metastasis elsewhere. The treatment is repeated twice after 2 months and 5 months. The patients died 11 months later, 6 months later than expected with this type of treatment and this stage of the disease.

Example 17—Method for Treating Pancreatic Cancer

A 48 year old woman is diagnosed with pancreatic cancer at an advanced stage. She receives an intravenous injection of a polypeptide of the present invention (eg. a botulinum type D neurotoxin protease, a botulinum type C neurotoxin translocation domain and an EGF peptide), optionally in combination with the chemotherapeutic agent, Gemcitabine. Within 3 weeks a significant reduction in primary tumour growth and a diminution in size of the metastases are observed without appearance of new metastasis elsewhere. The treatment is repeated twice after 2 months and 5 months. The patient died 12 months later, 6 months later than expected with this type of treatment and this stage of the disease.

Example 18—Method for Treating Metastatic Bone Cancer

A 71 year old man is diagnosed with a stage IV prostate cancer. To treat metastatic growth in his bone he receives an intravenous injection of a polypeptide of the present invention (eg. a botulinum type D neurotoxin protease, a botulinum type D neurotoxin translocation domain and a TGF-beta peptide), optionally in combination with external beam radiation plus hormone therapy. Within 4 weeks a significant shrinkage of the tumour at the metastatic sites is observed without appearance of metastasis elsewhere. The treatment is repeated 2 and 4 months later. After 6 months no detectable increase in tumour burden is observable anymore with the usual detection tools (X-ray, ProstaScint scan, MRI, CT scan, etc.).

Example 19—Method for Treating Metastatic Small Cell Lung Cancer in the Brain A 65 year old man diagnosed with a small cell lung cancer at an advanced stage also presents with multiple brain metastases. To treat, a polypeptide of the present invention (eg. a botulinum type A neurotoxin protease, a botulinum type A neurotoxin translocation domain, and a SDF-1 peptide) is delivered into his brain by convection enhanced delivery, optionally in combination with chemotherapy and whole brain radiation. Within 4 weeks significant shrinkage of the metastatic tumour sites is observed without appearance of metastasis elsewhere. The treatment is repeated at 2 months and 8 weeks later no metastatic tumour is observable anymore with the usual detection tools (X-rays, CT scan, MRI, PET scanning, Radionuclide imaging, etc.) or using the usual blood tests recommended for this cancer.

Example 20—Method for Treating Bowel Cancer

A 76 year old man is diagnosed with a stage II small bowel cancer. To treatment and/or to prevent metastasis he receives a direct injection of a polypeptide of the present invention (eg. a botulinum type A neurotoxin protease and translocation domain and an EGF peptide), optionally in combination with chemotherapy. Within 4 weeks a significant shrinkage of the tumour is observed without appearance of metastasis elsewhere and surgery is then realized to remove the tumour.

Example 21—Method for Treating Chronic Lymphocytic Leukaemia

A 54 year old man is diagnosed with relapsed chronic lymphocytic leukaemia. To treat, he receives an intravenous injection of a polypeptide of the present invention (eg. a botulinum type B neurotoxin protease, a botulinum type B neurotoxin translocation domain and an LIF-1 peptide), optionally in combination with chemotherapy. Within 2 weeks a significant reduction in tumour cell count in the patient's blood is observed which remains stable for an extended period of time as determined by microscopic examination and flow cytometric analysis of the patient's blood

Example 22—Method for Treating Liver Cancer

A 55 year old woman is diagnosed with a stage IV hepatic cancer. To treat, she receives an intravenous injection of a polypeptide of the present invention (eg. a botulinum type D neurotoxin protease, a botulinum type D neurotoxin translocation domain and a TGF-alpha peptide), optionally in combination with chemotherapy. Within 2 weeks a significant shrinkage of the tumour is observed on PET-CT imaging studies along with a reduction of alpha-fetoprotein in the blood, which was elevated prior to treatment.

Example 23—Method for Treating Hodgkin's Lymphoma

A 24 year old man is diagnosed with stage IVA Hodgkin's lymphoma. To treat, he receives repeated intravenous injections of a polypeptide of the present invention (eg. a botulinum type B neurotoxin protease, a botulinum type B neurotoxin translocation domain and an VEGF peptide), optionally in combination with chemotherapy. Within 2 weeks a significant reduction in tumour volume is observed and tumour blood flow using the usual detection tools (MRI, CT scans) and leads to complete remission within 2 months.

Example 24—Method for Treating Renal Cancer

A 54 year old man is diagnosed with advanced renal cell carcinoma. To treat, he receives an intravenous administration of a polypeptide of the present invention (eg. a botulinum type A neurotoxin protease, a botulinum type C neurotoxin translocation domain and a VEGF peptide), optionally in combination with the anti-angiogenic therapeutic, Sunitinib, a small molecule tyrosine kinase inhibitor (TKI). Within 14 days a significant shrinkage of the tumour over and above that expected with TKI alone is observed using the usual detection tools (CT, MRI scans, blood tests).

Example 25—Method for Treating Skin Cancer

A 31 year old woman is diagnosed with a facial melanoma. To treat, she receives direct administration of a polypeptide of the present invention (eg. a botulinum type D neurotoxin protease, a botulinum type C neurotoxin translocation domain, a GS20 linker, and a VEGF peptide), optionally in combination with chemotherapy and immunotherapy. Within 21 days a significant shrinkage of the tumour over and above that expected with chemo and immunotherapy alone is observed, allowing surgical resection with clear but much reduced margins.

Example 26—Method for Treating Oropharyngeal Cancer

A 63 year old man is diagnosed with a stage III head and neck cancer. To treat, he receives an intravenous injection of a polypeptide of the present invention (eg. a botulinum type D neurotoxin protease, a botulinum type D neurotoxin translocation domain and a TGF-alpha peptide), optionally in combination with radiotherapy and chemotherapy. Within 4 weeks a significant improvement in the patient's ability to swallow food is apparent which is maintained longer than would be expected with the combination therapy alone.

Example 27—Method for Treating Myeloma Cancer

A 73 year old woman diagnosed with multiple myeloma associated osteolytic bone lesions and hypercalcemia is treated with the standard chemotherapy. To improve the effects of the treatments she receives an intravenous injection of a polypeptide of the present invention (eg. a botulinum type D neurotoxin protease, a botulinum type C neurotoxin translocation domain and an IL-6 peptide). Within 4 weeks a significant reduction in the size of bone lesions and severity of hypercalcemia is observed without appearance of new lesions elsewhere using the usual detection tools (MRI, X-ray, blood tests).

Example 28—Method for Treating Soft Tissue Sarcoma Cancer

A 51 year old woman diagnosed with a fibrosarcoma of the leg is treated with radiation therapy in an attempt to reduce tumour size prior to surgical resection. To improve the effects of the radiation treatment she receives an intravenous injection of a polypeptide of the present invention (eg. a botulinum type D neurotoxin protease, a botulinum type C neurotoxin translocation domain, a GS20 linker, and a bFGF peptide). Within 14 days a significant shrinkage of the tumour over and above that expected with radiation therapy alone is observed, allowing surgical resection with clear margins.

Example 29—Method for Treating Gastric Cancer

A 84 year old man diagnosed with advanced gastric cancer and unable to undergo surgical resection is treated with radiation therapy to relieve tumour associated blockage. To improve the effects of the treatment he receives multiple direct injections of a polypeptide of the present invention (eg. a botulinum type A neurotoxin protease, a botulinum type A neurotoxin translocation domain, a GS20 linker, and a GRP peptide). Within 5 days a significant shrinkage of the tumour is observed with the usual detection tools (gastroscopic examination and CT scan). The treatment is repeated 1 month later and 4 months later tumour blockage has not recurred.

Example 30—Method for Treating Testicular Cancer

A 32 year old man is diagnosed with a stage I seminoma cancer. To treat and/or to prevent recurrence he receives a intravenous injection of a polypeptide of the present invention (eg. a botulinum type D neurotoxin protease, a botulinum type C neurotoxin translocation domain, a GS20 linker, and a VEGF peptide), optionally in combination with chemotherapy. Within 14 days a significant shrinkage of the tumour is observed. The treatment is repeated 1 month later and 6 weeks later no tumour is observable anymore with the usual detection tools (blood tests and CT scans).

Example 31—Method for Treating Uterine Cancer

A 76 year old woman diagnosed with a stage IIA endometrial cancer is treated with usual chemotherapy and radiotherapy. To improve the effects of the treatment and to prevent metastasis she receives a direct injection of a polypeptide of the present invention (eg. a botulinum type A neurotoxin protease and translocation domain and an EGF peptide). Within 6 weeks a significant shrinkage of the tumour is observed on direct visualization of the uterine cavity by hysteroscopy without appearance of metastasis elsewhere.

Example 32—Method for Treating Karposi Sarcoma

A 48 year old man is diagnosed with acquired immunity deficiency syndrome (AIDS) and presents with multiple Karposi sarcoma lesions. To treat, he receives an intravenous injection of a polypeptide of the present invention (eg. a botulinum type A neurotoxin protease, a botulinum type A neurotoxin translocation domain and an IL-6 peptide), optionally in combination with interferon alpha. Within 3 weeks a significant reduction in lesion size is observed without appearance of new lesions elsewhere. The treatment is repeated twice after 1 month and 3 months which effectively stops the progression of the Kaposi sarcoma.

Example 33—Method for Treating Primary Brain Cancer

A 45 year old woman is diagnosed with glioblastoma. To treat and/or to prevent further metastasis she receives an intracranial application of a polypeptide of the present invention (eg. a botulinum type C neurotoxin protease, a botulinum type C neurotoxin translocation domain and a VEGF peptide), optionally in combination with chemotherapy. Within 4 weeks a significant decrease in the size of the tumour is observed without appearance of metastasis elsewhere. The treatment is repeated 1 month later and 4 weeks later no tumour is observable anymore with the usual detection tools (X-rays, CT scan, etc.).

Example 34—Method for Treating Rectal Cancer

A 77 year old man diagnosed with a stage II rectal cancer is treated with a polypeptide of the present invention (eg. botulinum type A neurotoxin protease and an anti-EGFR antibody F(ab)'$_2$ fragment), optionally in combination with radiotherapy and surgery. He receives localised injections of polypeptide (eg. 3 days in advance of a standard regiment of fractionated radiation) and within 2 weeks a significant shrinkage of the tumour is observed which enables complete surgical resection. 12 months later no tumour recurrence is observable with the usual detection tools (colonoscopy, CT scan, PET scan, etc.) and the level of carcinoembryonic antigen (CEA) returned to the normal.

Example 35—Assessment of Proliferation Changes, Inhibition of Cellular Secretion and Concomitant SNARE Cleavage after Treatment of In Vitro Cultured Renal Cancer Cell Lines with a Polypeptide of the Present Invention Methods:
Proliferation Analysis:
An appropriate volume containing 1000 cells of a suitable renal cancer cell line, for example A498, ACHN or 786-0, are seeded into the wells of a 96-well cell culture plate in a suitable growth medium supplemented with 10% Foetal Bovine Serum and incubated at 37° C. in a humidified atmosphere with 5% $CO_2$. Cells are allowed to adhere overnight after which treatment with an EGF-liganded LHA molecule, such as an LHA molecule with a C-terminal presented EGF ligand, is initiated. After 24 hours, the treatment media are removed, cell monolayers are washed to remove traces of LHA-EGF and fresh medium applied to cells. After a further 24 hours a conventional colorimetric proliferation assay (based on the determination of the cleavage of the tetrazolium salt WST-1 to formazan by cellular enzymes) is performed. Specifically, WST-1 is added to the culture medium for 4 hours after which the optical density at 440 nm is determined for each treatment. FIGS. 50-52 demonstrate inhibition of in vitro proliferation from a renal cell carcinoma line by an EGF-LHA fusion.
Cellular Secretion Analysis:
10,000 cells of a suitable renal cancer cell line (for example 786-0, A498 or ACHN) are seeded in the wells of a 24 well plate in an appropriate culture medium containing 10% foetal bovine serum. Plates are incubated overnight in an incubator at 37° C. in a humidified atmosphere with 5% $CO_2$ to allow cells to adhere. Cell cultures are then treated with an appropriate polypeptide of the present invention which targets a specific receptor on the cells of interest (for the cell lines detailed above an appropriate molecule would be an EGF-liganded LHA as these 3 cell lines all express EGF receptors, FIG. 48). After 24 hours, the treatment medium is removed, cell monolayers refed with fresh culture medium and 24-48 hours later samples of the culture medium are removed to fresh microfuge tubes which are subsequently spun at 1500 rpm for 5 minutes to remove floating cells. The resultant supernatants are removed to fresh tubes and aliquots then used for the quantification of specific analytes (for example VEGF, TNF-alpha) by enzyme-linked immunosorbent assay or ELISA (FIG. 53). An example of analysis of inhibition of a secretion (GRP) from a small cell lung carcinoma cell line is provided in FIG. 54.

Western Blot Analysis to Detect SNARE Cleavage Due to Cellular Uptake of Polypeptides of the Present Invention:

Cell cultures are treated with polypeptides as detailed above for the analysis of cellular secretions. After removal of culture medium for subsequent ELISA analysis, cell monolayers in each well are washed three times with phosphate-buffered saline and protein extracts prepared by cellular lysis in standard Laemmli sample buffer. Cellular protein are separated on 12% SDS-polyacrylamide gels and electrophoretically transferred to a nitrocellulose membrane. After blocking of the membrane, primary antisera are used to probe for the SNARE protein of interest and detection of full length and/or cleaved forms is enabled by a peroxidase-conjugated anti-species IgG. In the case of treatment of the renal cell line 786-0 with an LHA-EGF molecule, cleavage of the SNARE SNAP-25 is observed (see FIG. 49).

SEQ ID NOs

1. DNA sequence of $LH_N$/A

```
ggatccATGGAGTTCGTTAACAAACAGTTCAACTATAAAGACCCAGTTAACGGTGTTGACATTGCTTAC

ATCAAAATCCCGAACGCTGGCCAGATGCAGCCGGTAAAGGCATTCAAAATCCACAACAAAATCTGGGTT

ATCCCGGAACGTGATACCTTTACTAACCCGGAAGAAGGTGACCTGAACCCGCCACCGGAAGCGAAACAG

GTGCCGGTATCTTACTATGACTCCACCTACCTGTCTACCGATAACGAAAAGGACAACTACCTGAAAGGT

GTTACTAAACTGTTCGAGCGTATTTACTCCACCGACCTGGGCCGTATGCTGCTGACTAGCATCGTTCGC

GGTATCCCGTTCTGGGGCGGTTCTACCATCGATACCGAACTGAAAGTAATCGACACTAACTGCATCAAC

GTTATTCAGCCGGACGGTTCCTATCGTTCCGAAGAACTGAACCTGGTGATCATCGGCCCGTCTGCTGAT

ATCATCCAGTTCGAGTGTCTGAGCTTTGGTCACGAAGTTCTGAACCTCACCCGTAACGGCTACGGTTCC

ACTCAGTACATCCGTTTCTCTCCGGACTTCACCTTCGGTTTTGAAGAATCCCTGGAAGTAGACACGAAC

CCACTGCTGGGCGCTGGTAAATTCGCAACTGATCCTGCGGTTACCCTGGCTCACGAACTGATTCATGCA

GGCCACCGCCTGTACGGTATCGCCATCAATCCGAACCGTGTCTTCAAAGTTAACACCAACGCGTATTAC

GAGATGTCCGGTCTGGAAGTTAGCTTCGAAGAACTGCGTACTTTTGGCGGTCACGACGCTAAATTCATC

GACTCTCTGCAAGAAAACGAGTTCCGTCTGTACTACTATAACAAGTTCAAAGATATCGCATCCACCCTG

AACAAAGCGAAATCCATCGTGGGTACCACTGCTTCTCTCCAGTACATGAAGAACGTTTTTAAAGAAAAA

TACCTGCTCAGCGAAGACACCTCCGGCAAATTCTCTGTAGACAAGTTGAAATTCGATAAACTTTACAAA

ATGCTGACTGAAATTTACACCGAAGACAACTTCGTTAAGTTCTTTAAAGTTCTGAACCGCAAAACCTAT

CTGAACTTCGACAAGGCAGTATTCAAAATCAACATCGTGCCGAAAGTTAACTACACTATCTACGATGGT

TTCAACCTGCGTAACACCAACCTGGCTGCTAATTTTAACGGCCAGAACACGGAAATCAACAACATGAAC

TTCACAAAACTGAAAAACTTCACTGGTCTGTTCGAGTTTTACAAGCTGCTGTGCGTCGACGGCATCATT

ACCTCCAAAACTAAATCTGACGATGACGATAAAAACAAAGCGCTGAACCTGCAGTGTATCAAGGTTAAC

AACTGGGATTTATTCTTCAGCCCGAGTGAAGACAACTTCACCAACGACCTGAACAAAGGTGAAGAAATC

ACCTCAGATACTAACATCGAAGCAGCCGAAGAAAACATCTCGCTGGACCTGATCCAGCAGTACTACCTG

ACCTTTAATTTCGACAACGAGCCGGAAAACATTTCTATCGAAAACCTGAGCTCTGATATCATCGGCCAG

CTGGAACTGATGCCGAACATCGAACGTTTCCCAAACGGTAAAAAGTACGAGCTGGACAAATATACCATG

TTCCACTACCTGCGCGCGCAGGAATTTGAACACGGCAAATCCCGTATCGCACTGACTAACTCCGTTAAC

GAAGCTCTGCTCAACCCGTCCCGTGTATACACCTTCTTCTCTAGCGACTACGTGAAAAAGGTCAACAAA

GCGACTGAAGCTGCAATGTTCTTGGGTTGGGTTGAACAGCTTGTTTATGATTTTACCGACGAGACGTCC

GAAGTATCTACTACCGACAAAATTGCGGATATCACTATCATCATCCCGTACATCGGTCCGGCTCTGAAC

ATTGGCAACATGCTGTACAAAGACGACTTCGTTGGCGCACTGATCTTCTCCGGTGCGGTGATCCTGCTG

GAGTTCATCCCGGAAATCGCCATCCCGGTACTGGGCACCTTTGCTCTGGTTTCTTACATTGCAAACAAG
```

-continued

GTTCTGACTGTACAAACCATCGACAACGCGCTGAGCAAACGTAACGAAAAATGGGATGAAGTTTACAAA

TATATCGTGACCAACTGGCTGGCTAAGGTTAATACTCAGATCGACCTCATCCGCAAAAAAATGAAAGAA

GCACTGGAAAACCAGGCGGAAGCTACCAAGGCAATCATTAACTACCAGTACAACCAGTACACCGAGGAA

GAAAAAAACAACATCAACTTCAACATCGACGATCTGTCCTCTAAACTGAACGAATCCATCAACAAAGCT

ATGATCAACATCAACAAGTTCCTGAACCAGTGCTCTGTAAGCTATCTGATGAACTCCATGATCCCGTAC

GGTGTTAAACGTCTGGAGGACTTCGATGCGTCTCTGAAAGACGCCCTGCTGAAATACATTTACGACAAC

CGTGGCACTCTGATCGGTCAGGTTGATCGTCTGAAGGACAAAGTGAACAATACCTTATCGACCGACATC

CCTTTTCAGCTCAGTAAATATGTCGATAACCAACGCCTTTTGTCCACTctagaataatgaaagctt

2. DNA sequence of LH$_N$/B

GGATCCATGCCGGTTACCATCAACAACTTCAACTACAACGACCCGATCGACAACAACAACATCATTATG

ATGGAACCGCCGTTCGCACGTGGTACCGGACGTTACTACAAGGCTTTTAAGATCACCGACCGTATCTGG

ATCATCCCGGAACGTTACACCTTCGGTTACAAACCTGAGGACTTCAACAAGAGTAGCGGGATTTTCAAT

CGTGACGTCTGCGAGTACTATGATCCAGATTATCTGAATACCAACGATAAGAAGAACATATTCCTTCAG

ACTATGATTAAACTCTTCAACCGTATCAAAAGCAAACCGCTCGGTGAAAAACTCCTCGAAATGATTATC

AACGGTATCCCGTACCTCGGTGACCGTCGTGTCCCGCTTGAAGAGTTCAACACCAACATCGCAAGCGTC

ACCGTCAACAAACTCATCAGCAACCCAGGTGAAGTCGAACGTAAAAAAGGTATCTTCGCAAACCTCATC

ATCTTCGGTCCGGGTCCGGTCCTCAACGAAAACGAAACCATCGACATCGGTATCCAGAACCACTTCGCA

AGCCGTGAAGGTTTCGGTGGTATCATGCAGATGAAATTCTGCCCGGAATACGTCAGTGTCTTCAACAAC

GTCCAGGAAAACAAAGGTGCAAGCATCTTCAACCGTCGTGGTTACTTCAGCGACCCGGCACTCATCCTC

ATGCATGAACTCATCCACGTCCTCCACGGTCTCTACGGTATCAAAGTTGACGACCTCCCGATCGTCCCG

AACGAGAAGAAATTCTTCATGCAGAGCACCGACGCAATCCAGGCTGAGGAACTCTACACCTTCGGTGGC

CAAGACCCAAGTATCATAACCCCGTCCACCGACAAAAGCATCTACGACAAAGTCCTCCAGAACTTCAGG

GGTATCGTGGACAGACTCAACAAAGTCCTCGTCTGCATCAGCGACCCGAACATCAATATCAACATATAC

AAGAACAAGTTCAAAGACAAGTACAAATTCGTCGAGGACAGCGAAGGCAAATACAGCATCGACGTAGAA

AGTTTCGACAAGCTCTACAAAAGCCTCATGTTCGGTTTCACCGAAACCAACATCGCCGAGAACTACAAG

ATCAAGACAAGGGCAAGTTACTTCAGCGACAGCCTCCCGCCTGTCAAAATCAAGAACCTCTTAGACAAC

GAGATTTACACAATTGAAGAGGGCTTCAACATCAGTGACAAAGACATGGAGAAGGAATACAGAGGTCAG

AACAAGGCTATCAACAAACAGGCATACGAGGAGATCAGCAAAGAACACCTCGCAGTCTACAAGATCCAG

ATGTGCGTCGACGGCATCATTACCTCCAAAACTAAATCTGACGATGACGATAAAAACAAAGCGCTGAAC

CTGCAGTGCATCGACGTTGACAACGAAGACCTGTTCTTCATCGCTGACAAAAACAGCTTCAGTGACGAC

CTGAGCAAAAACGAACGTATCGAATACAACACCCAGAGCAACTACATCGAAAACGACTTCCCGATCAAC

GAACTGATCCTGGACACCGACCTGATAAGTAAAATCGAACTGCCGAGCGAAAACACCGAAAGTCTGACC

GACTTCAACGTTGACGTTCCGGTTTACGAAAAACAGCCGGCTATCAAGAAAATCTTCACCGACGAAAAC

ACCATCTTCCAGTACCTGTACAGCCAGACCTTCCCGCTGGACATCCGTGACATCAGTCTGACCAGCAGT

TTCGACGACGCTCTGCTGTTCAGCAACAAAGTTTACAGTTTCTTCAGCATGGACTACATCAAAACCGCT

AACAAAGTTGTTGAAGCAGGGCTGTTCGCTGGTTGGGTTAAACAGATCGTTAACGACTTCGTTATCGAA

GCTAACAAAAGCAACACTATGGACAAAATCGCTGACATCAGTCTGATCGTTCCGTACATCGGTCTGGCT

CTGAACGTTGGTAACGAAACCGCTAAAGGTAACTTTGAAAACGCTTTCGAGATCGCTGGTGCAAGCATC

CTGCTGGAGTTCATCCCGGAACTGCTGATCCCGGTTGTTGGTGCTTTCCTGCTGGAAAGTTACATCGAC

AACAAAAACAAGATCATCAAAACCATCGACAACGCTCTGACCAAACGTAACGAAAAATGGAGTGATATG

TACGGTCTGATCGTTGCTCAGTGGCTGAGCACCGTCAACACCCAGTTCTACACCATCAAAGAAGGTATG

-continued

TACAAAGCTCTGAACTACCAGGCTCAGGCTCTGGAAGAGATCATCAAATACCGTTACAACATCTACAGT

GAGAAGGAAAAGAGTAACATCAACATCGACTTCAACGACATCAACAGCAAACTGAACGAAGGTATCAAC

CAGGCTATCGACAACATCAACAACTTCATCAACGGTTGCAGTGTTAGCTACCTGATGAAGAAGATGATC

CCGCTGGCTGTTGAAAAACTGCTGGACTTCGACAACACCCTGAAAAAGAACCTGCTGAACTACATCGAC

GAAAACAAGCTGTACCTGATCGGTAGTGCTGAATACGAAAAAAGTAAAGTGAACAAATACCTGAAGACC

ATCATGCCGTTCGACCTGAGTATCTACACCAACGACACCATCCTGATCGAAATGTTCAACAAATACAAC

TCtctagaataatgaaagctt

3. DNA sequence of LH$_N$/C ggatccATGCCGATCACCATCAACAACTTCAACTACAGCGATCCGGTGGATAACAAAAACATCCTGTAC

CTGGATACCCATCTGAATACCCTGGCGAACGAACCGGAAAAAGCGTTTCGTATCACCGGCAACATTTGG

GTTATTCCGGATCGTTTTAGCCGTAACAGCAACCCGAATCTGAATAAACCGCCGCGTGTTACCAGCCCG

AAAAGCGGTTATTACGATCCGAACTATCTGAGCACCGATAGCGATAAAGATACCTTCCTGAAAGAAATC

ATCAAACTGTTCAAACGCATCAACAGCCGTGAAATTGGCGAAGAACTGATCTATCGCCTGAGCACCGAT

ATTCCGTTTCCGGGCAACAACAACACCCCGATCAACACCTTTGATTTCGATGTGGATTTCAACAGCGTT

GATGTTAAAACCCGCCAGGGTAACAATTGGGTGAAAACCGGCAGCATTAACCCGAGCGTGATTATTACC

GGTCCGCGCGAAAACATTATTGATCCGGAAACCAGCACCTTTAAACTGACCAACAACACCTTTGCGGCG

CAGGAAGGTTTTGGCGCGCTGAGCATTATTAGCATTAGCCCGCGCTTTATGCTGACCTATAGCAACGCG

ACCAACGATGTTGGTGAAGGCCGTTTCAGCAAAAGCGAATTTTGCATGGACCCGATCCTGATCCTGATG

CATGAACTGAACCATGCGATGCATAACCTGTATGGCATCGCGATTCCGAACGATCAGACCATTAGCAGC

GTGACCAGCAACATCTTTTACAGCCAGTACAACGTGAAACTGGAATATGCGGAAATCTATGCGTTTGGC

GGTCCGACCATTGATCTGATTCCGAAAAGCGCGCGCAAATACTTCGAAGAAAAAGCGCTGGATTACTAT

CGCAGCATTGCGAAACGTCTGAACAGCATTACCACCGCGAATCCGAGCAGCTTCAACAAATATATCGGC

GAATATAAACAGAAACTGATCCGCAAATATCGCTTTGTGGTGGAAAGCAGCGGCGAAGTTACCGTTAAC

CGCAATAAATTCGTGGAACTGTACAACGAACTGACCCAGATCTTCACCGAATTTAACTATGCGAAAATC

TATAACGTGCAGAACCGTAAAATCTACCTGAGCAACGTGTATACCCCGGTGACCGCGAATATTCTGGAT

GATAACGTGTACGATATCCAGAACGGCTTTAACATCCCGAAAAGCAACCTGAACGTTCTGTTTATGGGC

CAGAACCTGAGCCGTAATCCGGCGCTGCGTAAAGTGAACCCGGAAAACATGCTGTACCTGTTCACCAAA

TTTTGCGTCGACGCGATTGATGGTCGTAGCCTGTACAACAAAACCCTGCAGTGTCGTGAACTGCTGGTG

AAAAACACCGATCTGCCGTTTATTGGCGATATCAGCGATGTGAAAACCGATATCTTCCTGCGCAAAGAT

ATCAACGAAGAAACCGAAGTGATCTACTACCCGGATAACGTGAGCGTTGATCAGGTGATCCTGAGCAAA

AACACCAGCGAACATGGTCAGCTGGATCTGCTGTATCCGAGCATTGATAGCGAAAGCGAAATTCTGCCG

GGCGAAAACCAGGTGTTTTACGATAACCGTACCCAGAACGTGGATTACCTGAACAGCTATTACTACCTG

GAAAGCCAGAAACTGAGCGATAACGTGGAAGATTTTACCTTTACCCGCAGCATTGAAGAAGCGCTGGAT

AACAGCGCGAAAGTTTACACCTATTTTCCGACCCTGGCGAACAAAGTTAATGCGGGTGTTCAGGGCGGT

CTGTTTCTGATGTGGGCGAACGATGTGGTGGAAGATTTCACCACCAACATCCTGCGTAAAGATACCCTG

GATAAAATCAGCGATGTTAGCGCGATTATTCCGTATATTGGTCCGGCGCTGAACATTAGCAATAGCGTG

CGTCGTGGCAATTTTACCGAAGCGTTTGCGGTTACCGGTGTGACCATTCTGCTGGAAGCGTTTCCGGAA

TTTACCATTCCGGCGCTGGGTGCGTTTGTGATCTATAGCAAAGTGCAGGAACGCAACGAAATCATCAAA

ACCATCGATAACTGCCTGGAACAGCGTATTAAACGCTGGAAAGATAGCTATGAATGGATGATGGGCACC

TGGCTGAGCCGTATTATCACCCAGTTCAACAACATCAGCTACCAGATGTACGATAGCCTGAACTATCAG

GCGGGTGCGATTAAAGCGAAAATCGATCTGGAATACAAAAAATACAGCGGCAGCGATAAAGAAAACATC

-continued

AAAAGCCAGGTTGAAAACCTGAAAAACAGCCTGGATGTGAAAATTAGCGAAGCGATGAATAACATCAAC

AAATTCATCCGCGAATGCAGCGTGACCTACCTGTTCAAAAACATGCTGCCGAAAGTGATCGATGAACTG

AACGAATTTGATCGCAACACCAAAGCGAAACTGATCAACCTGATCGATAGCCACAACATTATTCTGGTG

GGCGAAGTGGATAAACTGAAAGCGAAAGTTAACAACAGCTTCCAGAACACCATCCCGTTTAACATCTTC

AGCTATACCAACAACAGCCTGCTGAAAGATATCATCAACGAATACTTCAAtctagaataatgaaagctt

4. DNA sequence of LH$_N$/D ggatccATGACGTGGCCAGTTAAGGATTTCAACTACTCAGATCCTGTAAATGACAACGATATTCTGTAC

CTTCGCATTCCACAAAATAAACTGATCACCACACCAGTCAAAGCATTCATGATTACTCAAAACATTTGG

GTCATTCCAGAACGCTTTTCTAGTGACACAAATCCGAGTTTATCTAAACCTCCGCGTCCGACGTCCAAA

TATCAGAGCTATTACGATCCCTCATATCTCAGTACGGACGAACAAAAAGATACTTTCCTTAAAGGTATC

ATTAAACTGTTTAAGCGTATTAATGAGCGCGATATCGGGAAAAAGTTGATTAATTATCTTGTTGTGGGT

TCCCCGTTCATGGGCGATAGCTCTACCCCCGAAGACACTTTTGATTTTACCCGTCATACGACAAACATC

GCGGTAGAGAAGTTTGAGAACGGATCGTGGAAAGTCACAAACATCATTACACCTAGCGTCTTAATTTTT

GGTCCGCTGCCAAACATCTTAGATTATACAGCCAGCCTGACTTTGCAGGGGCAACAGTCGAATCCGAGT

TTCGAAGGTTTTGGTACCCTGAGCATTCTGAAAGTTGCCCCGGAATTTCTGCTCACTTTTTCAGATGTC

ACCAGCAACCAGAGCTCAGCAGTATTAGGAAAGTCAATTTTTTGCATGGACCCGGTTATTGCACTGATG

CACGAACTGACGCACTCTCTGCATCAACTGTATGGGATCAACATCCCCAGTGACAAACGTATTCGTCCC

CAGGTGTCTGAAGGATTTTTCTCACAGGATGGGCCGAACGTCCAGTTCGAAGAGTTGTATACTTTCGGA

GGCCTGGACGTAGAGATCATTCCCCAGATTGAGCGCAGTCAGCTGCGTGAGAAGGCATTGGGCCATTAT

AAGGATATTGCAAAACGCCTGAATAACATTAACAAAACGATTCCATCTTCGTGGATCTCGAATATTGAT

AAATATAAGAAAATTTTTAGCGAGAAATATAATTTTGATAAAGATAATACAGGTAACTTTGTGGTTAAC

ATTGACAAATTCAACTCCCTTTACAGTGATTTGACGAATGTAATGAGCGAAGTTGTGTATAGTTCCCAA

TACAACGTTAAGAATCGTACCCATTACTTCTCTCGTCACTACCTGCCGGTTTTCGCGAACATCCTTGAC

GATAATATTTACACTATTCGTGACGGCTTTAACTTGACCAACAAGGGCTTCAATATTGAAAATTCAGGC

CAGAACATTGAACGCAACCCGGCCTTGCAGAAACTGTCGAGTGAATCCGTGGTTGACCTGTTTACCAAA

GTCTGCGTCGACAAAAGCGAAGAGAAGCTGTACGATGACGATGACAAAGATCGTTGGGGATCGTCCCTG

CAGTGTATTAAAGTGAAAAACAATCGGCTGCCTTATGTAGCAGATAAAGATAGCATTAGTCAGGAGATT

TTCGAAAATAAAATTATCACTGACGAAACCAATGTTCAGAATTATTCAGATAAATTTTCACTGGACGAA

AGCATCTTAGATGGCCAAGTTCCGATTAACCCGGAAATTGTTGATCCGTTACTGCCGAACGTGAATATG

GAACCGTTAAACCTCCCTGGCAAGAGATCGTATTTTATGATGACATTACGAAATATGTGGACTACCTT

AATTCTTATTACTATTTGGAAAGCCAGAAACTGTCCAATAACGTGGAAAACATTACTCTGACCACAAGC

GTGGAAGAGGCTTTAGGCTACTCAAATAAGATTTATACCTTCCTCCCGTCGCTGGCGGAAAAAGTAAAT

AAAGGTGTGCAGGCTGGTCTGTTCCTCAACTGGGCGAATGAAGTTGTCGAAGACTTTACCACGAATATT

ATGAAAAAGGATACCCTGGATAAAATCTCCGACGTCTCGGTTATTATCCCATATATTGGCCCTGCGTTA

AATATCGGTAATAGTGCGCTGCGGGGAATTTTAACCAGGCCTTTGCTACCGCGGGCGTCGCGTTCCTC

CTGGAGGGCTTTCCTGAATTTACTATCCCGGCGCTCGGTGTTTTTACATTTTACTCTTCCATCCAGGAG

CGTGAGAAAATTATCAAAACCATCGAAAACTGCCTGGAGCAGCGGGTGAAACGCTGGAAAGATTCTTAT

CAATGGATGGTGTCAAACTGGTTATCTCGCATCACGACCCAATTCAACCATATTAATTACCAGATGTAT

GATAGTCTGTCGTACCAAGCTGACGCCATTAAAGCCAAAATTGATCTGGAATATAAAAGTACTCTGGT

AGCGATAAGGAGAACATCAAAAGCCAGGTGGAGAACCTTAAGAATAGTCTGGATGTGAAAATCTCTGAA

GCTATGAATAACATTAACAAATTCATTCGTGAATGTTCGGTGACGTACCTGTTCAAGAATATGCTGCCA

-continued

AAAGTTATTGATGAACTGAATAAATTTGATCTGCGTACCAAAACCGAACTTATCAACCTCATCGACTCC

CACAACATTATCCTTGTGGGCGAAGTGGATCGTCTGAAGGCCAAAGTAAACGAGAGCTTTGAAAATACG

ATGCCGTTTAATATTTTTTCATATACCAATAACTCCTTGCTGAAAGATATCATCAATGAATATTTCAAT ctagattaataagctt 5. DNA sequence of the CT-CST29 linker
GGATCCGTCGACCTGCAGGGTCTAGAAGGCGGTGGCGGTAGCGGCGGTGGCGGTAGCGGCGGTGGCGGT

AGCGGCGGTGGCGGTAGCGCACTAGTGCAGGAAAGACCTCCATTACAACAACCTCCACATCGCGATAAG

AAACCATGTAAGAATTTCTTTTGGAAAACATTTAGCAGTTGCAAATGATAAAAGCTT

6. DNA sequence of the LHD-CT-CST29 fusion
GGATCCATGACGTGGCCAGTTAAGGATTTCAACTACTCAGATCCTGTAAATGACAACGATATTCTGTAC

CTTCGCATTCCACAAAATAAACTGATCACCACACCAGTCAAAGCATTCATGATTACTCAAAACATTTGG

GTCATTCCAGAACGCTTTTCTAGTGACACAAATCCGAGTTTATCTAAACCTCCGCGTCCGACGTCCAAA

TATCAGAGCTATTACGATCCCTCATATCTCAGTACGGACGAACAAAAAGATACTTTCCTTAAAGGTATC

ATTAAACTGTTTAAGCGTATTAATGAGCGCGATATCGGGAAAAAGTTGATTAATTATCTTGTTGTGGGT

TCCCCGTTCATGGGCGATAGCTCTACCCCCGAAGACACTTTTGATTTTACCCGTCATACGACAAACATC

GCGGTAGAGAAGTTTGAGAACGGATCGTGGAAAGTCACAAACATCATTACACCTAGCGTCTTAATTTTT

GGTCCGCTGCCAAACATCTTAGATTATACAGCCAGCCTGACTTTGCAGGGGCAACAGTCGAATCCGAGT

TTCGAAGGTTTTGGTACCCTGAGCATTCTGAAAGTTGCCCCGGAATTTCTGCTCACTTTTTCAGATGTC

ACCAGCAACCAGAGCTCAGCAGTATTAGGAAAGTCAATTTTTTGCATGGACCCGGTTATTGCACTGATG

CACGAACTGACGCACTCTCTGCATCAACTGTATGGGATCAACATCCCCAGTGACAAACGTATTCGTCCC

CAGGTGTCTGAAGGATTTTTCTCACAGGATGGGCCGAACGTCCAGTTCGAAGAGTTGTATACTTTCGGA

GGCCTGGACGTAGAGATCATTCCCCAGATTGAGCGCAGTCAGCTGCGTGAGAAGGCATTGGGCCATTAT

AAGGATATTGCAAAACGCCTGAATAACATTAACAAAACGATTCCATCTTCGTGGATCTCGAATATTGAT

AAATATAAGAAAATTTTTAGCGAGAAATATAATTTTGATAAAGATAATACAGGTAACTTTGTGGTTAAC

ATTGACAAATTCAACTCCCTTTACAGTGATTTGACGAATGTAATGAGCGAAGTTGTGTATAGTTCCCAA

TACAACGTTAAGAATCGTACCCATTACTTCTCTCGTCACTACCTGCCGGTTTTCGCGAACATCCTTGAC

GATAATATTTACACTATTCGTGACGGCTTTAACTTGACCAACAAGGGCTTCAATATTGAAAATTCAGGC

CAGAACATTGAACGCAACCCGGCCTTGCAGAAACTGTCGAGTGAATCCGTGGTTGACCTGTTTACCAAA

GTCTGCGTCGACAAAAGCGAAGAGAAGCTGTACGATGACGATGACAAAGATCGTTGGGGATCGTCCCTG

CAGTGTATTAAAGTGAAAAACAATCGGCTGCCTTATGTAGCAGATAAAGATAGCATTAGTCAGGAGATT

TTCGAAAATAAAATTATCACTGACGAAACCAATGTTCAGAATTATTCAGATAAATTTTCACTGGACGAA

AGCATCTTAGATGGCCAAGTTCCGATTAACCCGGAAATTGTTGATCCGTTACTGCCGAACGTGAATATG

GAACCGTTAAACCTCCCTGGCGAAGAGATCGTATTTTATGATGACATTACGAAATATGTGGACTACCTT

AATTCTTATTACTATTTGGAAAGCCAGAAACTGTCCAATAACGTGGAAAACATTACTCTGACCACAAGC

GTGGAAGAGGCTTTAGGCTACTCAAATAAGATTTATACCTTCCTCCCGTCGCTGGCGGAAAAAGTAAAT

AAAGGTGTGCAGGCTGGTCTGTTCCTCAACTGGGCGAATGAAGTTGTCGAAGACTTTACCACGAATATT

ATGAAAAAGGATACCCTGGATAAAATCTCCGACGTCTCGGTTATTATCCCATATATTGGCCCTGCGTTA

AATATCGGTAATAGTGCGCTGCGGGGAATTTTAACCAGGCCTTTGCTACCGCGGGCGTCGCGTTCCTC

CTGGAGGGCTTTCCTGAATTTACTATCCCGGCGCTCGGTGTTTTTACATTTTACTCTTCCATCCAGGAG

CGTGAGAAAATTATCAAAACCATCGAAAACTGCCTGGAGCAGCGGGTGAAACGCTGGAAAGATTCTTAT

CAATGGATGGTGTCAAACTGGTTATCTCGCATCACGACCCAATTCAACCATATTAATTACCAGATGTAT

GATAGTCTGTCGTACCAAGCTGACGCCATTAAAGCCAAAATTGATCTGGAATATAAAAAGTACTCTGGT

-continued

AGCGATAAGGAGAACATCAAAAGCCAGGTGGAGAACCTTAAGAATAGTCTGGATGTGAAAATCTCTGAA

GCTATGAATAACATTAACAAATTCATTCGTGAATGTTCGGTGACGTACCTGTTCAAGAATATGCTGCCA

AAAGTTATTGATGAACTGAATAAATTTGATCTGCGTACCAAAACCGAACTTATCAACCTCATCGACTCC

CACAACATTATCCTTGTGGGCGAAGTGGATCGTCTGAAGGCCAAAGTAAACGAGAGCTTTGAAAATACG

ATGCCGTTTAATATTTTTTCATATACCAATAACTCCTTGCTGAAAGATATCATCAATGAATATTTCAAT

CTAGAAGGCGGTGGCGGTAGCGGCGGTGGCGGTAGCGGCGGTGGCGGTAGCGCACTAGTGCAGGAAAGA

CCTCCATTACAACAACCTCCACATCGCGATAAGAAACCATGTAAGAATTTCTTTTGGAAAACATTTAGC

AGTTGCAAAtaataagctt

7. Protein sequence of the LHD-CT-CST-29 fusion
TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDKSEEKLYDDDDKDRWGSSLQCIKVKNNRLPYVADKDSISQEIFEN

KIITDETNVQNYSDKFSLDESILDGQVPINPEIVDPLLPNVMEPLNLPGEEIVFYDDITKYVDYLNSY

YYLESQKLSNNVENITLTTSVEEALGYSNKIYTFLPSLAEKVNKGVQAGLFLNWANEVVEDFTTNIMKK

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALVQERPPL

QQPPHRDKKPCKNFFWKTFSSCK

8. DNA sequence of the CP-EGF linker
ggatccGTCGACaacaacaataacaacaacaataacaacaacgacgatgacgataaaAATTCAGATAGC

GAATGTCCACTTAGTCACGACGGGTACTGTTTGCATGATGGTGTGTGTATGTATATAGAAGCACTAGAC

AAATACGCTTGCAATTGCGTAGTTGGCTATATAGGAGAGCGATGCCAATATAGAGATCTGAAGTGGTGG

GAGTTAAGGGCAgaagcggcagccaaagaagcagccgctaaggcgctgcagagtctagaataataagct t

9. DNA sequence of the LHA-CP-EGF fusion
ggatccATGGAGTTCGTTAACAAACAGTTCAACTATAAAGACCCAGTTAACGGTGTTGACATTGCTTAC

ATCAAAATCCCGAACGCTGGCCAGATGCAGCCGGTAAAGGCATTCAAAATCCACAACAAAATCTGGGTT

ATCCCGGAACGTGATACCTTTACTAACCCGGAAGAAGGTGACCTGAACCCGCCACCGGAAGCGAAACAG

GTGCCGGTATCTTACTATGACTCCACCTACCTGTCTACCGATAACGAAAAGGACAACTACCTGAAAGGT

GTTACTAAACTGTTCGAGCGTATTTACTCCACCGACCTGGGCCGTATGCTGCTGACTAGCATCGTTCGC

GGTATCCCGTTCTGGGGCGGTTCTACCATCGATACCGAACTGAAAGTAATCGACACTAACTGCATCAAC

GTTATTCAGCCGGACGGTTCCTATCGTTCCGAAGAACTGAACCTGGTGATCATCGGCCCGTCTGCTGAT

ATCATCCAGTTCGAGTGTCTGAGCTTTGGTCACGAAGTTCTGAACCTCACCCGTAACGGCTACGGTTCC

ACTCAGTACATCCGTTTCTCTCCGGACTTCACCTTCGGTTTTGAAGAATCCCTGGAAGTAGACACGAAC

CCACTGCTGGGCGCTGGTAAATTCGCAACTGATCCTGCGGTTACCCTGGCTCACGAACTGATTCATGCA

GGCCACCGCCTGTACGGTATCGCCATCAATCCGAACCGTGTCTTCAAAGTTAACACCAACGCGTATTAC

GAGATGTCCGGTCTGGAAGTTAGCTTCGAAGAACTGCGTACTTTTGGCGGTCACGACGCTAAATTCATC

```
GACTCTCTGCAAGAAAACGAGTTCCGTCTGTACTACTATAACAAGTTCAAAGATATCGCATCCACCCTG

AACAAAGCGAAATCCATCGTGGGTACCACTGCTTCTCTCCAGTACATGAAGAACGTTTTTAAAGAAAAA

TACCTGCTCAGCGAAGACACCTCCGGCAAATTCTCTGTAGACAAGTTGAAATTCGATAAACTTTACAAA

ATGCTGACTGAAATTTACACCGAAGACAACTTCGTTAAGTTCTTTAAAGTTCTGAACCGCAAAACCTAT

CTGAACTTCGACAAGGCAGTATTCAAAATCAACATCGTGCCGAAAGTTAACTACACTATCTACGATGGT

TTCAACCTGCGTAACACCAACCTGGCTGCTAATTTTAACGGCCAGAACACGGAAATCAACAACATGAAC

TTCACAAAACTGAAAAACTTCACTGGTCTGTTCGAGTTTTACAAGCTGCTGTGCGTCGAcaacaacaat aacaacaacaataacaacaacgacgatgacgataaaAATTCAGATAGCGAATGTCCACTTAGTCACGAC

GGGTACTGTTTGCATGATGGTGTGTGTATGTATATAGAAGCACTAGACAAATACGCTTGCAATTGCGTA

GTTGGCTATATAGGAGAGCGATGCCAATATAGAGATCTGAAGTGGTGGGAGTTAAGGGCAgaagcggca gccaaagaagcagccgctaaggcgCTGCAGTGTATCAAGGTTAACAACTGGGATTTATTCTTCAGCCCG

AGTGAAGACAACTTCACCAACGACCTGAACAAAGGTGAAGAAATCACCTCAGATACTAACATCGAAGCA

GCCGAAGAAAACATCTCGCTGGACCTGATCCAGCAGTACTACCTGACCTTTAATTTCGACAACGAGCCG

GAAAACATTTCTATCGAAAACCTGAGCTCTGATATCATCGGCCAGCTGGAACTGATGCCGAACATCGAA

CGTTTCCCAAACGGTAAAAAGTACGAGCTGGACAAATATACCATGTTCCACTACCTGCGCGCGCAGGAA

TTTGAACACGGCAAATCCCGTATCGCACTGACTAACTCCGTTAACGAAGCTCTGCTCAACCCGTCCCGT

GTATACACCTTCTTCTCTAGCGACTACGTGAAAAAGGTCAACAAAGCGACTGAAGCTGCAATGTTCTTG

GGTTGGGTTGAACAGCTTGTTTATGATTTTACCGACGAGACGTCCGAAGTATCTACTACCGACAAAATT

GCGGATATCACTATCATCATCCCGTACATCGGTCCGGCTCTGAACATTGGCAACATGCTGTACAAAGAC

GACTTCGTTGGCGCACTGATCTTCTCCGGTGCGGTGATCCTGCTGGAGTTCATCCCGGAAATCGCCATC

CCGGTACTGGGCACCTTTGCTCTGGTTTCTTACATTGCAAACAAGGTTCTGACTGTACAAACCATCGAC

AACGCGCTGAGCAAACGTAACGAAAAATGGGATGAAGTTTACAAATATATCGTGACCAACTGGCTGGCT

AAGGTTAATACTCAGATCGACCTCATCCGCAAAAAAATGAAAGAAGCACTGGAAAACCAGGCGGAAGCT

ACCAAGGCAATCATTAACTACCAGTACAACCAGTACACCGAGGAAGAAAAAAACAACATCAACTTCAAC

ATCGACGATCTGTCCTCTAAACTGAACGAATCCATCAACAAAGCTATGATCAACATCAACAAGTTCCTG

AACCAGTGCTCTGTAAGCTATCTGATGAACTCCATGATCCCGTACGGTGTTAAACGTCTGGAGGACTTC

GATGCGTCTCTGAAAGACGCCCTGCTGAAATACATTTACGACAACCGTGGCACTCTGATCGGTCAGGTT

GATCGTCTGAAGGACAAAGTGAACAATACCTTATCGACCGACATCCCTTTTCAGCTCAGTAAATATGTC

GATAACCAACGCCTTTGTCCACTctagaataatgaaagctt
```

10. Protein sequence of the LHA-CP-EGF fusion

EFVNKQFNYKDPVNGVDIAYIKIPNAGQMQPVKAFKIHNKIWVIPERDTFTNPEEGDLNPPPEAKQVPV

SYYDSTYLSTDNEKDNYLKGVTKLFERIYSTDLGRMLLTSIVRGIPFWGGSTIDTELKVIDTNCINVIQ

PDGSYRSEELNLVIIGPSADIIQFECLSFGHEVLNLTRNGYGSTQYIRFSPDFTFGFEESLEVDTNPLL

GAGKFATDPAVTLAHELIHAGHRLYGIAINPNRVFKVNTNAYYEMSGLEVSFEELRTFGGHDAKFIDSL

QENEFRLYYYNKFKDIASTLNKAKSIVGTTASLQYMKNVFKEKYLLSEDTSGKFSVDKLKFDKLYKMLT

EIYTEDNFVKFFKVLNRKTYLNFDKAVFKINIVPKVNYTIYDGFNLRNTNLAANFNGQNTEINNMNFTK

LKNFTGLFEFYKLLCVDNNNNNNNNNNDDDDKNSDSECPLSHDGYCLHDGVCMYIEALDKYACNCVVGY

IGERCQYRDLKWWELRAEAAAKEAAAKALQCIKVNNWDLFFSPSEDNFTNDLNKGEEITSDTNIEAAEE

NISLDLIQQYYLTFNFDNEPENISIENLSSDIIGQLELMPNIERFPNGKKYELDKYTMFHYLRAQEFEH

GKSRIALTNSVNEALLNPSRVYTFFSSDYVKKVNKATEAAMFLGWVEQLVYDFTDETSEVSTTDKIADI

TIIIPYIGPALNIGNMLYKDDFVGALIFSGAVILLEFIPEIAIPVLGTFALVSYIANKVLTVQTIDNAL

-continued

SKRNEKWDEVYKYIVTNWLAKVNTQIDLIRKKMKEALENQAEATKAIINYQYNQYTEEEKNNINFNIDD
LSSKLNESINKAMININKFLNQCSVSYLMNSMIPYGVKRLEDFDASLKDALLKYIDNRGTLIGQVDRL
KDKVNNTLSTDIPFQLSKYVDNQRLLST

11. Protein sequence of $LH_N/A$
EFVNKQFNYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDTNCINVIQ
PDGSYRSEELNLVIIGPSADIIQFECKSFGHEVLNLTRNGYGSTQYIRFSPDFTFGFEESLEVDTNPLL
GAGKFATDPAVTLAHELIHAGHRLYGIAINPNRVFKVNTNAYYEMSGLEVSFEELRTFGGHDAKFIDSL
QENEFRLYYYNKFKDIASTLNKAKSIVGTTASLQYMKNVFKEKYLLSEDTSGKFSVDKLKFDKLYKMLT
EIYTEDNFVKFFKVLNRKTYLNFDKAVFKINIVPKVNYTIYDGFNLRNTNLAANFNGQNTEINNMNFTK
LKNFTGLFEFYKLLCVDGIITSKTKSDDDDKNKALNLQCIKVNNWDLFFSPSEDNFTNDLNKGEEITSD
TNIEAAEENISLDLIQQYYLTFNFDNEPENISIENLSSDIIGQLELMPNIERFPNGKKYELDKYTMFHY
LRAQEFEHGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINYQYNQYTEEEKN
NINFNIDDLSSKLNESINKAMININKFLNQCSVSYLMNSMIPYGVKRLEDFDASLKDALLKYIDNRGT
LIGQVDRLKDKVNNTLSTDIPFQLSKYVDNQRLLST 12. Protein sequence of $LH_N/B$
PVTINNFNYNDPIDNNNIIMMEPPFARGTGRYYKAFKITDRIWIIPERYTFGYKPEDFNKSSGIFNRDV
CEYYDPDYLNTNDKKNIFLQTMIKLFNRIKSKPLGEKLLEMIINGIPYLGDRRVPLEEFNTNIASVTVN
KLISNPGEVERKKGIFANLIIFGPGPVLNENETIDIGIQNHFASREGFGGIMQMKFCPEYVSVFNNVQE
NKGASIFNRRGYFSDPALILMHELIHVLHGLYGIKVDDLPIVPNEKKFFMQSTDAIQAEELYTFGGQDP
SIITPSTDKSIYDKVLQNFRGIVDRLNKVLVCISDPNININIYKNKFKDKYKFVEDSEGKYSIDVESFD
KLYKSLMFGFTETNIAENYKIKTRASYFSDSLPPVKIKNLLDNEIYTIEEGFNISDKDMEKEYRGQNKA
INKQAYEEISKEHLAVYKIQMCVDEEKLYDDDDKDRWGSSLQCIDVDNEDLFFIADKNSFSDDLSKNER
IEYNTQSNYIENDFPINELILDTDLISKIELPSENTESLTDFNVDVPVYEKQPAIKKIFTDENTIFQYL
YSQTFPLDIRDISLTSSFDDALLFSNKVYSFFSMDYIKTANKVVEAGLFAGWVKQIVNDFVIEANKSNT
MDAIADISLIVPYIGLALNVGNETAKGNFENAFEIAGASILLEFIPELLIPVVGAFLLESYIDNKNKII
KTIDNALTKRNEKWSDMYGLIVAQWLSTVNTQFYTIKEGMYKALNYQAQALEEIIKYRYNIYSEKEKSN
INIDFNDINSKLNEGINQAIDNINNFINGCSVSYLMKKMIPLAVEKLLDFDNTLKKNLLNYIDENKLYL
IGSAEYEKSKVNKYLKTIMPFDLSIYTNDTILIEMFNKYNS 13. Protein sequence of $LH_N/C$
PITINNFNYSDPVDNKNILYLDTHLNTLANEPEKAFRITGNIWVIPDRFSRNSNPNLNKPPRVTSPKSG
YYDPNYLSTDSDKDTFLKEIIKLFKRINSREIGEELIYRLSTDIPFPGNNNTPINTFDFDVDFNSVDVK
TRQGNNWVKTGSINPSVIITGPRENIIDPETSTFKLTNNTFAAQEGFGALSIISISPRFMLTYSNATND
VGEGRFSKSEFCMDPILILMHELNHAMHNLYGIAIPNDQTISSVTSNIFYSQYNVKLEYAEIYAFGGPT
IDLIPKSARKYFEEKALDYYRSIAKRLNSITTANPSSFNKYIGEYKQKLIRKYRFVVESSGEVTVNRNK
FVELYNELTQIFTEFNYAKIYNVQNRKIYLSNVYTPVTANILDDNVYDIQNGFNIPKSNLNVLFMGQNL
SRNPALRKVNPENMLYLFTKFCVDAIDGRSLYNKTLQCRELLVKNTDLPFIGDISDVKTDIFLRKDINE
ETEVIYYPDNVSVDQVILSKNTSEHGQLDLLYPSIDSESEILPGENQVFYDNRTQNVDYLNSYYYLESQ
KLSDNVEDFTFTRSIEEALDNSAKVYTYFPTLANKVNAGVQGGLFLMWANDVVEDFTTNILRKDTLDKI
SDVSAIIPYIGPALNISNSVRRGNFTEAFAVTGVTILLEAFPEFTIPALGAFVIYSKVQERNEIIKTID NCLEQRIKRWKDSYEWMMGTWLSRIITQFNNISYQMYDSLNYQAGAIKAKIDLEYKKYSGSDKENIKSQ
VENLKNSLDVKISEAMNNINKFIRECSVTYLFKNMLPKVIDELNEFDRNTKAKLINLIDSHNIILVGEV
DKLKAKVNNSFQNTIPFNIFSYTNNSLLKDIINEYFN 14. Protein sequence of LH$_N$/D
TWPVKDFNYSDPVNDNDILYLRIPQNKLITTPVKAFMITQNIWVIPERFSSDTNPSLSKPPRPTSKYQS
YYDPSYLSTDEQKDTFLKGIIKLFKRINERDIGKKLINYLVVGSPFMGDSSTPEDTFDFTRHTTNIAVE
KFENGSWKVTNIITPSVLIFGPLPNILDYTASLTLQGQQSNPSFEGFGTLSILKVAPEFLLTFSDVTSN
QSSAVLGKSIFCMDPVIALMHELTHSLHQLYGINIPSDKRIRPQVSEGFFSQDGPNVQFEELYTFGGLD
VEIIPQIERSQLREKALGHYKDIAKRLNNINKTIPSSWISNIDKYKKIFSEKYNFDKDNTGNFVVNIDK
FNSLYSDLTNVMSEVVYSSQYNVKNRTHYFSRHYLPVFANILDDNIYTIRDGFNLTNKGFNIENSGQNI
ERNPALQKLSSESVVDLFTKVCVDKSEEKLYDDDDKDRWGSSLQCIKVKNNRLPYVADKDSISQEIFEN
KIITDETNVQNYSDKFSLDESILDGQVPINPEIVDPLLPNVNMEPLNLPGEEIVFYDDITKYVDYLNSY
YYLESQKLSNNVENITLTTSVEEALGYSNKIYTFLPSLAEKVNKGVQAGLFLNWANEVVEDFTTNIMKK
DTLDKISDVSVIIPYIGPALNIGNSALRGNFNQAFATAGVAFLLEGFPEFTIPALGVFTFYSSIQEREK
IIKTIENCLEQRVKRWKDSYQWMVSNWLSRITTQFNHINYQMYDSLSYQADAIKAKIDLEYKKYSGSDK
ENIKSQVENLKNSLDVKISEAMNNINKFIRECSVTYLFKNMLPKVIDELNKFDLRTKTELINLIDSHNI
ILVGEVDRLKAKVNESFENTMPFNIFSYTNNSLLKDIINEYFN 15. Synthesised GnRH peptide
pGlu-His-Trp-Ser-Tyr-Gly-Cys-Arg-Pro-Gly-NH2

16. Protein sequence of the LHB-CT-SST28 fusion
PVTINNFNYNDPIDNNNIIMMEPPFARGTGRYYKAFKITDRIWIIPERYTFGYKPEDFNKSSGIFNRDV
CEYYDPDYLNTNDKKNIFLQTMIKLFNRIKSKPLGEKLLEMIINGIPYLGDRRVPLEEFNTNIASVTVN
KLISNPGEVERKKGIFANLIIFGPGPVLNENETIDIGIQNHFASREGFGGIMQMKFCPEYVSVFNNVQE
NKGASIFNRRGYFSDPALILMHELIHVLHGLYGIKVDDLPIVPNEKKFFMQSTDAIQAEELYTFGGQDP
SIITPSTDKSIYDKVLQNFRGIVDRLNKVLVCISDPNININIYKNKFKDKYKFVEDSEGKYSIDVESFD
KLYKSLMFGFTETNIAENYKIKTRASYFSDSLPPVKIKNLLDNEIYTIEEGFNISDKDMEKEYRGQNKA
INKQAYEEISKEHLAVYKIQMCVDGIITSKTKSDDDDKNKALNLQCIDVDNEDLFFIADKNSFSDDLSK
NERIEYNTQSNYIENDFPINELILDTDLISKIELPSENTESLTDFNVDVPVYEKQPAIKKIFTDENTIF
QYLYSQTFPLDIRDISLTSSFDDALLFSNKVYSFFSMDYIKTANKVVEAGLFAGWVKQIVNDFVIEANK
SNTMDKIADISLIVPYIGLALNVGNETAKGNFENAFEIAGASILLEFIPELLIPVVGAFLLESYIDNKN
KIIKTIDNALTKRNEKWSDMYGLIVAQWLSTVNTQFYTIKEGMYKALNYQAQALEEIIKYRYNIYSEKE
KSNINIDFNDINSKLNEGINQAIDNINNFINGCSVSYLMKKMIPLAVEKLLDFDNTLKKNLLNYIDENK
LYLIGSAEYEKSKVNKYLKTIMPFDLSIYTNDTILIEMFNKYNSLEGGGGSGGGGSGGGGSALDSANSN
PAMAPRERKAGCKNFFWKTFTSC 17. Protein sequence of the LHA-CP-SST28 fusion
EFVNKQFNYKDPVNGVDIAYI -continued

GGSGGGGSALVLQCIKVNNWDLFFSPSEDNFTNDLNKGEEITSDTNIEAAEENISLDLIQQYYLTFNFD

NEPENISIENLSSDIIGQLELMPNIERFPNGKKYELDKYTMFHYLRAQEFEHGKSRIALTNSVNEALLN

PSRVYTFFSSDYVKKVNKATEAAMFLGWVEQLVYDFTDETSEVSTTDKIADITIIIPYIGPALNIGNML

YKDDFVGALIFSGAVILLEFIPEIAIPVLGTFALVSYIANKVLTVQTIDNALSKRNEKWDEVYKYIVTN

WLAKVNTQIDLIRKKMKEALENQAEATKAIINYQYNQYTEEEKNNINFNIDDLSSKLNESINKAMININ

KFLNQCSVSYLMNSMIPYGVKRLEDFDASLKDALLKYIYDNRGTLIGQVDRLKDKVNNTLSTDIPFQLS

KYVDNQRLLST

18. Protein sequence of the LHD-CT-EGF fusion
TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDKSEEKLYDDDDKDRWGSSLQCIKVKNNRLPYVADKDSISQEIFEN

KIITDETNVQNYSDKFSLDESILDGQVPINPEIVDPLLPNVNMEPLNLPGEEIVFYDDITKYVDYLNSY

YYLESQKLSNNVENITLTTSVEEALGYSNKIYTFLPSLAEKVNKGVQAGLFLNWANEVVEDFTTNIMKK

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALVNSDSEC

PLSHDGYCLHDGVCMYIEALDKYACNCVVGYIGERCQYRDLKWWELR

19. Protein sequence of the LHD-CT-VIP fusion
TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDKSEEKLYDDDDKDRWGSSLQCIKVKNNRLPYVADKDSISQEIFEN

KIITDETNVQNYSDKFSLDESILDGQVPINPEIVDPLLPNVNMEPLNLPGEEIVFYDDITKYVDYLNSY

YYLESQKLSNNVENITLTTSVEEALGYSNKIYTFLPSLAEKVNKGVQAGLFLNWANEVVEDFTTNIMKK

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALVHSDAVF

TDNYTRLRKQMAVKKYLNSILN

20. Protein sequence of the LHC-CT-IGF1 fusion

PITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVK

TRQGNNWVKTGSINPSVIITGPRENIIDPETSTFKLTNNTFAAQEGFGALSIISISPRFMLTYSNATND

VGEGRFSKSEFCMDPILILMHELNHAMHNLYGIAIPNDQTISSVTSNIFYSQYNVKLEYAEIYAFGGPT

-continued

IDLIPKSARKYFEEKALDYYRSIAKRLNSITTANPSSFNKYIGEYKQKLIRKYRFVVESSGEVTVNRNK

FVELYNELTQIFTEFNYAKIYNVQNRKIYLSNVYTPVTANILDDNVYDIQNGFNIPKSNLNVLFMGQNL

SRNPALRKVNPENMLYLFTKFCVDAIDGRSLYNKTLQCRELLVKNTDLPFIGDISDVKTDIFLRKDINE

ETEVIYYPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKI

SDVSAIIPYIGPALNISNSVRRGNFTEAFAVTGVTILLEAFPEFTIPALGAFVIYSKVQERNEIIKTID

NCLEQRIKRWKDSYEWMMGTWLSRIITQFNNISYQMYDSLNYQAGAIKAKIDLEYKKYSGSDKENIKSQ

VENLKNSLDVKISEAMNNINKFIRECSVTYLFKNMLPKVIDELNEFDRNTKAKLINLIDSHNIILVGEV

DKLKAKVNNSFQNTIPFNIFSYTNNSLLKDIINEYFNLEGGGGSGGGGSGGGGSALVGPETLCGAELVD

ALQFVCGDRGFYFNKPTGYGSSSRRAPQTGIVDECCFRSCDLRRLEMYCAPLKPAKSA

21. Protein sequence of the LHD-CT-IGF1 fusion

TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDKSEEKLYDDDDKDRWGSSLQCIKVKNNRLPYVADKDSISQEIFEN

KIITDETNVQNYSDKFSLDESILDGQVPINPEIVDPLLPNVNMEPLNLPGEEIVFYDDITKYVDYLNSY

YYLESQKLSNNVENITLTTSVEEALGYSNKIYTFLPSLAEKVNKGVQAGLFLNWANEVVEDFTTNIMKK

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALVGPETLC

GAELVDALQFVCGDRGFYFNKPTGYGSSSRRAPQTGIVDECCFRSCDLRRLEMYCAPLKPAKSA

22. Protein sequence of the LHC-CT-VIP fusion

PITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVK

TRQGNNWVKTGSINPSVIITGPRENIIDPETSTFKLTNNTFAAQEGFGALSIISISPRFMLTYSNATND

VGEGRFSKSEFCMDPILILMHELNHAMHNLYGIAIPNDQTISSVTSNIFYSQYNVKLEYAEIYAFGGPT

IDLIPKSARKYFEEKALDYYRSIAKRLNSITTANPSSFNKYIGEYKQKLIRKYRFVVESSGEVTVNRNK

FVELYNELTQIFTEFNYAKIYNVQNRKIYLSNVYTPVTANILDDNVYDIQNGFNIPKSNLNVLFMGQNL

SRNPALRKVNPENMLYLFTKFCVDAIDGRSLYNKTLQCRELLVKNTDLPFIGDISDVKTDIFLRKDINE

ETEVIYYPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKI

SDVSAIIPYIGPALNISNSVRRGNFTEAFAVTGVTILLEAFPEFTIPALGAFVIYSKVQERNEIIKTID

NCLEQRIKRWKDSYEWMMGTWLSRIITQFNNISYQMYDSLNYQAGAIKAKIDLEYKKYSGSDKENIKSQ

VENLKNSLDVKISEAMNNINKFIRECSVTYLFKNMLPKVIDELNEFDRNTKAKLINLIDSHNIILVGEV

DKLKAKVNNSFQNTIPFNIFSYTNNSLLKDIINEYFNLEGGGGSGGGGSGGGGSALVHSDAVFTDNYTR

LRKQMAVKKYLNSILN

23. Protein sequence of the LHC-CT-GnRH fusion
PITINNFNYSDPVDNKNILYLDTHLNTLANEPEKAFRITGNIWVIPDRFSRNSNPNLNKPPRVTSPKSG
YYDPNYLSTDSDKDTFLKEIIKLFKRINSREIGEELIYRLSTDIPFPGNNNTPINTFDFDVDFNSVDVK
TRQGNNWVKTGSINPSVIITGPRENIIDPETSTFKLTNNTFAAQEGFGALSIISISPRFMLTYSNATND
VGEGRFSKSEFCMDPILILMHELNHAMHNLYGIAIPNDQTISSVTSNIFYSQYNVKLEYAEIYAFGGPT
IDLIPKSARKYFEEKALDYYRSIAKRLNSITTANPSSFNKYIGEYKQKLIRKYRFVVESSGEVTVNRNK
FVELYNELTQIFTEFNYAKIYNVQNRKIYLSNVYTPVTANILDDNVYDIQNGFNIPKSNLNVLFMGQNL
SRNPALRKVNPENMLYLFTKFCVDAIDGRSLYNKTLQCRELLVKNTDLPFIGDISDVKTDIFLRKDINE
ETEVIYYPDNVSVDQVILSKNTSEHGQLDLLYPSIDSESEILPGENQVFYDNRTQNVDYLNSYYYLESQ
KLSDNVEDFTFTRSIEEALDNSAKVYTYFPTLANKVNAGVQGGLFLMWANDVVEDFTTNILRKDTLDKI
SDVSAIIPYIGPALNISNSVRRGNFTEAFAVTGVTILLEAFPEFTIPALGAFVIYSKVQERNEIIKTID
NCLEQRIKRWKDSYEWMMGTWLSRIITQFNNISYQMYDSLNYQAGAIKAKIDLEYKKYSGSDKENIKSQ
VENLKNSLDVKISEAMNNINKFIRECSVTYLFKNMLPKVIDELNEFDRNTKAKLINLIDSHNIILVGEV
DKLKAKVNNSFQNTIPFNIFSYTNNSLLKDIINEYFNLEGGGGSGGGGSGGGGSALVMKPIQKLLAGLI
LLTWCVEGCSSQHWSYGLRPGGKRDAENLIDSFQEIVKEVGQLAETQRFECTTHQPRSPLRDLKGALES
LIEEETGQKKI 24. Protein sequence of the LHD-CT-GnRH fusion
TWPVKDFNYSDPVNDNDILYLRIPQNKLITTPVKAFMITQNIWVIPERFSSDTNPSLSKPPRPTSKYQS
YYDPSYLSTDEQKDTFLKGIIKLFKRINERDIGKKLINYLVVGSPFMGDSSTPEDTFDFTRHTTNIAVE
KFENGSWKVTNIITPSVLIFGPLPNILDYTASLTLQGQQSNPSFEGFGTLSILKVAPEFLLTFSDVTSN
QSSAVLGKSIFCMDPVIALMHELTHSLHQLYGINIPSDKRIRPQVSEGFFSQDGPNVQFEELYTFGGLD
VEIIPQIERSQLREKALGHYKDIAKRLNNINKTIPSSWISNIDKYKKIFSEKYNFDKDNTGNFVVNIDK
FNSLYSDLTNVMSEVVYSSQYNVKNRTHYFSRHYLPVFANILDDNIYTIRDGFNLTNKGFNIENSGQNI
ERNPALQKLSSESVVDLFTKVCVDKSEEKLYDDDDKDRWGSSLQCIKVKNNRLPYVADKDSISQEIFEN
KIITDETNVQNYSDKFSLDESILDGQVPINPEIVDPLLPNVNMEPLNLPGEEIVFYDDITKYVDYLNSY
YYLESQKLSNNVENITLTTSVEEALGYSNKIYTFLPSLAEKVNKGVQAGLFLNWANEVVEDFTTNIMKK
DTLDKISDVSVIIPYIGPALNIGNSALRGNFNQAFATAGVAFLLEGFPEFTIPALGVFTFYSSIQEREK
IIKTIENCLEQRVKRWKDSYQWMVSNWLSRITTQFNHINYQMYDSLSYQADAIKAKIDLEYKKYSGSDK
ENIKSQVENLKNSLDVKISEAMNNINKFIRECSVTYLFKNMLPKVIDELNKFDLRTKTELINLIDSHNI
ILVGEVDRLKAKVNESFENTMPFNIFSYTNNSLLKDIINEYFNLEGGGGSGGGGSGGGGSGGGGSALVM
KPIQKLLAGLILLTWCVEGCSSQHWSYGLRPGGKRDAENLIDSFQEIVKEVGQLAETQRFECTTHQPRS
PLRDLKGALESLIEEETGQKKI 25. Protein sequence of the LHD-CT-GRP fusion
TWPVKDFNYSDPVNDNDILYLRIPQNKLITTPVKAFMITQNIWVIPERFSSDTNPSLSKPPRPTSKYQS
YYDPSYLSTDEQKDTFLKGIIKLFKRINERDIGKKLINYLVVGSPFMGDSSTPEDTFDFTRHTTNIAVE
KFENGSWKVTNIITPSVLIFGPLPNILDYTASLTLQGQQSNPSFEGFGTLSILKVAPEFLLTFSDVTSN
QSSAVLGKSIFCMDPVIALMHELTHSLHQLYGINIPSDKRIRPQVSEGFFSQDGPNVQFEELYTFGGLD
VEIIPQIERSQLREKALGHYKDIAKRLNNINKTIPSSWISNIDKYKKIFSEKYNFDKDNTGNFVVNIDK
FNSLYSDLTNVMSEVVYSSQYNVKNRTHYFSRHYLPVFANILDDNIYTIRDGFNLTNKGFNIENSGQNI
ERNPALQKLSSESVVDLFTKVCVDKSEEKLYDDDDKDRWGSSLQCIKVKNNRLPYVADKDSISQEIFEN
KIITDETNVQNYSDKFSLDESILDGQVPINPEIVDPLLPNVNMEPLNLPGEEIVFYDDITKYVDYLNSY
YYLESQKLSNNVENITLTTSVEEALGYSNKIYTFLPSLAEKVNKGVQAGLFLNWANEVVEDFTTNIMKK -continued

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALVGNHWAV

GHLM

26. Protein sequence of the LHB-CT-GRP fusion
PVTINNFNYNDPIDNNNIIMMEPPFARGTGRYYKAFKITDRIWIIPERYTFGYKPEDFNKSSGIFNRDV

CEYYDPDYLNTNDKKNIFLQTMIKLFNRIKSKPLGEKLLEMIINGIPYLGDRRVPLEEFNTNIASVTVN

KLISNPGEVERKKGIFANLIIFGPGPVLNENETIDIGIQNHFASREGFGGIMQMKFCPEYVSVFNNVQE

NKGASIFNRRGYFSDPALILMHELIHVLHGLYGIKVDDLPIVPNEKKFFMQSTDAIQAEELYTFGGQDP

SIITPSTDKSIYDKVLQNFRGIVDRLNKVLVCISDPNINNINIYKNKFKDKYKFVEDSEGKYSIDVESFD

KLYKSLMFGFTETNIAENYKIKTRASYFSDSLPPVKIKNLLDNEIYTIEEGFNISDKDMEKEYRGQNKA

INKQAYEEISKEHLAVYKIQMCVDEEKLYDDDDKDRWGSSLQCIDVDNEDLFFIADKNSFSDDLSKNER

IEYNTQSNYIENDFPINELILDTDLISKIELPSENTESLTDFNVDVPVYEKQPAIKKIFTDENTIFQYL

YSQTFPLDIRDISLTSSFDDALLFSNKVYSFFSMDYIKTANKVVEAGLFAGWVKQIVNDFVIEANKSNT

MDAIADISLIVPYIGLALNVGNETAKGNFENAFEIAGASILLEFIPELLIPVVGAFLLESYIDNKNKII

KTIDNALTKRNEKWSDMYGLIVAQWLSTVNTQFYTIKEGMYKALNYQAQALEEIIKYRYNIYSEKEKSN

INIDFNDINSKLNEGINQAIDNINNFINGCSVSYLMKKMIPLAVEKLLDFDNTLKKNLLNYIDENKLYL

IGSAEYEKSKVNKYLKTIMPFDLSIYTNDTILIEMFNKYNSLEGGGGSGGGGSGGGGSALVGNHWAVGH

LM

27. Protein sequence of the LHC-CT-LIF fusion
PITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVK

TRQGNNWVKTGSINPSVIITGPRENIIDPETSTFKLTNNTFAAQEGFGALSIISISPRFMLTYSNATND

VGEGRFSKSEFCMDPILILMHELNHAMHNLYGIAIPNDQTISSVTSNIFYSQYNVKLEYAEIYAFGGPT

IDLIPKSARKYFEEKALDYYRSIAKRLNSITTANPSSFNKYIGEYKQKLIRKYRFVVESSGEVTVNRNK

FVELYNELTQIFTEFNYAKIYNVQNRKIYLSNVYTPVTANILDDNVYDIQNGFNIPKSNLNVLFMGQNL

SRNPALRKVNPENMLYLFTKFCVDAIDGRSLYNKTLQCRELLVKNTDLPFIGDISDVKTDIFLRKDINE

ETEVIYYPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKI

SDVSAIIPYIGPALNISNSVRRGNFTEAFAVTGVTILLEAFPEFTIPALGAFVIYSKVQERNEIIKTID

NCLEQRIKRWKDSYEWMMGTWLSRIITQFNNISYQMYDSLNYQAGAIKAKIDLEYKKYSGSDKENIKSQ

VENLKNSLDVKISEAMNNINKFIRECSVTYLFKNMLPKVIDELNEFDRNTKAKLINLIDSHNIILVGEV

DKLKAKVNNSFQNTIPFNIFSYTNNSLLKDIINEYFNLEGGGGSGGGGSGGGGSALVSPLPITPVNATC

AIRHPCHNNLMNQIRSQLAQLNGSANALFILYYTAQGEPFPNNLDKLCGPNVTDFPPFHANGTEKAKLV

ELYRIVVYLGTSLGNITRDQKILNPSALSHSKLNATADILRGLLSNVLCRLCSKYHVGHVDVTYGPDT

SGKDVFQKKKLGCQLLGKYKQIIAVLAQAF

28. Protein sequence of the LHB-CP-LIF fusion
PVTINNFNYNDPIDNNNIIMMEPPFARGTGRYYKAFKITDRIWIIPERYTFGYKPEDFNKSSGIFNRDV

CEYYDPDYLNTNDKKNIFLQTMIKLFNRIKSKPLGEKLLEMIINGIPYLGDRRVPLEEFNTNIASVTVN

KLISNPGEVERKKGIFANLIIFGPGPVLNENETIDIGIQNHFASREGFGGIMQMKFCPEYVSVFNNVQE

NKGASIFNRRGYFSDPALILMHELIHVLHGLYGIKVDDLPIVPNEKKFFMQSTDAIQAEELYTFGGQDP

SIITPSTDKSIYDKVLQNFRGIVDRLNKVLVCISDPNININIYKNKFKDKYKFVEDSEGKYSIDVESFD
KLYKSLMFGFTETNIAENYKIKTRASYFSDSLPPVKIKNLLDNEIYTIEEGFNISDKDMEKEYRGQNKA
INKQAYEEISKEHLAVYKIQMCVDNNNNNNNNNNDDDDKSPLPITPVNATCAIRHPCHNNLMNQIRSQL
AQLNGSANALFILYYTAQGEPFPNNLDKLCGPNVTDFPPFHANGTEKAKLVELYRIVVYLGTSLGNITR
DQKILNPSALSLHSKLNATADILRGLLSNVLCRLCSKYHVGHVDVTYGPDTSGKDVFQKKKLGCQLLGK
YKQIIAVLAQAFAEAAAKEAAAKALQCIDVDNEDLFFIADKNSFSDDLSKNERIEYNTQSNYIENDFPI
NELILDTDLISKIELPSENTESLTDFNVDVPVYEKQPAIKKIFTDENTIFQYLYSQTFPLDIRDISLTS
SFDDALLFSNKVYSFFSMDYIKTANKVVEAGLFAGWVKQIVNDFVIEANKSNTMDKIADISLIVPYIGL
ALNVGNETAKGNFENAFEIAGASILLEFIPELLIPVVGAFLLESYIDNKNKIIKTIDNALTKRNEKWSD
MYGLIVAQWLSTVNTQFYTIKEGMYKALNYQAQALEEIIKYRYNIYSEKEKSNINIDFNDINSKLNEGI
NQAIDNINNFINGCSVSYLMKKMIPLAVEKLLDFDNTLKKNLLNYIDENKLYLIGSAEYEKSKVNKYLK
TIMPFDLSIYTNDTILIEMFNKYNS

29. Protein sequence of the LHC-CT-FGF1 fusion
PITINNFNYSDPVDNKNILYLDTHLNTLANEPEKAFRITGNIWVIPDRFSRNSNPNLNKPPRVTSPKSG
YYDPNYLSTDSDKDTFLKEIIKLFKRINSREIGEELIYRLSTDIPFFPGNNNTPINTFDFDVDFNSVDVK
TRQGNNWVKTGSINPSVIITGPRENIIDPETSTFKLTNNTFAAQEGFGALSIISISPRFMLTYSNATND
VGEGRFSKSEFCMDPILILMHELNHAMHNLYGIAIPNDQTISSVTSNIFYSQYNVKLEYAEIYAFGGPT
IDLIPKSARKYFEEKALDYYRSIAKRLNSITTANPSSFNKYIGEYKQKLIRKYRFVVESSGEVTVNRNK
FVELYNELTQIFTEFNYAKIYNVQNRKIYLSNVYTPVTANILDDNVYDIQNGFNIPKSNLNVLFMGQNL
SRNPALRKVNPENMLYLFTKFCVDAIDGRSLYNKTLQCRELLVKNTDLPFIGDISDVKTDIFLRKDINE
ETEVIYYPDNVSVDQVILSKNTSEHGQLDLLYPSIDSESEILPGENQVFYDNRTQNVDYLNSYYYLESQ
KLSDNVEDFTFTRSIEEALDNSAKVYTYFPTLANKVNAGVQGGLFLMWANDVVEDFTTNILRKDTLDKI
SDVSAIIPYIGPALNISNSVRRGNFTEAFAVTGVTILLEAFPEFTIPALGAFVIYSKVQERNEIIKTID
NCLEQRIKRWKDSYEWMMGTWLSRIITQFNNISYQMYDSLNYQAGAIKAKIDLEYKKYSGSDKENIKSQ
VENLKNSLDVKISEAMNNINKFIRECSVTYLFKNMLPKVIDELNEFDRNTKAKLINLIDSHNIILVGEV
DKLKAKVNNSFQNTIPFNIFSYTNNSLLKDIINEYFNLEGGGGSGGGGSGGGGSALVMFNLPPGNYKKP
KLLYCSNGGHFLRILPDGTVDGTRDRSDQHIQLQLSAESVGEVYIKSTETGQYLAMDTDGLLYGSQTPN
EECLFLERLEENHYNTYISKKHAEKNWFVGLKKNGSCKRGPRTHYGQKAILFLPLPVSSD 30. Protein sequence of the LHA-CP-FGF1 fus -continued LGTFALVSYIANKVLTVQTIDNALSKRNEKWDEVYKYIVTNWLAKVNTQIDLIRKKMKEALENQAEATK
AIINYQYNQYTEEEKNNINFNIDDLSSKLNESINKAMININKFLNQCSVSYLMNSMIPYGVKRLEDFDA
SLKDALLKYIYDNRGTLIGQVDRLKDKVNNTLSTDIPFQLSKYVDNQRLLST 31. Protein sequence of the LHA-CT-FGF9 fusion
EFVNKQFNYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDTNCINVIQ
PDGSYRSEELNLVIIGPSADIIQFECLSFGHEVLNLTRNGYGSTQYIRFSPDFTFGFEESLEVDTNPLL
GAGKFATDPAVTLAHELIHAGHRLYGIAINPNRVFKVNTNAYYEMSGLEVSFEELRTFGGHDAKFIDSL
QENEFRLYYYNKFKDIASTLNKAKSIVGTTASLQYMKNVFKEKYLLSEDTSGKFSVDKLKFDKLYKMLT
EIYTEDNFVKFFKVLNRKTYLNFDKAVFKINIVPKVNYTIYDGFNLRNTNLAANFNGQNTEINNMNFTK
LKNFTGLFEFYKLLCVDGIITSKTKSDDDDKNKALNLQCIKVNNWDLFFSPSEDNFTNDLNKGEEITSD
TNIEAAEENISLDLIQQYYLTFNFDNEPENISIENLSSDIIGQLELMPNIERFPNGKKYELDKYTMFHY
LRAQEFEHGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINYQYNQYTEEEKN
NINFNIDDLSSKLNESINKAMININKFLNQCSVSYLMNSMIPYGVKRLEDFDASLKDALLKYIYDNRGT
LIGQVDRLKDKVNNTLSTDIPFQLSKYVDNQRLLSTLEGGGGSGGGGSGGGGSGGGGSALVDHLGQSEA
GGLPRGPAVTDLDHLKGILRRRQLYCRTGFHLEIFPNGTIQGTRKDHSRFGILEFISIAVGLVSIRGVD
SGLYLGMNEKGELYGSEKLTQECVFREQFEENWYNTYSSNLYKHVDTGRRYYVALNKDGTPREGTRTKR
HQKFTHFLPRPVDPDKVPELYKDILSQS 32. Protein sequence of the LHC-CP-FGF9 fusion
PITINNFNYSDPVDNKNILYLDTHLNTLANEPEKAFRITGNIWVIPDRFSRNSNPNLNKPPRVTSPKSG
YYDPNYLSTDSDKDTFLKEIIKLFKRINSREIGEELIYRLSTDIPFPGNNNTPINTFDFDVDFNSVDVK
TRQGNNWVKTGSINPSVIITGPRENIIDPETSTFKLTNNTFAAQEGFGALSIISISPRFMLTYSNATND
VGEGRFSKSEFCMDPILILMHELNHAMHNLYGIAIPNDQTISSVTSNIFYSQYNVKLEYAEIYAFGGPT
IDLIPKSARKYFEEKALDYYRSIAKRLNSITTANPSSFNKYIGEYKQKLIRKYRFVVESSGEVTVNRNK
FVELYNELTQIFTEFNYAKIYNVQNRKIYLSNVYTPVTANILDDNVYDIQNGFNIPKSNLNVLFMGQNL
SRNPALRKVNPENMLYLFTKFCVDNNNNNNNNNNDDDKDHLGQSEAGGLPRGPAVTDLDHLKGILRRR
QLYCRTGFHLEIFPNGTIQGTRKDHSRFGILEFISIAVGLVSIRGVDSGLYLGMNEKGELYGSEKLTQE
CVFREQFEENWYNTYSSNLYKHVDTGRRYYVALNKDGTPREGTRTKRHQKFTHFLPRPVDPDKVPELYK
DILSQSAEAAAKEAAAKALQCRELLVKNTDLPFIGDISDVKTDIFLRKDINEETEVIYYPDNVSVDQVI
LSKNTSEHGQLDLLYPSIDSESEILPGENQVFYDNRTQNVDYLNSYYYLESQKLSDNVEDFTFTRSIEE
ALDNSAKVYTYFPTLANKVNAGVQGGLFLMWANDVVEDFTTNILRKDTLDKISDVSAIIPYIGPALNIS
NSVRRGNFTEAFAVTGVTILLEAFPEFTIPALGAFVIYSKVQERNEIIKTIDNCLEQRIKRWKDSYEWM
MGTWLSRIITQFNNISYQMYDSLNYQAGAIKAKIDLEYKKYSGSDKENIKSQVENLKNSLDVKISEAMN
NINKFIRECSVTYLFKNMLPKVIDELNEFDRNTKAKLINLIDSHNIILVGEVDKLKAKVNNSFQNTIPF
NIFSYTNNSLLKDIINEYFN 33. Protein sequence of the IgA-H$_N$tet-CT-SST14 Fusion
ESNQPEKNGTATKPENSGNTTSENGQTEPEKKLELRNVSDIELYSQTNGTYRQHVSLDGIPENTDTYFV
KVKSSAFKDVYIPVASITEEKRNGQSVYKITAKAEKLQQELENKYVDNFTFYLDKKAKEENTNFTSFSN
LVKAINQNPSGTYHLAASLNANEVELGPDERSYIKDTFTGRLIGEKDGKNYAIYNLKKPLFENLSGATV
EKLSLKNVAISGKNDIGSLANEATNGTKIKQVHVDGCVDGIITSKTKSDDDDKNKALNLQCIKIKNEDL -continued TFIAEKNSFSEEPFQDEIVSYNTKNKPLNFNYSLDKIIVDYNLQSKITLPNDRTTPVTKGIPYAPEYKS
NAASTIEIHNIDDNTIYQYLYAQKSPTTLQRITMTNSVDDALINSTKIYSYFPSVISKVNQGAQGILFL
QWVRDIIDDFTNESSQKTTIDKISDVSTIVPYIGPALNIVKQGYEGNFIGALETTGVVLLLEYIPEITL
PVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEF
DTQSKNILMQYIKANSKFIGITELKKLESKINKVFSTPIPFSYSKNLDCWVDNEEDIDVLEGGGGSGGG
GSGGGGSALVAGCKNFFWKTFTSC 34. Protein sequence of the IgA-H$_N$tet-CP-SST14 fusion ESNQPEKNGTATKPENSGNTTSENGQTEPEKKLELRNVSDIELYSQTNGTYRQHVSLDGIPENTDTYFV
KVKSSAFKDVYIPVASITEEKRNGQSVYKITAKAEKLQQELENKYVDNFTFYLDKKAKEENTNFTSFSN
LVKAINQNPSGTYHLAASLNANEVELGPDERSYIKDTFTGRLIGEKDGKNYAIYNLKKPLFENLSGATV
EKLSLKNVAISGKNDIGSLANEATNGTKIKQVHVDGCVDGIITSKTKSDDDDKAGCKNFFWKTFTSCAL
AGGGGSGGGGSGGGGSALALQCIKIKNEDLTFIAEKNSFSEEPFQDEIVSYNTKNKPLNFNYSLDKIIV
DYNLQSKITLPNDRTTPVTKGIPYAPEYKSNAASTIEIHNIDDNTIYQYLYAQKSPTTLQRITMTNSVD
DALINSTKIYSYFPSVISKVNQGAQGILFLQWVRDIIDDFTNESSQKTTIDKISDVSTIVPYIGPALNI
VKQGYEGNFIGALETTGVVLLLEYIPEITLPVIAALSIAESSTQKEKIIKTIDNFLEKRYEKWIEVYKL
VKAKWLGTVNTQFQKRSYQMYRSLEYQVDAIKKIIDYEYKIYSGPDKEQIADEINNLKNKLEEKANKAM
ININIFMRESSRSFLVNQMINEAKKQLLEFDTQSKNILMQYIKANSKFIGITELKKLESKINKVFSTPI
PFSYSKNLDCWVDNEEDIDV 35. Protein sequence of the LHA-CT-SST14 fusion EFVNKQFNYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDTNCINVIQ
PDGSYRSEELNLVIIGPSADIIQFECLSFGHEVLNLTRNGYGSTQYIRFSPDFTFGFEESLEVDTNPLL
GAGKFATDPAVTLAHELIHAGHRLYGIAINPNRVFKVNTNAYYEMSGLEVSFEELRTFGGHDAKFIDSL
QENEFRLYYYNKFKDIASTLNKAKSIVGTTASLQYMKNVFKEKYLLSEDTSGKFSVDKLKFDKLYKMLT
EIYTEDNFVKFFKVLNRKTYLNFDKAVFKINIVPKVNYTIYDGFNLRNTNLAANFNGQNTEINNMNFTK
LKNFTGLFEFYKLLCVDGIITSKTKSDDDDKNKALNLQCIKVNNWDLFFSPSEDNFTNDLNKGEEITSD
TNIEAAEENISLDLIQQYYLTFNFDNEPENISIENLSSDIIGQLELMPNIERFPNGKKYELDKYTMFHY
LRAQEFEHGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINYQYNQYTEEEKN
NINFNIDDLSSKLNESINKAMININKFLNQCSVSYLMNSMIPYGVKRLEDFDASLKDALLKYIYDNRGT
LIGQVDRLKDKVNNTLSTDIPFQLSKYVDNQRLLSTLEGGGGSGGGGSGGGGSALVAGCKNFFWKTFTS
C 36. Protein sequence of the LHA-CT-EGFv3 fusion EFVNKQFNYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDTNCINVIQ
PDGSYRSEELNLVIIGPSADIIQFECLSFGHEVLNLTRNGYGSTQYIRFSPDFTFGFEESLEVDTNPLL
GAGKFATDPAVTLAHELIHAGHRLYGIAINPNRVFKVNTNAYYEMSGLEVSFEELRTFGGHDAKFIDSL
QENEFRLYYYNKFKDIASTLNKAKSIVGTTASLQYMKNVFKEKYLLSEDTSGKFSVDKLKFDKLYKMLT
EIYTEDNFVKFFKVLNRKTYLNFDKAVFKINIVPKVNYTIYDGFNLRNTNLAANFNGQNTEINNMNFTK
LKNFTGLFEFYKLLCVDGIITSKTKSDDDDKNKALNLQCIKVNNWDLFFSPSEDNFTNDLNKGEEITSD -continued

TNIEAAEENISLDLIQQYYLTFNFDNEPENISIENLSSDIIGQLELMPNIERFPNGKKYELDKYTMFHY
LRAQEFEHGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINYQYNQYTEEEKN
NINFNIDDLSSKLNESINKAMININKFLNQCSVSYLMNSMIPYGVKRLEDFDASLKDALLKYIYDNRGT
LIGQVDRLKDKVNNTLSTDIPFQLSKYVDNQRLLSTLEGGGGSGGGGSGGGGSGGGGSALVDNSDPKCP
LSHEGYCLNDGVCMYIGTLDRYACNCVVGYVGERCQYRDLKLAELR

37. Protein sequence of the LHE-CT-IL6 fusion

PKINSFNYNDPVNDRTILYIKPGGCQEFYKSFNIMKNIWIIPERNVIGTTPQDFHPPTSLKNGDSSYYD

PNYLQSDEEKDRFLKIVTKIFNRINNNLSGGILLEELSKANPYLGNDNTPDNQFHIGDASAVEIKFSNG

SQHILLPNVIIMGAEPDLFETNSSNISLRNNYMPSNHGFGSIAIVTFSPEYSFRFNDNSINEFIQDPAL

TLMHELIHSLHGLYGAKGITTTCIITQQQNPLITNRKGINIEEFLTFGGNDLNIITVAQYNDIYTNLLN

DYRKIASKLSKVQVSNPQLNPYKDIFQEKYGLDKDASGIYSVNINKFDDILKKLYSFTEFDLATKFQVK

CRETYIGQYKYFKLSNLLNDSIYNISEGYNINNLKVNFRGQNANLNPRIIKPITGRGLVKKIIRFCVDG

IITSKTKSLIEGRNKALNLQCIEINNGELFFVASENSYNDDNINTPKEIDDTVTSNNNYENDLDQVILN

FNSESAPGLSDEKLNLTIQNDAYIPKYDSNGTSDIEQHDVNELNVFFYLDAQKVPEGENNVNLTSSIDT

ALLEQPKIYTFFSSEFINNVNKPVQAALFVSWIQQVLVDFTTEANQKSTVDKIADISIVVPYIGLALNI

GNEAQKGNFKDALELLGAGILLEFEPELLIPTILVFTIKSFLGSSDNKNKVIKAINNALKERDEKWKEV

YSFIVSNWMTKINTQFNKRKEQMYQALQNQVNAIKTIIESKYNSYTLEEKNELTNKYDIKQIENELNQK

VSIAMNNIDRFLTESSISYLMKIINEVKINKLREYDENVKTYLLNYIIQHGSILGESQQELNSMVTDTL

NNSIPFKLSSYTDDKILISYFNKFFKLEGGGGSGGGGSGGGGSGGGGSALVPPGEDSKDVAAPHRQPLT

SSERIDKQIRYILDGISALRKETCNKSNMCESSKEALAENNLNLPKMAEKDGCFQSGFNEETCLVKIIT

GLLEFEVYLEYLQNRFESSEEQARAVQMSTKVLIQFLQKKAKNLDAITTPDPTTNASLLTKLQAQNQWL

QDMTTHLILRSFKEFLQSSLRALRQM

38. Protein sequence of the LHB-CT-IL8 fusion

PVTINNFNYNDPIDNNNIIMMEPPFARGTGRYYKAFKITDRIWIIPERYTFGYKPEDFNKSSGIFNRDV

CEYYDPDYLNTNDKKNIFLQTMIKLFNRIKSKPLGEKLLEMIINGIPYLGDRRVPLEEFNTNIASVTVN

KLISNPGEVERKKGIFANLIIFGPGPVLNENETIDIGIQNHFASREGFGGIMQMKFCPEYVSVFNNVQE

NKGASIFNRRGYFSDPALILMHELIHVLHGLYGIKVDDLPIVPNEKKFFMQSTDAIQAEELYTFGGQDP

SIITPSTDKSIYDKVLQNFRGIVDRLNKVLVCISDPNININIYKNKFKDKYKFVEDSEGKYSIDVESFD

KLYKSLMFGFTETNIAENYKIKTRASYFSDSLPPVKIKNLLDNEIYTIEEGFNISDKDMEKEYRGQNKA

INKQAYEEISKEHLAVYKIQMCVDGIITSKTKSLIEGRNKALNLQCIDVDNEDLFFIADKNSFSDDLSK

NERIEYNTQSNYIENDFPINELILDTDLISKIELPSENTESLTDFNVDVPVYEKQPAIKKIFTDENTIF

QYLYSQTFPLDIRDISLTSSFDDALLFSNKVYSFFSMDYIKTANKVVEAGLFAGWVKQIVNDFVIEANK

SNTMDKIADISLIVPYIGLALNVGNETAKGNFENAFEIAGASILLEFIPELLIPVVGAFLLESYIDNKN

KIIKTIDNALTKRNEKWSDMYGLIVAQWLSTVNTQFYTIKEGMYKALNYQAQALEEIIKYRYNIYSEKE

KSNINIDFNDINSKLNEGINQAIDNINNFINGCSVSYLMKKMIPLAVEKLLDFDNTLKKNLLNYIDENK

LYLIGSAEYEKSKVNKYLKTIMPFDLSIYTNDTILIEMFNKYNSLEGGGGSGGGGSGGGGSALVAKELR

CQCIKTYSKPFHPKFIKELRVIESGPHCANTEIIVKLSDGRELCLDPKENWVQRVVEKFLKRAENS

39. Protein sequence of the LHF-CP-GRAN4 fusion

PVAINSFNYNDPVNDDTILYMQIPYEEKSKKYYKAFEIMRNVWIIPERNTIGTNPSDFDPPASLKNGSS

AYYDPNYLTTDAEKDRYLKTTIKLFKRINSNPAGKVLLQEISYAKPYLGNDHTPIDEFSPVTRTTSVNI

-continued

KLSTNVESSMLLNLLVLGAGPDIFESCCYPVRKLIDPDVVYDPSNYGFGSINIVTFSPEYEYTFNDISG
GHNSSTESFIADPAISLAHELIHALHGLYGARGVTYEETIEVKQAPLMIAEKPIRLEEFLTFGGQDLNI
ITSAMKEKIYNNLLANYEKIATRLSEVNSAPPEYDINEYKDYFQWKYGLDKNADGSYTVNENKFNEIYK
KLYSFTESDLANKFKVKARNTYFIKYEFLKVPNLLDDDIYTVSEGFNIGNLAVNNRGQSIKLNPKIIDS
IPDKGLVEKIVKFAVENNNNNNNNNNLGCVDGIITSKTKSLIEGRDVKCDMEVSCPDGYTCCRLQSGAW
GCCPFTQAVCCEDHIHCCPAGFTCDTQKGTCEALAGGGGSGGGGSGGGGSALVLQCIEVNNSELFFVAS
ESSYNENDINTPKEIDDTTNLNNNYENNLDEVILDYNSQTIPQISNIENLNTLVQDNSYVPEYDSNGTS
EIEEYDVVDFNVFFYLHAQKVPEGETNISLTSSIDTALLEESKDIFFSSEFIDTINKPVNAALFIDWIS
KVIRDFTTEATQKSTVDKIADISLIVPYVGLALNIIIEAEKGNFEEAFELLGVGILLEFVPELTIPVIL
VFTIKSYIDSYENKNKAIKAINNSLIEREAKWKEIYSWIVSNWLTRINTQFNKRKEQMYQALQNQVDAI
KTAIEYKYNNYTSDEKNRLESEYNINNIEEELNKKVSLAMKNIERFMTESSISYLMKLINEAKVGKLKK

YDNHVKSDLLNYILDHRSILGEQTNELSDLVTSTLNSSIPFELSSYTNDKILIIYFNRLYKT

40. Protein sequence of the LHD-CP-TGFa fusion

TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDGGGGSGGGGSADDDDKVVSHFNDCPDSHTQFCFHGTCRFLVQEDK

PACVCHSGYVGARCEHADLLALAGGGGSGGGGSGGGGSALALQCIKVKNNRLPYVADKDSISQEIFENK

IITDETNVQNYSDKFSLDESILDGQVPINPEIVDPLLPNVNMEPLNLPGEEIVFYDDITKYVDYLNSYY

YLESQKLSNNVENITLTTSVEEALGYSNKIYTFLPSLAEKVNKGVQAGLFLNWANEVVEDFTTNIMKKD

TLDKISDVSVIIPYIGPALNIGNSALRGNFNQAFATAGVAFLLEGFPEFTIPALGVFTFYSSIQEREKI

IKTIENCLEQRVKRWKDSYQWMVSNWLSRITTQFNHINYQMYDSLSYQADAIKAKIDLEYKKYSGSDKE

NIKSQVENLKNSLDVKISEAMNNINKFIRECSVTYLFKNMLPKVIDELNKFDLRTKTELINLIDSHNII

LVGEVDRLKAKVNESFENTMPFNIFSYTNNSLLKDIINEYFN

41. Protein sequence of the LHD-CP-TGFb fusion

TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDGGGGSGGGGSADDDDKALDTNYCFSSTEKNCCVRQLYIDFRKDLG

WKWIHEPKGYHANFCLGPCPYIWSLDTQYSKVLALYNQHNPGASAAPCCVPQALEPLPIVYYVGRKPKV

EQLSNMIVRSCKCSALAGGGGSGGGGSGGGGSALALQCIKVKNNRLPYVADKDSISQEIFENKIITDET

NVQNYSDKFSLDESILDGQVPINPEIVDPLLPNVNMEPLNLPGEEIVFYDDITKYVDYLNSYYYLESQK

LSNNVENITLTTSVEEALGYSNKIYTFLPSLAEKVNKGVQAGLFLNWANEVVEDFTTNIMKKDTLDKIS

DVSVIIPYIGPALNIGNSALRGNFNQAFATAGVAFLLEGFPEFTIPALGVFTFYSSIQEREKIIKTIEN

CLEQRVKRWKDSYQWMVSNWLSRITTQFNHINYQMYDSLSYQADAIKAKIDLEYKKYSGSDKENIKSQV

-continued

ENLKNSLDVKISEAMNNINKFIRECSVTYLFKNMLPKVIDELNKFDLRTKTELINLIDSHNIILVGEVD
RLKAKVNESFENTMPFNIFSYTNNSLLKDIINEYFN

42. Protein sequence of the LHB-CT-TNFa fusion
PVTINNFNYNDPIDNNNIIMMEPPFARGTGRYYKAFKITDRIWIIPERYTFGYKPEDFNKSSGIFNRDV
CEYYDPDYLNTNDKKNIFLQTMIKLFNRIKSKPLGEKLLEMIINGIPYLGDRRVPLEEFNTNIASVTVN
KLISNPGEVERKKGIFANLIIFGPGPVLNENETIDIGIQNHFASREGFGGIMQMKFCPEYVSVFNNVQE

NKGASIFNRRGYFSDPALILMHELIHVLHGLYGIKVDDLPIVPNEKKFFMQSTDAIQAEELYTFGGQDP

SIITPSTDKSIYDKVLQNFRGIVDRLNKVLVCISDPNININIYKNKFKDKYKFVEDSEGKYSIDVESFD

KLYKSLMFGFTETNIAENYKIKTRASYFSDSLPPVKIKNLLDNEIYTIEEGFNISDKDMEKEYRGQNKA

INKQAYEEISKEHLAVYKIQMCVDEEKLYDDDDKDRWGSSLQCIDVDNEDLFFIADKNSFSDDLSKNER

IEYNTQSNYIENDFPINELILDTDLISKIELPSENTESLTDFNVDVPVYEKQPAIKKIFTDENTIFQYL

YSQTFPLDIRDISLTSSFDDALLFSNKVYSFFSMDYIKTANKVVEAGLFAGWVKQIVNDFVIEANKSNT

MDAIADISLIVPYIGLALNVGNETAKGNFENAFEIAGASILLEFIPELLIPVVGAFLLESYIDNKNKII

KTIDNALTKRNEKWSDMYGLIVAQWLSTVNTQFYTIKEGMYKALNYQAQALEEIIKYRYNIYSEKEKSN

INIDFNDINSKLNEGINQAIDNINNFINGCSVSYLMKKMIPLAVEKLLDFDNTLKKNLLNYIDENKLYL

IGSAEYEKSKVNKYLKTIMPFDLSIYTNDTILIEMFNKYNSLEGGGGSGGGGSGGGGSALVRSSSRTPS

DKPVAHVVANPQAEGQLQWLNRRANALLANGVELRDNQLVVPSEGLYLIYSQVLFKGQGCPSTHVLLTH

TISRIAVSYQTKVNLLSAIKSPCQRETPEGAEAKPWYEPIYLGGVFQLEKGDRLSAEINRPDYLDFAES

GQVYFGIIAL

43. Protein sequence of the LHD-CT-SDF1 fusion
TWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVE

KFENGSWKVTNIITPSVLIFGPLPNILDYTASLTLQGQQSNPSFEGFGTLSILKVAPEFLLTFSDVTSN

QSSAVLGKSIFCMDPVIALMHELTHSLHQLYGINIPSDKRIRPQVSEGFFSQDGPNVQFEELYTFGGLD

VEIIPQIERSQLREKALGHYKDIAKRLNNINKTIPSSWISNIDKYKKIFSEKYNFDKDNTGNFVVNIDK

FNSLYSDLTNVMSEVVYSSQYNVKNRTHYFSRHYLPVFANILDDNIYTIRDGFNLTNKGFNIENSGQNI

ERNPALQKLSSESVVDLFTKVCVDKSEEKLYDDDDKDRWGSSLQCIKVKNNRLPYVADKDSISQEIFEN

KIITDETNVQNYSDKFSLDESILDGQVPINPEIVDPLLPNVNMEPLNLPGEEIVFYDDITKYVDYLNSY

YYLESQKLSNNVENITLTTSVEEALGYSNKIYTFLPSLAEKVNKGVQAGLFLNWANEVVEDFTTNIMKK

DTLDKISDVSVIIPYIGPALNIGNSALRGNFNQAFATAGVAFLLEGFPEFTIPALGVFTFYSSIQEREK

IIKTIENCLEQRVKRWKDSYQWMVSNWLSRITTQFNHINYQMYDSLSYQADAIKAKIDLEYKKYSGSDK

ENIKSQVENLKNSLDVKISEAMNNINKFIRECSVTYLFKNMLPKVIDELNKFDLRTKTELINLIDSHNI

ILVGEVDRLKAKVNESFENTMPFNIFSYTNNSLLKDIINEYFNLEGGGGSGGGGSGGGGSALKPVSLSY

RCPCRFFESHVARANVKHLKILNTPNCALQIVARLKNNNRQVCIDPKLKWIQEYLEKALNKRFKM

44. Protein sequence of the LHC-CT-VEGF fusion
PITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVK

TRQGNNWVKTGSINPSVIITGPRENIIDPETSTFKLTNNTFAAQEGFGALSIISISPRFMLTYSNATND

VGEGRFSKSEFCMDPILILMHELNHAMHNLYGIAIPNDQTISSVTSNIFYSQYNVKLEYAEIYAFGGPT

IDLIPKSARKYFEEKALDYYRSIAKRLNSITTANPSSFNKYIGEYKQKLIRKYRFVVESSGEVTVNRNK

FVELYNELTQIFTEFNYAKIYNVQNRKIYLSNVYTPVTANILDDNVYDIQNGFNIPKSNLNVLFMGQNL

SRNPALRKVNPENMLYLFTKFCVDAIDGRSLYNKTLQCRELLVKNTDLPFIGDISDVKTDIFLRKDINE

-continued

ETEVIYYPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKI

SDVSAIIPYIGPALNISNSVRRGNFTEAFAVTGVTILLEAFPEFTIPALGAFVIYSKVQERNEIIKTID

NCLEQRIKRWKDSYEWMMGTWLSRIITQFNNISYQMYDSLNYQAGAIKAKIDLEYKKYSGSDKENIKSQ

VENLKNSLDVKISEAMNNINKFIRECSVTYLFKNMLPKVIDELNEFDRNTKAKLINLIDSHNIILVGEV

DKLKAKVNNSFQNTIPFNIFSYTNNSLLKDIINEYFNLEGGGGSGGGGSGGGGSALAPMAEGGGQNHHE

VVKFMDVYQRSYCHPIETLVDIFQEYPDEIEYIFKPSCVPLMRCGGCCNDEGLECVPTEESNITMQIMR

IKPHQGQHIGEMSFLQHNKCECRPKKDRARQEKKSVRGKGKGQKRKRKKSRYKSWSVYVGARCCLMPWS

LPGPHPCGPCSERRKHLFVQDPQTCKCSCKNTDSRCKARQLELNERTCRCDKPRR

---

SEQUENCE LISTING

<160> NUMBER OF SEQ ID NOS: 177

<210> SEQ ID NO 1
<211> LENGTH: 2619
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

```
ggatccatgg agttcgttaa caaacagttc aactataaag acccagttaa cggtgttgac        60
attgcttaca tcaaaatccc gaacgctggc cagatgcagc cggtaaaggc attcaaaatc       120
cacaacaaaa tctgggttat cccggaacgt gataccttta ctaacccgga agaaggtgac       180
ctgaacccgc caccggaagc gaaacaggtg ccggtatctt actatgactc cacctacctg       240
tctaccgata cgaaaagga caactacctg aaaggtgtta ctaaactgtt cgagcgtatt       300
tactccaccg acctgggccg tatgctgctg actagcatcg ttcgcggtat cccgttctgg       360
ggcggttcta ccatcgatac cgaactgaaa gtaatcgaca ctaactgcat caacgttatt       420
cagccggacg gttcctatcg ttccgaagaa ctgaacctgg tgatcatcgg cccgtctgct       480
gatatcatcc agttcgagtg tctgagcttt ggtcacgaag ttctgaacct cacccgtaac       540
ggctacggtt ccactcagta catccgtttc tctccggact tcaccttcgg ttttgaagaa       600
tccctggaag tagacacgaa cccactgctg ggcgctggta attcgcaac tgatcctgcg       660 gttaccctgg ctcacgaact gattcatgca ggccaccgcc tgtacggtat cgccatcaat       720
ccgaaccgtg tcttcaaagt taacaccaac gcgtattacg agatgtccgg tctggaagtt       780
agcttcgaag aactgcgtac ttttggcggt cacgacgcta aattcatcga ctctctgcaa       840
gaaaacgagt ccgtctgta ctactataac aagttcaaag atatcgcatc caccctgaac       900
aaagcgaaat ccatcgtggg taccactgct tctctccagt acatgaagaa cgttttttaaa       960 gaaaaatacc tgctcagcga agacacctcc ggcaaattct ctgtagacaa gttgaaattc      1020
gataaacttt acaaaatgct gactgaaatt tacaccgaag acaacttcgt taagttcttt      1080
aaagttctga accgcaaaac ctatctgaac ttcgacaagg cagtattcaa atcaacatc      1140 gtgccgaaag ttaactacac tatctacgat ggtttcaacc tgcgtaacac caacctggct      1200 gctaattta acggcagaa cacggaaatc aacaacatga acttcacaaa actgaaaac      1260 ttcactggtc tgttcgagtt ttacaagctg ctgtgcgtcg acggcatcat tacctccaaa      1320
```

```
actaaatctg acgatgacga taaaaacaaa gcgctgaacc tgcagtgtat caaggttaac    1380
aactgggatt tattcttcag cccgagtgaa gacaacttca ccaacgacct gaacaaaggt    1440
gaagaaatca cctcagatac taacatcgaa gcagccgaag aaaacatctc gctggacctg    1500
atccagcagt actacctgac ctttaatttc gacaacgagc cggaaaacat ttctatcgaa    1560
aacctgagct ctgatatcat cggccagctg gaactgatgc cgaacatcga acgtttccca    1620
aacggtaaaa agtacgagct ggacaaatat accatgttcc actacctgcg cgcgcaggaa    1680
tttgaacacg gcaaatcccg tatcgcactg actaactccg ttaacgaagc tctgctcaac    1740
ccgtcccgtg tatacacctt cttctctagc gactacgtga aaaaggtcaa caaagcgact    1800
gaagctgcaa tgttcttggg ttgggttgaa cagcttgttt atgattttac cgacgagacg    1860
tccgaagtat ctactaccga caaaattgcg gatatcacta tcatcatccc gtacatcggt    1920
ccggctctga acattggcaa catgctgtac aaagacgact tcgttggcgc actgatcttc    1980
tccggtgcgg tgatcctgct ggagttcatc ccggaaatcg ccatcccggt actgggcacc    2040
tttgctctgg tttcttacat tgcaaacaag gttctgactg tacaaaccat cgacaacgcg    2100
ctgagcaaac gtaacgaaaa atgggatgaa gtttacaaat atatcgtgac caactggctg    2160
gctaaggtta atactcagat cgacctcatc cgcaaaaaaa tgaagaagc actggaaaac    2220 caggcggaag ctaccaaggc aatcattaac taccagtaca accagtacac cgaggaagaa    2280
aaaaacaaca tcaacttcaa catcgacgat ctgtcctcta aactgaacga atccatcaac    2340
aaagctatga tcaacatcaa caagttcctg aaccagtgct ctgtaagcta tctgatgaac    2400
tccatgatcc cgtacggtgt taaacgtctg gaggacttcg atgcgtctct gaaagacgcc    2460
ctgctgaaat acatttacga caaccgtggc actctgatcg gtcaggttga tcgtctgaag    2520
gacaaagtga acaataccct tatcgaccga catcccttttc agctcagtaa atatgtcgat    2580
aaccaacgcc ttttgtccac tctagaataa tgaaagctt                           2619
```

<210> SEQ ID NO 2
<211> LENGTH: 2643
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

```
ggatccatgc cggttaccat caacaacttc aactacaacg acccgatcga caacaacaac     60
atcattatga tggaaccgcc gttcgcacgt ggtaccggac gttactacaa ggcttttaag    120
atcaccgacc gtatctggat catcccggaa cgttacacct tcggttacaa acctgaggac    180
ttcaacaaga gtagcgggat tttcaatcgt gacgtctgcg agtactatga tccagattat    240
ctgaatacca acgataagaa gaacatattc cttcagacta tgattaaact cttcaaccgt    300
atcaaaagca aaccgctcgg tgaaaaactc ctcgaaatga ttatcaacgg tatcccgtac    360
ctcggtgacc gtcgtgtccc gcttgaagag ttcaacacca acatcgcaag cgtcaccgtc    420
aacaaactca tcagcaaccc aggtgaagtc gaacgtaaaa aaggtatctt cgcaaacctc    480
atcatcttcg gtccgggtcc ggtcctcaac gaaaacgaaa ccatcgacat cggtatccag    540
aaccacttcg caagccgtga aggtttcggt ggtatcatgc agatgaaatt ctgcccggaa    600
tacgtcagtg tcttcaacaa cgtccaggaa aacaaaggt caagcatctt caaccgtcgt    660
```

```
ggttacttca gcgacccggc actcatcctc atgcatgaac tcatccacgt cctccacggt    720
ctctacggta tcaaagttga cgacctcccg atcgtcccga acgagaagaa attcttcatg    780
cagagcaccg acgcaatcca ggctgaggaa ctctacacct tcggtggcca agacccaagt    840
atcataaccc cgtccaccga caaaagcatc tacgacaaag tcctccagaa cttcaggggt    900
atcgtggaca gactcaacaa agtcctcgtc tgcatcagcg acccgaacat caatatcaac    960
atatacaaga caagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag acaagggcaa gttacttcag cgacagcctc    1140
ccgcctgtca aaatcaagaa cctcttagac aacgagattt acacaattga gagggcttc    1200 aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gacggcatca ttacctccaa aactaaatct gacgatgacg ataaaaacaa agcgctgaac    1380
ctgcagtgca tcgacgttga caacgaagac ctgttcttca tcgctgacaa aaacagcttc    1440
agtgacgacc tgagcaaaaa cgaacgtatc gaatacaaca cccagagcaa ctacatcgaa    1500
aacgacttcc cgatcaacga actgatcctg acaccgacc tgataagtaa aatcgaactg    1560
ccgagcgaaa acaccgaaag tctgaccgac ttcaacgttg acgttccggt ttacgaaaaa    1620
cagccggcta tcaagaaaat cttcaccgac gaaaacacca tcttccagta cctgtacagc    1680
cagaccttcc cgctggacat ccgtgacatc agtctgacca gcagtttcga cgacgctctg    1740
ctgttcagca acaaagttta cagtttcttc agcatggact acatcaaaac cgctaacaaa    1800
gttgttgaag cagggctgtt cgctggttgg gttaaacaga tcgttaacga cttcgttatc    1860
gaagctaaca aaagcaacac tatggacaaa atcgctgaca tcagtctgat cgttccgtac    1920
atcggtctgg ctctgaacgt tggtaacgaa accgctaaag gtaactttga aaacgctttc    1980
gagatcgctg gtgcaagcat cctgctggag ttcatcccgg aactgctgat cccggttgtt    2040
ggtgctttcc tgctggaaag ttacatcgac aacaaaaaca agatcatcaa aaccatcgac    2100
aacgctctga ccaaacgtaa cgaaaaatgg agtgatatgt acggtctgat cgttgctcag    2160
tggctgagca ccgtcaacac ccagttctac accatcaaag aaggtatgta caagctctg    2220 aactaccagg ctcaggctct ggaagagatc atcaaatacc gttacaacat ctacagtgag    2280
aaggaaaaga gtaacatcaa catcgacttc aacgacatca acagcaaact gaacgaaggt    2340
atcaaccagg ctatcgacaa catcaacaac ttcatcaacg gttgcagtgt tagctacctg    2400
atgaagaaga tgatcccgct ggctgttgaa aaactgctgg acttcgacaa caccctgaaa    2460
aagaacctgc tgaactacat cgacgaaaac aagctgtacc tgatcggtag tgctgaatac    2520 gaaaaagta aagtgaacaa atacctgaag accatcatgc cgttcgacct gagtatctac    2580
accaacgaca ccatcctgat cgaaatgttc aacaaataca actctctaga ataatgaaag    2640
ctt                                                                  2643
```

<210> SEQ ID NO 3
<211> LENGTH: 2622
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3

```
ggatccatgc cgatcaccat caacaacttc aactacagcg atccggtgga taacaaaaac    60
atcctgtacc tggatcccca tctgaatacc ctggcgaacg aaccggaaaa agcgtttcgt   120
atcaccggca acatttgggt tattccggat cgttttagcc gtaacagcaa cccgaatctg   180
aataaaccgc gcgtgttaca cagcccgaaa agcggttatt acgatccgaa ctatctgagc   240
accgatagcg ataaagatac cttcctgaaa gaaatcatca aactgttcaa acgcatcaac   300
agccgtgaaa ttggcgaaga actgatctat cgcctgagca ccgatattcc gtttccgggc   360
aacaacaaca ccccgatcaa cacctttgat tcgatgtgg atttcaacag cgttgatgtt    420 aaacccgcc agggtaacaa ttgggtgaaa accggcagca ttaacccgag cgtgattatt    480
accggtccgc gcgaaaacat tattgatccg gaaaccagca cctttaaact gaccaacaac   540
acctttgcgg cgcaggaagg ttttggcgcg ctgagcatta ttagcattag cccgcgcttt   600
atgctgacct atagcaacgc gaccaacgat gttggtgaag ccgtttcag caaaagcgaa    660 ttttgcatgg acccgatcct gatcctgatg catgaactga accatgcgat gcataacctg   720
tatggcatcg cgattccgaa cgatcagacc attagcagcg tgaccagcaa catctttttac  780 agccagtaca acgtgaaact ggaatatgcg gaaatctatg cgtttggcgg tccgaccatt   840
gatctgattc cgaaaagcgc gcgcaaatac ttcgaagaaa agcgctgga ttactatcgc    900 agcattgcga acgtctgaa cagcattacc accgcgaatc cgagcagctt caacaaatat    960
atcggcgaat ataaacagaa actgatccgc aaatatcgct tgtggtgga aagcagcggc   1020 gaagttaccg ttaaccgcaa taaattcgtg gaactgtaca acgaactgac ccagatcttc   1080
accgaattta actatgcgaa atctataac gtgcagaacc gtaaaatcta cctgagcaac    1140
gtgtataccc cggtgaccgc gaatattctg gatgataacg tgtacgatat ccagaacggc   1200
tttaacatcc cgaaaagcaa cctgaacgtt ctgtttatgg ccagaaccct gagccgtaat   1260
ccggcgctgc gtaaagtgaa cccggaaaac atgctgtacc tgttcaccaa attttgcgtc   1320
gacgcgattg atggtcgtag cctgtacaac aaaaaccctgc agtgtcgtga actgctggtg   1380
aaaaacaccg atctgccgtt tattggcgat atcagcgatg tgaaaaccga tatcttcctg   1440
cgcaaagata tcaacgaaga aaccgaagtg atctactacc cggataacgt gagcgttgat   1500
caggtgatcc tgagcaaaaa caccagcgaa catggtcagc tggatctgct gtatccgagc   1560
attgatagcg aaagcgaaat tctgccgggc gaaaaccagg tgttttacga taaccgtacc   1620
cagaacgtgg attacctgaa cagctattac tacctggaaa gccagaaact gagcgataac   1680
gtggaagatt ttacctttac ccgcagcatt gaagaagcgc tggataacag cgcgaaagtt   1740
tacacctatt ttccgaccct ggcgaacaaa gttaatgcgg tgttcagggg cggtctgttt   1800
ctgatgtggg cgaacgatgt ggtggaagat ttcaccacca catcctgcg taaagatacc    1860 ctggataaaa tcagcgatgt tagcgcgatt attccgtata ttggtccggc gctgaacatt   1920
agcaatagcg tgcgtcgtgg caatttttacc gaagcgtttg cggttaccgg tgtgaccatt   1980
ctgctggaag cgtttccgga atttaccatt ccggcgctgg tgcgtttgt gatctatagc    2040 aaagtgcagg aacgcaacga aatcatcaaa accatcgata actgcctgga acagcgtatt   2100
aaacgctgga agatagcta tgaatggatg atgggcacct ggctgagccg tattatcacc    2160
cagttcaaca catcagcta ccagatgtac gatagcctga actatcaggc gggtgcgatt   2220
aaagcgaaaa tcgatctgga atacaaaaaa tacagcggca cgataaagaa aaacatcaaa   2280
agccaggttg aaaacctgaa aaacagcctg gatgtgaaaa ttagcgaagc gatgaataac   2340
```

| | | |
|---|---|---|
| atcaacaaat tcatccgcga atgcagcgtg acctacctgt caaaaacat gctgccgaaa | 2400 |
| gtgatcgatg aactgaacga atttgatcgc aacaccaaag cgaaactgat caacctgatc | 2460 |
| gatagccaca acattattct ggtgggcgaa gtggataaac tgaaagcgaa agttaacaac | 2520 |
| agcttccaga acaccatccc gtttaacatc ttcagctata ccaacaacag cctgctgaaa | 2580 |
| gatatcatca acgaatactt caatctagaa taatgaaagc tt | 2622 |

```
<210> SEQ ID NO 4
<211> LENGTH: 2638
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
```

| | |
|---|---|
| ggatccatga cgtggccagt taaggatttc aactactcag atcctgtaaa tgacaacgat | 60 |
| attctgtacc ttcgcattcc acaaaataaa ctgatcacca caccagtcaa agcattcatg | 120 |
| attactcaaa acatttgggt cattccagaa cgcttttcta gtgacacaaa tccgagttta | 180 |
| tctaaacctc cgcgtccgac gtccaaatat cagagctatt acgatccctc atatctcagt | 240 |
| acggacgaac aaaaagatac tttccttaaa ggtatcatta aactgtttaa gcgtattaat | 300 |
| gagcgcgata tcgggaaaaa gttgattaat tatcttgttg tgggttcccc gttcatgggc | 360 |
| gatagctcta cccccgaaga cactttgat tttacccgtc atacgacaaa catcgcggta | 420 |
| gagaagtttg agaacggatc gtggaaagtc acaaacatca ttacacctag cgtcttaatt | 480 |
| tttggtccgc tgccaaacat cttagattat acagccagcc tgactttgca ggggcaacag | 540 |
| tcgaatccga gtttcgaagg ttttggtacc ctgagcattg tgaaagttgc cccggaattt | 600 |
| ctgctcactt tttcagatgt caccagcaac cagagctcag cagtattagg aaagtcaatt | 660 |
| ttttgcatgg acccggttat tgcactgatg cacgaactga cgcactctct gcatcaactg | 720 |
| tatgggatca acatccccag tgacaaacgt attcgtcccc aggtgtctga aggattttc | 780 |
| tcacaggatg gccgaacgt ccagttcgaa gagttgtata ctttcggagg cctggacgta | 840 |
| gagatcattc cccagattga gcgcagtcag ctgcgtgaga aggcattggg ccattataag | 900 |
| gatattgcaa aacgcctgaa taacattaac aaaacgattc catcttcgtg gatctcgaat | 960 |
| attgataaat ataagaaaat ttttagcgag aaatataatt ttgataaaga taatacaggt | 1020 |
| aactttgtgg ttaacattga caaattcaac tcccttttaca gtgatttgac gaatgtaatg | 1080 |
| agcgaagttg tgtatagttc ccaatacaac gttaagaatc gtacccatta cttctctcgt | 1140 |
| cactacctgc cggttttcgc gaacatcctt gacgataata tttacactat tcgtgacggc | 1200 |
| tttaacttga ccaacaaggg cttcaatatt gaaaattcag gccagaacat tgaacgcaac | 1260 |
| ccggccttgc agaaactgtc gagtgaatcc gtggttgacc tgtttaccaa agtctgcgtc | 1320 |
| gacaaaagcg aagagaagct gtacgatgac gatgacaaag atcgttgggg atcgtccctg | 1380 |
| cagtgtatta aagtgaaaaa caatcggctg ccttatgtag cagataaaga tagcattagt | 1440 |
| caggagattt tcgaaaataa aattatcact gacgaaacca atgttcagaa ttattcagat | 1500 |
| aaattttcac tggacgaaag catcttagat ggccaagttc cgattaaccc ggaaattgtt | 1560 |
| gatccgttac tgccgaacgt gaatatggaa ccgttaaacc tccctggcga agatcgta | 1620 |
| ttttatgatg acattacgaa atatgtggac taccttaatt cttattacta tttggaaagc | 1680 |
| cagaaactgt ccaataacgt ggaaaacatt actctgacca caagcgtgga agaggcttta | 1740 |

```
ggctactcaa ataagattta taccttcctc ccgtcgctgg cggaaaaagt aaataaaggt   1800
gtgcaggctg gtctgttcct caactgggcg aatgaagttg tcgaagactt taccacgaat   1860
attatgaaaa aggatacccct ggataaaatc tccgacgtct cggttattat cccatatatt   1920
ggccctgcgt taaatatcgg taatagtgcg ctgcggggga atttaaccca ggcctttgct   1980
accgcgggcg tcgcgttcct cctggagggc tttcctgaat ttactatccc ggcgctcggt   2040 gttttacat tttactcttc catccaggag cgtgagaaaa ttatcaaaac catcgaaaac   2100
tgcctggagc agcgggtgaa acgctggaaa gattcttatc aatggatggt gtcaaactgg   2160
ttatctcgca tcacgaccca attcaaccat attaattacc agatgtatga tagtctgtcg   2220
taccaagctg acgccattaa agccaaaatt gatctggaat ataaaaagta ctctggtagc   2280
gataaggaga acatcaaaag ccaggtggag aaccttaaga atagtctgga tgtgaaaatc   2340
tctgaagcta tgaataacat taacaaattc attcgtgaat gttcggtgac gtacctgttc   2400
aagaatatgc tgccaaaagt tattgatgaa ctgaataaat ttgatctgcg taccaaaacc   2460
gaacttatca acctcatcga ctcccacaac attatccttg tgggcgaagt ggatcgtctg   2520
aaggccaaag taaacgagag cttttgaaaat acgatgccgt ttaatatttt ttcatatacc   2580
aataactcct tgctgaaaga tatcatcaat gaatatttca atctagatta ataagctt     2638

<210> SEQ ID NO 5
<211> LENGTH: 195
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
ggatccgtcg acctgcaggg tctagaaggc ggtggcggta gcggcggtgg cggtagcggc     60
ggtggcggta gcggcggtgg cggtagcgca ctagtgcagg aaagacctcc attacaacaa    120
cctccacatc gcgataagaa accatgtaag aatttctttt ggaaaacatt tagcagttgc    180
aaatgataaa agctt                                                    195

<210> SEQ ID NO 6
<211> LENGTH: 2779
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
ggatccatga cgtggccagt taaggatttc aactactcag atcctgtaaa tgacaacgat     60
attctgtacc ttcgcattcc acaaaataaa ctgatcacca ccagtcaa agcattcatg      120 attactcaaa acatttgggt cattccagaa cgcttttcta gtgacacaaa tccgagttta    180
tctaaacctc cgcgtccgac gtccaaatat cagagctatt acgatccctc atatctcagt    240
acggacgaac aaaaagatac tttccttaaa ggtatcatta actgtttaa gcgtattaat    300 gagcgcgata tcgggaaaaa gttgattaat tatcttgttg tgggttcccc gttcatgggc    360
gatagctcta cccccgaaga cacttttgat tttacccgtc atacgacaaa catcgcggta    420
gagaagtttg agaacggatc gtggaaagtc acaaacatca ttacacctag cgtcttaatt    480
```

```
tttggtccgc tgccaaacat cttagattat acagccagcc tgactttgca ggggcaacag    540
tcgaatccga gtttcgaagg ttttggtacc ctgagcattc tgaaagttgc cccggaattt    600
ctgctcactt tttcagatgt caccagcaac cagagctcag cagtattagg aaagtcaatt    660
ttttgcatgg acccggttat tgcactgatg cacgaactga cgcactctct gcatcaactg    720
tatgggatca acatccccag tgacaaacgt attcgtcccc aggtgtctga aggatttttc    780
tcacaggatg ggccgaacgt ccagttcgaa gagttgtata ctttcggagg cctggacgta    840
gagatcattc cccagattga gcgcagtcag ctgcgtgaga aggcattggg ccattataag    900
gatattgcaa aacgcctgaa taacattaac aaaacgattc catcttcgtg gatctcgaat    960
attgataaat ataagaaaat ttttagcgag aaatataatt ttgataaaga taatacaggt   1020
aactttgtgg ttaacattga caaattcaac tcccttttaca gtgatttgac gaatgtaatg   1080
agcgaagttg tgtatagttc ccaatacaac gttaagaatc gtacccatta cttctctcgt   1140
cactacctgc cggttttcgc gaacatcctt gacgataata tttacactat tcgtgacggc   1200
tttaacttga ccaacaaggg cttcaatatt gaaaattcag ccagaacat tgaacgcaac   1260 ccggccttgc agaaactgtc gagtgaatcc gtggttgacc tgtttaccaa agtctgcgtc   1320
gacaaaagcg aagagaagct gtacgatgac gatgacaaag atcgttgggg atcgtccctg   1380
cagtgtatta aagtgaaaaa caatcggctg ccttatgtag cagataaaga tagcattagt   1440
caggagattt tcgaaaataa aattatcact gacgaaacca atgttcagaa ttattcgat    1500 aaattttcac tggacgaaag catcttagat ggccaagttc cgattaaccc ggaaattgtt   1560
gatccgttac tgccgaacgt gaatatgaaa ccgttaaacc tccctggcga agagatcgta   1620
ttttatgatg acattacgaa atatgtggac taccttaatt cttattacta tttggaaagc   1680
cagaaactgt ccaataacgt ggaaaacatt actctgacca caagcgtgga agaggcttta   1740
ggctactcaa ataagattta taccttcctc ccgtcgctgg cggaaaaagt aaataaaggt   1800
gtgcaggctg gtctgttcct caactgggcg aatgaagttg tcgaagactt taccacgaat   1860
attatgaaaa aggataccct ggataaaatc tccgacgtct cggttattat cccatatatt   1920
ggccctgcgt taaatatcgg taatagtgcg ctgcgggga attttaaccca ggcctttgct   1980 accgcgggcg tcgcgttcct cctggagggc tttcctgaat ttactatccc ggcgctcggt   2040 gttttacat tttactcttc catccaggag cgtgagaaaa ttatcaaaac catcgaaaac   2100
tgcctggagc agcgggtgaa acgctggaaa gattcttatc aatggatggt gtcaaactgg   2160
ttatctcgca tcacgaccca attcaaccat attaattacc agatgtatga tagtctgtcg   2220
taccaagctg acgccattaa agccaaaatt gatctggaat ataaaaagta ctctggtagc   2280
gataaggaga acatcaaaag ccaggtggag aaccttaaga atagtctgga tgtgaaaatc   2340
tctgaagcta tgaataacat taacaaattc attcgtgaat gttcggtgac gtacctgttc   2400
aagaatatgc tgccaaaagt tattgatgaa ctgaataaat ttgatctgcg taccaaaacc   2460
gaacttatca acctcatcga ctcccacaac attatccttg tgggcgaagt ggatcgtctg   2520
aaggccaaag taaacgagag ctttgaaaat acgatgccgt ttaatatttt ttcatatacc   2580
aataactcct tgctgaaaga tatcatcaat gaatatttca atctagaagg cggtggcggt   2640
agcggcggtg gcggtagcgg cggtggcggt agcgcactag tgcaggaaag acctccatta   2700
caacaacctc cacatcgcga taagaaacca tgtaagaatt tcttttggaa aacatttagc   2760
agttgcaaat aataagctt                                                2779
```

```
<210> SEQ ID NO 7
<211> LENGTH: 920
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
                20                  25                  30

Val Lys Ala Phe Met Ile Thr Gln Asn Ile Trp Val Ile Pro Glu Arg
            35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
                100                 105                 110

Ser Pro Phe Met Gly Asp Ser Ser Thr Pro Glu Asp Thr Phe Asp Phe
            115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
                180                 185                 190

Val Ala Pro Glu Phe Leu Leu Thr Phe Ser Asp Val Thr Ser Asn Gln
            195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
                260                 265                 270

Gly Gly Leu Asp Val Glu Ile Ile Pro Gln Ile Glu Arg Ser Gln Leu
            275                 280                 285

Arg Glu Lys Ala Leu Gly His Tyr Lys Asp Ile Ala Lys Arg Leu Asn
290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
                340                 345                 350

Leu Thr Asn Val Met Ser Glu Val Val Tyr Ser Ser Gln Tyr Asn Val
            355                 360                 365
```

-continued

Lys Asn Arg Thr His Tyr Phe Ser Arg His Tyr Leu Pro Val Phe Ala
370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
            405                 410                 415

Asn Pro Ala Leu Gln Lys Leu Ser Ser Glu Ser Val Val Asp Leu Phe
            420                 425                 430

Thr Lys Val Cys Val Asp Lys Ser Glu Glu Lys Leu Tyr Asp Asp Asp
            435                 440                 445

Asp Lys Asp Arg Trp Gly Ser Ser Leu Gln Cys Ile Lys Val Lys Asn
450                 455                 460

Asn Arg Leu Pro Tyr Val Ala Asp Lys Asp Ser Ile Ser Gln Glu Ile
465                 470                 475                 480

Phe Glu Asn Lys Ile Ile Thr Asp Glu Thr Asn Val Gln Asn Tyr Ser
                485                 490                 495

Asp Lys Phe Ser Leu Asp Glu Ser Ile Leu Asp Gly Gln Val Pro Ile
            500                 505                 510

Asn Pro Glu Ile Val Asp Pro Leu Leu Pro Asn Val Asn Met Glu Pro
515                 520                 525

Leu Asn Leu Pro Gly Glu Glu Ile Val Phe Tyr Asp Asp Ile Thr Lys
530                 535                 540

Tyr Val Asp Tyr Leu Asn Ser Tyr Tyr Tyr Leu Glu Ser Gln Lys Leu
545                 550                 555                 560

Ser Asn Asn Val Glu Asn Ile Thr Leu Thr Thr Ser Val Glu Glu Ala
                565                 570                 575

Leu Gly Tyr Ser Asn Lys Ile Tyr Thr Phe Leu Pro Ser Leu Ala Glu
            580                 585                 590

Lys Val Asn Lys Gly Val Gln Ala Gly Leu Phe Leu Asn Trp Ala Asn
            595                 600                 605

Glu Val Val Glu Asp Phe Thr Thr Asn Ile Met Lys Lys Asp Thr Leu
610                 615                 620

Asp Lys Ile Ser Asp Val Ser Val Ile Ile Pro Tyr Ile Gly Pro Ala
625                 630                 635                 640

Leu Asn Ile Gly Asn Ser Ala Leu Arg Gly Asn Phe Asn Gln Ala Phe
                645                 650                 655

Ala Thr Ala Gly Val Ala Phe Leu Leu Glu Gly Phe Pro Glu Phe Thr
            660                 665                 670

Ile Pro Ala Leu Gly Val Phe Thr Phe Tyr Ser Ser Ile Gln Glu Arg
            675                 680                 685

Glu Lys Ile Ile Lys Thr Ile Glu Asn Cys Leu Glu Gln Arg Val Lys
            690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
                725                 730                 735

Ser Tyr Gln Ala Asp Ala Ile Lys Ala Lys Ile Asp Leu Glu Tyr Lys
            740                 745                 750

Lys Tyr Ser Gly Ser Asp Lys Glu Asn Ile Lys Ser Gln Val Glu Asn
            755                 760                 765

Leu Lys Asn Ser Leu Asp Val Lys Ile Ser Glu Ala Met Asn Asn Ile
770                 775                 780

```
Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
            805                 810                 815

Thr Glu Leu Ile Asn Leu Ile Asp Ser His Asn Ile Ile Leu Val Gly
        820                 825                 830

Glu Val Asp Arg Leu Lys Ala Lys Val Asn Glu Ser Phe Glu Asn Thr
    835                 840                 845

Met Pro Phe Asn Ile Phe Ser Tyr Thr Asn Asn Ser Leu Leu Lys Asp
850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Val Gln Glu Arg Pro Pro
            885                 890                 895

Leu Gln Gln Pro Pro His Arg Asp Lys Lys Pro Cys Lys Asn Phe Phe
                900                 905                 910

Trp Lys Thr Phe Ser Ser Cys Lys
        915                 920

<210> SEQ ID NO 8
<211> LENGTH: 277
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
ggatccgtcg acaacaacaa taacaacaac aataacaaca acgacgatga cgataaaaat     60
tcagatagcg aatgtccact tagtcacgac gggtactgtt tgcatgatgg tgtgtgtatg    120
tatatagaag cactagacaa atacgcttgc aattgcgtag ttggctatat aggagagcga    180
tgccaatata gagatctgaa gtggtgggag ttaagggcag aagcggcagc caaagaagca    240
gccgctaagg cgctgcagag tctagaataa taagctt                             277

<210> SEQ ID NO 9
<211> LENGTH: 2802
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc accggaagc gaaacaggtg ccggtatctt actatgactc cacctacctg    240
tctaccgata cgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agtcgagtg tctgagcttt ggtcacgaag ttctgaacct cacccgtaac    540
```

-continued

| | |
|---|---|
| ggctacggtt ccactcagta catccgtttc tctccggact tcaccttcgg ttttgaagaa | 600 |
| tccctggaag tagacacgaa cccactgctg ggcgctggta aattcgcaac tgatcctgcg | 660 |
| gttaccctgg ctcacgaact gattcatgca ggccaccgcc tgtacggtat cgccatcaat | 720 |
| ccgaaccgtg tcttcaaagt taacaccaac gcgtattacg agatgtccgg tctggaagtt | 780 |
| agcttcgaag aactgcgtac ttttggcggt cacgacgcta aattcatcga ctctctgcaa | 840 |
| gaaaacgagt tccgtctgta ctactataac aagttcaaag atatcgcatc caccctgaac | 900 |
| aaagcgaaat ccatcgtggg taccactgct tctctccagt acatgaagaa cgttttttaaa | 960 |
| gaaaaatacc tgctcagcga agacacctcc ggcaaattct ctgtagacaa gttgaaattc | 1020 |
| gataaacttt acaaaatgct gactgaaatt tacaccgaag acaacttcgt taagttcttt | 1080 |
| aaagttctga accgcaaaac ctatctgaac ttcgacaagg cagtattcaa atcaacatc | 1140 |
| gtgccgaaag ttaactacac tatctacgat ggtttcaacc tgcgtaacac caacctggct | 1200 |
| gctaatttta acggccagaa cacgaaatc aacaacatga acttcacaaa actgaaaaac | 1260 |
| ttcactggtc tgttcgagtt ttacaagctg ctgtgcgtcg acaacaacaa taacaacaac | 1320 |
| aataacaaca acgacgatga cgataaaaat tcagatagcg aatgtccact tagtcacgac | 1380 |
| gggtactgtt tgcatgatgg tgtgtgtatg tatatagaag cactagacaa atacgcttgc | 1440 |
| aattgcgtag ttggctatat aggagagcga tgccaatata gagatctgaa gtggtgggag | 1500 |
| ttaagggcag aagcggcagc caaagaagca gccgctaagg cgctgcagtg tatcaaggtt | 1560 |
| aacaactggg atttattctt cagcccgagt gaagacaact tcaccaacga cctgaacaaa | 1620 |
| ggtgaagaaa tcacctcaga tactaacatc gaagcagccg aagaaaacat ctcgctggac | 1680 |
| ctgatccagc agtactacct gacctttaat ttcgacaacg agccggaaaa catttctatc | 1740 |
| gaaaacctga gctctgatat catcggccag ctggaactga tgccgaacat cgaacgtttc | 1800 |
| ccaaacggta aaagtacga gctggacaaa tataccatgt tccactacct gcgcgcgcag | 1860 |
| gaatttgaac acggcaaatc ccgtatcgca ctgactaact ccgttaacga agctctgctc | 1920 |
| aacccgtccc gtgtatacac cttcttctct agcgactacg tgaaaaaggt caacaaagcg | 1980 |
| actgaagctg caatgttctt gggttgggtt aacagcttg tttatgattt taccgacgag | 2040 |
| acgtccgaag tatctactac cgacaaaatt gcggatatca ctatcatcat cccgtacatc | 2100 |
| ggtccggctc tgaacattgg caacatgctg tacaaagacg acttcgttgg cgcactgatc | 2160 |
| ttctccggtg cggtgatcct gctggagttc atcccggaaa tcgccatccc ggtactgggc | 2220 |
| acctttgctc tggtttctta cattgcaaac aaggttctga ctgtacaaac catcgacaac | 2280 |
| gcgctgagca acgtaacga aaaatgggat gaagtttaca atatatcgt gaccaactgg | 2340 |
| ctggctaagg ttaatactca gatcgacctc atccgcaaaa aaatgaaaga agcactggaa | 2400 |
| aaccaggcgg aagctaccaa ggcaatcatt aactaccagt acaaccagta caccgaggaa | 2460 |
| gaaaaaaaca acatcaactt caacatcgac gatctgtcct ctaaactgaa cgaatccatc | 2520 |
| aacaaagcta tgatcaacat caacaagttc ctgaaccagt gctctgtaag ctatctgatg | 2580 |
| aactccatga tcccgtacgg tgttaaacgt ctggaggact cgatgcgtc tctgaaagac | 2640 |
| gccctgctga aatacatttta cgacaaccgt ggcactctga tcggtcaggt tgatcgtctg | 2700 |
| aaggacaaag tgaacaatac cttatcgacc gacatcccctt ttcagctcag taaatatgtc | 2760 |
| gataaccaac gccttttgtc cactctagaa taatgaaagc tt | 2802 |

<210> SEQ ID NO 10
<211> LENGTH: 925

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
        355                 360                 365

Asp Lys Ala Val Phe Lys Ile Asn Ile Val Pro Lys Val Asn Tyr Thr

```
              370                 375                 380
Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Asn
                420                 425                 430

Asn Asn Asn Asn Asn Asn Asn Asn Asp Asp Asp Lys Asn Ser
            435                 440                 445

Asp Ser Glu Cys Pro Leu Ser His Asp Gly Tyr Cys Leu His Asp Gly
            450                 455                 460

Val Cys Met Tyr Ile Glu Ala Leu Asp Lys Tyr Ala Cys Asn Cys Val
465                 470                 475                 480

Val Gly Tyr Ile Gly Glu Arg Cys Gln Tyr Arg Asp Leu Lys Trp Trp
                485                 490                 495

Glu Leu Arg Ala Glu Ala Ala Lys Glu Ala Ala Lys Ala Leu
            500                 505                 510

Gln Cys Ile Lys Val Asn Asn Trp Asp Leu Phe Phe Ser Pro Ser Glu
            515                 520                 525

Asp Asn Phe Thr Asn Asp Leu Asn Lys Gly Glu Glu Ile Thr Ser Asp
            530                 535                 540

Thr Asn Ile Glu Ala Ala Glu Glu Asn Ile Ser Leu Asp Leu Ile Gln
545                 550                 555                 560

Gln Tyr Tyr Leu Thr Phe Asn Phe Asp Asn Glu Pro Glu Asn Ile Ser
                565                 570                 575

Ile Glu Asn Leu Ser Ser Asp Ile Ile Gly Gln Leu Glu Leu Met Pro
            580                 585                 590

Asn Ile Glu Arg Phe Pro Asn Gly Lys Lys Tyr Glu Leu Asp Lys Tyr
            595                 600                 605

Thr Met Phe His Tyr Leu Arg Ala Gln Glu Phe Glu His Gly Lys Ser
            610                 615                 620

Arg Ile Ala Leu Thr Asn Ser Val Asn Glu Ala Leu Leu Asn Pro Ser
625                 630                 635                 640

Arg Val Tyr Thr Phe Phe Ser Ser Asp Tyr Val Lys Lys Val Asn Lys
                645                 650                 655

Ala Thr Glu Ala Ala Met Phe Leu Gly Trp Val Glu Gln Leu Val Tyr
                660                 665                 670

Asp Phe Thr Asp Glu Thr Ser Glu Val Ser Thr Thr Asp Lys Ile Ala
            675                 680                 685

Asp Ile Thr Ile Ile Ile Pro Tyr Ile Gly Pro Ala Leu Asn Ile Gly
            690                 695                 700

Asn Met Leu Tyr Lys Asp Asp Phe Val Gly Ala Leu Ile Phe Ser Gly
705                 710                 715                 720

Ala Val Ile Leu Leu Glu Phe Ile Pro Glu Ile Ala Ile Pro Val Leu
                725                 730                 735

Gly Thr Phe Ala Leu Val Ser Tyr Ile Ala Asn Lys Val Leu Thr Val
                740                 745                 750

Gln Thr Ile Asp Asn Ala Leu Ser Lys Arg Asn Glu Lys Trp Asp Glu
            755                 760                 765

Val Tyr Lys Tyr Ile Val Thr Asn Trp Leu Ala Lys Val Asn Thr Gln
            770                 775                 780

Ile Asp Leu Ile Arg Lys Lys Met Lys Glu Ala Leu Glu Asn Gln Ala
785                 790                 795                 800
```

```
Glu Ala Thr Lys Ala Ile Ile Asn Tyr Gln Tyr Asn Gln Tyr Thr Glu
                805                 810                 815

Glu Glu Lys Asn Asn Ile Asn Phe Asn Ile Asp Asp Leu Ser Ser Lys
            820                 825                 830

Leu Asn Glu Ser Ile Asn Lys Ala Met Ile Asn Ile Asn Lys Phe Leu
        835                 840                 845

Asn Gln Cys Ser Val Ser Tyr Leu Met Asn Ser Met Ile Pro Tyr Gly
    850                 855                 860

Val Lys Arg Leu Glu Asp Phe Asp Ala Ser Leu Lys Asp Ala Leu Leu
865                 870                 875                 880

Lys Tyr Ile Tyr Asp Asn Arg Gly Thr Leu Ile Gly Gln Val Asp Arg
                885                 890                 895

Leu Lys Asp Lys Val Asn Asn Thr Leu Ser Thr Asp Ile Pro Phe Gln
            900                 905                 910

Leu Ser Lys Tyr Val Asp Asn Gln Arg Leu Leu Ser Thr
        915                 920                 925

<210> SEQ ID NO 11
<211> LENGTH: 864
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220
```

-continued

```
Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
        355                 360                 365

Asp Lys Ala Val Phe Lys Ile Asn Ile Val Pro Lys Val Asn Tyr Thr
    370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Gly
            420                 425                 430

Ile Ile Thr Ser Lys Thr Lys Ser Asp Asp Asp Lys Asn Lys Ala
        435                 440                 445

Leu Asn Leu Gln Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
                485                 490                 495

Leu Ile Gln Gln Tyr Tyr Leu Thr Phe Asn Phe Asp Asn Glu Pro Glu
            500                 505                 510

Asn Ile Ser Ile Glu Asn Leu Ser Ser Asp Ile Ile Gly Gln Leu Glu
        515                 520                 525

Leu Met Pro Asn Ile Glu Arg Phe Pro Asn Gly Lys Lys Tyr Glu Leu
530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
        595                 600                 605

Leu Val Tyr Asp Phe Thr Asp Glu Thr Ser Glu Val Ser Thr Thr Asp
    610                 615                 620

Lys Ile Ala Asp Ile Thr Ile Ile Pro Tyr Ile Gly Pro Ala Leu
625                 630                 635                 640

Asn Ile Gly Asn Met Leu Tyr Lys Asp Asp Phe Val Gly Ala Leu Ile
```

```
                    645                 650                 655
Phe Ser Gly Ala Val Ile Leu Leu Glu Phe Ile Pro Glu Ile Ala Ile
                660                 665                 670

Pro Val Leu Gly Thr Phe Ala Leu Val Ser Tyr Ile Ala Asn Lys Val
            675                 680                 685

Leu Thr Val Gln Thr Ile Asp Asn Ala Leu Ser Lys Arg Asn Glu Lys
        690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
                740                 745                 750

Tyr Thr Glu Glu Glu Lys Asn Asn Ile Asn Phe Asn Ile Asp Asp Leu
            755                 760                 765

Ser Ser Lys Leu Asn Glu Ser Ile Asn Lys Ala Met Ile Asn Ile Asn
        770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
                820                 825                 830

Val Asp Arg Leu Lys Asp Lys Val Asn Asn Thr Leu Ser Thr Asp Ile
            835                 840                 845

Pro Phe Gln Leu Ser Lys Tyr Val Asp Asn Gln Arg Leu Leu Ser Thr
        850                 855                 860

<210> SEQ ID NO 12
<211> LENGTH: 869
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
    50                  55                  60

Phe Asn Arg Asp Val Cys Glu Tyr Tyr Asp Pro Asp Tyr Leu Asn Thr
65              70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
    130                 135                 140
```

```
Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
            165                 170                 175

Gln Asn His Phe Ala Ser Arg Glu Gly Phe Gly Gly Ile Met Gln Met
            180                 185                 190

Lys Phe Cys Pro Glu Tyr Val Ser Val Phe Asn Asn Val Gln Glu Asn
            195                 200                 205

Lys Gly Ala Ser Ile Phe Asn Arg Arg Gly Tyr Phe Ser Asp Pro Ala
            210                 215                 220

Leu Ile Leu Met His Glu Leu Ile His Val Leu His Gly Leu Tyr Gly
225                 230                 235                 240

Ile Lys Val Asp Asp Leu Pro Ile Val Pro Asn Glu Lys Lys Phe Phe
            245                 250                 255

Met Gln Ser Thr Asp Ala Ile Gln Ala Glu Glu Leu Tyr Thr Phe Gly
            260                 265                 270

Gly Gln Asp Pro Ser Ile Ile Thr Pro Ser Thr Asp Lys Ser Ile Tyr
            275                 280                 285

Asp Lys Val Leu Gln Asn Phe Arg Gly Ile Val Asp Arg Leu Asn Lys
            290                 295                 300

Val Leu Val Cys Ile Ser Asp Pro Asn Ile Asn Ile Asn Ile Tyr Lys
305                 310                 315                 320

Asn Lys Phe Lys Asp Lys Tyr Lys Phe Val Glu Asp Ser Glu Gly Lys
            325                 330                 335

Tyr Ser Ile Asp Val Glu Ser Phe Asp Lys Leu Tyr Lys Ser Leu Met
            340                 345                 350

Phe Gly Phe Thr Glu Thr Asn Ile Ala Glu Asn Tyr Lys Ile Lys Thr
            355                 360                 365

Arg Ala Ser Tyr Phe Ser Asp Ser Leu Pro Pro Val Lys Ile Lys Asn
            370                 375                 380

Leu Leu Asp Asn Glu Ile Tyr Thr Ile Glu Glu Gly Phe Asn Ile Ser
385                 390                 395                 400

Asp Lys Asp Met Glu Lys Glu Tyr Arg Gly Gln Asn Lys Ala Ile Asn
            405                 410                 415

Lys Gln Ala Tyr Glu Glu Ile Ser Lys Glu His Leu Ala Val Tyr Lys
            420                 425                 430

Ile Gln Met Cys Val Asp Glu Glu Lys Leu Tyr Asp Asp Asp Asp Lys
            435                 440                 445

Asp Arg Trp Gly Ser Ser Leu Gln Cys Ile Asp Val Asp Asn Glu Asp
            450                 455                 460

Leu Phe Phe Ile Ala Asp Lys Asn Ser Phe Ser Asp Asp Leu Ser Lys
465                 470                 475                 480

Asn Glu Arg Ile Glu Tyr Asn Thr Gln Ser Asn Tyr Ile Glu Asn Asp
            485                 490                 495

Phe Pro Ile Asn Glu Leu Ile Leu Asp Thr Asp Leu Ile Ser Lys Ile
            500                 505                 510

Glu Leu Pro Ser Glu Asn Thr Glu Ser Leu Thr Asp Phe Asn Val Asp
            515                 520                 525

Val Pro Val Tyr Glu Lys Gln Pro Ala Ile Lys Lys Ile Phe Thr Asp
            530                 535                 540

Glu Asn Thr Ile Phe Gln Tyr Leu Tyr Ser Gln Thr Phe Pro Leu Asp
545                 550                 555                 560
```

```
Ile Arg Asp Ile Ser Leu Thr Ser Ser Phe Asp Asp Ala Leu Leu Phe
            565                 570                 575

Ser Asn Lys Val Tyr Ser Phe Phe Ser Met Asp Tyr Ile Lys Thr Ala
        580                 585                 590

Asn Lys Val Val Glu Ala Gly Leu Phe Ala Gly Trp Val Lys Gln Ile
        595                 600                 605

Val Asn Asp Phe Val Ile Glu Ala Asn Lys Ser Asn Thr Met Asp Ala
    610                 615                 620

Ile Ala Asp Ile Ser Leu Ile Val Pro Tyr Ile Gly Leu Ala Leu Asn
625                 630                 635                 640

Val Gly Asn Glu Thr Ala Lys Gly Asn Phe Glu Asn Ala Phe Glu Ile
            645                 650                 655

Ala Gly Ala Ser Ile Leu Leu Glu Phe Ile Pro Glu Leu Leu Ile Pro
        660                 665                 670

Val Val Gly Ala Phe Leu Leu Glu Ser Tyr Ile Asp Asn Lys Asn Lys
        675                 680                 685

Ile Ile Lys Thr Ile Asp Asn Ala Leu Thr Lys Arg Asn Glu Lys Trp
    690                 695                 700

Ser Asp Met Tyr Gly Leu Ile Val Ala Gln Trp Leu Ser Thr Val Asn
705                 710                 715                 720

Thr Gln Phe Tyr Thr Ile Lys Glu Gly Met Tyr Lys Ala Leu Asn Tyr
            725                 730                 735

Gln Ala Gln Ala Leu Glu Glu Ile Ile Lys Tyr Arg Tyr Asn Ile Tyr
        740                 745                 750

Ser Glu Lys Glu Lys Ser Asn Ile Asn Ile Asp Phe Asn Asp Ile Asn
        755                 760                 765

Ser Lys Leu Asn Glu Gly Ile Asn Gln Ala Ile Asp Asn Ile Asn Asn
    770                 775                 780

Phe Ile Asn Gly Cys Ser Val Ser Tyr Leu Met Lys Lys Met Ile Pro
785                 790                 795                 800

Leu Ala Val Glu Lys Leu Leu Asp Phe Asp Asn Thr Leu Lys Lys Asn
            805                 810                 815

Leu Leu Asn Tyr Ile Asp Glu Asn Lys Leu Tyr Leu Ile Gly Ser Ala
        820                 825                 830

Glu Tyr Glu Lys Ser Lys Val Asn Lys Tyr Leu Lys Thr Ile Met Pro
        835                 840                 845

Phe Asp Leu Ser Ile Tyr Thr Asn Asp Thr Ile Leu Ile Glu Met Phe
    850                 855                 860

Asn Lys Tyr Asn Ser
865

<210> SEQ ID NO 13
<211> LENGTH: 865
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
```

```
                35                  40                  45
Phe Ser Arg Asn Ser Asn Pro Asn Leu Asn Lys Pro Pro Arg Val Thr
        50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Leu Ile Tyr Arg Leu Ser Thr Asp
            100                 105                 110

Ile Pro Phe Pro Gly Asn Asn Thr Pro Ile Asn Thr Phe Asp Phe
            115                 120                 125

Asp Val Asp Phe Asn Ser Val Asp Val Lys Thr Arg Gln Gly Asn Asn
        130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
                180                 185                 190

Ile Ser Pro Arg Phe Met Leu Thr Tyr Ser Asn Ala Thr Asn Asp Val
            195                 200                 205

Gly Glu Gly Arg Phe Ser Lys Ser Glu Phe Cys Met Asp Pro Ile Leu
            210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
            275                 280                 285

Glu Glu Lys Ala Leu Asp Tyr Tyr Arg Ser Ile Ala Lys Arg Leu Asn
        290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
            355                 360                 365

Gln Asn Arg Lys Ile Tyr Leu Ser Asn Val Tyr Thr Pro Val Thr Ala
        370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
            420                 425                 430

Thr Lys Phe Cys Val Asp Ala Ile Asp Gly Arg Ser Leu Tyr Asn Lys
        435                 440                 445

Thr Leu Gln Cys Arg Glu Leu Leu Val Lys Asn Thr Asp Leu Pro Phe
            450                 455                 460
```

```
Ile Gly Asp Ile Ser Asp Val Lys Thr Asp Ile Phe Leu Arg Lys Asp
465                 470                 475                 480

Ile Asn Glu Glu Thr Glu Val Ile Tyr Tyr Pro Asp Asn Val Ser Val
                485                 490                 495

Asp Gln Val Ile Leu Ser Lys Asn Thr Ser Glu His Gly Gln Leu Asp
            500                 505                 510

Leu Leu Tyr Pro Ser Ile Asp Ser Glu Ser Glu Ile Leu Pro Gly Glu
            515                 520                 525

Asn Gln Val Phe Tyr Asp Asn Arg Thr Gln Asn Val Asp Tyr Leu Asn
            530                 535                 540

Ser Tyr Tyr Tyr Leu Glu Ser Gln Lys Leu Ser Asp Asn Val Glu Asp
545                 550                 555                 560

Phe Thr Phe Thr Arg Ser Ile Glu Glu Ala Leu Asp Asn Ser Ala Lys
                565                 570                 575

Val Tyr Thr Tyr Phe Pro Thr Leu Ala Asn Lys Val Asn Ala Gly Val
            580                 585                 590

Gln Gly Gly Leu Phe Leu Met Trp Ala Asn Asp Val Glu Asp Phe
            595                 600                 605

Thr Thr Asn Ile Leu Arg Lys Asp Thr Leu Asp Lys Ile Ser Asp Val
            610                 615                 620

Ser Ala Ile Ile Pro Tyr Ile Gly Pro Ala Leu Asn Ile Ser Asn Ser
625                 630                 635                 640

Val Arg Arg Gly Asn Phe Thr Glu Ala Phe Ala Val Thr Gly Val Thr
                645                 650                 655

Ile Leu Leu Glu Ala Phe Pro Glu Phe Thr Ile Pro Ala Leu Gly Ala
            660                 665                 670

Phe Val Ile Tyr Ser Lys Val Gln Glu Arg Asn Glu Ile Ile Lys Thr
            675                 680                 685

Ile Asp Asn Cys Leu Glu Gln Arg Ile Lys Arg Trp Lys Asp Ser Tyr
            690                 695                 700

Glu Trp Met Met Gly Thr Trp Leu Ser Arg Ile Ile Thr Gln Phe Asn
705                 710                 715                 720

Asn Ile Ser Tyr Gln Met Tyr Asp Ser Leu Asn Tyr Gln Ala Gly Ala
                725                 730                 735

Ile Lys Ala Lys Ile Asp Leu Glu Tyr Lys Lys Tyr Ser Gly Ser Asp
            740                 745                 750

Lys Glu Asn Ile Lys Ser Gln Val Glu Asn Leu Lys Asn Ser Leu Asp
            755                 760                 765

Val Lys Ile Ser Glu Ala Met Asn Asn Ile Asn Lys Phe Ile Arg Glu
            770                 775                 780

Cys Ser Val Thr Tyr Leu Phe Lys Asn Met Leu Pro Lys Val Ile Asp
785                 790                 795                 800

Glu Leu Asn Glu Phe Asp Arg Asn Thr Lys Ala Lys Leu Ile Asn Leu
                805                 810                 815

Ile Asp Ser His Asn Ile Ile Leu Val Gly Glu Val Asp Lys Leu Lys
            820                 825                 830

Ala Lys Val Asn Asn Ser Phe Gln Asn Thr Ile Pro Phe Asn Ile Phe
            835                 840                 845

Ser Tyr Thr Asn Asn Ser Leu Leu Lys Asp Ile Ile Asn Glu Tyr Phe
            850                 855                 860

Asn
865
```

<210> SEQ ID NO 14
<211> LENGTH: 871
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
            340                 345                 350

Leu Thr Asn Val Met Ser Glu Val Val Tyr Ser Ser Gln Tyr Asn Val
```

```
            355                 360                 365
Lys Asn Arg Thr His Tyr Phe Ser Arg His Tyr Leu Pro Val Phe Ala
        370                 375                 380
Asn Ile Leu Asp Asp Asn Ile Tyr Thr Ile Arg Asp Gly Phe Asn Leu
385                 390                 395                 400
Thr Asn Lys Gly Phe Asn Ile Glu Asn Ser Gly Gln Asn Ile Glu Arg
                405                 410                 415
Asn Pro Ala Leu Gln Lys Leu Ser Ser Glu Ser Val Val Asp Leu Phe
            420                 425                 430
Thr Lys Val Cys Val Asp Lys Ser Glu Glu Lys Leu Tyr Asp Asp Asp
                435                 440                 445
Asp Lys Asp Arg Trp Gly Ser Ser Leu Gln Cys Ile Lys Val Lys Asn
            450                 455                 460
Asn Arg Leu Pro Tyr Val Ala Asp Lys Asp Ser Ile Ser Gln Glu Ile
465                 470                 475                 480
Phe Glu Asn Lys Ile Ile Thr Asp Glu Thr Asn Val Gln Asn Tyr Ser
                485                 490                 495
Asp Lys Phe Ser Leu Asp Glu Ser Ile Leu Asp Gly Gln Val Pro Ile
                500                 505                 510
Asn Pro Glu Ile Val Asp Pro Leu Leu Pro Asn Val Asn Met Glu Pro
            515                 520                 525
Leu Asn Leu Pro Gly Glu Glu Ile Val Phe Tyr Asp Asp Ile Thr Lys
        530                 535                 540
Tyr Val Asp Tyr Leu Asn Ser Tyr Tyr Leu Glu Ser Gln Lys Leu
545                 550                 555                 560
Ser Asn Asn Val Glu Asn Ile Thr Leu Thr Thr Ser Val Glu Glu Ala
                565                 570                 575
Leu Gly Tyr Ser Asn Lys Ile Tyr Thr Phe Leu Pro Ser Leu Ala Glu
            580                 585                 590
Lys Val Asn Lys Gly Val Gln Ala Gly Leu Phe Leu Asn Trp Ala Asn
            595                 600                 605
Glu Val Val Glu Asp Phe Thr Thr Asn Ile Met Lys Lys Asp Thr Leu
        610                 615                 620
Asp Lys Ile Ser Asp Val Ser Val Ile Ile Pro Tyr Ile Gly Pro Ala
625                 630                 635                 640
Leu Asn Ile Gly Asn Ser Ala Leu Arg Gly Asn Phe Asn Gln Ala Phe
                645                 650                 655
Ala Thr Ala Gly Val Ala Phe Leu Leu Glu Gly Phe Pro Glu Phe Thr
            660                 665                 670
Ile Pro Ala Leu Gly Val Phe Thr Phe Tyr Ser Ser Ile Gln Glu Arg
            675                 680                 685
Glu Lys Ile Ile Lys Thr Ile Glu Asn Cys Leu Glu Gln Arg Val Lys
            690                 695                 700
Arg Trp Lys Asp Ser Tyr Gln Trp Met Val Ser Asn Trp Leu Ser Arg
705                 710                 715                 720
Ile Thr Thr Gln Phe Asn His Ile Asn Tyr Gln Met Tyr Asp Ser Leu
                725                 730                 735
Ser Tyr Gln Ala Asp Ala Ile Lys Ala Lys Ile Asp Leu Glu Tyr Lys
            740                 745                 750
Lys Tyr Ser Gly Ser Asp Lys Glu Asn Ile Lys Ser Gln Val Glu Asn
                755                 760                 765
Leu Lys Asn Ser Leu Asp Val Lys Ile Ser Glu Ala Met Asn Asn Ile
        770                 775                 780
```

```
Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
            805                 810                 815

Thr Glu Leu Ile Asn Leu Ile Asp Ser His Asn Ile Ile Leu Val Gly
            820                 825                 830

Glu Val Asp Arg Leu Lys Ala Lys Val Asn Glu Ser Phe Glu Asn Thr
            835                 840                 845

Met Pro Phe Asn Ile Phe Ser Tyr Thr Asn Asn Ser Leu Leu Lys Asp
850                 855                 860

Ile Ile Asn Glu Tyr Phe Asn
865                 870
```

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

```
Glu His Trp Ser Tyr Gly Cys Arg Pro Gly
1               5                   10
```

<210> SEQ ID NO 16
<211> LENGTH: 920
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
            35                  40                  45

Tyr Thr Phe Gly Tyr Lys Pro Glu Asp Phe Asn Lys Ser Ser Gly Ile
    50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
            115                 120                 125

Asn Thr Asn Ile Ala Ser Val Thr Val Asn Lys Leu Ile Ser Asn Pro
    130                 135                 140

Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175
```

-continued

```
Gln Asn His Phe Ala Ser Arg Glu Gly Phe Gly Ile Met Gln Met
                180                 185                 190
Lys Phe Cys Pro Glu Tyr Val Ser Val Phe Asn Asn Val Gln Glu Asn
            195                 200                 205
Lys Gly Ala Ser Ile Phe Asn Arg Arg Gly Tyr Phe Ser Asp Pro Ala
        210                 215                 220
Leu Ile Leu Met His Glu Leu Ile His Val Leu His Gly Leu Tyr Gly
225                 230                 235                 240
Ile Lys Val Asp Asp Leu Pro Ile Val Pro Asn Glu Lys Lys Phe Phe
                245                 250                 255
Met Gln Ser Thr Asp Ala Ile Gln Ala Glu Glu Leu Tyr Thr Phe Gly
            260                 265                 270
Gly Gln Asp Pro Ser Ile Ile Thr Pro Ser Thr Asp Lys Ser Ile Tyr
        275                 280                 285
Asp Lys Val Leu Gln Asn Phe Arg Gly Ile Val Asp Arg Leu Asn Lys
290                 295                 300
Val Leu Val Cys Ile Ser Asp Pro Asn Ile Asn Ile Asn Ile Tyr Lys
305                 310                 315                 320
Asn Lys Phe Lys Asp Lys Tyr Lys Phe Val Glu Asp Ser Glu Gly Lys
                325                 330                 335
Tyr Ser Ile Asp Val Glu Ser Phe Asp Lys Leu Tyr Lys Ser Leu Met
            340                 345                 350
Phe Gly Phe Thr Glu Thr Asn Ile Ala Glu Asn Tyr Lys Ile Lys Thr
        355                 360                 365
Arg Ala Ser Tyr Phe Ser Asp Ser Leu Pro Pro Val Lys Ile Lys Asn
370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
                405                 410                 415
Lys Gln Ala Tyr Glu Glu Ile Ser Lys Glu His Leu Ala Val Tyr Lys
            420                 425                 430
Ile Gln Met Cys Val Asp Gly Ile Ile Thr Ser Lys Thr Lys Ser Asp
        435                 440                 445
Asp Asp Asp Lys Asn Lys Ala Leu Asn Leu Gln Cys Ile Asp Val Asp
450                 455                 460
Asn Glu Asp Leu Phe Phe Ile Ala Asp Lys Asn Ser Phe Ser Asp Asp
465                 470                 475                 480
Leu Ser Lys Asn Glu Arg Ile Glu Tyr Asn Thr Gln Ser Asn Tyr Ile
                485                 490                 495
Glu Asn Asp Phe Pro Ile Asn Glu Leu Ile Leu Asp Thr Asp Leu Ile
            500                 505                 510
Ser Lys Ile Glu Leu Pro Ser Glu Asn Thr Glu Ser Leu Thr Asp Phe
        515                 520                 525
Asn Val Asp Val Pro Val Tyr Gly Lys Gln Pro Ala Ile Lys Lys Ile
530                 535                 540
Phe Thr Asp Glu Asn Thr Ile Phe Gln Tyr Leu Tyr Ser Gln Thr Phe
545                 550                 555                 560
Pro Leu Asp Ile Arg Asp Ile Ser Leu Thr Ser Ser Phe Asp Asp Ala
                565                 570                 575
Leu Leu Phe Ser Asn Lys Val Tyr Ser Phe Phe Ser Met Asp Tyr Ile
            580                 585                 590
Lys Thr Ala Asn Lys Val Val Glu Ala Gly Leu Phe Ala Gly Trp Val
```

```
            595                 600                 605
Lys Gln Ile Val Asn Asp Phe Val Ile Glu Ala Asn Lys Ser Asn Thr
            610                 615                 620
Met Asp Lys Ile Ala Asp Ile Ser Leu Ile Val Pro Tyr Ile Gly Leu
625                 630                 635                 640
Ala Leu Asn Val Gly Asn Glu Thr Ala Lys Gly Asn Phe Glu Asn Ala
                    645                 650                 655
Phe Glu Ile Ala Gly Ala Ser Ile Leu Leu Glu Phe Ile Pro Glu Leu
                660                 665                 670
Leu Ile Pro Val Val Gly Ala Phe Leu Leu Glu Ser Tyr Ile Asp Asn
            675                 680                 685
Lys Asn Lys Ile Ile Lys Thr Ile Asp Asn Ala Leu Thr Lys Arg Asn
            690                 695                 700
Glu Lys Trp Ser Asp Met Tyr Gly Leu Ile Val Ala Gln Trp Leu Ser
705                 710                 715                 720
Thr Val Asn Thr Gln Phe Tyr Thr Ile Lys Glu Gly Met Tyr Lys Ala
                    725                 730                 735
Leu Asn Tyr Gln Ala Gln Ala Leu Glu Glu Ile Ile Lys Tyr Arg Tyr
                740                 745                 750
Asn Ile Tyr Ser Glu Lys Glu Lys Ser Asn Ile Asn Ile Asp Phe Asn
            755                 760                 765
Asp Ile Asn Ser Lys Leu Asn Glu Gly Ile Asn Gln Ala Ile Asp Asn
            770                 775                 780
Ile Asn Asn Phe Ile Asn Gly Cys Ser Val Ser Tyr Leu Met Lys Lys
785                 790                 795                 800
Met Ile Pro Leu Ala Val Glu Lys Leu Leu Asp Phe Asp Asn Thr Leu
                    805                 810                 815
Lys Lys Asn Leu Leu Asn Tyr Ile Asp Glu Asn Lys Leu Tyr Leu Ile
                820                 825                 830
Gly Ser Ala Glu Tyr Glu Lys Ser Lys Val Asn Lys Tyr Leu Lys Thr
            835                 840                 845
Ile Met Pro Phe Asp Leu Ser Ile Tyr Thr Asn Asp Thr Ile Leu Ile
            850                 855                 860
Glu Met Phe Asn Lys Tyr Asn Ser Leu Glu Gly Gly Gly Ser Gly
865                 870                 875                 880
Gly Gly Gly Ser Gly Gly Gly Ser Ala Leu Asp Ser Ala Asn Ser
                    885                 890                 895
Asn Pro Ala Met Ala Pro Arg Glu Arg Lys Ala Gly Cys Lys Asn Phe
                900                 905                 910
Phe Trp Lys Thr Phe Thr Ser Cys
                915                 920

<210> SEQ ID NO 17
<211> LENGTH: 908
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Phe Val Asn Lys Gln Phe Asn Tyr Lys Asp Pro Val Asn Gly Val
1               5                   10                  15
Asp Ile Ala Tyr Ile Lys Ile Pro Asn Ala Gly Gln Met Gln Pro Val
                20                  25                  30
```

-continued

Lys Ala Phe Lys Ile His Asn Lys Ile Trp Val Ile Pro Glu Arg Asp
            35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
            115                 120                 125

Ile Asp Thr Asn Cys Ile Asn Val Ile Gln Pro Asp Gly Ser Tyr Arg
            130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
            195                 200                 205

Ala Gly Lys Phe Ala Thr Asp Pro Ala Val Thr Leu Ala His Glu Leu
            210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
                260                 265                 270

Ile Asp Ser Leu Gln Glu Asn Glu Phe Arg Leu Tyr Tyr Tyr Asn Lys
            275                 280                 285

Phe Lys Asp Ile Ala Ser Thr Leu Asn Lys Ala Lys Ser Ile Val Gly
            290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
            355                 360                 365

Asp Lys Ala Val Phe Lys Ile Asn Ile Val Pro Lys Val Asn Tyr Thr
            370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Gly
            420                 425                 430

Ile Ile Thr Ser Lys Thr Lys Ser Asp Asp Asp Lys Ser Ala Asn
            435                 440                 445

```
Ser Asn Pro Ala Met Ala Pro Arg Glu Arg Lys Ala Gly Cys Lys Asn
    450             455                 460
Phe Phe Trp Lys Thr Phe Thr Ser Cys Ala Leu Ala Gly Gly Gly Gly
465             470                 475                 480
Ser Gly Gly Gly Ser Gly Gly Gly Ser Ala Leu Val Leu Gln
                485             490                 495
Cys Ile Lys Val Asn Asn Trp Asp Leu Phe Phe Ser Pro Ser Glu Asp
                500             505                 510
Asn Phe Thr Asn Asp Leu Asn Lys Gly Glu Glu Ile Thr Ser Asp Thr
        515             520                 525
Asn Ile Glu Ala Ala Glu Glu Asn Ile Ser Leu Asp Leu Ile Gln Gln
530             535                 540
Tyr Tyr Leu Thr Phe Asn Phe Asp Asn Glu Pro Glu Asn Ile Ser Ile
545             550                 555                 560
Glu Asn Leu Ser Ser Asp Ile Ile Gly Gln Leu Glu Leu Met Pro Asn
                565             570                 575
Ile Glu Arg Phe Pro Asn Gly Lys Lys Tyr Glu Leu Asp Lys Tyr Thr
                580             585                 590
Met Phe His Tyr Leu Arg Ala Gln Glu Phe Glu His Gly Lys Ser Arg
        595             600                 605
Ile Ala Leu Thr Asn Ser Val Asn Glu Ala Leu Leu Asn Pro Ser Arg
610             615                 620
Val Tyr Thr Phe Phe Ser Ser Asp Tyr Val Lys Val Asn Lys Ala
625             630                 635                 640
Thr Glu Ala Ala Met Phe Leu Gly Trp Val Glu Gln Leu Val Tyr Asp
                645             650                 655
Phe Thr Asp Glu Thr Ser Glu Val Ser Thr Thr Asp Lys Ile Ala Asp
                660             665                 670
Ile Thr Ile Ile Ile Pro Tyr Ile Gly Pro Ala Leu Asn Ile Gly Asn
        675             680                 685
Met Leu Tyr Lys Asp Asp Phe Val Gly Ala Leu Ile Phe Ser Gly Ala
        690             695                 700
Val Ile Leu Leu Glu Phe Ile Pro Glu Ile Ala Ile Pro Val Leu Gly
705             710                 715                 720
Thr Phe Ala Leu Val Ser Tyr Ile Ala Asn Lys Val Leu Thr Val Gln
                725             730                 735
Thr Ile Asp Asn Ala Leu Ser Lys Arg Asn Glu Lys Trp Asp Glu Val
                740             745                 750
Tyr Lys Tyr Ile Val Thr Asn Trp Leu Ala Lys Val Asn Thr Gln Ile
        755             760                 765
Asp Leu Ile Arg Lys Lys Met Lys Glu Ala Leu Glu Asn Gln Ala Glu
    770             775                 780
Ala Thr Lys Ala Ile Ile Asn Tyr Gln Tyr Asn Gln Tyr Thr Glu Glu
785             790                 795                 800
Glu Lys Asn Asn Ile Asn Phe Asn Ile Asp Asp Leu Ser Ser Lys Leu
                805             810                 815
Asn Glu Ser Ile Asn Lys Ala Met Ile Asn Ile Asn Lys Phe Leu Asn
                820             825                 830
Gln Cys Ser Val Ser Tyr Leu Met Asn Ser Met Ile Pro Tyr Gly Val
        835             840                 845
Lys Arg Leu Glu Asp Phe Asp Ala Ser Leu Lys Asp Ala Leu Leu Lys
    850             855                 860
Tyr Ile Tyr Asp Asn Arg Gly Thr Leu Ile Gly Gln Val Asp Arg Leu
```

```
                865                 870                 875                 880

Lys Asp Lys Val Asn Asn Thr Leu Ser Thr Asp Ile Pro Phe Gln Leu
                    885                 890                 895

Ser Lys Tyr Val Asp Asn Gln Arg Leu Leu Ser Thr
                    900                 905

<210> SEQ ID NO 18
<211> LENGTH: 944
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
290                 295                 300

Asn Ile Asn Lys Thr Ile Pro Ser Ser Trp Ile Ser Asn Ile Asp Lys
305                 310                 315                 320
```

-continued

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
                340                 345                 350

Leu Thr Asn Val Met Ser Glu Val Val Tyr Ser Ser Gln Tyr Asn Val
                355                 360                 365

Lys Asn Arg Thr His Tyr Phe Ser Arg His Tyr Leu Pro Val Phe Ala
    370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
                405                 410                 415

Asn Pro Ala Leu Gln Lys Leu Ser Ser Glu Ser Val Val Asp Leu Phe
                420                 425                 430

Thr Lys Val Cys Val Asp Lys Ser Glu Glu Lys Leu Tyr Asp Asp Asp
                435                 440                 445

Asp Lys Asp Arg Trp Gly Ser Ser Leu Gln Cys Ile Lys Val Lys Asn
    450                 455                 460

Asn Arg Leu Pro Tyr Val Ala Asp Lys Asp Ser Ile Ser Gln Glu Ile
465                 470                 475                 480

Phe Glu Asn Lys Ile Ile Thr Asp Glu Thr Asn Val Gln Asn Tyr Ser
                485                 490                 495

Asp Lys Phe Ser Leu Asp Glu Ser Ile Leu Asp Gly Gln Val Pro Ile
                500                 505                 510

Asn Pro Glu Ile Val Asp Pro Leu Leu Pro Asn Val Asn Met Glu Pro
                515                 520                 525

Leu Asn Leu Pro Gly Glu Glu Ile Val Phe Tyr Asp Asp Ile Thr Lys
                530                 535                 540

Tyr Val Asp Tyr Leu Asn Ser Tyr Tyr Tyr Leu Glu Ser Gln Lys Leu
545                 550                 555                 560

Ser Asn Asn Val Glu Asn Ile Thr Leu Thr Thr Ser Val Glu Glu Ala
                565                 570                 575

Leu Gly Tyr Ser Asn Lys Ile Tyr Thr Phe Leu Pro Ser Leu Ala Glu
                580                 585                 590

Lys Val Asn Lys Gly Val Gln Ala Gly Leu Phe Leu Asn Trp Ala Asn
                595                 600                 605

Glu Val Val Glu Asp Phe Thr Thr Asn Ile Met Lys Lys Asp Thr Leu
                610                 615                 620

Asp Lys Ile Ser Asp Val Ser Val Ile Ile Pro Tyr Ile Gly Pro Ala
625                 630                 635                 640

Leu Asn Ile Gly Asn Ser Ala Leu Arg Gly Asn Phe Asn Gln Ala Phe
                645                 650                 655

Ala Thr Ala Gly Val Ala Phe Leu Leu Glu Gly Phe Pro Glu Phe Thr
                660                 665                 670

Ile Pro Ala Leu Gly Val Phe Thr Phe Tyr Ser Ser Ile Gln Glu Arg
                675                 680                 685

Glu Lys Ile Ile Lys Thr Ile Glu Asn Cys Leu Glu Gln Arg Val Lys
                690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
                725                 730                 735

```
Ser Tyr Gln Ala Asp Ala Ile Lys Ala Lys Ile Asp Leu Glu Tyr Lys
            740                 745                 750

Lys Tyr Ser Gly Ser Asp Lys Glu Asn Ile Lys Ser Gln Val Glu Asn
        755                 760                 765

Leu Lys Asn Ser Leu Asp Val Lys Ile Ser Glu Ala Met Asn Asn Ile
    770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
                805                 810                 815

Thr Glu Leu Ile Asn Leu Ile Asp Ser His Asn Ile Ile Leu Val Gly
            820                 825                 830

Glu Val Asp Arg Leu Lys Ala Lys Val Asn Glu Ser Phe Glu Asn Thr
        835                 840                 845

Met Pro Phe Asn Ile Phe Ser Tyr Thr Asn Asn Ser Leu Leu Lys Asp
    850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Val Asn Ser Asp Ser Glu
            885                 890                 895

Cys Pro Leu Ser His Asp Gly Tyr Cys Leu His Asp Gly Val Cys Met
                900                 905                 910

Tyr Ile Glu Ala Leu Asp Lys Tyr Ala Cys Asn Cys Val Val Gly Tyr
            915                 920                 925

Ile Gly Glu Arg Cys Gln Tyr Arg Asp Leu Lys Trp Trp Glu Leu Arg
930                 935                 940

<210> SEQ ID NO 19
<211> LENGTH: 919
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
```

-continued

```
              145                 150                 155                 160
Leu Pro Asn Ile Leu Asp Tyr Thr Ala Ser Leu Thr Leu Gln Gly Gln
              165                 170                 175

Gln Ser Asn Pro Ser Phe Glu Gly Phe Gly Thr Leu Ser Ile Leu Lys
              180                 185                 190

Val Ala Pro Glu Phe Leu Leu Thr Phe Ser Asp Val Thr Ser Asn Gln
              195                 200                 205

Ser Ser Ala Val Leu Gly Lys Ser Ile Phe Cys Met Asp Pro Val Ile
              210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
              245                 250                 255

Phe Ser Gln Asp Gly Pro Asn Val Gln Phe Glu Glu Leu Tyr Thr Phe
              260                 265                 270

Gly Gly Leu Asp Val Glu Ile Ile Pro Gln Ile Glu Arg Ser Gln Leu
              275                 280                 285

Arg Glu Lys Ala Leu Gly His Tyr Lys Asp Ile Ala Lys Arg Leu Asn
              290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
              325                 330                 335

Gly Asn Phe Val Val Asn Ile Asp Lys Phe Asn Ser Leu Tyr Ser Asp
              340                 345                 350

Leu Thr Asn Val Met Ser Glu Val Val Tyr Ser Ser Gln Tyr Asn Val
              355                 360                 365

Lys Asn Arg Thr His Tyr Phe Ser Arg His Tyr Leu Pro Val Phe Ala
              370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
              405                 410                 415

Asn Pro Ala Leu Gln Lys Leu Ser Ser Glu Ser Val Val Asp Leu Phe
              420                 425                 430

Thr Lys Val Cys Val Asp Lys Ser Glu Lys Leu Tyr Asp Asp Asp
              435                 440                 445

Asp Lys Asp Arg Trp Gly Ser Ser Leu Gln Cys Ile Lys Val Lys Asn
450                 455                 460

Asn Arg Leu Pro Tyr Val Ala Asp Lys Asp Ser Ile Ser Gln Glu Ile
465                 470                 475                 480

Phe Glu Asn Lys Ile Ile Thr Asp Glu Thr Asn Val Gln Asn Tyr Ser
              485                 490                 495

Asp Lys Phe Ser Leu Asp Glu Ser Ile Leu Asp Gly Gln Val Pro Ile
              500                 505                 510

Asn Pro Glu Ile Val Asp Pro Leu Leu Pro Asn Val Asn Met Glu Pro
              515                 520                 525

Leu Asn Leu Pro Gly Glu Glu Ile Val Phe Tyr Asp Asp Ile Thr Lys
              530                 535                 540

Tyr Val Asp Tyr Leu Asn Ser Tyr Tyr Tyr Leu Glu Ser Gln Lys Leu
545                 550                 555                 560

Ser Asn Asn Val Glu Asn Ile Thr Leu Thr Thr Ser Val Glu Glu Ala
              565                 570                 575
```

Leu Gly Tyr Ser Asn Lys Ile Tyr Thr Phe Leu Pro Ser Leu Ala Glu
            580                 585                 590

Lys Val Asn Lys Gly Val Gln Ala Gly Leu Phe Leu Asn Trp Ala Asn
        595                 600                 605

Glu Val Val Glu Asp Phe Thr Thr Asn Ile Met Lys Lys Asp Thr Leu
    610                 615                 620

Asp Lys Ile Ser Asp Val Ser Val Ile Ile Pro Tyr Ile Gly Pro Ala
625                 630                 635                 640

Leu Asn Ile Gly Asn Ser Ala Leu Arg Gly Asn Phe Asn Gln Ala Phe
            645                 650                 655

Ala Thr Ala Gly Val Ala Phe Leu Leu Glu Gly Phe Pro Glu Phe Thr
        660                 665                 670

Ile Pro Ala Leu Gly Val Phe Thr Phe Tyr Ser Ser Ile Gln Glu Arg
    675                 680                 685

Glu Lys Ile Ile Lys Thr Ile Glu Asn Cys Leu Glu Gln Arg Val Lys
690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
            725                 730                 735

Ser Tyr Gln Ala Asp Ala Ile Lys Ala Lys Ile Asp Leu Glu Tyr Lys
        740                 745                 750

Lys Tyr Ser Gly Ser Asp Lys Glu Asn Ile Lys Ser Gln Val Glu Asn
    755                 760                 765

Leu Lys Asn Ser Leu Asp Val Lys Ile Ser Glu Ala Met Asn Asn Ile
770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
            805                 810                 815

Thr Glu Leu Ile Asn Leu Ile Asp Ser His Asn Ile Ile Leu Val Gly
        820                 825                 830

Glu Val Asp Arg Leu Lys Ala Lys Val Asn Glu Ser Phe Glu Asn Thr
    835                 840                 845

Met Pro Phe Asn Ile Phe Ser Tyr Thr Asn Asn Ser Leu Leu Lys Asp
850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Val His Ser Asp Ala Val
            885                 890                 895

Phe Thr Asp Asn Tyr Thr Arg Leu Arg Lys Gln Met Ala Val Lys Lys
        900                 905                 910

Tyr Leu Asn Ser Ile Leu Asn
        915

<210> SEQ ID NO 20
<211> LENGTH: 955
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

```
Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
50                      55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
```

```
            420             425             430
Thr Lys Phe Cys Val Asp Ala Ile Asp Gly Arg Ser Leu Tyr Asn Lys
            435                 440                 445
Thr Leu Gln Cys Arg Glu Leu Leu Val Lys Asn Thr Asp Leu Pro Phe
            450                 455                 460
Ile Gly Asp Ile Ser Asp Val Lys Thr Asp Ile Phe Leu Arg Lys Asp
465                 470                 475                 480
Ile Asn Glu Glu Thr Glu Val Ile Tyr Tyr Pro Asp Asn Val Ser Val
                    485                 490                 495
Asp Gln Val Ile Leu Ser Lys Asn Thr Ser Glu His Gly Gln Leu Asp
                500                 505                 510
Leu Leu Tyr Pro Ser Ile Asp Ser Glu Ser Glu Ile Leu Pro Gly Glu
            515                 520                 525
Asn Gln Val Phe Tyr Asp Asn Arg Thr Gln Asn Val Asp Tyr Leu Asn
            530                 535                 540
Ser Tyr Tyr Tyr Leu Glu Ser Gln Lys Leu Ser Asp Asn Val Glu Asp
545                 550                 555                 560
Phe Thr Phe Thr Arg Ser Ile Glu Glu Ala Leu Asp Asn Ser Ala Lys
                    565                 570                 575
Val Tyr Thr Tyr Phe Pro Thr Leu Ala Asn Lys Val Asn Ala Gly Val
                580                 585                 590
Gln Gly Gly Leu Phe Leu Met Trp Ala Asn Asp Val Val Glu Asp Phe
            595                 600                 605
Thr Thr Asn Ile Leu Arg Lys Asp Thr Leu Asp Lys Ile Ser Asp Val
            610                 615                 620
Ser Ala Ile Ile Pro Tyr Ile Gly Pro Ala Leu Asn Ile Ser Asn Ser
625                 630                 635                 640
Val Arg Arg Gly Asn Phe Thr Glu Ala Phe Ala Val Thr Gly Val Thr
                    645                 650                 655
Ile Leu Leu Glu Ala Phe Pro Glu Phe Thr Ile Pro Ala Leu Gly Ala
                660                 665                 670
Phe Val Ile Tyr Ser Lys Val Gln Glu Arg Asn Glu Ile Ile Lys Thr
            675                 680                 685
Ile Asp Asn Cys Leu Glu Gln Arg Ile Lys Arg Trp Lys Asp Ser Tyr
            690                 695                 700
Glu Trp Met Met Gly Thr Trp Leu Ser Arg Ile Ile Thr Gln Phe Asn
705                 710                 715                 720
Asn Ile Ser Tyr Gln Met Tyr Asp Ser Leu Asn Tyr Gln Ala Gly Ala
                    725                 730                 735
Ile Lys Ala Lys Ile Asp Leu Glu Tyr Lys Lys Tyr Ser Gly Ser Asp
                740                 745                 750
Lys Glu Asn Ile Lys Ser Gln Val Glu Asn Leu Lys Asn Ser Leu Asp
            755                 760                 765
Val Lys Ile Ser Glu Ala Met Asn Asn Ile Asn Lys Phe Ile Arg Glu
            770                 775                 780
Cys Ser Val Thr Tyr Leu Phe Lys Asn Met Leu Pro Lys Val Ile Asp
785                 790                 795                 800
Glu Leu Asn Glu Phe Asp Arg Asn Thr Lys Ala Lys Leu Ile Asn Leu
                    805                 810                 815
Ile Asp Ser His Asn Ile Ile Leu Val Gly Glu Val Asp Lys Leu Lys
                820                 825                 830
Ala Lys Val Asn Asn Ser Phe Gln Asn Thr Ile Pro Phe Asn Ile Phe
            835                 840                 845
```

```
Ser Tyr Thr Asn Asn Ser Leu Leu Lys Asp Ile Ile Asn Glu Tyr Phe
            850                 855                 860

Asn Leu Glu Gly Gly Gly Ser Gly Gly Gly Ser Gly Gly Gly
865                 870                 875                 880

Gly Ser Ala Leu Val Gly Pro Glu Thr Leu Cys Gly Ala Glu Leu Val
                885                 890                 895

Asp Ala Leu Gln Phe Val Cys Gly Asp Arg Gly Phe Tyr Phe Asn Lys
            900                 905                 910

Pro Thr Gly Tyr Gly Ser Ser Arg Arg Ala Pro Gln Thr Gly Ile
            915                 920                 925

Val Asp Glu Cys Cys Phe Arg Ser Cys Asp Leu Arg Arg Leu Glu Met
            930                 935                 940

Tyr Cys Ala Pro Leu Lys Pro Ala Lys Ser Ala
945                 950                 955
```

<210> SEQ ID NO 21
<211> LENGTH: 961
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
            35                  40                  45

Phe Ser Ser Asp Thr Asn Pro Ser Leu Ser Lys Pro Pro Arg Pro Thr
50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
            85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
            115                 120                 125

Thr Arg His Thr Thr Asn Ile Ala Val Glu Lys Phe Glu Asn Gly Ser
            130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
            165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
            195                 200                 205

Ser Ser Ala Val Leu Gly Lys Ser Ile Phe Cys Met Asp Pro Val Ile
            210                 215                 220

Ala Leu Met His Glu Leu Thr His Ser Leu His Gln Leu Tyr Gly Ile
225                 230                 235                 240
```

```
Asn Ile Pro Ser Asp Lys Arg Ile Arg Pro Gln Val Ser Glu Gly Phe
                245                 250                 255
Phe Ser Gln Asp Gly Pro Asn Val Gln Phe Glu Glu Leu Tyr Thr Phe
            260                 265                 270
Gly Gly Leu Asp Val Glu Ile Ile Pro Gln Ile Glu Arg Ser Gln Leu
        275                 280                 285
Arg Glu Lys Ala Leu Gly His Tyr Lys Asp Ile Ala Lys Arg Leu Asn
    290                 295                 300
Asn Ile Asn Lys Thr Ile Pro Ser Ser Trp Ile Ser Asn Ile Asp Lys
305                 310                 315                 320
Tyr Lys Lys Ile Phe Ser Glu Lys Tyr Asn Phe Asp Lys Asp Asn Thr
                325                 330                 335
Gly Asn Phe Val Val Asn Ile Asp Lys Phe Asn Ser Leu Tyr Ser Asp
            340                 345                 350
Leu Thr Asn Val Met Ser Glu Val Val Tyr Ser Ser Gln Tyr Asn Val
        355                 360                 365
Lys Asn Arg Thr His Tyr Phe Ser Arg His Tyr Leu Pro Val Phe Ala
    370                 375                 380
Asn Ile Leu Asp Asp Asn Ile Tyr Thr Ile Arg Asp Gly Phe Asn Leu
385                 390                 395                 400
Thr Asn Lys Gly Phe Asn Ile Glu Asn Ser Gly Gln Asn Ile Glu Arg
                405                 410                 415
Asn Pro Ala Leu Gln Lys Leu Ser Ser Glu Ser Val Val Asp Leu Phe
            420                 425                 430
Thr Lys Val Cys Val Asp Lys Ser Glu Lys Leu Tyr Asp Asp Asp
        435                 440                 445
Asp Lys Asp Arg Trp Gly Ser Ser Leu Gln Cys Ile Lys Val Lys Asn
    450                 455                 460
Asn Arg Leu Pro Tyr Val Ala Asp Lys Asp Ser Ile Ser Gln Glu Ile
465                 470                 475                 480
Phe Glu Asn Lys Ile Ile Thr Asp Glu Thr Asn Val Gln Asn Tyr Ser
                485                 490                 495
Asp Lys Phe Ser Leu Asp Glu Ser Ile Leu Asp Gly Gln Val Pro Ile
            500                 505                 510
Asn Pro Glu Ile Val Asp Pro Leu Leu Pro Asn Val Asn Met Glu Pro
        515                 520                 525
Leu Asn Leu Pro Gly Glu Glu Ile Val Phe Tyr Asp Asp Ile Thr Lys
    530                 535                 540
Tyr Val Asp Tyr Leu Asn Ser Tyr Tyr Tyr Leu Glu Ser Gln Lys Leu
545                 550                 555                 560
Ser Asn Asn Val Glu Asn Ile Thr Leu Thr Thr Ser Val Glu Glu Ala
                565                 570                 575
Leu Gly Tyr Ser Asn Lys Ile Tyr Thr Phe Leu Pro Ser Leu Ala Glu
            580                 585                 590
Lys Val Asn Lys Gly Val Gln Ala Gly Leu Phe Leu Asn Trp Ala Asn
        595                 600                 605
Glu Val Val Glu Asp Phe Thr Thr Asn Ile Met Lys Lys Asp Thr Leu
    610                 615                 620
Asp Lys Ile Ser Asp Val Ser Val Ile Ile Pro Tyr Ile Gly Pro Ala
625                 630                 635                 640
Leu Asn Ile Gly Asn Ser Ala Leu Arg Gly Asn Phe Asn Gln Ala Phe
                645                 650                 655
Ala Thr Ala Gly Val Ala Phe Leu Leu Glu Gly Phe Pro Glu Phe Thr
```

Ile Pro Ala Leu Gly Val Phe Thr Phe Tyr Ser Ser Ile Gln Glu Arg
            675                 680                 685

Glu Lys Ile Ile Lys Thr Ile Glu Asn Cys Leu Glu Gln Arg Val Lys
        690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
                725                 730                 735

Ser Tyr Gln Ala Asp Ala Ile Lys Ala Lys Ile Asp Leu Glu Tyr Lys
            740                 745                 750

Lys Tyr Ser Gly Ser Asp Lys Glu Asn Ile Lys Ser Gln Val Glu Asn
        755                 760                 765

Leu Lys Asn Ser Leu Asp Val Lys Ile Ser Glu Ala Met Asn Asn Ile
    770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
                805                 810                 815

Thr Glu Leu Ile Asn Leu Ile Asp Ser His Asn Ile Ile Leu Val Gly
            820                 825                 830

Glu Val Asp Arg Leu Lys Ala Lys Val Asn Glu Ser Phe Glu Asn Thr
        835                 840                 845

Met Pro Phe Asn Ile Phe Ser Tyr Thr Asn Asn Ser Leu Leu Lys Asp
    850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Val Gly Pro Glu Thr Leu
                885                 890                 895

Cys Gly Ala Glu Leu Val Asp Ala Leu Gln Phe Val Cys Gly Asp Arg
            900                 905                 910

Gly Phe Tyr Phe Asn Lys Pro Thr Gly Tyr Gly Ser Ser Ser Arg Arg
        915                 920                 925

Ala Pro Gln Thr Gly Ile Val Asp Glu Cys Cys Phe Arg Ser Cys Asp
    930                 935                 940

Leu Arg Arg Leu Glu Met Tyr Cys Ala Pro Leu Lys Pro Ala Lys Ser
945                 950                 955                 960

Ala

<210> SEQ ID NO 22
<211> LENGTH: 913
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

-continued

```
Phe Ser Arg Asn Ser Asn Pro Asn Leu Asn Lys Pro Pro Arg Val Thr
 50                  55                  60

Ser Pro Lys Ser Gly Tyr Tyr Asp Pro Asn Tyr Leu Ser Thr Asp Ser
 65                  70                  75                  80

Asp Lys Asp Thr Phe Leu Lys Glu Ile Ile Lys Leu Phe Lys Arg Ile
                 85                  90                  95

Asn Ser Arg Glu Ile Gly Glu Glu Leu Ile Tyr Arg Leu Ser Thr Asp
                100                 105                 110

Ile Pro Phe Pro Gly Asn Asn Asn Thr Pro Ile Asn Thr Phe Asp Phe
             115                 120                 125

Asp Val Asp Phe Asn Ser Val Asp Val Lys Thr Arg Gln Gly Asn Asn
 130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                 165                 170                 175

Asn Thr Phe Ala Ala Gln Glu Gly Phe Gly Ala Leu Ser Ile Ile Ser
             180                 185                 190

Ile Ser Pro Arg Phe Met Leu Thr Tyr Ser Asn Ala Thr Asn Asp Val
             195                 200                 205

Gly Glu Gly Arg Phe Ser Lys Ser Glu Phe Cys Met Asp Pro Ile Leu
210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
             245                 250                 255

Tyr Ser Gln Tyr Asn Val Lys Leu Glu Tyr Ala Glu Ile Tyr Ala Phe
             260                 265                 270

Gly Gly Pro Thr Ile Asp Leu Ile Pro Lys Ser Ala Arg Lys Tyr Phe
             275                 280                 285

Glu Glu Lys Ala Leu Asp Tyr Tyr Arg Ser Ile Ala Lys Arg Leu Asn
 290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                 325                 330                 335

Gly Glu Val Thr Val Asn Arg Asn Lys Phe Val Glu Leu Tyr Asn Glu
             340                 345                 350

Leu Thr Gln Ile Phe Thr Glu Phe Asn Tyr Ala Lys Ile Tyr Asn Val
             355                 360                 365

Gln Asn Arg Lys Ile Tyr Leu Ser Asn Val Tyr Thr Pro Val Thr Ala
 370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                 405                 410                 415

Asn Pro Ala Leu Arg Lys Val Asn Pro Glu Asn Met Leu Tyr Leu Phe
             420                 425                 430

Thr Lys Phe Cys Val Asp Ala Ile Asp Gly Arg Ser Leu Tyr Asn Lys
             435                 440                 445

Thr Leu Gln Cys Arg Glu Leu Leu Val Lys Asn Thr Asp Leu Pro Phe
 450                 455                 460

Ile Gly Asp Ile Ser Asp Val Lys Thr Asp Ile Phe Leu Arg Lys Asp
```

-continued

```
              465                 470                 475                 480
Ile Asn Glu Glu Thr Glu Val Ile Tyr Tyr Pro Asp Asn Val Ser Val
                    485                 490                 495
Asp Gln Val Ile Leu Ser Lys Asn Thr Ser Glu His Gly Gln Leu Asp
                    500                 505                 510
Leu Leu Tyr Pro Ser Ile Asp Ser Glu Ser Glu Ile Leu Pro Gly Glu
                    515                 520                 525
Asn Gln Val Phe Tyr Asp Asn Arg Thr Gln Asn Val Asp Tyr Leu Asn
                    530                 535                 540
Ser Tyr Tyr Tyr Leu Glu Ser Gln Lys Leu Ser Asp Asn Val Glu Asp
545                 550                 555                 560
Phe Thr Phe Thr Arg Ser Ile Glu Glu Ala Leu Asp Asn Ser Ala Lys
                    565                 570                 575
Val Tyr Thr Tyr Phe Pro Thr Leu Ala Asn Lys Val Asn Ala Gly Val
                    580                 585                 590
Gln Gly Gly Leu Phe Leu Met Trp Ala Asn Asp Val Val Glu Asp Phe
                    595                 600                 605
Thr Thr Asn Ile Leu Arg Lys Asp Thr Leu Asp Lys Ile Ser Asp Val
                    610                 615                 620
Ser Ala Ile Ile Pro Tyr Ile Gly Pro Ala Leu Asn Ile Ser Asn Ser
625                 630                 635                 640
Val Arg Arg Gly Asn Phe Thr Glu Ala Phe Ala Val Thr Gly Val Thr
                    645                 650                 655
Ile Leu Leu Glu Ala Phe Pro Glu Phe Thr Ile Pro Ala Leu Gly Ala
                    660                 665                 670
Phe Val Ile Tyr Ser Lys Val Gln Glu Arg Asn Glu Ile Ile Lys Thr
                    675                 680                 685
Ile Asp Asn Cys Leu Glu Gln Arg Ile Lys Arg Trp Lys Asp Ser Tyr
                    690                 695                 700
Glu Trp Met Met Gly Thr Trp Leu Ser Arg Ile Ile Thr Gln Phe Asn
705                 710                 715                 720
Asn Ile Ser Tyr Gln Met Tyr Asp Ser Leu Asn Tyr Gln Ala Gly Ala
                    725                 730                 735
Ile Lys Ala Lys Ile Asp Leu Glu Tyr Lys Lys Tyr Ser Gly Ser Asp
                    740                 745                 750
Lys Glu Asn Ile Lys Ser Gln Val Glu Asn Leu Lys Asn Ser Leu Asp
                    755                 760                 765
Val Lys Ile Ser Glu Ala Met Asn Asn Ile Asn Lys Phe Ile Arg Glu
                    770                 775                 780
Cys Ser Val Thr Tyr Leu Phe Lys Asn Met Leu Pro Lys Val Ile Asp
785                 790                 795                 800
Glu Leu Asn Glu Phe Asp Arg Asn Thr Lys Ala Lys Leu Ile Asn Leu
                    805                 810                 815
Ile Asp Ser His Asn Ile Ile Leu Val Gly Glu Val Asp Lys Leu Lys
                    820                 825                 830
Ala Lys Val Asn Asn Ser Phe Gln Asn Thr Ile Pro Phe Asn Ile Phe
                    835                 840                 845
Ser Tyr Thr Asn Asn Ser Leu Leu Lys Asp Ile Ile Asn Glu Tyr Phe
                    850                 855                 860
Asn Leu Glu Gly Gly Gly Ser Gly Gly Gly Ser Gly Gly Gly
865                 870                 875                 880
Gly Ser Ala Leu Val His Ser Asp Ala Val Phe Thr Asp Asn Tyr Thr
                    885                 890                 895
```

```
Arg Leu Arg Lys Gln Met Ala Val Lys Lys Tyr Leu Asn Ser Ile Leu
                900                 905                 910

Asn

<210> SEQ ID NO 23
<211> LENGTH: 977
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
                20                  25                  30

Glu Lys Ala Phe Arg Ile Thr Gly Asn Ile Trp Val Ile Pro Asp Arg
            35                  40                  45

Phe Ser Arg Asn Ser Asn Pro Asn Leu Asn Lys Pro Pro Arg Val Thr
50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
```

-continued

```
            325                 330                 335
Gly Glu Val Thr Val Asn Arg Asn Lys Phe Val Glu Leu Tyr Asn Glu
            340                 345                 350
Leu Thr Gln Ile Phe Thr Glu Phe Asn Tyr Ala Lys Ile Tyr Asn Val
            355                 360                 365
Gln Asn Arg Lys Ile Tyr Leu Ser Asn Val Tyr Thr Pro Val Thr Ala
            370                 375                 380
Asn Ile Leu Asp Asp Asn Val Tyr Asp Ile Gln Asn Gly Phe Asn Ile
385                 390                 395                 400
Pro Lys Ser Asn Leu Asn Val Leu Phe Met Gly Gln Asn Leu Ser Arg
            405                 410                 415
Asn Pro Ala Leu Arg Lys Val Asn Pro Glu Asn Met Leu Tyr Leu Phe
            420                 425                 430
Thr Lys Phe Cys Val Asp Ala Ile Asp Gly Arg Ser Leu Tyr Asn Lys
            435                 440                 445
Thr Leu Gln Cys Arg Glu Leu Leu Val Lys Asn Thr Asp Leu Pro Phe
            450                 455                 460
Ile Gly Asp Ile Ser Asp Val Lys Thr Asp Ile Phe Leu Arg Lys Asp
465                 470                 475                 480
Ile Asn Glu Glu Thr Glu Val Ile Tyr Tyr Pro Asp Asn Val Ser Val
            485                 490                 495
Asp Gln Val Ile Leu Ser Lys Asn Thr Ser Glu His Gly Gln Leu Asp
            500                 505                 510
Leu Leu Tyr Pro Ser Ile Asp Ser Glu Ser Glu Ile Leu Pro Gly Glu
            515                 520                 525
Asn Gln Val Phe Tyr Asp Asn Arg Thr Gln Asn Val Asp Tyr Leu Asn
            530                 535                 540
Ser Tyr Tyr Tyr Leu Glu Ser Gln Lys Leu Ser Asp Asn Val Glu Asp
545                 550                 555                 560
Phe Thr Phe Thr Arg Ser Ile Glu Glu Ala Leu Asp Asn Ser Ala Lys
            565                 570                 575
Val Tyr Thr Tyr Phe Pro Thr Leu Ala Asn Lys Val Asn Ala Gly Val
            580                 585                 590
Gln Gly Gly Leu Phe Leu Met Trp Ala Asn Asp Val Glu Asp Phe
            595                 600                 605
Thr Thr Asn Ile Leu Arg Lys Asp Thr Leu Asp Lys Ile Ser Asp Val
            610                 615                 620
Ser Ala Ile Ile Pro Tyr Ile Gly Pro Ala Leu Asn Ile Ser Asn Ser
625                 630                 635                 640
Val Arg Arg Gly Asn Phe Thr Glu Ala Phe Ala Val Thr Gly Val Thr
            645                 650                 655
Ile Leu Leu Glu Ala Phe Pro Glu Phe Thr Ile Pro Ala Leu Gly Ala
            660                 665                 670
Phe Val Ile Tyr Ser Lys Val Gln Glu Arg Asn Glu Ile Ile Lys Thr
            675                 680                 685
Ile Asp Asn Cys Leu Glu Gln Arg Ile Lys Arg Trp Lys Asp Ser Tyr
            690                 695                 700
Glu Trp Met Met Gly Thr Trp Leu Ser Arg Ile Ile Thr Gln Phe Asn
705                 710                 715                 720
Asn Ile Ser Tyr Gln Met Tyr Asp Ser Leu Asn Tyr Gln Ala Gly Ala
            725                 730                 735
Ile Lys Ala Lys Ile Asp Leu Glu Tyr Lys Lys Tyr Ser Gly Ser Asp
            740                 745                 750
```

Lys Glu Asn Ile Lys Ser Gln Val Glu Asn Leu Lys Asn Ser Leu Asp
            755                 760                 765

Val Lys Ile Ser Glu Ala Met Asn Asn Ile Asn Lys Phe Ile Arg Glu
    770                 775                 780

Cys Ser Val Thr Tyr Leu Phe Lys Asn Met Leu Pro Lys Val Ile Asp
785                 790                 795                 800

Glu Leu Asn Glu Phe Asp Arg Asn Thr Lys Ala Lys Leu Ile Asn Leu
                805                 810                 815

Ile Asp Ser His Asn Ile Ile Leu Val Gly Glu Val Asp Lys Leu Lys
            820                 825                 830

Ala Lys Val Asn Asn Ser Phe Gln Asn Thr Ile Pro Phe Asn Ile Phe
                835                 840                 845

Ser Tyr Thr Asn Asn Ser Leu Leu Lys Asp Ile Ile Asn Glu Tyr Phe
        850                 855                 860

Asn Leu Glu Gly Gly Gly Gly Ser Gly Gly Gly Ser Gly Gly Gly
865                 870                 875                 880

Gly Ser Ala Leu Val Met Lys Pro Ile Gln Lys Leu Leu Ala Gly Leu
                885                 890                 895

Ile Leu Leu Thr Trp Cys Val Glu Gly Cys Ser Ser Gln His Trp Ser
            900                 905                 910

Tyr Gly Leu Arg Pro Gly Gly Lys Arg Asp Ala Glu Asn Leu Ile Asp
        915                 920                 925

Ser Phe Gln Glu Ile Val Lys Glu Val Gly Gln Leu Ala Glu Thr Gln
    930                 935                 940

Arg Phe Glu Cys Thr Thr His Gln Pro Arg Ser Pro Leu Arg Asp Leu
945                 950                 955                 960

Lys Gly Ala Leu Glu Ser Leu Ile Glu Glu Thr Gly Gln Lys Lys
                965                 970                 975

Ile

<210> SEQ ID NO 24
<211> LENGTH: 988
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65              70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe

-continued

```
                115                 120                 125
Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
            340                 345                 350

Leu Thr Asn Val Met Ser Glu Val Val Tyr Ser Ser Gln Tyr Asn Val
        355                 360                 365

Lys Asn Arg Thr His Tyr Phe Ser Arg His Tyr Leu Pro Val Phe Ala
    370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
                405                 410                 415

Asn Pro Ala Leu Gln Lys Leu Ser Ser Glu Ser Val Val Asp Leu Phe
            420                 425                 430

Thr Lys Val Cys Val Asp Lys Ser Glu Glu Lys Leu Tyr Asp Asp Asp
        435                 440                 445

Asp Lys Asp Arg Trp Gly Ser Ser Leu Gln Cys Ile Lys Val Lys Asn
    450                 455                 460

Asn Arg Leu Pro Tyr Val Ala Asp Lys Asp Ser Ile Ser Gln Glu Ile
465                 470                 475                 480

Phe Glu Asn Lys Ile Ile Thr Asp Glu Thr Asn Val Gln Asn Tyr Ser
                485                 490                 495

Asp Lys Phe Ser Leu Asp Glu Ser Ile Leu Asp Gly Gln Val Pro Ile
            500                 505                 510

Asn Pro Glu Ile Val Asp Pro Leu Leu Pro Asn Val Asn Met Glu Pro
        515                 520                 525

Leu Asn Leu Pro Gly Glu Glu Ile Val Phe Tyr Asp Asp Ile Thr Lys
    530                 535                 540
```

-continued

Tyr Val Asp Tyr Leu Asn Ser Tyr Tyr Leu Glu Ser Gln Lys Leu
545                 550                 555                 560

Ser Asn Asn Val Glu Asn Ile Thr Leu Thr Thr Ser Val Glu Ala
                565                 570                 575

Leu Gly Tyr Ser Asn Lys Ile Tyr Thr Phe Leu Pro Ser Leu Ala Glu
            580                 585                 590

Lys Val Asn Lys Gly Val Gln Ala Gly Leu Phe Leu Asn Trp Ala Asn
        595                 600                 605

Glu Val Val Glu Asp Phe Thr Thr Asn Ile Met Lys Lys Asp Thr Leu
    610                 615                 620

Asp Lys Ile Ser Asp Val Ser Val Ile Ile Pro Tyr Ile Gly Pro Ala
625                 630                 635                 640

Leu Asn Ile Gly Asn Ser Ala Leu Arg Gly Asn Phe Asn Gln Ala Phe
                645                 650                 655

Ala Thr Ala Gly Val Ala Phe Leu Leu Glu Gly Phe Pro Glu Phe Thr
            660                 665                 670

Ile Pro Ala Leu Gly Val Phe Thr Phe Tyr Ser Ser Ile Gln Glu Arg
        675                 680                 685

Glu Lys Ile Ile Lys Thr Ile Glu Asn Cys Leu Glu Gln Arg Val Lys
    690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
                725                 730                 735

Ser Tyr Gln Ala Asp Ala Ile Lys Ala Lys Ile Asp Leu Glu Tyr Lys
            740                 745                 750

Lys Tyr Ser Gly Ser Asp Lys Glu Asn Ile Lys Ser Gln Val Glu Asn
        755                 760                 765

Leu Lys Asn Ser Leu Asp Val Lys Ile Ser Glu Ala Met Asn Asn Ile
    770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
                805                 810                 815

Thr Glu Leu Ile Asn Leu Ile Asp Ser His Asn Ile Ile Leu Val Gly
            820                 825                 830

Glu Val Asp Arg Leu Lys Ala Lys Val Asn Glu Ser Phe Glu Asn Thr
        835                 840                 845

Met Pro Phe Asn Ile Phe Ser Tyr Thr Asn Asn Ser Leu Leu Lys Asp
    850                 855                 860

Ile Ile Asn Glu Tyr Phe Asn Leu Glu Gly Gly Gly Ser Gly Gly
865                 870                 875                 880

Gly Gly Ser Gly Gly Gly Gly Ser Gly Gly Gly Gly Ser Ala Leu Val
                885                 890                 895

Met Lys Pro Ile Gln Lys Leu Leu Ala Gly Leu Ile Leu Leu Thr Trp
            900                 905                 910

Cys Val Glu Gly Cys Ser Ser Gln His Trp Ser Tyr Gly Leu Arg Pro
        915                 920                 925

Gly Gly Lys Arg Asp Ala Glu Asn Leu Ile Asp Ser Phe Gln Glu Ile
    930                 935                 940

Val Lys Glu Val Gly Gln Leu Ala Glu Thr Gln Arg Phe Glu Cys Thr
945                 950                 955                 960

-continued

```
Thr His Gln Pro Arg Ser Pro Leu Arg Asp Leu Lys Gly Ala Leu Glu
            965                 970                 975

Ser Leu Ile Glu Glu Thr Gly Gln Lys Lys Ile
            980                 985

<210> SEQ ID NO 25
<211> LENGTH: 901
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
```

```
                        325                 330                 335
Gly Asn Phe Val Val Asn Ile Asp Lys Phe Asn Ser Leu Tyr Ser Asp
                340                 345                 350
Leu Thr Asn Val Met Ser Glu Val Val Tyr Ser Ser Gln Tyr Asn Val
                355                 360                 365
Lys Asn Arg Thr His Tyr Phe Ser Arg His Tyr Leu Pro Val Phe Ala
                370                 375                 380
Asn Ile Leu Asp Asp Asn Ile Tyr Thr Ile Arg Asp Gly Phe Asn Leu
385                 390                 395                 400
Thr Asn Lys Gly Phe Asn Ile Glu Asn Ser Gly Gln Asn Ile Glu Arg
                405                 410                 415
Asn Pro Ala Leu Gln Lys Leu Ser Ser Glu Ser Val Val Asp Leu Phe
                420                 425                 430
Thr Lys Val Cys Val Asp Lys Ser Glu Glu Lys Leu Tyr Asp Asp Asp
                435                 440                 445
Asp Lys Asp Arg Trp Gly Ser Ser Leu Gln Cys Ile Lys Val Lys Asn
                450                 455                 460
Asn Arg Leu Pro Tyr Val Ala Asp Lys Asp Ser Ile Ser Gln Glu Ile
465                 470                 475                 480
Phe Glu Asn Lys Ile Ile Thr Asp Glu Thr Asn Val Gln Asn Tyr Ser
                485                 490                 495
Asp Lys Phe Ser Leu Asp Glu Ser Ile Leu Asp Gly Gln Val Pro Ile
                500                 505                 510
Asn Pro Glu Ile Val Asp Pro Leu Leu Pro Asn Val Asn Met Glu Pro
                515                 520                 525
Leu Asn Leu Pro Gly Glu Glu Ile Val Phe Tyr Asp Asp Ile Thr Lys
                530                 535                 540
Tyr Val Asp Tyr Leu Asn Ser Tyr Tyr Tyr Leu Glu Ser Gln Lys Leu
545                 550                 555                 560
Ser Asn Asn Val Glu Asn Ile Thr Leu Thr Thr Ser Val Glu Glu Ala
                565                 570                 575
Leu Gly Tyr Ser Asn Lys Ile Tyr Thr Phe Leu Pro Ser Leu Ala Glu
                580                 585                 590
Lys Val Asn Lys Gly Val Gln Ala Gly Leu Phe Leu Asn Trp Ala Asn
                595                 600                 605
Glu Val Val Glu Asp Phe Thr Thr Asn Ile Met Lys Lys Asp Thr Leu
                610                 615                 620
Asp Lys Ile Ser Asp Val Ser Val Ile Ile Pro Tyr Ile Gly Pro Ala
625                 630                 635                 640
Leu Asn Ile Gly Asn Ser Ala Leu Arg Gly Asn Phe Asn Gln Ala Phe
                645                 650                 655
Ala Thr Ala Gly Val Ala Phe Leu Leu Glu Gly Phe Pro Glu Phe Thr
                660                 665                 670
Ile Pro Ala Leu Gly Val Phe Thr Phe Tyr Ser Ser Ile Gln Glu Arg
                675                 680                 685
Glu Lys Ile Ile Lys Thr Ile Glu Asn Cys Leu Glu Gln Arg Val Lys
                690                 695                 700
Arg Trp Lys Asp Ser Tyr Gln Trp Met Val Ser Asn Trp Leu Ser Arg
705                 710                 715                 720
Ile Thr Thr Gln Phe Asn His Ile Asn Tyr Gln Met Tyr Asp Ser Leu
                725                 730                 735
Ser Tyr Gln Ala Asp Ala Ile Lys Ala Lys Ile Asp Leu Glu Tyr Lys
                740                 745                 750
```

```
Lys Tyr Ser Gly Ser Asp Lys Glu Asn Ile Lys Ser Gln Val Glu Asn
            755                 760                 765

Leu Lys Asn Ser Leu Asp Val Lys Ile Ser Glu Ala Met Asn Asn Ile
770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
                805                 810                 815

Thr Glu Leu Ile Asn Leu Ile Asp Ser His Asn Ile Ile Leu Val Gly
            820                 825                 830

Glu Val Asp Arg Leu Lys Ala Lys Val Asn Gly Ser Phe Glu Asn Thr
            835                 840                 845

Met Pro Phe Asn Ile Phe Ser Tyr Thr Asn Asn Ser Leu Leu Lys Asp
        850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Val Gly Asn His Trp Ala
                885                 890                 895

Val Gly His Leu Met
            900

<210> SEQ ID NO 26
<211> LENGTH: 899
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
    50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
    130                 135                 140

Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190
```

```
Lys Phe Cys Pro Glu Tyr Val Ser Val Phe Asn Asn Val Gln Glu Asn
        195                 200                 205
Lys Gly Ala Ser Ile Phe Asn Arg Arg Gly Tyr Phe Ser Asp Pro Ala
    210                 215                 220
Leu Ile Leu Met His Glu Leu Ile His Val Leu His Gly Leu Tyr Gly
225                 230                 235                 240
Ile Lys Val Asp Asp Leu Pro Ile Val Pro Asn Glu Lys Lys Phe Phe
                245                 250                 255
Met Gln Ser Thr Asp Ala Ile Gln Ala Glu Glu Leu Tyr Thr Phe Gly
            260                 265                 270
Gly Gln Asp Pro Ser Ile Ile Thr Pro Ser Thr Asp Lys Ser Ile Tyr
        275                 280                 285
Asp Lys Val Leu Gln Asn Phe Arg Gly Ile Val Asp Arg Leu Asn Lys
    290                 295                 300
Val Leu Val Cys Ile Ser Asp Pro Asn Ile Asn Ile Asn Ile Tyr Lys
305                 310                 315                 320
Asn Lys Phe Lys Asp Lys Tyr Lys Phe Val Glu Asp Ser Glu Gly Lys
                325                 330                 335
Tyr Ser Ile Asp Val Glu Ser Phe Asp Lys Leu Tyr Lys Ser Leu Met
            340                 345                 350
Phe Gly Phe Thr Glu Thr Asn Ile Ala Glu Asn Tyr Lys Ile Lys Thr
        355                 360                 365
Arg Ala Ser Tyr Phe Ser Asp Ser Leu Pro Pro Val Lys Ile Lys Asn
    370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
                405                 410                 415
Lys Gln Ala Tyr Glu Glu Ile Ser Lys Glu His Leu Ala Val Tyr Lys
            420                 425                 430
Ile Gln Met Cys Val Asp Glu Glu Lys Leu Tyr Asp Asp Asp Asp Lys
        435                 440                 445
Asp Arg Trp Gly Ser Ser Leu Gln Cys Ile Asp Val Asp Asn Glu Asp
    450                 455                 460
Leu Phe Phe Ile Ala Asp Lys Asn Ser Phe Ser Asp Asp Leu Ser Lys
465                 470                 475                 480
Asn Glu Arg Ile Glu Tyr Asn Thr Gln Ser Asn Tyr Ile Glu Asn Asp
                485                 490                 495
Phe Pro Ile Asn Glu Leu Ile Leu Asp Thr Asp Leu Ile Ser Lys Ile
            500                 505                 510
Glu Leu Pro Ser Glu Asn Thr Glu Ser Leu Thr Asp Phe Asn Val Asp
        515                 520                 525
Val Pro Val Tyr Glu Lys Gln Pro Ala Ile Lys Lys Ile Phe Thr Asp
    530                 535                 540
Glu Asn Thr Ile Phe Gln Tyr Leu Tyr Ser Gln Thr Phe Pro Leu Asp
545                 550                 555                 560
Ile Arg Asp Ile Ser Leu Thr Ser Ser Phe Asp Asp Ala Leu Leu Phe
                565                 570                 575
Ser Asn Lys Val Tyr Ser Phe Phe Ser Met Asp Tyr Ile Lys Thr Ala
            580                 585                 590
Asn Lys Val Val Glu Ala Gly Leu Phe Ala Gly Trp Val Lys Gln Ile
        595                 600                 605
Val Asn Asp Phe Val Ile Glu Ala Asn Lys Ser Asn Thr Met Asp Ala
```

Ile Ala Asp Ile Ser Leu Ile Val Pro Tyr Ile Gly Leu Ala Leu Asn
625                 630                 635                 640

Val Gly Asn Glu Thr Ala Lys Gly Asn Phe Glu Asn Ala Phe Glu Ile
                645                 650                 655

Ala Gly Ala Ser Ile Leu Leu Glu Phe Ile Pro Glu Leu Leu Ile Pro
            660                 665                 670

Val Val Gly Ala Phe Leu Leu Glu Ser Tyr Ile Asp Asn Lys Asn Lys
        675                 680                 685

Ile Ile Lys Thr Ile Asp Asn Ala Leu Thr Lys Arg Asn Glu Lys Trp
690                 695                 700

Ser Asp Met Tyr Gly Leu Ile Val Ala Gln Trp Leu Ser Thr Val Asn
705                 710                 715                 720

Thr Gln Phe Tyr Thr Ile Lys Glu Gly Met Tyr Lys Ala Leu Asn Tyr
                725                 730                 735

Gln Ala Gln Ala Leu Glu Glu Ile Ile Lys Tyr Arg Tyr Asn Ile Tyr
            740                 745                 750

Ser Glu Lys Glu Lys Ser Asn Ile Asn Ile Asp Phe Asn Asp Ile Asn
        755                 760                 765

Ser Lys Leu Asn Glu Gly Ile Asn Gln Ala Ile Asp Asn Ile Asn Asn
770                 775                 780

Phe Ile Asn Gly Cys Ser Val Ser Tyr Leu Met Lys Lys Met Ile Pro
785                 790                 795                 800

Leu Ala Val Glu Lys Leu Leu Asp Phe Asp Asn Thr Leu Lys Lys Asn
                805                 810                 815

Leu Leu Asn Tyr Ile Asp Glu Asn Lys Leu Tyr Leu Ile Gly Ser Ala
            820                 825                 830

Glu Tyr Glu Lys Ser Lys Val Asn Lys Tyr Leu Lys Thr Ile Met Pro
        835                 840                 845

Phe Asp Leu Ser Ile Tyr Thr Asn Asp Thr Ile Leu Ile Glu Met Phe
850                 855                 860

Asn Lys Tyr Asn Ser Leu Glu Gly Gly Gly Ser Gly Gly Gly Gly
865                 870                 875                 880

Ser Gly Gly Gly Gly Ser Ala Leu Val Gly Asn His Trp Ala Val Gly
                885                 890                 895

His Leu Met

<210> SEQ ID NO 27
<211> LENGTH: 1065
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 27

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

```
Ser Pro Lys Ser Gly Tyr Tyr Asp Pro Asn Tyr Leu Ser Thr Asp Ser
 65                  70                  75                  80

Asp Lys Asp Thr Phe Leu Lys Glu Ile Ile Lys Leu Phe Lys Arg Ile
                 85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
            420                 425                 430

Thr Lys Phe Cys Val Asp Ala Ile Asp Gly Arg Ser Leu Tyr Asn Lys
        435                 440                 445

Thr Leu Gln Cys Arg Glu Leu Leu Val Lys Asn Thr Asp Leu Pro Phe
    450                 455                 460

Ile Gly Asp Ile Ser Asp Val Lys Thr Asp Ile Phe Leu Arg Lys Asp
465                 470                 475                 480

Ile Asn Glu Glu Thr Glu Val Ile Tyr Tyr Pro Asp Asn Val Ser Val
```

```
            485                 490                 495
Asp Gln Val Ile Leu Ser Lys Asn Thr Ser Glu His Gly Gln Leu Asp
            500                 505                 510

Leu Leu Tyr Pro Ser Ile Asp Ser Glu Ser Glu Ile Leu Pro Gly Glu
            515                 520                 525

Asn Gln Val Phe Tyr Asp Asn Arg Thr Gln Asn Val Asp Tyr Leu Asn
            530                 535                 540

Ser Tyr Tyr Tyr Leu Glu Ser Gln Lys Leu Ser Asp Asn Val Glu Asp
545                 550                 555                 560

Phe Thr Phe Thr Arg Ser Ile Glu Glu Ala Leu Asp Asn Ser Ala Lys
                565                 570                 575

Val Tyr Thr Tyr Phe Pro Thr Leu Ala Asn Lys Val Asn Ala Gly Val
                580                 585                 590

Gln Gly Gly Leu Phe Leu Met Trp Ala Asn Asp Val Val Glu Asp Phe
                595                 600                 605

Thr Thr Asn Ile Leu Arg Lys Asp Thr Leu Asp Lys Ile Ser Asp Val
                610                 615                 620

Ser Ala Ile Ile Pro Tyr Ile Gly Pro Ala Leu Asn Ile Ser Asn Ser
625                 630                 635                 640

Val Arg Arg Gly Asn Phe Thr Glu Ala Phe Ala Val Thr Gly Val Thr
                645                 650                 655

Ile Leu Leu Glu Ala Phe Pro Glu Phe Thr Ile Pro Ala Leu Gly Ala
                660                 665                 670

Phe Val Ile Tyr Ser Lys Val Gln Glu Arg Asn Glu Ile Ile Lys Thr
                675                 680                 685

Ile Asp Asn Cys Leu Glu Gln Arg Ile Lys Arg Trp Lys Asp Ser Tyr
            690                 695                 700

Glu Trp Met Met Gly Thr Trp Leu Ser Arg Ile Ile Thr Gln Phe Asn
705                 710                 715                 720

Asn Ile Ser Tyr Gln Met Tyr Asp Ser Leu Asn Tyr Gln Ala Gly Ala
                725                 730                 735

Ile Lys Ala Lys Ile Asp Leu Glu Tyr Lys Lys Tyr Ser Gly Ser Asp
                740                 745                 750

Lys Glu Asn Ile Lys Ser Gln Val Glu Asn Leu Lys Asn Ser Leu Asp
                755                 760                 765

Val Lys Ile Ser Glu Ala Met Asn Asn Ile Asn Lys Phe Ile Arg Glu
                770                 775                 780

Cys Ser Val Thr Tyr Leu Phe Lys Asn Met Leu Pro Lys Val Ile Asp
785                 790                 795                 800

Glu Leu Asn Glu Phe Asp Arg Asn Thr Lys Ala Lys Leu Ile Asn Leu
                805                 810                 815

Ile Asp Ser His Asn Ile Ile Leu Val Gly Glu Val Asp Lys Leu Lys
                820                 825                 830

Ala Lys Val Asn Asn Ser Phe Gln Asn Thr Ile Pro Phe Asn Ile Phe
                835                 840                 845

Ser Tyr Thr Asn Asn Ser Leu Leu Lys Asp Ile Ile Asn Glu Tyr Phe
            850                 855                 860

Asn Leu Glu Gly Gly Gly Ser Gly Gly Gly Ser Gly Gly Gly Gly Gly
865                 870                 875                 880

Gly Ser Ala Leu Val Ser Pro Leu Pro Ile Thr Pro Val Asn Ala Thr
                885                 890                 895

Cys Ala Ile Arg His Pro Cys His Asn Asn Leu Met Asn Gln Ile Arg
                900                 905                 910
```

```
Ser Gln Leu Ala Gln Leu Asn Gly Ser Ala Asn Ala Leu Phe Ile Leu
            915                 920                 925

Tyr Tyr Thr Ala Gln Gly Glu Pro Phe Pro Asn Asn Leu Asp Lys Leu
        930                 935                 940

Cys Gly Pro Asn Val Thr Asp Phe Pro Pro His Ala Asn Gly Thr
945                 950                 955                 960

Glu Lys Ala Lys Leu Val Glu Leu Tyr Arg Ile Val Val Tyr Leu Gly
            965                 970                 975

Thr Ser Leu Gly Asn Ile Thr Arg Asp Gln Lys Ile Leu Asn Pro Ser
        980                 985                 990

Ala Leu Ser Leu His Ser Lys Leu Asn Ala Thr Ala Asp Ile Leu Arg
            995                1000                1005

Gly Leu Leu Ser Asn Val Leu Cys Arg Leu Cys Ser Lys Tyr His
       1010                1015                1020

Val Gly His Val Asp Val Thr Tyr Gly Pro Asp Thr Ser Gly Lys
       1025                1030                1035

Asp Val Phe Gln Lys Lys Lys Leu Gly Cys Gln Leu Leu Gly Lys
       1040                1045                1050

Tyr Lys Gln Ile Ile Ala Val Leu Ala Gln Ala Phe
       1055                1060                1065

<210> SEQ ID NO 28
<211> LENGTH: 1060
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Pro Val Thr Ile Asn Asn Phe Asn Tyr Asn Asp Pro Ile Asp Asn Asn
1               5                  10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
    50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
    130                 135                 140

Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190
```

```
Lys Phe Cys Pro Glu Tyr Val Ser Val Phe Asn Asn Val Gln Glu Asn
        195                 200                 205
Lys Gly Ala Ser Ile Phe Asn Arg Arg Gly Tyr Phe Ser Asp Pro Ala
    210                 215                 220
Leu Ile Leu Met His Glu Leu Ile His Val Leu His Gly Leu Tyr Gly
225                 230                 235                 240
Ile Lys Val Asp Asp Leu Pro Ile Val Pro Asn Glu Lys Lys Phe Phe
                245                 250                 255
Met Gln Ser Thr Asp Ala Ile Gln Ala Glu Leu Tyr Thr Phe Gly
            260                 265                 270
Gly Gln Asp Pro Ser Ile Ile Thr Pro Ser Thr Asp Lys Ser Ile Tyr
        275                 280                 285
Asp Lys Val Leu Gln Asn Phe Arg Gly Ile Val Asp Arg Leu Asn Lys
    290                 295                 300
Val Leu Val Cys Ile Ser Asp Pro Asn Ile Asn Ile Asn Ile Tyr Lys
305                 310                 315                 320
Asn Lys Phe Lys Asp Lys Tyr Lys Phe Val Glu Asp Ser Glu Gly Lys
                325                 330                 335
Tyr Ser Ile Asp Val Glu Ser Phe Asp Lys Leu Tyr Lys Ser Leu Met
            340                 345                 350
Phe Gly Phe Thr Glu Thr Asn Ile Ala Glu Asn Tyr Lys Ile Lys Thr
        355                 360                 365
Arg Ala Ser Tyr Phe Ser Asp Ser Leu Pro Pro Val Lys Ile Lys Asn
    370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
                405                 410                 415
Lys Gln Ala Tyr Glu Glu Ile Ser Lys Glu His Leu Ala Val Tyr Lys
            420                 425                 430
Ile Gln Met Cys Val Asp Asn Asn Asn Asn Asn Asn Asn Asn Asn Asn
        435                 440                 445
Asp Asp Asp Asp Lys Ser Pro Leu Pro Ile Thr Pro Val Asn Ala Thr
450                 455                 460
Cys Ala Ile Arg His Pro Cys His Asn Asn Leu Met Asn Gln Ile Arg
465                 470                 475                 480
Ser Gln Leu Ala Gln Leu Asn Gly Ser Ala Asn Ala Leu Phe Ile Leu
                485                 490                 495
Tyr Tyr Thr Ala Gln Gly Glu Pro Phe Pro Asn Asn Leu Asp Lys Leu
            500                 505                 510
Cys Gly Pro Asn Val Thr Asp Phe Pro Pro Phe His Ala Asn Gly Thr
        515                 520                 525
Glu Lys Ala Lys Leu Val Glu Leu Tyr Arg Ile Val Val Tyr Leu Gly
    530                 535                 540
Thr Ser Leu Gly Asn Ile Thr Arg Asp Gln Lys Ile Leu Asn Pro Ser
545                 550                 555                 560
Ala Leu Ser Leu His Ser Lys Leu Asn Ala Thr Ala Asp Ile Leu Arg
                565                 570                 575
Gly Leu Leu Ser Asn Val Leu Cys Arg Leu Cys Ser Lys Tyr His Val
            580                 585                 590
Gly His Val Asp Val Thr Tyr Gly Pro Asp Thr Ser Gly Lys Asp Val
        595                 600                 605
Phe Gln Lys Lys Lys Leu Gly Cys Gln Leu Leu Gly Lys Tyr Lys Gln
```

```
              610                 615                 620
Ile Ile Ala Val Leu Ala Gln Ala Phe Ala Glu Ala Ala Lys Glu
625                 630                 635                 640

Ala Ala Ala Lys Ala Leu Gln Cys Ile Asp Val Asp Asn Glu Asp Leu
                645                 650                 655

Phe Phe Ile Ala Asp Lys Asn Ser Phe Ser Asp Leu Ser Lys Asn
                660                 665                 670

Glu Arg Ile Glu Tyr Asn Thr Gln Ser Asn Tyr Ile Glu Asn Asp Phe
            675                 680                 685

Pro Ile Asn Glu Leu Ile Leu Asp Thr Asp Leu Ile Ser Lys Ile Glu
            690                 695                 700

Leu Pro Ser Glu Asn Thr Glu Ser Leu Thr Asp Phe Asn Val Asp Val
705                 710                 715                 720

Pro Val Tyr Glu Lys Gln Pro Ala Ile Lys Lys Ile Phe Thr Asp Glu
                725                 730                 735

Asn Thr Ile Phe Gln Tyr Leu Tyr Ser Gln Thr Phe Pro Leu Asp Ile
                740                 745                 750

Arg Asp Ile Ser Leu Thr Ser Ser Phe Asp Asp Ala Leu Leu Phe Ser
            755                 760                 765

Asn Lys Val Tyr Ser Phe Phe Ser Met Asp Tyr Ile Lys Thr Ala Asn
770                 775                 780

Lys Val Val Glu Ala Gly Leu Phe Ala Gly Trp Val Lys Gln Ile Val
785                 790                 795                 800

Asn Asp Phe Val Ile Glu Ala Asn Lys Ser Asn Thr Met Asp Lys Ile
                805                 810                 815

Ala Asp Ile Ser Leu Ile Val Pro Tyr Ile Gly Leu Ala Leu Asn Val
                820                 825                 830

Gly Asn Glu Thr Ala Lys Gly Asn Phe Glu Asn Ala Phe Glu Ile Ala
            835                 840                 845

Gly Ala Ser Ile Leu Leu Glu Phe Ile Pro Glu Leu Leu Ile Pro Val
850                 855                 860

Val Gly Ala Phe Leu Leu Glu Ser Tyr Ile Asp Asn Lys Asn Lys Ile
865                 870                 875                 880

Ile Lys Thr Ile Asp Asn Ala Leu Thr Lys Arg Asn Glu Lys Trp Ser
                885                 890                 895

Asp Met Tyr Gly Leu Ile Val Ala Gln Trp Leu Ser Thr Val Asn Thr
                900                 905                 910

Gln Phe Tyr Thr Ile Lys Glu Gly Met Tyr Lys Ala Leu Asn Tyr Gln
            915                 920                 925

Ala Gln Ala Leu Glu Glu Ile Ile Lys Tyr Arg Tyr Asn Ile Tyr Ser
930                 935                 940

Glu Lys Glu Lys Ser Asn Ile Asn Ile Asp Phe Asn Asp Ile Asn Ser
945                 950                 955                 960

Lys Leu Asn Glu Gly Ile Asn Gln Ala Ile Asp Asn Ile Asn Asn Phe
                965                 970                 975

Ile Asn Gly Cys Ser Val Ser Tyr Leu Met Lys Lys Met Ile Pro Leu
                980                 985                 990

Ala Val Glu Lys Leu Leu Asp Phe Asp Asn Thr Leu Lys Lys Asn Leu
            995                 1000                1005

Leu Asn Tyr Ile Asp Glu Asn Lys Leu Tyr Leu Ile Gly Ser Ala
   1010                1015                1020

Glu Tyr Glu Lys Ser Lys Val Asn Lys Tyr Leu Lys Thr Ile Met
   1025                1030                1035
```

```
Pro Phe Asp Leu Ser Ile Tyr Thr Asn Asp Thr Ile Leu Ile Glu
    1040                1045                1050

Met Phe Asn Lys Tyr Asn Ser
    1055                1060

<210> SEQ ID NO 29
<211> LENGTH: 1026
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320
```

Tyr Lys Gln Lys Leu Ile Arg Lys Tyr Arg Phe Val Val Glu Ser Ser
            325                 330                 335

Gly Glu Val Thr Val Asn Arg Asn Lys Phe Val Glu Leu Tyr Asn Glu
        340                 345                 350

Leu Thr Gln Ile Phe Thr Glu Phe Asn Tyr Ala Lys Ile Tyr Asn Val
            355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
                420                 425                 430

Thr Lys Phe Cys Val Asp Ala Ile Asp Gly Arg Ser Leu Tyr Asn Lys
            435                 440                 445

Thr Leu Gln Cys Arg Glu Leu Leu Val Lys Asn Thr Asp Leu Pro Phe
    450                 455                 460

Ile Gly Asp Ile Ser Asp Val Lys Thr Asp Ile Phe Leu Arg Lys Asp
465                 470                 475                 480

Ile Asn Glu Glu Thr Glu Val Ile Tyr Tyr Pro Asp Asn Val Ser Val
                485                 490                 495

Asp Gln Val Ile Leu Ser Lys Asn Thr Ser Glu His Gly Gln Leu Asp
                500                 505                 510

Leu Leu Tyr Pro Ser Ile Asp Ser Glu Ser Ile Leu Pro Gly Glu
                515                 520                 525

Asn Gln Val Phe Tyr Asp Asn Arg Thr Gln Asn Val Asp Tyr Leu Asn
    530                 535                 540

Ser Tyr Tyr Tyr Leu Glu Ser Gln Lys Leu Ser Asp Asn Val Glu Asp
545                 550                 555                 560

Phe Thr Phe Thr Arg Ser Ile Glu Glu Ala Leu Asp Asn Ser Ala Lys
                565                 570                 575

Val Tyr Thr Tyr Phe Pro Thr Leu Ala Asn Lys Val Asn Ala Gly Val
                580                 585                 590

Gln Gly Gly Leu Phe Leu Met Trp Ala Asn Asp Val Val Glu Asp Phe
            595                 600                 605

Thr Thr Asn Ile Leu Arg Lys Asp Thr Leu Asp Lys Ile Ser Asp Val
    610                 615                 620

Ser Ala Ile Ile Pro Tyr Ile Gly Pro Ala Leu Asn Ile Ser Asn Ser
625                 630                 635                 640

Val Arg Arg Gly Asn Phe Thr Glu Ala Phe Ala Val Thr Gly Val Thr
                645                 650                 655

Ile Leu Leu Glu Ala Phe Pro Glu Phe Thr Ile Pro Ala Leu Gly Ala
                660                 665                 670

Phe Val Ile Tyr Ser Lys Val Gln Glu Arg Asn Glu Ile Ile Lys Thr
            675                 680                 685

Ile Asp Asn Cys Leu Glu Gln Arg Ile Lys Arg Trp Lys Asp Ser Tyr
    690                 695                 700

Glu Trp Met Met Gly Thr Trp Leu Ser Arg Ile Ile Thr Gln Phe Asn
705                 710                 715                 720

Asn Ile Ser Tyr Gln Met Tyr Asp Ser Leu Asn Tyr Gln Ala Gly Ala
                725                 730                 735

Ile Lys Ala Lys Ile Asp Leu Glu Tyr Lys Lys Tyr Ser Gly Ser Asp 740                 745                 750
Lys Glu Asn Ile Lys Ser Gln Val Glu Asn Leu Lys Asn Ser Leu Asp
                755                 760                 765
Val Lys Ile Ser Glu Ala Met Asn Asn Ile Asn Lys Phe Ile Arg Glu
            770                 775                 780
Cys Ser Val Thr Tyr Leu Phe Lys Asn Met Leu Pro Lys Val Ile Asp
785                 790                 795                 800
Glu Leu Asn Glu Phe Asp Arg Asn Thr Lys Ala Lys Leu Ile Asn Leu
                805                 810                 815
Ile Asp Ser His Asn Ile Ile Leu Val Gly Glu Val Asp Lys Leu Lys
                820                 825                 830
Ala Lys Val Asn Asn Ser Phe Gln Asn Thr Ile Pro Phe Asn Ile Phe
                835                 840                 845
Ser Tyr Thr Asn Asn Ser Leu Leu Lys Asp Ile Ile Asn Glu Tyr Phe
                850                 855                 860
Asn Leu Glu Gly Gly Gly Gly Ser Gly Gly Gly Ser Gly Gly Gly
865                 870                 875                 880
Gly Ser Ala Leu Val Met Phe Asn Leu Pro Pro Gly Asn Tyr Lys Lys
                885                 890                 895
Pro Lys Leu Leu Tyr Cys Ser Asn Gly Gly His Phe Leu Arg Ile Leu
                900                 905                 910
Pro Asp Gly Thr Val Asp Gly Thr Arg Asp Arg Ser Asp Gln His Ile
                915                 920                 925
Gln Leu Gln Leu Ser Ala Glu Ser Val Gly Glu Val Tyr Ile Lys Ser
            930                 935                 940
Thr Glu Thr Gly Gln Tyr Leu Ala Met Asp Thr Asp Gly Leu Leu Tyr
945                 950                 955                 960
Gly Ser Gln Thr Pro Asn Glu Glu Cys Leu Phe Leu Glu Arg Leu Glu
                965                 970                 975
Glu Asn His Tyr Asn Thr Tyr Ile Ser Lys Lys His Ala Glu Lys Asn
                980                 985                 990
Trp Phe Val Gly Leu Lys Lys Asn  Gly Ser Cys Lys Arg  Gly Pro Arg
                995                 1000                1005
Thr His  Tyr Gly Gln Lys Ala  Ile Leu Phe Leu Pro  Leu Pro Val
    1010                1015                1020
Ser Ser  Asp
    1025

<210> SEQ ID NO 30
<211> LENGTH: 1018
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 30

Glu Phe Val Asn Lys Gln Phe Asn Tyr Lys Asp Pro Val Asn Gly Val
1               5                   10                  15
Asp Ile Ala Tyr Ile Lys Ile Pro Asn Ala Gly Gln Met Gln Pro Val
            20                  25                  30
Lys Ala Phe Lys Ile His Asn Lys Ile Trp Val Ile Pro Glu Arg Asp
        35                  40                  45
Thr Phe Thr Asn Pro Glu Glu Gly Asp Leu Asn Pro Pro Glu Ala
    50                  55                  60

```
Lys Gln Val Pro Val Ser Tyr Asp Ser Thr Tyr Leu Ser Thr Asp
 65                  70                  75                  80

Asn Glu Lys Asp Asn Tyr Leu Lys Gly Val Thr Lys Leu Phe Glu Arg
                 85                  90                  95

Ile Tyr Ser Thr Asp Leu Gly Arg Met Leu Leu Thr Ser Ile Val Arg
                100                 105                 110

Gly Ile Pro Phe Trp Gly Gly Ser Thr Ile Asp Thr Glu Leu Lys Val
            115                 120                 125

Ile Asp Thr Asn Cys Ile Asn Val Ile Gln Pro Asp Gly Ser Tyr Arg
        130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
        355                 360                 365

Asp Lys Ala Val Phe Lys Ile Asn Ile Val Pro Lys Val Asn Tyr Thr
    370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Gly
            420                 425                 430

Ile Ile Thr Ser Lys Thr Lys Ser Asp Asp Asp Lys Met Phe Asn
        435                 440                 445

Leu Pro Pro Gly Asn Tyr Lys Lys Pro Lys Leu Leu Tyr Cys Ser Asn
    450                 455                 460

Gly Gly His Phe Leu Arg Ile Leu Pro Asp Gly Thr Val Asp Gly Thr
465                 470                 475                 480
```

-continued

Arg Asp Arg Ser Asp Gln His Ile Gln Leu Gln Leu Ser Ala Glu Ser
            485                 490                 495

Val Gly Glu Val Tyr Ile Lys Ser Thr Glu Thr Gly Gln Tyr Leu Ala
            500                 505                 510

Met Asp Thr Asp Gly Leu Leu Tyr Gly Ser Gln Thr Pro Asn Glu Glu
            515                 520                 525

Cys Leu Phe Leu Glu Arg Leu Glu Glu Asn His Tyr Asn Thr Tyr Ile
            530                 535                 540

Ser Lys Lys His Ala Glu Lys Asn Trp Phe Val Gly Leu Lys Lys Asn
545                 550                 555                 560

Gly Ser Cys Lys Arg Gly Pro Arg Thr His Tyr Gly Gln Lys Ala Ile
            565                 570                 575

Leu Phe Leu Pro Leu Pro Val Ser Ser Asp Gly Gly Gly Ser Gly
            580                 585                 590

Gly Gly Gly Ser Gly Gly Gly Ser Ala Leu Val Leu Gln Cys Ile
            595                 600                 605

Lys Val Asn Asn Trp Asp Leu Phe Phe Ser Pro Ser Glu Asp Asn Phe
            610                 615                 620

Thr Asn Asp Leu Asn Lys Gly Glu Glu Ile Thr Ser Asp Thr Asn Ile
625                 630                 635                 640

Glu Ala Ala Glu Glu Asn Ile Ser Leu Asp Leu Ile Gln Gln Tyr Tyr
            645                 650                 655

Leu Thr Phe Asn Phe Asp Asn Glu Pro Glu Asn Ile Ser Ile Glu Asn
            660                 665                 670

Leu Ser Ser Asp Ile Ile Gly Gln Leu Glu Leu Met Pro Asn Ile Glu
            675                 680                 685

Arg Phe Pro Asn Gly Lys Lys Tyr Glu Leu Asp Lys Tyr Thr Met Phe
            690                 695                 700

His Tyr Leu Arg Ala Gln Glu Phe Glu His Gly Lys Ser Arg Ile Ala
705                 710                 715                 720

Leu Thr Asn Ser Val Asn Glu Ala Leu Leu Asn Pro Ser Arg Val Tyr
            725                 730                 735

Thr Phe Phe Ser Ser Asp Tyr Val Lys Lys Val Asn Lys Ala Thr Glu
            740                 745                 750

Ala Ala Met Phe Leu Gly Trp Val Glu Gln Leu Val Tyr Asp Phe Thr
            755                 760                 765

Asp Glu Thr Ser Glu Val Ser Thr Thr Asp Lys Ile Ala Asp Ile Thr
            770                 775                 780

Ile Ile Ile Pro Tyr Ile Gly Pro Ala Leu Asn Ile Gly Asn Met Leu
785                 790                 795                 800

Tyr Lys Asp Asp Phe Val Gly Ala Leu Ile Phe Ser Gly Ala Val Ile
            805                 810                 815

Leu Leu Glu Phe Ile Pro Glu Ile Ala Ile Pro Val Leu Gly Thr Phe
            820                 825                 830

Ala Leu Val Ser Tyr Ile Ala Asn Lys Val Leu Thr Val Gln Thr Ile
            835                 840                 845

Asp Asn Ala Leu Ser Lys Arg Asn Glu Lys Trp Asp Glu Val Tyr Lys
            850                 855                 860

Tyr Ile Val Thr Asn Trp Leu Ala Lys Val Asn Thr Gln Ile Asp Leu
865                 870                 875                 880

Ile Arg Lys Lys Met Lys Glu Ala Leu Glu Asn Gln Ala Glu Ala Thr
            885                 890                 895

Lys Ala Ile Ile Asn Tyr Gln Tyr Asn Gln Tyr Thr Glu Glu Glu Lys

```
                900           905           910
Asn Asn Ile Asn Phe Asn Ile Asp Asp Leu Ser Ser Lys Leu Asn Glu
        915                 920                 925

Ser Ile Asn Lys Ala Met Ile Asn Ile Asn Lys Phe Leu Asn Gln Cys
        930                 935                 940

Ser Val Ser Tyr Leu Met Asn Ser Met Ile Pro Tyr Gly Val Lys Arg
945                 950                 955                 960

Leu Glu Asp Phe Asp Ala Ser Leu Lys Asp Ala Leu Leu Lys Tyr Ile
                965                 970                 975

Tyr Asp Asn Arg Gly Thr Leu Ile Gly Gln Val Asp Arg Leu Lys Asp
                980                 985                 990

Lys Val Asn Asn Thr Leu Ser Thr Asp Ile Pro Phe Gln Leu Ser Lys
        995                 1000                1005

Tyr Val Asp Asn Gln Arg Leu Leu Ser Thr
        1010                1015

<210> SEQ ID NO 31
<211> LENGTH: 1063
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
                20                  25                  30

Lys Ala Phe Lys Ile His Asn Lys Ile Trp Val Ile Pro Glu Arg Asp
            35                  40                  45

Thr Phe Thr Asn Pro Glu Glu Gly Asp Leu Asn Pro Pro Pro Glu Ala
        50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
                100                 105                 110

Gly Ile Pro Phe Trp Gly Gly Ser Thr Ile Asp Thr Glu Leu Lys Val
            115                 120                 125

Ile Asp Thr Asn Cys Ile Asn Val Ile Gln Pro Asp Gly Ser Tyr Arg
        130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
                180                 185                 190

Phe Gly Phe Glu Glu Ser Leu Glu Val Asp Thr Asn Pro Leu Leu Gly
            195                 200                 205

Ala Gly Lys Phe Ala Thr Asp Pro Ala Val Thr Leu Ala His Glu Leu
        210                 215                 220

Ile His Ala Gly His Arg Leu Tyr Gly Ile Ala Ile Asn Pro Asn Arg
225                 230                 235                 240
```

```
Val Phe Lys Val Asn Thr Asn Ala Tyr Tyr Glu Met Ser Gly Leu Glu
            245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
            275                 280                 285

Phe Lys Asp Ile Ala Ser Thr Leu Asn Lys Ala Lys Ser Ile Val Gly
            290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
            325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
            355                 360                 365

Asp Lys Ala Val Phe Lys Ile Asn Ile Val Pro Lys Val Asn Tyr Thr
            370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
            405                 410                 415

Asn Phe Thr Gly Leu Phe Glu Phe Tyr Lys Leu Leu Cys Val Asp Gly
            420                 425                 430

Ile Ile Thr Ser Lys Thr Lys Ser Asp Asp Asp Lys Asn Lys Ala
            435                 440                 445

Leu Asn Leu Gln Cys Ile Lys Val Asn Asn Trp Asp Leu Phe Phe Ser
            450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
            485                 490                 495

Leu Ile Gln Gln Tyr Tyr Leu Thr Phe Asn Phe Asp Asn Glu Pro Glu
            500                 505                 510

Asn Ile Ser Ile Glu Asn Leu Ser Ser Asp Ile Ile Gly Gln Leu Glu
            515                 520                 525

Leu Met Pro Asn Ile Glu Arg Phe Pro Asn Gly Lys Lys Tyr Glu Leu
            530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
            565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
            595                 600                 605

Leu Val Tyr Asp Phe Thr Asp Glu Thr Ser Glu Val Ser Thr Thr Asp
            610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
            645                 650                 655
```

```
Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
            675                 680                 685

Leu Thr Val Gln Thr Ile Asp Asn Ala Leu Ser Lys Arg Asn Glu Lys
            690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
            755                 760                 765

Ser Ser Lys Leu Asn Glu Ser Ile Asn Lys Ala Met Ile Asn Ile Asn
            770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
            805                 810                 815

Ala Leu Leu Lys Tyr Ile Tyr Asp Asn Arg Gly Thr Leu Ile Gly Gln
            820                 825                 830

Val Asp Arg Leu Lys Asp Lys Val Asn Asn Thr Leu Ser Thr Asp Ile
            835                 840                 845

Pro Phe Gln Leu Ser Lys Tyr Val Asp Asn Gln Arg Leu Leu Ser Thr
            850                 855                 860

Leu Glu Gly Gly Gly Gly Ser Gly Gly Gly Gly Ser Gly Gly Gly Gly
865                 870                 875                 880

Ser Gly Gly Gly Gly Ser Ala Leu Val Asp His Leu Gly Gln Ser Glu
            885                 890                 895

Ala Gly Gly Leu Pro Arg Gly Pro Ala Val Thr Asp Leu Asp His Leu
            900                 905                 910

Lys Gly Ile Leu Arg Arg Arg Gln Leu Tyr Cys Arg Thr Gly Phe His
            915                 920                 925

Leu Glu Ile Phe Pro Asn Gly Thr Ile Gln Gly Thr Arg Lys Asp His
            930                 935                 940

Ser Arg Phe Gly Ile Leu Glu Phe Ile Ser Ile Ala Val Gly Leu Val
945                 950                 955                 960

Ser Ile Arg Gly Val Asp Ser Gly Leu Tyr Leu Gly Met Asn Glu Lys
            965                 970                 975

Gly Glu Leu Tyr Gly Ser Glu Lys Leu Thr Gln Glu Cys Val Phe Arg
            980                 985                 990

Glu Gln Phe Glu Glu Asn Trp Tyr Asn Thr Tyr Ser Ser Asn Leu Tyr
            995                1000                1005

Lys His Val Asp Thr Gly Arg Arg Tyr Tyr Val Ala Leu Asn Lys
            1010                1015                1020

Asp Gly Thr Pro Arg Glu Gly Thr Arg Thr Lys Arg His Gln Lys
            1025                1030                1035

Phe Thr His Phe Leu Pro Arg Pro Val Asp Pro Asp Lys Val Pro
            1040                1045                1050

Glu Leu Tyr Lys Asp Ile Leu Ser Gln Ser
            1055                1060
```

```
<210> SEQ ID NO 32
<211> LENGTH: 1055
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32
```

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

-continued

```
Gln Asn Arg Lys Ile Tyr Leu Ser Asn Val Tyr Thr Pro Val Thr Ala
    370                 375                 380
Asn Ile Leu Asp Asp Asn Val Tyr Asp Ile Gln Asn Gly Phe Asn Ile
385                 390                 395                 400
Pro Lys Ser Asn Leu Asn Val Leu Phe Met Gly Gln Asn Leu Ser Arg
                405                 410                 415
Asn Pro Ala Leu Arg Lys Val Asn Pro Glu Asn Met Leu Tyr Leu Phe
            420                 425                 430
Thr Lys Phe Cys Val Asp Asn Asn Asn Asn Asn Asn Asn Asn Asn Asn
        435                 440                 445
Asp Asp Asp Asp Lys Asp His Leu Gly Gln Ser Glu Ala Gly Gly Leu
    450                 455                 460
Pro Arg Gly Pro Ala Val Thr Asp Leu Asp His Leu Lys Gly Ile Leu
465                 470                 475                 480
Arg Arg Arg Gln Leu Tyr Cys Arg Thr Gly Phe His Leu Glu Ile Phe
                485                 490                 495
Pro Asn Gly Thr Ile Gln Gly Thr Arg Lys Asp His Ser Arg Phe Gly
            500                 505                 510
Ile Leu Glu Phe Ile Ser Ile Ala Val Gly Leu Val Ser Ile Arg Gly
    515                 520                 525
Val Asp Ser Gly Leu Tyr Leu Gly Met Asn Glu Lys Gly Glu Leu Tyr
530                 535                 540
Gly Ser Glu Lys Leu Thr Gln Glu Cys Val Phe Arg Glu Gln Phe Glu
545                 550                 555                 560
Glu Asn Trp Tyr Asn Thr Tyr Ser Ser Asn Leu Tyr Lys His Val Asp
                565                 570                 575
Thr Gly Arg Arg Tyr Tyr Val Ala Leu Asn Lys Asp Gly Thr Pro Arg
            580                 585                 590
Glu Gly Thr Arg Thr Lys Arg His Gln Lys Phe Thr His Phe Leu Pro
        595                 600                 605
Arg Pro Val Asp Pro Asp Lys Val Pro Glu Leu Tyr Lys Asp Ile Leu
    610                 615                 620
Ser Gln Ser Ala Glu Ala Ala Lys Glu Ala Ala Lys Ala Leu
625                 630                 635                 640
Gln Cys Arg Glu Leu Leu Val Lys Asn Thr Asp Leu Pro Phe Ile Gly
                645                 650                 655
Asp Ile Ser Asp Val Lys Thr Asp Ile Phe Leu Arg Lys Asp Ile Asn
            660                 665                 670
Glu Glu Thr Glu Val Ile Tyr Tyr Pro Asp Asn Val Ser Val Asp Gln
        675                 680                 685
Val Ile Leu Ser Lys Asn Thr Ser Glu His Gly Gln Leu Asp Leu Leu
    690                 695                 700
Tyr Pro Ser Ile Asp Ser Glu Ser Glu Ile Leu Pro Gly Glu Asn Gln
705                 710                 715                 720
Val Phe Tyr Asp Asn Arg Thr Gln Asn Val Asp Tyr Leu Asn Ser Tyr
                725                 730                 735
Tyr Tyr Leu Glu Ser Gln Lys Leu Ser Asp Asn Val Glu Asp Phe Thr
            740                 745                 750
Phe Thr Arg Ser Ile Glu Glu Ala Leu Asp Asn Ser Ala Lys Val Tyr
        755                 760                 765
Thr Tyr Phe Pro Thr Leu Ala Asn Lys Val Asn Ala Gly Val Gln Gly
    770                 775                 780
```

```
Gly Leu Phe Leu Met Trp Ala Asn Asp Val Val Glu Asp Phe Thr Thr
785                 790                 795                 800

Asn Ile Leu Arg Lys Asp Thr Leu Asp Lys Ile Ser Asp Val Ser Ala
                805                 810                 815

Ile Ile Pro Tyr Ile Gly Pro Ala Leu Asn Ile Ser Asn Ser Val Arg
            820                 825                 830

Arg Gly Asn Phe Thr Glu Ala Phe Ala Val Thr Gly Val Thr Ile Leu
        835                 840                 845

Leu Glu Ala Phe Pro Glu Phe Thr Ile Pro Ala Leu Gly Ala Phe Val
    850                 855                 860

Ile Tyr Ser Lys Val Gln Glu Arg Asn Glu Ile Ile Lys Thr Ile Asp
865                 870                 875                 880

Asn Cys Leu Glu Gln Arg Ile Lys Arg Trp Lys Asp Ser Tyr Glu Trp
                885                 890                 895

Met Met Gly Thr Trp Leu Ser Arg Ile Ile Thr Gln Phe Asn Asn Ile
            900                 905                 910

Ser Tyr Gln Met Tyr Asp Ser Leu Asn Tyr Gln Ala Gly Ala Ile Lys
        915                 920                 925

Ala Lys Ile Asp Leu Glu Tyr Lys Lys Tyr Ser Gly Ser Asp Lys Glu
    930                 935                 940

Asn Ile Lys Ser Gln Val Glu Asn Leu Lys Asn Ser Leu Asp Val Lys
945                 950                 955                 960

Ile Ser Glu Ala Met Asn Asn Ile Asn Lys Phe Ile Arg Glu Cys Ser
                965                 970                 975

Val Thr Tyr Leu Phe Lys Asn Met Leu Pro Lys Val Ile Asp Glu Leu
            980                 985                 990

Asn Glu Phe Asp Arg Asn Thr Lys Ala Lys Leu Ile Asn Leu Ile Asp
        995                 1000                1005

Ser His Asn Ile Ile Leu Val Gly Glu Val Asp Lys Leu Lys Ala
    1010                1015                1020

Lys Val Asn Asn Ser Phe Gln Asn Thr Ile Pro Phe Asn Ile Phe
    1025                1030                1035

Ser Tyr Thr Asn Asn Ser Leu Leu Lys Asp Ile Ile Asn Glu Tyr
    1040                1045                1050

Phe Asn
    1055

<210> SEQ ID NO 33
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Ser Asn Gln Pro Gly Lys Asn Gly Thr Ala Thr Lys Pro Glu Asn
1               5                   10                  15

Ser Gly Asn Thr Thr Ser Glu Asn Gly Gln Thr Glu Pro Glu Lys Lys
            20                  25                  30

Leu Glu Leu Arg Asn Val Ser Asp Ile Glu Leu Tyr Ser Gln Thr Asn
        35                  40                  45

Gly Thr Tyr Arg Gln His Val Ser Leu Asp Gly Ile Pro Glu Asn Thr
    50                  55                  60

Asp Thr Tyr Phe Val Lys Val Lys Ser Ser Ala Phe Lys Asp Val Tyr
```

```
                65                  70                  75                  80
            Ile Pro Val Ala Ser Ile Thr Glu Glu Lys Arg Asn Gly Gln Ser Val
                            85                  90                  95
            Tyr Lys Ile Thr Ala Lys Ala Glu Lys Leu Gln Gln Glu Leu Glu Asn
                        100                 105                 110
            Lys Tyr Val Asp Asn Phe Thr Phe Tyr Leu Asp Lys Lys Ala Lys Glu
                    115                 120                 125
            Glu Asn Thr Asn Phe Thr Ser Phe Ser Asn Leu Val Lys Ala Ile Asn
                130                 135                 140
            Gln Asn Pro Ser Gly Thr Tyr His Leu Ala Ala Ser Leu Asn Ala Asn
            145                 150                 155                 160
            Glu Val Glu Leu Gly Pro Asp Glu Arg Ser Tyr Ile Lys Asp Thr Phe
                            165                 170                 175
            Thr Gly Arg Leu Ile Gly Glu Lys Asp Gly Lys Asn Tyr Ala Ile Tyr
                        180                 185                 190
            Asn Leu Lys Lys Pro Leu Phe Glu Asn Leu Ser Gly Ala Thr Val Glu
                    195                 200                 205
            Lys Leu Ser Leu Lys Asn Val Ala Ile Ser Gly Lys Asn Asp Ile Gly
                210                 215                 220
            Ser Leu Ala Asn Glu Ala Thr Asn Gly Thr Lys Ile Lys Gln Val His
            225                 230                 235                 240
            Val Asp Gly Cys Val Asp Gly Ile Ile Thr Ser Lys Thr Lys Ser Asp
                            245                 250                 255
            Asp Asp Asp Lys Asn Lys Ala Leu Asn Leu Gln Cys Ile Lys Ile Lys
                        260                 265                 270
            Asn Glu Asp Leu Thr Phe Ile Ala Glu Lys Asn Ser Phe Ser Glu Glu
                    275                 280                 285
            Pro Phe Gln Asp Glu Ile Val Ser Tyr Asn Thr Lys Asn Lys Pro Leu
                290                 295                 300
            Asn Phe Asn Tyr Ser Leu Asp Lys Ile Ile Val Asp Tyr Asn Leu Gln
            305                 310                 315                 320
            Ser Lys Ile Thr Leu Pro Asn Asp Arg Thr Thr Pro Val Thr Lys Gly
                            325                 330                 335
            Ile Pro Tyr Ala Pro Glu Tyr Lys Ser Asn Ala Ala Ser Thr Ile Glu
                        340                 345                 350
            Ile His Asn Ile Asp Asp Asn Thr Ile Tyr Gln Tyr Leu Tyr Ala Gln
                    355                 360                 365
            Lys Ser Pro Thr Thr Leu Gln Arg Ile Thr Met Thr Asn Ser Val Asp
                370                 375                 380
            Asp Ala Leu Ile Asn Ser Thr Lys Ile Tyr Ser Tyr Phe Pro Ser Val
            385                 390                 395                 400
            Ile Ser Lys Val Asn Gln Gly Ala Gln Gly Ile Leu Phe Leu Gln Trp
                            405                 410                 415
            Val Arg Asp Ile Ile Asp Asp Phe Thr Asn Glu Ser Ser Gln Lys Thr
                        420                 425                 430
            Thr Ile Asp Lys Ile Ser Asp Val Ser Thr Ile Val Pro Tyr Ile Gly
                    435                 440                 445
            Pro Ala Leu Asn Ile Val Lys Gln Gly Tyr Glu Gly Asn Phe Ile Gly
                450                 455                 460
            Ala Leu Glu Thr Thr Gly Val Val Leu Leu Leu Glu Tyr Ile Pro Glu
            465                 470                 475                 480
            Ile Thr Leu Pro Val Ile Ala Ala Leu Ser Ile Ala Glu Ser Ser Thr
                            485                 490                 495
```

```
Gln Lys Glu Lys Ile Ile Lys Thr Ile Asp Asn Phe Leu Glu Lys Arg
            500                 505                 510

Tyr Glu Lys Trp Ile Glu Val Tyr Lys Leu Val Lys Ala Lys Trp Leu
        515                 520                 525

Gly Thr Val Asn Thr Gln Phe Gln Lys Arg Ser Tyr Gln Met Tyr Arg
    530                 535                 540

Ser Leu Glu Tyr Gln Val Asp Ala Ile Lys Lys Ile Asp Tyr Glu
545                 550                 555                 560

Tyr Lys Ile Tyr Ser Gly Pro Asp Lys Glu Gln Ile Ala Asp Glu Ile
                565                 570                 575

Asn Asn Leu Lys Asn Lys Leu Glu Glu Lys Ala Asn Lys Ala Met Ile
            580                 585                 590

Asn Ile Asn Ile Phe Met Arg Glu Ser Ser Arg Ser Phe Leu Val Asn
        595                 600                 605

Gln Met Ile Asn Glu Ala Lys Lys Gln Leu Leu Glu Phe Asp Thr Gln
    610                 615                 620

Ser Lys Asn Ile Leu Met Gln Tyr Ile Lys Ala Asn Ser Lys Phe Ile
625                 630                 635                 640

Gly Ile Thr Glu Leu Lys Lys Leu Glu Ser Lys Ile Asn Lys Val Phe
                645                 650                 655

Ser Thr Pro Ile Pro Phe Ser Tyr Ser Lys Asn Leu Asp Cys Trp Val
            660                 665                 670

Asp Asn Glu Glu Asp Ile Asp Val Leu Glu Gly Gly Gly Ser Gly
        675                 680                 685

Gly Gly Gly Ser Gly Gly Gly Ser Ala Leu Val Ala Gly Cys Lys
    690                 695                 700

Asn Phe Phe Trp Lys Thr Phe Thr Ser Cys
705                 710

<210> SEQ ID NO 34
<211> LENGTH: 710
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Ser Asn Gln Pro Glu Lys Asn Gly Thr Ala Thr Lys Pro Glu Asn
1               5                   10                  15

Ser Gly Asn Thr Thr Ser Glu Asn Gly Gln Thr Glu Pro Glu Lys Lys
            20                  25                  30

Leu Glu Leu Arg Asn Val Ser Asp Ile Glu Leu Tyr Ser Gln Thr Asn
        35                  40                  45

Gly Thr Tyr Arg Gln His Val Ser Leu Asp Gly Ile Pro Glu Asn Thr
    50                  55                  60

Asp Thr Tyr Phe Val Lys Val Lys Ser Ser Ala Phe Lys Asp Val Tyr
65                  70                  75                  80

Ile Pro Val Ala Ser Ile Thr Glu Glu Lys Arg Asn Gly Gln Ser Val
            85                  90                  95

Tyr Lys Ile Thr Ala Lys Ala Glu Lys Leu Gln Gln Glu Leu Glu Asn
            100                 105                 110

Lys Tyr Val Asp Asn Phe Thr Phe Tyr Leu Asp Lys Lys Ala Lys Glu
        115                 120                 125
```

```
Glu Asn Thr Asn Phe Thr Ser Phe Ser Asn Leu Val Lys Ala Ile Asn
    130                 135                 140

Gln Asn Pro Ser Gly Thr Tyr His Leu Ala Ala Ser Leu Asn Ala Asn
145                 150                 155                 160

Glu Val Glu Leu Gly Pro Asp Glu Arg Ser Tyr Ile Lys Asp Thr Phe
                165                 170                 175

Thr Gly Arg Leu Ile Gly Glu Lys Asp Gly Lys Asn Tyr Ala Ile Tyr
                180                 185                 190

Asn Leu Lys Lys Pro Leu Phe Glu Asn Leu Ser Gly Ala Thr Val Glu
                195                 200                 205

Lys Leu Ser Leu Lys Asn Val Ala Ile Ser Gly Lys Asn Asp Ile Gly
    210                 215                 220

Ser Leu Ala Asn Glu Ala Thr Asn Gly Thr Lys Ile Lys Gln Val His
225                 230                 235                 240

Val Asp Gly Cys Val Asp Gly Ile Ile Thr Ser Lys Thr Lys Ser Asp
                245                 250                 255

Asp Asp Asp Lys Ala Gly Cys Lys Asn Phe Phe Trp Lys Thr Phe Thr
                260                 265                 270

Ser Cys Ala Leu Ala Gly Gly Gly Ser Gly Gly Gly Gly Ser Gly
                275                 280                 285

Gly Gly Gly Ser Ala Leu Ala Leu Gln Cys Ile Lys Ile Lys Asn Glu
    290                 295                 300

Asp Leu Thr Phe Ile Ala Glu Lys Asn Ser Phe Ser Glu Glu Pro Phe
305                 310                 315                 320

Gln Asp Glu Ile Val Ser Tyr Asn Thr Lys Asn Lys Pro Leu Asn Phe
                325                 330                 335

Asn Tyr Ser Leu Asp Lys Ile Ile Val Asp Tyr Asn Leu Gln Ser Lys
                340                 345                 350

Ile Thr Leu Pro Asn Asp Arg Thr Thr Pro Val Thr Lys Gly Ile Pro
                355                 360                 365

Tyr Ala Pro Glu Tyr Lys Ser Asn Ala Ala Ser Thr Ile Glu Ile His
    370                 375                 380

Asn Ile Asp Asp Asn Thr Ile Tyr Gln Tyr Leu Tyr Ala Gln Lys Ser
385                 390                 395                 400

Pro Thr Thr Leu Gln Arg Ile Thr Met Thr Asn Ser Val Asp Asp Ala
                405                 410                 415

Leu Ile Asn Ser Thr Lys Ile Tyr Ser Tyr Phe Pro Ser Val Ile Ser
                420                 425                 430

Lys Val Asn Gln Gly Ala Gln Gly Ile Leu Phe Leu Gln Trp Val Arg
    435                 440                 445

Asp Ile Ile Asp Asp Phe Thr Asn Glu Ser Ser Gln Lys Thr Thr Ile
450                 455                 460

Asp Lys Ile Ser Asp Val Ser Thr Ile Val Pro Tyr Ile Gly Pro Ala
465                 470                 475                 480

Leu Asn Ile Val Lys Gln Gly Tyr Glu Gly Asn Phe Ile Gly Ala Leu
                485                 490                 495

Glu Thr Thr Gly Val Val Leu Leu Glu Tyr Ile Pro Glu Ile Thr
                500                 505                 510

Leu Pro Val Ile Ala Ala Leu Ser Ile Ala Glu Ser Ser Thr Gln Lys
                515                 520                 525

Glu Lys Ile Ile Lys Thr Ile Asp Asn Phe Leu Glu Lys Arg Tyr Glu
    530                 535                 540

Lys Trp Ile Glu Val Tyr Lys Leu Val Lys Ala Lys Trp Leu Gly Thr
```

```
                545                 550                 555                 560
Val Asn Thr Gln Phe Gln Lys Arg Ser Tyr Gln Met Tyr Arg Ser Leu
                    565                 570                 575

Glu Tyr Gln Val Asp Ala Ile Lys Lys Ile Ile Asp Tyr Glu Tyr Lys
                    580                 585                 590

Ile Tyr Ser Gly Pro Asp Lys Glu Gln Ile Ala Asp Glu Ile Asn Asn
                    595                 600                 605

Leu Lys Asn Lys Leu Glu Glu Lys Ala Asn Lys Ala Met Ile Asn Ile
                    610                 615                 620

Asn Ile Phe Met Arg Glu Ser Ser Arg Ser Phe Leu Val Asn Gln Met
625                 630                 635                 640

Ile Asn Glu Ala Lys Lys Gln Leu Leu Glu Phe Asp Thr Gln Ser Lys
                    645                 650                 655

Asn Ile Leu Met Gln Tyr Ile Lys Ala Asn Ser Lys Phe Ile Gly Ile
                    660                 665                 670

Thr Glu Leu Lys Lys Leu Glu Ser Lys Ile Asn Lys Val Phe Ser Thr
                    675                 680                 685

Pro Ile Pro Phe Ser Tyr Ser Lys Asn Leu Asp Cys Trp Val Asp Asn
                    690                 695                 700

Glu Glu Asp Ile Asp Val
705                 710

<210> SEQ ID NO 35
<211> LENGTH: 898
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
                20                  25                  30

Lys Ala Phe Lys Ile His Asn Lys Ile Trp Val Ile Pro Glu Arg Asp
                35                  40                  45

Thr Phe Thr Asn Pro Glu Glu Gly Asp Leu Asn Pro Pro Pro Glu Ala
            50                  55                  60

Lys Gln Val Pro Val Ser Tyr Tyr Asp Ser Thr Tyr Leu Ser Thr Asp
65              70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
                100                 105                 110

Gly Ile Pro Phe Trp Gly Gly Ser Thr Ile Asp Thr Glu Leu Lys Val
                115                 120                 125

Ile Asp Thr Asn Cys Ile Asn Val Ile Gln Pro Asp Gly Ser Tyr Arg
            130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
                180                 185                 190
```

-continued

Phe Gly Phe Glu Glu Ser Leu Glu Val Asp Thr Asn Pro Leu Leu Gly
              195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
                260                 265                 270

Ile Asp Ser Leu Gln Glu Asn Glu Phe Arg Leu Tyr Tyr Tyr Asn Lys
                275                 280                 285

Phe Lys Asp Ile Ala Ser Thr Leu Asn Lys Ala Lys Ser Ile Val Gly
                290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
                340                 345                 350

Phe Val Lys Phe Phe Lys Val Leu Asn Arg Lys Thr Tyr Leu Asn Phe
                355                 360                 365

Asp Lys Ala Val Phe Lys Ile Asn Ile Val Pro Lys Val Asn Tyr Thr
                370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Gly
                420                 425                 430

Ile Ile Thr Ser Lys Thr Lys Ser Asp Asp Asp Lys Asn Lys Ala
                435                 440                 445

Leu Asn Leu Gln Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
                485                 490                 495

Leu Ile Gln Gln Tyr Tyr Leu Thr Phe Asn Phe Asp Asn Glu Pro Glu
                500                 505                 510

Asn Ile Ser Ile Glu Asn Leu Ser Ser Asp Ile Ile Gly Gln Leu Glu
                515                 520                 525

Leu Met Pro Asn Ile Glu Arg Phe Pro Asn Gly Lys Lys Tyr Glu Leu
    530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
                580                 585                 590

Val Asn Lys Ala Thr Glu Ala Ala Met Phe Leu Gly Trp Val Glu Gln
    595                 600                 605

```
Leu Val Tyr Asp Phe Thr Asp Glu Thr Ser Glu Val Ser Thr Thr Asp
    610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Glu Phe Ile Pro Glu Ile Ala Ile
                660                 665                 670

Pro Val Leu Gly Thr Phe Ala Leu Val Ser Tyr Ile Ala Asn Lys Val
                675                 680                 685

Leu Thr Val Gln Thr Ile Asp Asn Ala Leu Ser Lys Arg Asn Glu Lys
690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
                740                 745                 750

Tyr Thr Glu Glu Glu Lys Asn Asn Ile Asn Phe Asn Ile Asp Asp Leu
                755                 760                 765

Ser Ser Lys Leu Asn Glu Ser Ile Asn Lys Ala Met Ile Asn Ile Asn
770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
                820                 825                 830

Val Asp Arg Leu Lys Asp Lys Val Asn Asn Thr Leu Ser Thr Asp Ile
                835                 840                 845

Pro Phe Gln Leu Ser Lys Tyr Val Asp Asn Gln Arg Leu Leu Ser Thr
                850                 855                 860

Leu Glu Gly Gly Gly Gly Ser Gly Gly Gly Gly Ser Gly Gly Gly Gly
865                 870                 875                 880

Ser Ala Leu Val Ala Gly Cys Lys Asn Phe Phe Trp Lys Thr Phe Thr
                885                 890                 895

Ser Cys

<210> SEQ ID NO 36
<211> LENGTH: 943
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
                20                  25                  30

Lys Ala Phe Lys Ile His Asn Lys Ile Trp Val Ile Pro Glu Arg Asp
            35                  40                  45

Thr Phe Thr Asn Pro Glu Glu Gly Asp Leu Asn Pro Pro Pro Glu Ala
        50                  55                  60
```

```
Lys Gln Val Pro Val Ser Tyr Asp Ser Thr Tyr Leu Ser Thr Asp
 65                  70                  75                  80

Asn Glu Lys Asp Asn Tyr Leu Lys Gly Val Thr Lys Leu Phe Glu Arg
                 85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
130                 135                 140

Ser Glu Glu Leu Asn Leu Val Ile Ile Gly Pro Ser Ala Asp Ile Ile
145                 150                 155                 160

Gln Phe Glu Cys Leu Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
        355                 360                 365

Asp Lys Ala Val Phe Lys Ile Asn Ile Val Pro Lys Val Asn Tyr Thr
    370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Asp Gly
            420                 425                 430

Ile Ile Thr Ser Lys Thr Lys Ser Asp Asp Asp Lys Asn Lys Ala
        435                 440                 445

Leu Asn Leu Gln Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480
```

-continued

```
Thr Ser Asp Thr Asn Ile Glu Ala Ala Glu Glu Asn Ile Ser Leu Asp
            485                 490                 495
Leu Ile Gln Gln Tyr Tyr Leu Thr Phe Asn Phe Asp Asn Glu Pro Glu
        500                 505                 510
Asn Ile Ser Ile Glu Asn Leu Ser Ser Asp Ile Ile Gly Gln Leu Glu
    515                 520                 525
Leu Met Pro Asn Ile Glu Arg Phe Pro Asn Gly Lys Lys Tyr Glu Leu
530                 535                 540
Asp Lys Tyr Thr Met Phe His Tyr Leu Arg Ala Gln Glu Phe Glu His
545                 550                 555                 560
Gly Lys Ser Arg Ile Ala Leu Thr Asn Ser Val Asn Glu Ala Leu Leu
                565                 570                 575
Asn Pro Ser Arg Val Tyr Thr Phe Phe Ser Ser Asp Tyr Val Lys Lys
            580                 585                 590
Val Asn Lys Ala Thr Glu Ala Ala Met Phe Leu Gly Trp Val Glu Gln
        595                 600                 605
Leu Val Tyr Asp Phe Thr Asp Glu Thr Ser Glu Val Ser Thr Thr Asp
    610                 615                 620
Lys Ile Ala Asp Ile Thr Ile Ile Pro Tyr Ile Gly Pro Ala Leu
625                 630                 635                 640
Asn Ile Gly Asn Met Leu Tyr Lys Asp Asp Phe Val Gly Ala Leu Ile
                645                 650                 655
Phe Ser Gly Ala Val Ile Leu Leu Glu Phe Ile Pro Glu Ile Ala Ile
            660                 665                 670
Pro Val Leu Gly Thr Phe Ala Leu Val Ser Tyr Ile Ala Asn Lys Val
        675                 680                 685
Leu Thr Val Gln Thr Ile Asp Asn Ala Leu Ser Lys Arg Asn Glu Lys
    690                 695                 700
Trp Asp Glu Val Tyr Lys Tyr Ile Val Thr Asn Trp Leu Ala Lys Val
705                 710                 715                 720
Asn Thr Gln Ile Asp Leu Ile Arg Lys Lys Met Lys Glu Ala Leu Glu
                725                 730                 735
Asn Gln Ala Glu Ala Thr Lys Ala Ile Ile Asn Tyr Gln Tyr Asn Gln
            740                 745                 750
Tyr Thr Glu Glu Glu Lys Asn Asn Ile Asn Phe Asn Ile Asp Asp Leu
        755                 760                 765
Ser Ser Lys Leu Asn Glu Ser Ile Asn Lys Ala Met Ile Asn Ile Asn
    770                 775                 780
Lys Phe Leu Asn Gln Cys Ser Val Ser Tyr Leu Met Asn Ser Met Ile
785                 790                 795                 800
Pro Tyr Gly Val Lys Arg Leu Glu Asp Phe Asp Ala Ser Leu Lys Asp
                805                 810                 815
Ala Leu Leu Lys Tyr Ile Tyr Asp Asn Arg Gly Thr Leu Ile Gly Gln
            820                 825                 830
Val Asp Arg Leu Lys Asp Lys Val Asn Asn Thr Leu Ser Thr Asp Ile
        835                 840                 845
Pro Phe Gln Leu Ser Lys Tyr Val Asp Asn Gln Arg Leu Leu Ser Thr
    850                 855                 860
Leu Glu Gly Gly Gly Gly Ser Gly Gly Gly Ser Gly Gly Gly Gly
865                 870                 875                 880
Ser Gly Gly Gly Gly Ser Ala Leu Val Asp Asn Ser Asp Pro Lys Cys
                885                 890                 895
Pro Leu Ser His Glu Gly Tyr Cys Leu Asn Asp Gly Val Cys Met Tyr
```

```
              900                 905                 910
Ile Gly Thr Leu Asp Arg Tyr Ala Cys Asn Cys Val Val Gly Tyr Val
        915                 920                 925

Gly Glu Arg Cys Gln Tyr Arg Asp Leu Lys Leu Ala Glu Leu Arg
        930                 935                 940

<210> SEQ ID NO 37
<211> LENGTH: 1061
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Pro Lys Ile Asn Ser Phe Asn Tyr Asn Asp Pro Val Asn Asp Arg Thr
1               5                  10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln His Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Ile Asn Glu Phe Ile Gln Asp Pro Ala Leu Thr
        195                 200                 205

Leu Met His Glu Leu Ile His Ser Leu His Gly Leu Tyr Gly Ala Lys
    210                 215                 220

Gly Ile Thr Thr Thr Cys Ile Ile Thr Gln Gln Asn Pro Leu Ile
225                 230                 235                 240

Thr Asn Arg Lys Gly Ile Asn Ile Glu Glu Phe Leu Thr Phe Gly Gly
                245                 250                 255

Asn Asp Leu Asn Ile Ile Thr Val Ala Gln Tyr Asn Asp Ile Tyr Thr
            260                 265                 270

Asn Leu Leu Asn Asp Tyr Arg Lys Ile Ala Ser Lys Leu Ser Lys Val
        275                 280                 285

Gln Val Ser Asn Pro Gln Leu Asn Pro Tyr Lys Asp Ile Phe Gln Glu
    290                 295                 300

Lys Tyr Gly Leu Asp Lys Asp Ala Ser Gly Ile Tyr Ser Val Asn Ile
305                 310                 315                 320
```

```
Asn Lys Phe Asp Asp Ile Leu Lys Lys Leu Tyr Ser Phe Thr Glu Phe
                325                 330                 335

Asp Leu Ala Thr Lys Phe Gln Val Lys Cys Arg Glu Thr Tyr Ile Gly
            340                 345                 350

Gln Tyr Lys Tyr Phe Lys Leu Ser Asn Leu Leu Asn Asp Ser Ile Tyr
            355                 360                 365

Asn Ile Ser Glu Gly Tyr Asn Ile Asn Asn Leu Lys Val Asn Phe Arg
        370                 375                 380

Gly Gln Asn Ala Asn Leu Asn Pro Arg Ile Ile Lys Pro Ile Thr Gly
385                 390                 395                 400

Arg Gly Leu Val Lys Lys Ile Ile Arg Phe Cys Val Asp Gly Ile Ile
                405                 410                 415

Thr Ser Lys Thr Lys Ser Leu Ile Glu Gly Arg Asn Lys Ala Leu Asn
                420                 425                 430

Leu Gln Cys Ile Glu Ile Asn Asn Gly Glu Leu Phe Phe Val Ala Ser
        435                 440                 445

Glu Asn Ser Tyr Asn Asp Asn Ile Asn Thr Pro Lys Glu Ile Asp
        450                 455                 460

Asp Thr Val Thr Ser Asn Asn Asn Tyr Glu Asn Asp Leu Asp Gln Val
465                 470                 475                 480

Ile Leu Asn Phe Asn Ser Glu Ser Ala Pro Gly Leu Ser Asp Glu Lys
                485                 490                 495

Leu Asn Leu Thr Ile Gln Asn Asp Ala Tyr Ile Pro Lys Tyr Asp Ser
            500                 505                 510

Asn Gly Thr Ser Asp Ile Glu Gln His Asp Val Asn Glu Leu Asn Val
        515                 520                 525

Phe Phe Tyr Leu Asp Ala Gln Lys Val Pro Glu Gly Glu Asn Asn Val
530                 535                 540

Asn Leu Thr Ser Ser Ile Asp Thr Ala Leu Leu Glu Gln Pro Lys Ile
545                 550                 555                 560

Tyr Thr Phe Phe Ser Ser Glu Phe Ile Asn Asn Val Asn Lys Pro Val
                565                 570                 575

Gln Ala Ala Leu Phe Val Ser Trp Ile Gln Gln Val Leu Val Asp Phe
            580                 585                 590

Thr Thr Glu Ala Asn Gln Lys Ser Thr Val Asp Lys Ile Ala Asp Ile
            595                 600                 605

Ser Ile Val Val Pro Tyr Ile Gly Leu Ala Leu Asn Ile Gly Asn Glu
        610                 615                 620

Ala Gln Lys Gly Asn Phe Lys Asp Ala Leu Glu Leu Leu Gly Ala Gly
625                 630                 635                 640

Ile Leu Leu Glu Phe Glu Pro Glu Leu Leu Ile Pro Thr Ile Leu Val
                645                 650                 655

Phe Thr Ile Lys Ser Phe Leu Gly Ser Ser Asp Asn Lys Asn Lys Val
                660                 665                 670

Ile Lys Ala Ile Asn Asn Ala Leu Lys Glu Arg Asp Glu Lys Trp Lys
        675                 680                 685

Glu Val Tyr Ser Phe Ile Val Ser Asn Trp Met Thr Lys Ile Asn Thr
        690                 695                 700

Gln Phe Asn Lys Arg Lys Glu Gln Met Tyr Gln Ala Leu Gln Asn Gln
705                 710                 715                 720

Val Asn Ala Ile Lys Thr Ile Ile Glu Ser Lys Tyr Asn Ser Tyr Thr
                725                 730                 735
```

Leu Glu Glu Lys Asn Glu Leu Thr Asn Lys Tyr Asp Ile Lys Gln Ile
            740                 745                 750

Glu Asn Glu Leu Asn Gln Lys Val Ser Ile Ala Met Asn Asn Ile Asp
            755                 760                 765

Arg Phe Leu Thr Glu Ser Ser Ile Ser Tyr Leu Met Lys Ile Ile Asn
            770                 775                 780

Glu Val Lys Ile Asn Lys Leu Arg Glu Tyr Asp Glu Asn Val Lys Thr
785                 790                 795                 800

Tyr Leu Leu Asn Tyr Ile Ile Gln His Gly Ser Ile Leu Gly Glu Ser
            805                 810                 815

Gln Gln Glu Leu Asn Ser Met Val Thr Asp Thr Leu Asn Asn Ser Ile
            820                 825                 830

Pro Phe Lys Leu Ser Ser Tyr Thr Asp Asp Lys Ile Leu Ile Ser Tyr
            835                 840                 845

Phe Asn Lys Phe Phe Lys Leu Glu Gly Gly Gly Ser Gly Gly Gly
            850                 855                 860

Gly Ser Gly Gly Gly Ser Gly Gly Gly Ser Ala Leu Val Pro
865                 870                 875                 880

Pro Gly Glu Asp Ser Lys Asp Val Ala Ala Pro His Arg Gln Pro Leu
            885                 890                 895

Thr Ser Ser Glu Arg Ile Asp Lys Gln Ile Arg Tyr Ile Leu Asp Gly
            900                 905                 910

Ile Ser Ala Leu Arg Lys Glu Thr Cys Asn Lys Ser Asn Met Cys Glu
            915                 920                 925

Ser Ser Lys Glu Ala Leu Ala Glu Asn Asn Leu Asn Leu Pro Lys Met
            930                 935                 940

Ala Glu Lys Asp Gly Cys Phe Gln Ser Gly Phe Asn Glu Glu Thr Cys
945                 950                 955                 960

Leu Val Lys Ile Ile Thr Gly Leu Leu Glu Phe Glu Val Tyr Leu Glu
            965                 970                 975

Tyr Leu Gln Asn Arg Phe Glu Ser Ser Glu Glu Gln Ala Arg Ala Val
            980                 985                 990

Gln Met Ser Thr Lys Val Leu Ile Gln Phe Leu Gln Lys Lys Ala Lys
            995                 1000                1005

Asn Leu Asp Ala Ile Thr Thr Pro Asp Pro Thr Thr Asn Ala Ser
            1010                1015                1020

Leu Leu Thr Lys Leu Gln Ala Gln Asn Gln Trp Leu Gln Asp Met
            1025                1030                1035

Thr Thr His Leu Ile Leu Arg Ser Phe Lys Glu Phe Leu Gln Ser
            1040                1045                1050

Ser Leu Arg Ala Leu Arg Gln Met
            1055                1060

<210> SEQ ID NO 38
<211> LENGTH: 963
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 38

Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr

-continued

```
                20                  25                  30
Tyr Lys Ala Phe Lys Ile Thr Asp Arg Ile Trp Ile Ile Pro Glu Arg
            35                  40                  45
Tyr Thr Phe Gly Tyr Lys Pro Glu Asp Phe Asn Lys Ser Ser Gly Ile
 50                  55                  60
Phe Asn Arg Asp Val Cys Glu Tyr Tyr Asp Pro Asp Tyr Leu Asn Thr
 65                  70                  75                  80
Asn Asp Lys Lys Asn Ile Phe Leu Gln Thr Met Ile Lys Leu Phe Asn
                85                  90                  95
Arg Ile Lys Ser Lys Pro Leu Gly Glu Lys Leu Leu Glu Met Ile Ile
            100                 105                 110
Asn Gly Ile Pro Tyr Leu Gly Asp Arg Arg Val Pro Leu Glu Glu Phe
            115                 120                 125
Asn Thr Asn Ile Ala Ser Val Thr Val Asn Lys Leu Ile Ser Asn Pro
            130                 135                 140
Gly Glu Val Glu Arg Lys Lys Gly Ile Phe Ala Asn Leu Ile Ile Phe
145                 150                 155                 160
Gly Pro Gly Pro Val Leu Asn Glu Asn Glu Thr Ile Asp Ile Gly Ile
                165                 170                 175
Gln Asn His Phe Ala Ser Arg Glu Gly Phe Gly Ile Met Gln Met
            180                 185                 190
Lys Phe Cys Pro Glu Tyr Val Ser Val Phe Asn Asn Val Gln Glu Asn
            195                 200                 205
Lys Gly Ala Ser Ile Phe Asn Arg Arg Gly Tyr Phe Ser Asp Pro Ala
            210                 215                 220
Leu Ile Leu Met His Glu Leu Ile His Val Leu His Gly Leu Tyr Gly
225                 230                 235                 240
Ile Lys Val Asp Asp Leu Pro Ile Val Pro Asn Glu Lys Lys Phe Phe
            245                 250                 255
Met Gln Ser Thr Asp Ala Ile Gln Ala Glu Glu Leu Tyr Thr Phe Gly
            260                 265                 270
Gly Gln Asp Pro Ser Ile Ile Thr Pro Ser Thr Asp Lys Ser Ile Tyr
            275                 280                 285
Asp Lys Val Leu Gln Asn Phe Arg Gly Ile Val Asp Arg Leu Asn Lys
            290                 295                 300
Val Leu Val Cys Ile Ser Asp Pro Asn Ile Asn Ile Asn Ile Tyr Lys
305                 310                 315                 320
Asn Lys Phe Lys Asp Lys Tyr Lys Phe Val Glu Asp Ser Glu Gly Lys
            325                 330                 335
Tyr Ser Ile Asp Val Glu Ser Phe Asp Lys Leu Tyr Lys Ser Leu Met
            340                 345                 350
Phe Gly Phe Thr Glu Thr Asn Ile Ala Glu Asn Tyr Lys Ile Lys Thr
            355                 360                 365
Arg Ala Ser Tyr Phe Ser Asp Ser Leu Pro Pro Val Lys Ile Lys Asn
            370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
            405                 410                 415
Lys Gln Ala Tyr Glu Glu Ile Ser Lys Glu His Leu Ala Val Tyr Lys
            420                 425                 430
Ile Gln Met Cys Val Asp Gly Ile Ile Thr Ser Lys Thr Lys Ser Leu
            435                 440                 445
```

```
Ile Glu Gly Arg Asn Lys Ala Leu Asn Leu Gln Cys Ile Asp Val Asp
    450                 455                 460

Asn Glu Asp Leu Phe Phe Ile Ala Asp Lys Asn Ser Phe Ser Asp Asp
465                 470                 475                 480

Leu Ser Lys Asn Glu Arg Ile Glu Tyr Asn Thr Gln Ser Asn Tyr Ile
                485                 490                 495

Glu Asn Asp Phe Pro Ile Asn Glu Leu Ile Leu Asp Thr Asp Leu Ile
            500                 505                 510

Ser Lys Ile Glu Leu Pro Ser Glu Asn Thr Glu Ser Leu Thr Asp Phe
        515                 520                 525

Asn Val Asp Val Pro Val Tyr Glu Lys Gln Pro Ala Ile Lys Lys Ile
530                 535                 540

Phe Thr Asp Glu Asn Thr Ile Phe Gln Tyr Leu Tyr Ser Gln Thr Phe
545                 550                 555                 560

Pro Leu Asp Ile Arg Asp Ile Ser Leu Thr Ser Ser Phe Asp Asp Ala
                565                 570                 575

Leu Leu Phe Ser Asn Lys Val Tyr Ser Phe Phe Ser Met Asp Tyr Ile
            580                 585                 590

Lys Thr Ala Asn Lys Val Val Glu Ala Gly Leu Phe Ala Gly Trp Val
        595                 600                 605

Lys Gln Ile Val Asn Asp Phe Val Ile Glu Ala Asn Lys Ser Asn Thr
    610                 615                 620

Met Asp Lys Ile Ala Asp Ile Ser Leu Ile Val Pro Tyr Ile Gly Leu
625                 630                 635                 640

Ala Leu Asn Val Gly Asn Glu Thr Ala Lys Gly Asn Phe Glu Asn Ala
                645                 650                 655

Phe Glu Ile Ala Gly Ala Ser Ile Leu Leu Glu Phe Ile Pro Glu Leu
            660                 665                 670

Leu Ile Pro Val Val Gly Ala Phe Leu Leu Glu Ser Tyr Ile Asp Asn
        675                 680                 685

Lys Asn Lys Ile Ile Lys Thr Ile Asp Asn Ala Leu Thr Lys Arg Asn
    690                 695                 700

Glu Lys Trp Ser Asp Met Tyr Gly Leu Ile Val Ala Gln Trp Leu Ser
705                 710                 715                 720

Thr Val Asn Thr Gln Phe Tyr Thr Ile Lys Glu Gly Met Tyr Lys Ala
                725                 730                 735

Leu Asn Tyr Gln Ala Gln Ala Leu Glu Glu Ile Ile Lys Tyr Arg Tyr
            740                 745                 750

Asn Ile Tyr Ser Glu Lys Glu Lys Ser Asn Ile Asn Ile Asp Phe Asn
        755                 760                 765

Asp Ile Asn Ser Lys Leu Asn Glu Gly Ile Asn Gln Ala Ile Asp Asn
    770                 775                 780

Ile Asn Asn Phe Ile Asn Gly Cys Ser Val Ser Tyr Leu Met Lys Lys
785                 790                 795                 800

Met Ile Pro Leu Ala Val Glu Lys Leu Leu Asp Phe Asp Asn Thr Leu
                805                 810                 815

Lys Lys Asn Leu Leu Asn Tyr Ile Asp Glu Asn Lys Leu Tyr Leu Ile
            820                 825                 830

Gly Ser Ala Glu Tyr Glu Lys Ser Lys Val Asn Lys Tyr Leu Lys Thr
        835                 840                 845

Ile Met Pro Phe Asp Leu Ser Ile Tyr Thr Asn Asp Thr Ile Leu Ile
    850                 855                 860
```

```
Glu Met Phe Asn Lys Tyr Asn Ser Leu Glu Gly Gly Gly Ser Gly
865                 870                 875                 880

Gly Gly Gly Ser Gly Gly Gly Ser Ala Leu Val Ala Lys Glu Leu
                885                 890                 895

Arg Cys Gln Cys Ile Lys Thr Tyr Ser Lys Pro Phe His Pro Lys Phe
            900                 905                 910

Ile Lys Glu Leu Arg Val Ile Glu Ser Gly Pro His Cys Ala Asn Thr
            915                 920                 925

Glu Ile Ile Val Lys Leu Ser Asp Gly Arg Glu Leu Cys Leu Asp Pro
            930                 935                 940

Lys Glu Asn Trp Val Gln Arg Val Val Glu Lys Phe Leu Lys Arg Ala
945                 950                 955                 960

Glu Asn Ser

<210> SEQ ID NO 39
<211> LENGTH: 959
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Pro Val Ala Ile Asn Ser Phe Asn Tyr Asn Asp Pro Val Asn Asp Asp
1               5                   10                  15

Thr Ile Leu Tyr Met Gln Ile Pro Tyr Glu Glu Lys Ser Lys Lys Tyr
            20                  25                  30

Tyr Lys Ala Phe Glu Ile Met Arg Asn Val Trp Ile Ile Pro Glu Arg
        35                  40                  45

Asn Thr Ile Gly Thr Asn Pro Ser Asp Phe Asp Pro Pro Ala Ser Leu
    50                  55                  60

Lys Asn Gly Ser Ser Ala Tyr Tyr Asp Pro Asn Tyr Leu Thr Thr Asp
65                  70                  75                  80

Ala Glu Lys Asp Arg Tyr Leu Lys Thr Thr Ile Lys Leu Phe Lys Arg
                85                  90                  95

Ile Asn Ser Asn Pro Ala Gly Lys Val Leu Leu Gln Glu Ile Ser Tyr
            100                 105                 110

Ala Lys Pro Tyr Leu Gly Asn Asp His Thr Pro Ile Asp Glu Phe Ser
        115                 120                 125

Pro Val Thr Arg Thr Thr Ser Val Asn Ile Lys Leu Ser Thr Asn Val
130                 135                 140

Glu Ser Ser Met Leu Leu Asn Leu Leu Val Leu Gly Ala Gly Pro Asp
145                 150                 155                 160

Ile Phe Glu Ser Cys Cys Tyr Pro Val Arg Lys Leu Ile Asp Pro Asp
                165                 170                 175

Val Val Tyr Asp Pro Ser Asn Tyr Gly Phe Gly Ser Ile Asn Ile Val
            180                 185                 190

Thr Phe Ser Pro Glu Tyr Glu Tyr Thr Phe Asn Asp Ile Ser Gly Gly
        195                 200                 205

His Asn Ser Ser Thr Glu Ser Phe Ile Ala Asp Pro Ala Ile Ser Leu
    210                 215                 220

Ala His Glu Leu Ile His Ala Leu His Gly Leu Tyr Gly Ala Arg Gly
225                 230                 235                 240

Val Thr Tyr Glu Glu Thr Ile Glu Val Lys Gln Ala Pro Leu Met Ile
                245                 250                 255
```

```
Ala Glu Lys Pro Ile Arg Leu Glu Glu Phe Leu Thr Phe Gly Gly Gln
            260                 265                 270

Asp Leu Asn Ile Ile Thr Ser Ala Met Lys Glu Lys Ile Tyr Asn Asn
            275                 280                 285

Leu Leu Ala Asn Tyr Glu Lys Ile Ala Thr Arg Leu Ser Glu Val Asn
        290                 295                 300

Ser Ala Pro Pro Glu Tyr Asp Ile Asn Glu Tyr Lys Asp Tyr Phe Gln
305                 310                 315                 320

Trp Lys Tyr Gly Leu Asp Lys Asn Ala Asp Gly Ser Tyr Thr Val Asn
                325                 330                 335

Glu Asn Lys Phe Asn Glu Ile Tyr Lys Lys Leu Tyr Ser Phe Thr Glu
            340                 345                 350

Ser Asp Leu Ala Asn Lys Phe Lys Val Lys Ala Arg Asn Thr Tyr Phe
        355                 360                 365

Ile Lys Tyr Glu Phe Leu Lys Val Pro Asn Leu Leu Asp Asp Asp Ile
    370                 375                 380

Tyr Thr Val Ser Glu Gly Phe Asn Ile Gly Asn Leu Ala Val Asn Asn
385                 390                 395                 400

Arg Gly Gln Ser Ile Lys Leu Asn Pro Lys Ile Ile Asp Ser Ile Pro
                405                 410                 415

Asp Lys Gly Leu Val Glu Lys Ile Val Lys Phe Ala Val Glu Asn Asn
            420                 425                 430

Asn Asn Asn Asn Asn Asn Asn Asn Leu Gly Cys Val Asp Gly Ile Ile
        435                 440                 445

Thr Ser Lys Thr Lys Ser Leu Ile Glu Gly Arg Asp Val Lys Cys Asp
    450                 455                 460

Met Glu Val Ser Cys Pro Asp Gly Tyr Thr Cys Cys Arg Leu Gln Ser
465                 470                 475                 480

Gly Ala Trp Gly Cys Cys Pro Phe Thr Gln Ala Val Cys Cys Glu Asp
                485                 490                 495

His Ile His Cys Cys Pro Ala Gly Phe Thr Cys Asp Thr Gln Lys Gly
            500                 505                 510

Thr Cys Glu Ala Leu Ala Gly Gly Gly Ser Gly Gly Gly Ser
        515                 520                 525

Gly Gly Gly Gly Ser Ala Leu Val Leu Gln Cys Ile Glu Val Asn Asn
530                 535                 540

Ser Glu Leu Phe Phe Val Ala Ser Glu Ser Tyr Asn Glu Asn Asp
545                 550                 555                 560

Ile Asn Thr Pro Lys Glu Ile Asp Asp Thr Thr Asn Leu Asn Asn Asn
                565                 570                 575

Tyr Glu Asn Asn Leu Asp Glu Val Ile Leu Asp Tyr Asn Ser Gln Thr
            580                 585                 590

Ile Pro Gln Ile Ser Asn Ile Glu Asn Leu Asn Thr Leu Val Gln Asp
        595                 600                 605

Asn Ser Tyr Val Pro Glu Tyr Asp Ser Asn Gly Thr Ser Glu Ile Glu
    610                 615                 620

Glu Tyr Asp Val Val Asp Phe Asn Val Phe Phe Tyr Leu His Ala Gln
625                 630                 635                 640

Lys Val Pro Glu Gly Glu Thr Asn Ile Ser Leu Thr Ser Ser Ile Asp
                645                 650                 655

Thr Ala Leu Leu Glu Glu Ser Lys Asp Ile Phe Phe Ser Glu Phe
            660                 665                 670
```

```
Ile Asp Thr Ile Asn Lys Pro Val Asn Ala Ala Leu Phe Ile Asp Trp
            675                 680                 685

Ile Ser Lys Val Ile Arg Asp Phe Thr Thr Glu Ala Thr Gln Lys Ser
690                 695                 700

Thr Val Asp Lys Ile Ala Asp Ile Ser Leu Ile Val Pro Tyr Val Gly
705                 710                 715                 720

Leu Ala Leu Asn Ile Ile Ile Glu Ala Glu Lys Gly Asn Phe Glu Glu
                725                 730                 735

Ala Phe Glu Leu Leu Gly Val Gly Ile Leu Leu Glu Phe Val Pro Glu
            740                 745                 750

Leu Thr Ile Pro Val Ile Leu Val Phe Thr Ile Lys Ser Tyr Ile Asp
            755                 760                 765

Ser Tyr Glu Asn Lys Asn Lys Ala Ile Lys Ala Ile Asn Asn Ser Leu
770                 775                 780

Ile Glu Arg Glu Ala Lys Trp Lys Glu Ile Tyr Ser Trp Ile Val Ser
785                 790                 795                 800

Asn Trp Leu Thr Arg Ile Asn Thr Gln Phe Asn Lys Arg Lys Glu Gln
                805                 810                 815

Met Tyr Gln Ala Leu Gln Asn Gln Val Asp Ala Ile Lys Thr Ala Ile
            820                 825                 830

Glu Tyr Lys Tyr Asn Asn Tyr Thr Ser Asp Glu Lys Asn Arg Leu Glu
            835                 840                 845

Ser Glu Tyr Asn Ile Asn Asn Ile Glu Glu Glu Leu Asn Lys Lys Val
            850                 855                 860

Ser Leu Ala Met Lys Asn Ile Glu Arg Phe Met Thr Glu Ser Ser Ile
865                 870                 875                 880

Ser Tyr Leu Met Lys Leu Ile Asn Glu Ala Lys Val Gly Lys Leu Lys
                885                 890                 895

Lys Tyr Asp Asn His Val Lys Ser Asp Leu Leu Asn Tyr Ile Leu Asp
            900                 905                 910

His Arg Ser Ile Leu Gly Glu Gln Thr Asn Glu Leu Ser Asp Leu Val
            915                 920                 925

Thr Ser Thr Leu Asn Ser Ser Ile Pro Phe Glu Leu Ser Ser Tyr Thr
            930                 935                 940

Asn Asp Lys Ile Leu Ile Ile Tyr Phe Asn Arg Leu Tyr Lys Thr
945                 950                 955
```

<210> SEQ ID NO 40
<211> LENGTH: 939
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 40

```
Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
```

```
                65                  70                  75                  80
        Gln Lys Asp Thr Phe Leu Lys Gly Ile Ile Lys Leu Phe Lys Arg Ile
                        85                  90                  95

Asn Glu Arg Asp Ile Gly Lys Lys Leu Ile Asn Tyr Leu Val Val Gly
                        100                 105                 110

Ser Pro Phe Met Gly Asp Ser Thr Pro Glu Asp Thr Phe Asp Phe
                        115                 120                 125

Thr Arg His Thr Thr Asn Ile Ala Val Glu Lys Phe Glu Asn Gly Ser
                        130                 135                 140

Trp Lys Val Thr Asn Ile Ile Thr Pro Ser Val Leu Ile Phe Gly Pro
        145                 150                 155                 160

Leu Pro Asn Ile Leu Asp Tyr Thr Ala Ser Leu Thr Leu Gln Gly Gln
                        165                 170                 175

Gln Ser Asn Pro Ser Phe Glu Gly Phe Gly Thr Leu Ser Ile Leu Lys
                        180                 185                 190

Val Ala Pro Glu Phe Leu Leu Thr Phe Ser Asp Val Thr Ser Asn Gln
                        195                 200                 205

Ser Ser Ala Val Leu Gly Lys Ser Ile Phe Cys Met Asp Pro Val Ile
                210                 215                 220

Ala Leu Met His Glu Leu Thr His Ser Leu His Gln Leu Tyr Gly Ile
        225                 230                 235                 240

Asn Ile Pro Ser Asp Lys Arg Ile Arg Pro Gln Val Ser Glu Gly Phe
                        245                 250                 255

Phe Ser Gln Asp Gly Pro Asn Val Gln Phe Glu Glu Leu Tyr Thr Phe
                        260                 265                 270

Gly Gly Leu Asp Val Glu Ile Ile Pro Gln Ile Glu Arg Ser Gln Leu
                        275                 280                 285

Arg Glu Lys Ala Leu Gly His Tyr Lys Asp Ile Ala Lys Arg Leu Asn
                        290                 295                 300

Asn Ile Asn Lys Thr Ile Pro Ser Ser Trp Ile Ser Asn Ile Asp Lys
        305                 310                 315                 320

Tyr Lys Lys Ile Phe Ser Glu Lys Tyr Asn Phe Asp Lys Asp Asn Thr
                        325                 330                 335

Gly Asn Phe Val Val Asn Ile Asp Lys Phe Asn Ser Leu Tyr Ser Asp
                        340                 345                 350

Leu Thr Asn Val Met Ser Glu Val Val Tyr Ser Ser Gln Tyr Asn Val
                        355                 360                 365

Lys Asn Arg Thr His Tyr Phe Ser Arg His Tyr Leu Pro Val Phe Ala
        370                 375                 380

Asn Ile Leu Asp Asp Asn Ile Tyr Thr Ile Arg Asp Gly Phe Asn Leu
        385                 390                 395                 400

Thr Asn Lys Gly Phe Asn Ile Glu Asn Ser Gly Gln Asn Ile Glu Arg
                        405                 410                 415

Asn Pro Ala Leu Gln Lys Leu Ser Ser Glu Ser Val Val Asp Leu Phe
                        420                 425                 430

Thr Lys Val Cys Val Asp Gly Gly Gly Ser Gly Gly Gly Ser
                        435                 440                 445

Ala Asp Asp Asp Lys Val Val Ser His Phe Asn Asp Cys Pro Asp
                        450                 455                 460

Ser His Thr Gln Phe Cys Phe His Gly Thr Cys Arg Phe Leu Val Gln
        465                 470                 475                 480

Glu Asp Lys Pro Ala Cys Val Cys His Ser Gly Tyr Val Gly Ala Arg
                        485                 490                 495
```

```
Cys Glu His Ala Asp Leu Leu Ala Leu Ala Gly Gly Gly Ser Gly
            500                 505                 510
Gly Gly Gly Ser Gly Gly Gly Ser Ala Leu Ala Leu Gln Cys Ile
        515                 520                 525
Lys Val Lys Asn Asn Arg Leu Pro Tyr Val Ala Asp Lys Asp Ser Ile
    530                 535                 540
Ser Gln Glu Ile Phe Glu Asn Lys Ile Ile Thr Asp Glu Thr Asn Val
545                 550                 555                 560
Gln Asn Tyr Ser Asp Lys Phe Ser Leu Asp Glu Ser Ile Leu Asp Gly
                565                 570                 575
Gln Val Pro Ile Asn Pro Glu Ile Val Asp Pro Leu Leu Pro Asn Val
            580                 585                 590
Asn Met Glu Pro Leu Asn Leu Pro Gly Glu Glu Ile Val Phe Tyr Asp
        595                 600                 605
Asp Ile Thr Lys Tyr Val Asp Tyr Leu Asn Ser Tyr Tyr Tyr Leu Glu
    610                 615                 620
Ser Gln Lys Leu Ser Asn Asn Val Glu Asn Ile Thr Leu Thr Thr Ser
625                 630                 635                 640
Val Glu Glu Ala Leu Gly Tyr Ser Asn Lys Ile Tyr Thr Phe Leu Pro
                645                 650                 655
Ser Leu Ala Glu Lys Val Asn Lys Gly Val Gln Ala Gly Leu Phe Leu
            660                 665                 670
Asn Trp Ala Asn Glu Val Val Glu Asp Phe Thr Thr Asn Ile Met Lys
        675                 680                 685
Lys Asp Thr Leu Asp Lys Ile Ser Asp Val Ser Val Ile Ile Pro Tyr
    690                 695                 700
Ile Gly Pro Ala Leu Asn Ile Gly Asn Ser Ala Leu Arg Gly Asn Phe
705                 710                 715                 720
Asn Gln Ala Phe Ala Thr Ala Gly Val Ala Phe Leu Leu Glu Gly Phe
                725                 730                 735
Pro Glu Phe Thr Ile Pro Ala Leu Gly Val Phe Thr Phe Tyr Ser Ser
            740                 745                 750
Ile Gln Glu Arg Glu Lys Ile Ile Lys Thr Ile Glu Asn Cys Leu Glu
        755                 760                 765
Gln Arg Val Lys Arg Trp Lys Asp Ser Tyr Gln Trp Met Val Ser Asn
    770                 775                 780
Trp Leu Ser Arg Ile Thr Thr Gln Phe Asn His Ile Asn Tyr Gln Met
785                 790                 795                 800
Tyr Asp Ser Leu Ser Tyr Gln Ala Asp Ala Ile Lys Ala Lys Ile Asp
                805                 810                 815
Leu Glu Tyr Lys Lys Tyr Ser Gly Ser Asp Lys Glu Asn Ile Lys Ser
            820                 825                 830
Gln Val Glu Asn Leu Lys Asn Ser Leu Asp Val Lys Ile Ser Glu Ala
        835                 840                 845
Met Asn Asn Ile Asn Lys Phe Ile Arg Glu Cys Ser Val Thr Tyr Leu
    850                 855                 860
Phe Lys Asn Met Leu Pro Lys Val Ile Asp Glu Leu Asn Lys Phe Asp
865                 870                 875                 880
Leu Arg Thr Lys Thr Glu Leu Ile Asn Leu Ile Asp Ser His Asn Ile
                885                 890                 895
Ile Leu Val Gly Glu Val Asp Arg Leu Lys Ala Lys Val Asn Glu Ser
            900                 905                 910
```

-continued

```
Phe Glu Asn Thr Met Pro Phe Asn Ile Phe Ser Tyr Thr Asn Asn Ser
            915                 920                 925

Leu Leu Lys Asp Ile Ile Asn Glu Tyr Phe Asn
        930                 935

<210> SEQ ID NO 41
<211> LENGTH: 1002
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
```

-continued

```
              325                 330                 335
Gly Asn Phe Val Val Asn Ile Asp Lys Phe Asn Ser Leu Tyr Ser Asp
            340                 345                 350
Leu Thr Asn Val Met Ser Glu Val Tyr Ser Ser Gln Tyr Asn Val
            355                 360                 365
Lys Asn Arg Thr His Tyr Phe Ser Arg His Tyr Leu Pro Val Phe Ala
            370                 375                 380
Asn Ile Leu Asp Asp Asn Ile Tyr Thr Ile Arg Asp Gly Phe Asn Leu
385                 390                 395                 400
Thr Asn Lys Gly Phe Asn Ile Glu Asn Ser Gly Gln Asn Ile Glu Arg
                405                 410                 415
Asn Pro Ala Leu Gln Lys Leu Ser Ser Glu Ser Val Val Asp Leu Phe
            420                 425                 430
Thr Lys Val Cys Val Asp Gly Gly Gly Ser Gly Gly Gly Gly Ser
            435                 440                 445
Ala Asp Asp Asp Asp Lys Ala Leu Asp Thr Asn Tyr Cys Phe Ser Ser
450                 455                 460
Thr Glu Lys Asn Cys Cys Val Arg Gln Leu Tyr Ile Asp Phe Arg Lys
465                 470                 475                 480
Asp Leu Gly Trp Lys Trp Ile His Glu Pro Lys Gly Tyr His Ala Asn
                485                 490                 495
Phe Cys Leu Gly Pro Cys Pro Tyr Ile Trp Ser Leu Asp Thr Gln Tyr
                500                 505                 510
Ser Lys Val Leu Ala Leu Tyr Asn Gln His Asn Pro Gly Ala Ser Ala
                515                 520                 525
Ala Pro Cys Cys Val Pro Gln Ala Leu Glu Pro Leu Pro Ile Val Tyr
            530                 535                 540
Tyr Val Gly Arg Lys Pro Lys Val Glu Gln Leu Ser Asn Met Ile Val
545                 550                 555                 560
Arg Ser Cys Lys Cys Ser Ala Leu Ala Gly Gly Gly Ser Gly Gly
                565                 570                 575
Gly Gly Ser Gly Gly Gly Ser Ala Leu Ala Leu Gln Cys Ile Lys
            580                 585                 590
Val Lys Asn Asn Arg Leu Pro Tyr Val Ala Asp Lys Asp Ser Ile Ser
                595                 600                 605
Gln Glu Ile Phe Glu Asn Lys Ile Ile Thr Asp Glu Thr Asn Val Gln
610                 615                 620
Asn Tyr Ser Asp Lys Phe Ser Leu Asp Glu Ser Ile Leu Asp Gly Gln
625                 630                 635                 640
Val Pro Ile Asn Pro Glu Ile Val Asp Pro Leu Leu Pro Asn Val Asn
                645                 650                 655
Met Glu Pro Leu Asn Leu Pro Gly Glu Glu Ile Val Phe Tyr Asp Asp
                660                 665                 670
Ile Thr Lys Tyr Val Asp Tyr Leu Asn Ser Tyr Tyr Leu Glu Ser
                675                 680                 685
Gln Lys Leu Ser Asn Asn Val Glu Asn Ile Thr Leu Thr Thr Ser Val
            690                 695                 700
Glu Glu Ala Leu Gly Tyr Ser Asn Lys Ile Tyr Thr Phe Leu Pro Ser
705                 710                 715                 720
Leu Ala Glu Lys Val Asn Lys Gly Val Gln Ala Gly Leu Phe Leu Asn
                725                 730                 735
Trp Ala Asn Glu Val Val Glu Asp Phe Thr Thr Asn Ile Met Lys Lys
                740                 745                 750
```

```
Asp Thr Leu Asp Lys Ile Ser Asp Val Ser Val Ile Ile Pro Tyr Ile
        755                 760                 765

Gly Pro Ala Leu Asn Ile Gly Asn Ser Ala Leu Arg Gly Asn Phe Asn
        770                 775                 780

Gln Ala Phe Ala Thr Ala Gly Val Ala Phe Leu Leu Glu Gly Phe Pro
785                 790                 795                 800

Glu Phe Thr Ile Pro Ala Leu Gly Val Phe Thr Phe Tyr Ser Ser Ile
                805                 810                 815

Gln Glu Arg Glu Lys Ile Ile Lys Thr Ile Glu Asn Cys Leu Glu Gln
                820                 825                 830

Arg Val Lys Arg Trp Lys Asp Ser Tyr Gln Trp Met Val Ser Asn Trp
        835                 840                 845

Leu Ser Arg Ile Thr Thr Gln Phe Asn His Ile Asn Tyr Gln Met Tyr
        850                 855                 860

Asp Ser Leu Ser Tyr Gln Ala Asp Ala Ile Lys Ala Lys Ile Asp Leu
865                 870                 875                 880

Glu Tyr Lys Lys Tyr Ser Gly Ser Asp Lys Glu Asn Ile Lys Ser Gln
                885                 890                 895

Val Glu Asn Leu Lys Asn Ser Leu Asp Val Lys Ile Ser Glu Ala Met
                900                 905                 910

Asn Asn Ile Asn Lys Phe Ile Arg Glu Cys Ser Val Thr Tyr Leu Phe
        915                 920                 925

Lys Asn Met Leu Pro Lys Val Ile Asp Glu Leu Asn Lys Phe Asp Leu
        930                 935                 940

Arg Thr Lys Thr Glu Leu Ile Asn Leu Ile Asp Ser His Asn Ile Ile
945                 950                 955                 960

Leu Val Gly Glu Val Asp Arg Leu Lys Ala Lys Val Asn Glu Ser Phe
                965                 970                 975

Glu Asn Thr Met Pro Phe Asn Ile Phe Ser Tyr Thr Asn Asn Ser Leu
                980                 985                 990

Leu Lys Asp Ile Ile Asn Glu Tyr  Phe Asn
        995                 1000
```

<210> SEQ ID NO 42
<211> LENGTH: 1045
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr
                20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
        50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95
```

-continued

Arg Ile Lys Ser Lys Pro Leu Gly Glu Lys Leu Leu Glu Met Ile Ile
            100                 105                 110
Asn Gly Ile Pro Tyr Leu Gly Asp Arg Arg Val Pro Leu Glu Glu Phe
            115                 120                 125
Asn Thr Asn Ile Ala Ser Val Thr Val Asn Lys Leu Ile Ser Asn Pro
        130                 135                 140
Gly Glu Val Glu Arg Lys Lys Gly Ile Phe Ala Asn Leu Ile Ile Phe
145                 150                 155                 160
Gly Pro Gly Pro Val Leu Asn Glu Asn Glu Thr Ile Asp Ile Gly Ile
                165                 170                 175
Gln Asn His Phe Ala Ser Arg Glu Gly Phe Gly Gly Ile Met Gln Met
            180                 185                 190
Lys Phe Cys Pro Glu Tyr Val Ser Val Phe Asn Asn Val Gln Glu Asn
            195                 200                 205
Lys Gly Ala Ser Ile Phe Asn Arg Arg Gly Tyr Phe Ser Asp Pro Ala
        210                 215                 220
Leu Ile Leu Met His Glu Leu Ile His Val Leu His Gly Leu Tyr Gly
225                 230                 235                 240
Ile Lys Val Asp Asp Leu Pro Ile Val Pro Asn Glu Lys Lys Phe Phe
                245                 250                 255
Met Gln Ser Thr Asp Ala Ile Gln Ala Glu Glu Leu Tyr Thr Phe Gly
            260                 265                 270
Gly Gln Asp Pro Ser Ile Ile Thr Pro Ser Thr Asp Lys Ser Ile Tyr
            275                 280                 285
Asp Lys Val Leu Gln Asn Phe Arg Gly Ile Val Asp Arg Leu Asn Lys
        290                 295                 300
Val Leu Val Cys Ile Ser Asp Pro Asn Ile Asn Ile Asn Ile Tyr Lys
305                 310                 315                 320
Asn Lys Phe Lys Asp Lys Tyr Lys Phe Val Glu Asp Ser Glu Gly Lys
                325                 330                 335
Tyr Ser Ile Asp Val Glu Ser Phe Asp Lys Leu Tyr Lys Ser Leu Met
            340                 345                 350
Phe Gly Phe Thr Glu Thr Asn Ile Ala Glu Asn Tyr Lys Ile Lys Thr
            355                 360                 365
Arg Ala Ser Tyr Phe Ser Asp Ser Leu Pro Pro Val Lys Ile Lys Asn
        370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
                405                 410                 415
Lys Gln Ala Tyr Glu Glu Ile Ser Lys Glu His Leu Ala Val Tyr Lys
            420                 425                 430
Ile Gln Met Cys Val Asp Glu Lys Leu Tyr Asp Asp Asp Lys
            435                 440                 445
Asp Arg Trp Gly Ser Ser Leu Gln Cys Ile Asp Val Asp Asn Glu Asp
        450                 455                 460
Leu Phe Phe Ile Ala Asp Lys Asn Ser Phe Ser Asp Asp Leu Ser Lys
465                 470                 475                 480
Asn Glu Arg Ile Glu Tyr Asn Thr Gln Ser Asn Tyr Ile Glu Asn Asp
                485                 490                 495
Phe Pro Ile Asn Glu Leu Ile Leu Asp Thr Asp Leu Ile Ser Lys Ile
            500                 505                 510
Glu Leu Pro Ser Glu Asn Thr Glu Ser Leu Thr Asp Phe Asn Val Asp

-continued

|  |  | 515 |  |  |  | 520 |  |  |  | 525 |  |  |
|---|---|---|---|---|---|---|---|---|---|---|---|---|

Val Pro Val Tyr Glu Lys Gln Pro Ala Ile Lys Lys Ile Phe Thr Asp
530                 535                 540

Glu Asn Thr Ile Phe Gln Tyr Leu Tyr Ser Gln Thr Phe Pro Leu Asp
545                 550                 555                 560

Ile Arg Asp Ile Ser Leu Thr Ser Ser Phe Asp Asp Ala Leu Leu Phe
                565                 570                 575

Ser Asn Lys Val Tyr Ser Phe Phe Ser Met Asp Tyr Ile Lys Thr Ala
                580                 585                 590

Asn Lys Val Val Glu Ala Gly Leu Phe Ala Gly Trp Val Lys Gln Ile
                595                 600                 605

Val Asn Asp Phe Val Ile Glu Ala Asn Lys Ser Asn Thr Met Asp Ala
610                 615                 620

Ile Ala Asp Ile Ser Leu Ile Val Pro Tyr Ile Gly Leu Ala Leu Asn
625                 630                 635                 640

Val Gly Asn Glu Thr Ala Lys Gly Asn Phe Glu Asn Ala Phe Glu Ile
                645                 650                 655

Ala Gly Ala Ser Ile Leu Leu Glu Phe Ile Pro Glu Leu Leu Ile Pro
                660                 665                 670

Val Val Gly Ala Phe Leu Leu Glu Ser Tyr Ile Asp Asn Lys Asn Lys
                675                 680                 685

Ile Ile Lys Thr Ile Asp Asn Ala Leu Thr Lys Arg Asn Glu Lys Trp
690                 695                 700

Ser Asp Met Tyr Gly Leu Ile Val Ala Gln Trp Leu Ser Thr Val Asn
705                 710                 715                 720

Thr Gln Phe Tyr Thr Ile Lys Glu Gly Met Tyr Lys Ala Leu Asn Tyr
                725                 730                 735

Gln Ala Gln Ala Leu Glu Glu Ile Ile Lys Tyr Arg Tyr Asn Ile Tyr
                740                 745                 750

Ser Glu Lys Glu Lys Ser Asn Ile Asn Ile Asp Phe Asn Asp Ile Asn
                755                 760                 765

Ser Lys Leu Asn Glu Gly Ile Asn Gln Ala Ile Asp Asn Ile Asn Asn
                770                 775                 780

Phe Ile Asn Gly Cys Ser Val Ser Tyr Leu Met Lys Lys Met Ile Pro
785                 790                 795                 800

Leu Ala Val Glu Lys Leu Leu Asp Phe Asp Asn Thr Leu Lys Lys Asn
                805                 810                 815

Leu Leu Asn Tyr Ile Asp Glu Asn Lys Leu Tyr Leu Ile Gly Ser Ala
                820                 825                 830

Glu Tyr Glu Lys Ser Lys Val Asn Lys Tyr Leu Lys Thr Ile Met Pro
                835                 840                 845

Phe Asp Leu Ser Ile Tyr Thr Asn Asp Thr Ile Leu Ile Glu Met Phe
850                 855                 860

Asn Lys Tyr Asn Ser Leu Glu Gly Gly Gly Ser Gly Gly Gly Gly
865                 870                 875                 880

Ser Gly Gly Gly Gly Ser Ala Leu Val Arg Ser Ser Arg Thr Pro
                885                 890                 895

Ser Asp Lys Pro Val Ala His Val Ala Asn Pro Gln Ala Glu Gly
                900                 905                 910

Gln Leu Gln Trp Leu Asn Arg Arg Ala Asn Ala Leu Leu Ala Asn Gly
                915                 920                 925

Val Glu Leu Arg Asp Asn Gln Leu Val Val Pro Ser Glu Gly Leu Tyr
                930                 935                 940

```
Leu Ile Tyr Ser Gln Val Leu Phe Lys Gly Gln Gly Cys Pro Ser Thr
945                 950                 955                 960

His Val Leu Leu Thr His Thr Ile Ser Arg Ile Ala Val Ser Tyr Gln
                965                 970                 975

Thr Lys Val Asn Leu Leu Ser Ala Ile Lys Ser Pro Cys Gln Arg Glu
            980                 985                 990

Thr Pro Glu Gly Ala Glu Ala Lys Pro Trp Tyr Glu Pro Ile Tyr Leu
        995                 1000                1005

Gly Gly Val Phe Gln Leu Glu Lys Gly Asp Arg Leu Ser Ala Glu
    1010                1015                1020

Ile Asn Arg Pro Asp Tyr Leu Asp Phe Ala Glu Ser Gly Gln Val
    1025                1030                1035

Tyr Phe Gly Ile Ile Ala Leu
    1040                1045
```

<210> SEQ ID NO 43
<211> LENGTH: 962
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Ile Trp Val Ile Pro Glu Arg
        35                  40                  45

Phe Ser Ser Asp Thr Asn Pro Ser Leu Ser Lys Pro Pro Arg Pro Thr
50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
210                 215                 220

Ala Leu Met His Glu Leu Thr His Ser Leu His Gln Leu Tyr Gly Ile
225                 230                 235                 240
```

```
Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Pro Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
            340                 345                 350

Leu Thr Asn Val Met Ser Glu Val Val Tyr Ser Ser Gln Tyr Asn Val
        355                 360                 365

Lys Asn Arg Thr His Tyr Phe Ser Arg His Tyr Leu Pro Val Phe Ala
    370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
                405                 410                 415

Asn Pro Ala Leu Gln Lys Leu Ser Ser Glu Ser Val Val Asp Leu Phe
            420                 425                 430

Thr Lys Val Cys Val Asp Lys Ser Glu Glu Lys Leu Tyr Asp Asp Asp
        435                 440                 445

Asp Lys Asp Arg Trp Gly Ser Ser Leu Gln Cys Ile Lys Val Lys Asn
    450                 455                 460

Asn Arg Leu Pro Tyr Val Ala Asp Lys Asp Ser Ile Ser Gln Glu Ile
465                 470                 475                 480

Phe Glu Asn Lys Ile Ile Thr Asp Glu Thr Asn Val Gln Asn Tyr Ser
                485                 490                 495

Asp Lys Phe Ser Leu Asp Glu Ser Ile Leu Asp Gly Gln Val Pro Ile
            500                 505                 510

Asn Pro Glu Ile Val Asp Pro Leu Leu Pro Asn Val Asn Met Glu Pro
        515                 520                 525

Leu Asn Leu Pro Gly Glu Glu Ile Val Phe Tyr Asp Asp Ile Thr Lys
    530                 535                 540

Tyr Val Asp Tyr Leu Asn Ser Tyr Tyr Tyr Leu Glu Ser Gln Lys Leu
545                 550                 555                 560

Ser Asn Asn Val Glu Asn Ile Thr Leu Thr Thr Ser Val Glu Glu Ala
                565                 570                 575

Leu Gly Tyr Ser Asn Lys Ile Tyr Thr Phe Leu Pro Ser Leu Ala Glu
            580                 585                 590

Lys Val Asn Lys Gly Val Gln Ala Gly Leu Phe Leu Asn Trp Ala Asn
        595                 600                 605

Glu Val Val Glu Asp Phe Thr Thr Asn Ile Met Lys Lys Asp Thr Leu
    610                 615                 620

Asp Lys Ile Ser Asp Val Ser Val Ile Ile Pro Tyr Ile Gly Pro Ala
625                 630                 635                 640

Leu Asn Ile Gly Asn Ser Ala Leu Arg Gly Asn Phe Asn Gln Ala Phe
                645                 650                 655

Ala Thr Ala Gly Val Ala Phe Leu Leu Glu Gly Phe Pro Glu Phe Thr
```

```
                    660                 665                 670
Ile Pro Ala Leu Gly Val Phe Thr Phe Tyr Ser Ser Ile Gln Glu Arg
            675                 680                 685

Glu Lys Ile Ile Lys Thr Ile Glu Asn Cys Leu Glu Gln Arg Val Lys
            690                 695                 700

Arg Trp Lys Asp Ser Tyr Gln Trp Met Val Ser Asn Trp Leu Ser Arg
705                 710                 715                 720

Ile Thr Thr Gln Phe Asn His Ile Asn Tyr Gln Met Tyr Asp Ser Leu
                725                 730                 735

Ser Tyr Gln Ala Asp Ala Ile Lys Ala Lys Ile Asp Leu Glu Tyr Lys
            740                 745                 750

Lys Tyr Ser Gly Ser Asp Lys Glu Asn Ile Lys Ser Gln Val Glu Asn
            755                 760                 765

Leu Lys Asn Ser Leu Asp Val Lys Ile Ser Glu Ala Met Asn Asn Ile
            770                 775                 780

Asn Lys Phe Ile Arg Glu Cys Ser Val Thr Tyr Leu Phe Lys Asn Met
785                 790                 795                 800

Leu Pro Lys Val Ile Asp Glu Leu Asn Lys Phe Asp Leu Arg Thr Lys
                805                 810                 815

Thr Glu Leu Ile Asn Leu Ile Asp Ser His Asn Ile Ile Leu Val Gly
                820                 825                 830

Glu Val Asp Arg Leu Lys Ala Lys Val Asn Glu Ser Phe Glu Asn Thr
            835                 840                 845

Met Pro Phe Asn Ile Phe Ser Tyr Thr Asn Asn Ser Leu Leu Lys Asp
850                 855                 860

Ile Ile Asn Glu Tyr Phe Asn Leu Glu Gly Gly Gly Ser Gly Gly
865                 870                 875                 880

Gly Gly Ser Gly Gly Gly Ser Ala Leu Lys Pro Val Ser Leu Ser
                885                 890                 895

Tyr Arg Cys Pro Cys Arg Phe Phe Glu Ser His Val Ala Arg Ala Asn
            900                 905                 910

Val Lys His Leu Lys Ile Leu Asn Thr Pro Asn Cys Ala Leu Gln Ile
            915                 920                 925

Val Ala Arg Leu Lys Asn Asn Asn Arg Gln Val Cys Ile Asp Pro Lys
            930                 935                 940

Leu Lys Trp Ile Gln Glu Tyr Leu Glu Lys Ala Leu Asn Lys Arg Phe
945                 950                 955                 960

Lys Met

<210> SEQ ID NO 44
<211> LENGTH: 1090
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45
```

```
Phe Ser Arg Asn Ser Asn Pro Asn Leu Asn Lys Pro Pro Arg Val Thr
 50                  55                  60

Ser Pro Lys Ser Gly Tyr Tyr Asp Pro Asn Tyr Leu Ser Thr Asp Ser
 65                  70                  75                  80

Asp Lys Asp Thr Phe Leu Lys Glu Ile Ile Lys Leu Phe Lys Arg Ile
                 85                  90                  95

Asn Ser Arg Glu Ile Gly Glu Leu Ile Tyr Arg Leu Ser Thr Asp
            100                 105                 110

Ile Pro Phe Pro Gly Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
                180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
            420                 425                 430

Thr Lys Phe Cys Val Asp Ala Ile Asp Gly Arg Ser Leu Tyr Asn Lys
        435                 440                 445

Thr Leu Gln Cys Arg Glu Leu Leu Val Lys Asn Thr Asp Leu Pro Phe
    450                 455                 460

Ile Gly Asp Ile Ser Asp Val Lys Thr Asp Ile Phe Leu Arg Lys Asp
```

```
             465                 470                 475                 480
        Ile Asn Glu Glu Thr Glu Val Ile Tyr Tyr Pro Asp Asn Val Ser Val
                            485                 490                 495

Asp Gln Val Ile Leu Ser Lys Asn Thr Ser Glu His Gly Gln Leu Asp
                            500                 505                 510

Leu Leu Tyr Pro Ser Ile Asp Ser Glu Ser Glu Ile Leu Pro Gly Glu
                            515                 520                 525

Asn Gln Val Phe Tyr Asp Asn Arg Thr Gln Asn Val Asp Tyr Leu Asn
                    530                 535                 540

Ser Tyr Tyr Leu Glu Ser Gln Lys Leu Ser Asp Asn Val Glu Asp
        545                 550                 555                 560

Phe Thr Phe Thr Arg Ser Ile Glu Glu Ala Leu Asp Asn Ser Ala Lys
                            565                 570                 575

Val Tyr Thr Tyr Phe Pro Thr Leu Ala Asn Lys Val Asn Ala Gly Val
                            580                 585                 590

Gln Gly Gly Leu Phe Leu Met Trp Ala Asn Asp Val Val Glu Asp Phe
                    595                 600                 605

Thr Thr Asn Ile Leu Arg Lys Asp Thr Leu Asp Lys Ile Ser Asp Val
                    610                 615                 620

Ser Ala Ile Ile Pro Tyr Ile Gly Pro Ala Leu Asn Ile Ser Asn Ser
        625                 630                 635                 640

Val Arg Arg Gly Asn Phe Thr Glu Ala Phe Ala Val Thr Gly Val Thr
                            645                 650                 655

Ile Leu Leu Glu Ala Phe Pro Glu Phe Thr Ile Pro Ala Leu Gly Ala
                            660                 665                 670

Phe Val Ile Tyr Ser Lys Val Gln Glu Arg Asn Glu Ile Ile Lys Thr
                            675                 680                 685

Ile Asp Asn Cys Leu Glu Gln Arg Ile Lys Arg Trp Lys Asp Ser Tyr
                    690                 695                 700

Glu Trp Met Met Gly Thr Trp Leu Ser Arg Ile Ile Thr Gln Phe Asn
        705                 710                 715                 720

Asn Ile Ser Tyr Gln Met Tyr Asp Ser Leu Asn Tyr Gln Ala Gly Ala
                            725                 730                 735

Ile Lys Ala Lys Ile Asp Leu Glu Tyr Lys Lys Tyr Ser Gly Ser Asp
                            740                 745                 750

Lys Glu Asn Ile Lys Ser Gln Val Glu Asn Leu Lys Asn Ser Leu Asp
                            755                 760                 765

Val Lys Ile Ser Glu Ala Met Asn Asn Ile Asn Lys Phe Ile Arg Glu
                    770                 775                 780

Cys Ser Val Thr Tyr Leu Phe Lys Asn Met Leu Pro Lys Val Ile Asp
        785                 790                 795                 800

Glu Leu Asn Glu Phe Asp Arg Asn Thr Lys Ala Lys Leu Ile Asn Leu
                            805                 810                 815

Ile Asp Ser His Asn Ile Ile Leu Val Gly Glu Val Asp Lys Leu Lys
                            820                 825                 830

Ala Lys Val Asn Asn Ser Phe Gln Asn Thr Ile Pro Phe Asn Ile Phe
                    835                 840                 845

Ser Tyr Thr Asn Asn Ser Leu Leu Lys Asp Ile Ile Asn Glu Tyr Phe
                    850                 855                 860

Asn Leu Glu Gly Gly Gly Ser Gly Gly Gly Ser Gly Gly Gly
        865                 870                 875                 880

Gly Ser Ala Leu Ala Pro Met Ala Glu Gly Gly Gln Asn His His
                            885                 890                 895
```

```
Glu Val Val Lys Phe Met Asp Val Tyr Gln Arg Ser Tyr Cys His Pro
              900                 905                 910

Ile Glu Thr Leu Val Asp Ile Phe Gln Glu Tyr Pro Asp Glu Ile Glu
              915                 920                 925

Tyr Ile Phe Lys Pro Ser Cys Val Pro Leu Met Arg Cys Gly Gly Cys
              930                 935                 940

Cys Asn Asp Glu Gly Leu Glu Cys Val Pro Thr Glu Glu Ser Asn Ile
945                 950                 955                 960

Thr Met Gln Ile Met Arg Ile Lys Pro His Gln Gly Gln His Ile Gly
                965                 970                 975

Glu Met Ser Phe Leu Gln His Asn Lys Cys Glu Cys Arg Pro Lys Lys
              980                 985                 990

Asp Arg Ala Arg Gln Glu Lys Lys  Ser Val Arg Gly Lys  Gly Lys Gly
              995                 1000                1005

Gln Lys  Arg Lys Arg Lys Lys  Ser Arg Tyr Lys Ser  Trp Ser Val
    1010                 1015                1020

Tyr Val  Gly Ala Arg Cys Cys  Leu Met Pro Trp Ser  Leu Pro Gly
    1025                 1030                1035

Pro His  Pro Cys Gly Pro Cys  Ser Glu Arg Arg Lys  His Leu Phe
    1040                 1045                1050

Val Gln  Asp Pro Gln Thr Cys  Lys Cys Ser Cys Lys  Asn Thr Asp
    1055                 1060                1065

Ser Arg  Cys Lys Ala Arg Gln  Leu Glu Leu Asn Glu  Arg Thr Cys
    1070                 1075                1080

Arg Cys  Asp Lys Pro Arg Arg
    1085                 1090

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glutamate

<400> SEQUENCE: 45

Glu His Trp Ser Tyr Gly Leu Arg Pro Gly
1               5                   10

<210> SEQ ID NO 46
<211> LENGTH: 6
<212> TYPE: PRT
<213> ORGANISM: Unknown
<220> FEATURE:
<221> NAME/KEY: source
<223> OTHER INFORMATION: /note="Description of Unknown: Transforming
      growth factor alpha peptide"

<400> SEQUENCE: 46

Trp Ser His Phe Asn Asp
1               5

<210> SEQ ID NO 47
<211> LENGTH: 5
<212> TYPE: PRT
<213> ORGANISM: Unknown
```

```
<220> FEATURE:
<221> NAME/KEY: source
<223> OTHER INFORMATION: /note="Description of Unknown: Neuregulin
      peptide"

<400> SEQUENCE: 47

Ser His Leu Val Lys
1               5

<210> SEQ ID NO 48
<211> LENGTH: 5
<212> TYPE: PRT
<213> ORGANISM: Unknown
<220> FEATURE:
<221> NAME/KEY: source
<223> OTHER INFORMATION: /note="Description of Unknown: Epidermal
      growth factor peptide"

<400> SEQUENCE: 48

Asn Ser Asp Ser Glu
1               5

<210> SEQ ID NO 49
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 50
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 51
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Tyr Ala Asp Ala Ile Phe Thr Asn Ser Tyr Arg Lys Ile Leu Gly Gln
1               5                   10                  15
```

Leu Ser Ala Arg Lys Leu Leu Gln Asp Ile Met Asn Arg Gln Gln Gly
            20                  25                  30

Glu Arg Asn Gln Glu Gln Gly Ala Lys Val Arg Leu
        35                  40

<210> SEQ ID NO 52
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala Lys Val Arg Leu
        35                  40

<210> SEQ ID NO 53
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

His Val Asp Ala Ile Phe Thr Gln Ser Tyr Arg Lys Val Leu Ala Gln
1               5                   10                  15

Leu Ser Ala Arg Lys Leu Leu Gln Asp Ile Leu Asn Arg
            20                  25

<210> SEQ ID NO 54
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

His Val Asp Ala Ile Phe Thr Gln Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 55
<211> LENGTH: 14
<212> TYPE: PRT
<213> ORGANISM: Unknown
<220> FEATURE:
<221> NAME/KEY: source
<223> OTHER INFORMATION: /note="Description of Unknown: Frog bombesin
      peptide"
<220> FEATURE:
<221> NAME/KEY: MOD_RES
<222> LOCATION: (1)..(1)
<223> OTHER INFORMATION: pyro-Glutamate

<400> SEQUENCE: 55

Glu Gln Arg Leu Gly Asn Gln Trp Ala Val Gly His Leu Met
1               5                   10

<210> SEQ ID NO 56
<211> LENGTH: 27
<212> TYPE: PRT
<213> ORGANISM: Unknown
<220> FEATURE:
<221> NAME/KEY: source
<223> OTHER INFORMATION: /note="Description of Unknown: Porcine gastrin releasing peptide"

<400> SEQUENCE: 56

Ala Pro Val Ser Val Gly Gly Thr Val Leu Ala Lys Met Tyr Pro
1               5                   10                  15

Arg Gly Asn His Trp Ala Val Gly His Leu Met
            20                  25

<210> SEQ ID NO 57
<211> LENGTH: 27
<212> TYPE: PRT
<213> ORGANISM: Homo sapiens

<400> SEQUENCE: 57

Val Pro Leu Pro Ala Gly Gly Thr Val Leu Thr Lys Met Tyr Pro
1               5                   10                  15

Arg Gly Asn His Trp Ala Val Gly His Leu Met
            20                  25

<210> SEQ ID NO 58
<211> LENGTH: 5
<212> TYPE: PRT
<213> ORGANISM: Unknown
<220> FEATURE:
<221> NAME/KEY: source
<223> OTHER INFORMATION: /note="Description of Unknown: Enterokinase peptide"

<400> SEQUENCE: 58

Asp Asp Asp Asp Lys
1               5

<210> SEQ ID NO 59
<211> LENGTH: 4
<212> TYPE: PRT
<213> ORGANISM: Unknown
<220> FEATURE:
<221> NAME/KEY: source
<223> OTHER INFORMATION: /note="Description of Unknown: Factor Xa peptide"

<400> SEQUENCE: 59

Ile Glu Gly Arg
1

<210> SEQ ID NO 60
<211> LENGTH: 4
<212> TYPE: PRT
<213> ORGANISM: Unknown
<220> FEATURE:
<221> NAME/KEY: source
<223> OTHER INFORMATION: /note="Description of Unknown: Factor Xa peptide"

<400> SEQUENCE: 60

Ile Asp Gly Arg
1

<210> SEQ ID NO 61
<211> LENGTH: 7
<212> TYPE: PRT
<213> ORGANISM: Tobacco etch virus

<400> SEQUENCE: 61

Glu Asn Leu Tyr Phe Gln Gly
1               5

<210> SEQ ID NO 62
<211> LENGTH: 6
<212> TYPE: PRT
<213> ORGANISM: Unknown
<220> FEATURE:
<221> NAME/KEY: source
<223> OTHER INFORMATION: /note="Description of Unknown: Thrombin
      peptide"

<400> SEQUENCE: 62

Leu Val Pro Arg Gly Ser
1               5

<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Leu Glu Val Leu Phe Gln Gly Pro
1               5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 64

His His His His His His
1               5

<210> SEQ ID NO 65
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 3
      peptide"

<400> SEQUENCE: 65

Asp Met Gln Asp
1

<210> SEQ ID NO 66
<211> LENGTH: 6
<212> TYPE: PRT

```
<213> ORGANISM: Unknown
<220> FEATURE:
<221> NAME/KEY: source
<223> OTHER INFORMATION: /note="Description of Unknown: Thrombin
      peptide"

<400> SEQUENCE: 66

Leu Val Pro Arg Gly Ser
1               5

<210> SEQ ID NO 67
<211> LENGTH: 10
<212> TYPE: PRT
<213> ORGANISM: Unknown
<220> FEATURE:
<221> NAME/KEY: source
<223> OTHER INFORMATION: /note="Description of Unknown: ADAM17 peptide"

<400> SEQUENCE: 67

Pro Leu Ala Gln Ala Val Arg Ser Ser Ser
1               5                   10

<210> SEQ ID NO 68
<211> LENGTH: 10
<212> TYPE: PRT
<213> ORGANISM: Homo sapiens

<400> SEQUENCE: 68

Ser Lys Gly Arg Ser Leu Ile Gly Arg Val
1               5                   10

<210> SEQ ID NO 69
<211> LENGTH: 6
<212> TYPE: PRT
<213> ORGANISM: Unknown
<220> FEATURE:
<221> NAME/KEY: source
<223> OTHER INFORMATION: /note="Description of Unknown: Elastase
      peptide"

<400> SEQUENCE: 69

Met Glu Ala Val Thr Tyr
1               5

<210> SEQ ID NO 70
<211> LENGTH: 4
<212> TYPE: PRT
<213> ORGANISM: Unknown
<220> FEATURE:
<221> NAME/KEY: source
<223> OTHER INFORMATION: /note="Description of Unknown: Granzyme
      peptide"

<400> SEQUENCE: 70

Ile Glu Pro Asp
1

<210> SEQ ID NO 71
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 2
      peptide"

<400> SEQUENCE: 71

Asp Val Ala Asp
```

```
<210> SEQ ID NO 72
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 4
      peptide"

<400> SEQUENCE: 72

Leu Glu Val Asp
1

<210> SEQ ID NO 73
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 7
      peptide"

<400> SEQUENCE: 73

Asp Glu Val Asp
1

<210> SEQ ID NO 74
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 9
      peptide"

<400> SEQUENCE: 74

Leu Glu His Asp
1

<210> SEQ ID NO 75
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase 10
      peptide"

<400> SEQUENCE: 75

Ile Glu His Asp
1

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Cys-methyl ester

<400> SEQUENCE: 76

Cys His Ser Gly Tyr Val Gly Ala Arg Cys
```

```
<210> SEQ ID NO 77
<211> LENGTH: 12
<212> TYPE: PRT
<213> ORGANISM: Unknown
<220> FEATURE:
<221> NAME/KEY: source
<223> OTHER INFORMATION: /note="Description of Unknown: Epidermal growth
      factor peptide"

<400> SEQUENCE: 77

Tyr His Trp Tyr Gly Tyr Thr Pro Gln Asn Val Ile
1               5                   10

<210> SEQ ID NO 78
<211> LENGTH: 116
<212> TYPE: PRT
<213> ORGANISM: Homo sapiens

<400> SEQUENCE: 78

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
                20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 79
<211> LENGTH: 155
<212> TYPE: PRT
<213> ORGANISM: Homo sapiens

<400> SEQUENCE: 79

Met Tyr Arg His Lys Asn Ser Trp Arg Leu Gly Leu Lys Tyr Pro Pro
1               5                   10                  15

Ser Ser Lys Glu Glu Thr Gln Val Pro Lys Thr Leu Ile Ser Gly Leu
                20                  25                  30

Pro Gly Arg Lys Ser Ser Arg Val Gly Glu Lys Leu Gln Ser Ala
        35                  40                  45

His Lys Met Pro Leu Ser Pro Gly Leu Leu Leu Leu Leu Ser Gly
    50                  55                  60

Ala Thr Ala Thr Ala Ala Leu Pro Leu Glu Gly Gly Pro Thr Gly Arg
65                  70                  75                  80

Asp Ser Glu His Met Gln Glu Ala Ala Gly Ile Arg Lys Ser Ser Leu
                85                  90                  95

Leu Thr Phe Leu Ala Trp Trp Phe Glu Trp Thr Ser Gln Ala Ser Ala
            100                 105                 110

Gly Pro Leu Ile Gly Glu Glu Ala Arg Glu Val Ala Arg Arg Gln Glu
```

```
                115                 120                 125
Gly Ala Pro Pro Gln Gln Ser Ala Arg Arg Asp Arg Met Pro Cys Arg
        130                 135                 140

Asn Phe Phe Trp Lys Thr Phe Ser Ser Cys Lys
145                 150                 155
```

<210> SEQ ID NO 80
<211> LENGTH: 7
<212> TYPE: PRT
<213> ORGANISM: Homo sapiens

<400> SEQUENCE: 80

```
Asn Phe Phe Trp Lys Thr Phe
1               5
```

<210> SEQ ID NO 81
<211> LENGTH: 8
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Lys"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"

<400> SEQUENCE: 81

```
Arg Asn Phe Phe Trp Lys Thr Phe
1               5
```

<210> SEQ ID NO 82
<211> LENGTH: 9
<212> TYPE: PRT
<213> ORGANISM: Homo sapiens
<220> FEATURE:
<221> NAME/KEY: VARIANT
<222> LOCATION: (2)..(2)
<223> OTHER INFORMATION: /replace="Lys"
<220> FEATURE:
<221> NAME/KEY: misc_feature
<222> LOCATION: (2)..(2)
<223> OTHER INFORMATION: /note="Residue given in the sequence has no
      preference with respect to the residue in the annotation for said
      position"

<400> SEQUENCE: 82

```
Cys Arg Asn Phe Phe Trp Lys Thr Phe
1               5
```

<210> SEQ ID NO 83
<211> LENGTH: 10
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (3)..(3)

```
<223> OTHER INFORMATION: /replace="Lys"
<220> FEATURE:
<221> NAME/KEY: misc_feature
<222> LOCATION: (3)..(3)
<223> OTHER INFORMATION: /note="Residue given in the sequence has no
      preference with respect to the residue in the annotation for said
      position"

<400> SEQUENCE: 83

Pro Cys Arg Asn Phe Phe Trp Lys Thr Phe
1               5                   10

<210> SEQ ID NO 84
<211> LENGTH: 8
<212> TYPE: PRT
<213> ORGANISM: Homo sapiens
<220> FEATURE:
<221> NAME/KEY: VARIANT
<222> LOCATION: (8)..(8)
<223> OTHER INFORMATION: /replace="Thr"
<220> FEATURE:
<221> NAME/KEY: misc_feature
<222> LOCATION: (8)..(8)
<223> OTHER INFORMATION: /note="Residue given in the sequence has no
      preference with respect to the residue in the annotation for said
      position"

<400> SEQUENCE: 84

Asn Phe Phe Trp Lys Thr Phe Ser
1               5

<210> SEQ ID NO 85
<211> LENGTH: 9
<212> TYPE: PRT
<213> ORGANISM: Homo sapiens
<220> FEATURE:
<221> NAME/KEY: VARIANT
<222> LOCATION: (8)..(8)
<223> OTHER INFORMATION: /replace="Thr"
<220> FEATURE:
<221> NAME/KEY: misc_feature
<222> LOCATION: (8)..(8)
<223> OTHER INFORMATION: /note="Residue given in the sequence has no
      preference with respect to the residue in the annotation for said
      position"

<400> SEQUENCE: 85

Asn Phe Phe Trp Lys Thr Phe Ser Ser
1               5

<210> SEQ ID NO 86
<211> LENGTH: 10
<212> TYPE: PRT
<213> ORGANISM: Homo sapiens
<220> FEATURE:
<221> NAME/KEY: VARIANT
<222> LOCATION: (8)..(8)
<223> OTHER INFORMATION: /replace="Thr"
<220> FEATURE:
<221> NAME/KEY: misc_feature
<222> LOCATION: (8)..(8)
<223> OTHER INFORMATION: /note="Residue given in the sequence has no
      preference with respect to the residue in the annotation for said
      position"

<400> SEQUENCE: 86

Asn Phe Phe Trp Lys Thr Phe Ser Ser Cys
1               5                   10

<210> SEQ ID NO 87
<211> LENGTH: 9
```

```
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Lys"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (9)..(9)
<223> OTHER INFORMATION: /replace="Thr"
<220> FEATURE:
<221> NAME/KEY: misc_feature
<222> LOCATION: (9)..(9)
<223> OTHER INFORMATION: /note="Residue given in the sequence has no
      preference with respect to the residue in the annotation for said
      position"

<400> SEQUENCE: 87

Arg Asn Phe Phe Trp Lys Thr Phe Ser
1               5

<210> SEQ ID NO 88
<211> LENGTH: 10
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Lys"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (9)..(9)
<223> OTHER INFORMATION: /replace="Thr"
<220> FEATURE:
<221> NAME/KEY: misc_feature
<222> LOCATION: (9)..(9)
<223> OTHER INFORMATION: /note="Residue given in the sequence has no
      preference with respect to the residue in the annotation for said
      position"

<400> SEQUENCE: 88

Arg Asn Phe Phe Trp Lys Thr Phe Ser Ser
1               5                   10

<210> SEQ ID NO 89
<211> LENGTH: 11
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Lys"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (9)..(9)
<223> OTHER INFORMATION: /replace="Thr"
<220> FEATURE:
```

```
<221> NAME/KEY: misc_feature
<222> LOCATION: (9)..(9)
<223> OTHER INFORMATION: /note="Residue given in the sequence has no
      preference with respect to the residue in the annotation for said
      position"

<400> SEQUENCE: 89

Arg Asn Phe Phe Trp Lys Thr Phe Ser Ser Cys
1               5                   10

<210> SEQ ID NO 90
<211> LENGTH: 10
<212> TYPE: PRT
<213> ORGANISM: Homo sapiens
<220> FEATURE:
<221> NAME/KEY: VARIANT
<222> LOCATION: (2)..(2)
<223> OTHER INFORMATION: /replace="Lys"
<220> FEATURE:
<221> NAME/KEY: misc_feature
<222> LOCATION: (2)..(2)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: misc_feature
<222> LOCATION: (10)..(10)
<223> OTHER INFORMATION: /note="Residue given in the sequence has no
      preference with respect to the residue in the annotation for said
      position"

<400> SEQUENCE: 90

Cys Arg Asn Phe Phe Trp Lys Thr Phe Ser
1               5                   10

<210> SEQ ID NO 91
<211> LENGTH: 11
<212> TYPE: PRT
<213> ORGANISM: Homo sapiens
<220> FEATURE:
<221> NAME/KEY: VARIANT
<222> LOCATION: (2)..(2)
<223> OTHER INFORMATION: /replace="Lys"
<220> FEATURE:
<221> NAME/KEY: misc_feature
<222> LOCATION: (2)..(2)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: misc_feature
<222> LOCATION: (10)..(10)
<223> OTHER INFORMATION: /note="Residue given in the sequence has no
      preference with respect to the residue in the annotation for said
      position"

<400> SEQUENCE: 91

Cys Arg Asn Phe Phe Trp Lys Thr Phe Ser Ser
1               5                   10

<210> SEQ ID NO 92
<211> LENGTH: 12
<212> TYPE: PRT
<213> ORGANISM: Homo sapiens
<220> FEATURE:
```

<221> NAME/KEY: VARIANT
<222> LOCATION: (2)..(2)
<223> OTHER INFORMATION: /replace="Lys"
<220> FEATURE:
<221> NAME/KEY: misc_feature
<222> LOCATION: (2)..(2)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: misc_feature
<222> LOCATION: (10)..(10)
<223> OTHER INFORMATION: /note="Residue given in the sequence has no
      preference with respect to the residue in the annotation for said
      position"

<400> SEQUENCE: 92

Cys Arg Asn Phe Phe Trp Lys Thr Phe Ser Ser Cys
1               5                   10

<210> SEQ ID NO 93
<211> LENGTH: 11
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: misc_feature
<222> LOCATION: (3)..(3)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (11)..(11)
<223> OTHER INFORMATION: /replace="Thr"
<220> FEATURE:
<221> NAME/KEY: misc_feature
<222> LOCATION: (11)..(11)
<223> OTHER INFORMATION: /note="Residue given in the sequence has no
      preference with respect to the residue in the annotation for said
      position"

<400> SEQUENCE: 93

Pro Cys Arg Asn Phe Phe Trp Lys Thr Phe Ser
1               5                   10

<210> SEQ ID NO 94
<211> LENGTH: 12
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no preference with respect to the residue in the annotation for said
       position"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: misc_feature
<222> LOCATION: (3)..(3)
<223> OTHER INFORMATION: /note="Residue given in the sequence has no
       preference with respect to the residue in the annotation for said
       position"
<220> FEATURE:
<221> NAME/KEY: VARIANT
<222> LOCATION: (11)..(11)
<223> OTHER INFORMATION: /replace="Thr"
<220> FEATURE:
<221> NAME/KEY: misc_feature
<222> LOCATION: (11)..(11)
<223> OTHER INFORMATION: /note="Residue given in the sequence has no
       preference with respect to the residue in the annotation for said
       position"

<400> SEQUENCE: 94

Pro Cys Arg Asn Phe Phe Trp Lys Thr Phe Ser Ser
1               5                   10

<210> SEQ ID NO 95
<211> LENGTH: 12
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
       preference with respect to the residue in the annotation for said
       position"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: misc_feature
<222> LOCATION: (3)..(3)
<223> OTHER INFORMATION: /note="Residue given in the sequence has no
       preference with respect to the residue in the annotation for said
       position"
<220> FEATURE:
<221> NAME/KEY: VARIANT
<222> LOCATION: (11)..(11)
<223> OTHER INFORMATION: /replace="Thr"
<220> FEATURE:
<221> NAME/KEY: misc_feature
<222> LOCATION: (11)..(11)
<223> OTHER INFORMATION: /note="Residue given in the sequence has no
       preference with respect to the residue in the annotation for said
       position"

<400> SEQUENCE: 95

Pro Cys Arg Asn Phe Phe Trp Lys Thr Phe Ser Cys
1               5                   10

<210> SEQ ID NO 96
<211> LENGTH: 28
<212> TYPE: PRT
<213> ORGANISM: Homo sapiens

<400> SEQUENCE: 96

Ser Ala Asn Ser Asn Pro Ala Met Ala Pro Arg Glu Arg Lys Ala Gly
1               5                   10                  15

```
Cys Lys Asn Phe Phe Trp Lys Thr Phe Thr Ser Cys
        20                  25
```

<210> SEQ ID NO 97
<211> LENGTH: 14
<212> TYPE: PRT
<213> ORGANISM: Homo sapiens

<400> SEQUENCE: 97

```
Ala Gly Cys Lys Asn Phe Phe Trp Lys Thr Phe Thr Ser Cys
1               5                   10
```

<210> SEQ ID NO 98
<211> LENGTH: 29
<212> TYPE: PRT
<213> ORGANISM: Homo sapiens

<400> SEQUENCE: 98

```
Gln Glu Gly Ala Pro Pro Gln Gln Ser Ala Arg Arg Asp Arg Met Pro
1               5                   10                  15

Cys Arg Asn Phe Phe Trp Lys Thr Phe Ser Ser Cys Lys
            20                  25
```

<210> SEQ ID NO 99
<211> LENGTH: 29
<212> TYPE: PRT
<213> ORGANISM: Homo sapiens

<400> SEQUENCE: 99

```
Gln Glu Arg Pro Pro Leu Gln Gln Pro Pro His Arg Asp Lys Lys Pro
1               5                   10                  15

Cys Lys Asn Phe Phe Trp Lys Thr Phe Ser Ser Cys Lys
            20                  25
```

<210> SEQ ID NO 100
<211> LENGTH: 29
<212> TYPE: PRT
<213> ORGANISM: Homo sapiens

<400> SEQUENCE: 100

```
Gln Glu Arg Pro Pro Pro Gln Gln Pro Pro His Leu Asp Lys Lys Pro
1               5                   10                  15

Cys Lys Asn Phe Phe Trp Lys Thr Phe Ser Ser Cys Lys
            20                  25
```

<210> SEQ ID NO 101
<211> LENGTH: 17
<212> TYPE: PRT
<213> ORGANISM: Homo sapiens

<400> SEQUENCE: 101

```
Asp Arg Met Pro Cys Arg Asn Phe Phe Trp Lys Thr Phe Ser Ser Cys
1               5                   10                  15

Lys
```

<210> SEQ ID NO 102
<211> LENGTH: 14
<212> TYPE: PRT
<213> ORGANISM: Homo sapiens

<400> SEQUENCE: 102

```
Pro Cys Arg Asn Phe Phe Trp Lys Thr Phe Ser Ser Cys Lys
```

```
                                         1               5                   10

<210> SEQ ID NO 103
<211> LENGTH: 14
<212> TYPE: PRT
<213> ORGANISM: Homo sapiens

<400> SEQUENCE: 103

Pro Cys Lys Asn Phe Phe Trp Lys Thr Phe Ser Ser Cys Lys
1               5                   10

<210> SEQ ID NO 104
<211> LENGTH: 10
<212> TYPE: PRT
<213> ORGANISM: Unknown
<220> FEATURE:
<221> NAME/KEY: source
<223> OTHER INFORMATION: /note="Description of Unknown: Bombesin
      peptide"

<400> SEQUENCE: 104

Gly Asn Gln Trp Ala Val Gly His Leu Met
1               5                   10

<210> SEQ ID NO 105
<211> LENGTH: 10
<212> TYPE: PRT
<213> ORGANISM: Unknown
<220> FEATURE:
<221> NAME/KEY: source
<223> OTHER INFORMATION: /note="Description of Unknown: Neuromedin B
      peptide"

<400> SEQUENCE: 105

Gly Asn Leu Trp Ala Thr Gly His Phe Met
1               5                   10

<210> SEQ ID NO 106
<211> LENGTH: 10
<212> TYPE: PRT
<213> ORGANISM: Unknown
<220> FEATURE:
<221> NAME/KEY: source
<223> OTHER INFORMATION: /note="Description of Unknown: Neuromedin C
      peptide"

<400> SEQUENCE: 106

Gly Asn His Trp Ala Val Gly His Leu Met
1               5                   10

<210> SEQ ID NO 107
<211> LENGTH: 9
<212> TYPE: PRT
<213> ORGANISM: Unknown
<220> FEATURE:
<221> NAME/KEY: source
<223> OTHER INFORMATION: /note="Description of Unknown: Litorin
      peptide"
<220> FEATURE:
<221> NAME/KEY: MOD_RES
<222> LOCATION: (1)..(1)
<223> OTHER INFORMATION: pyro-Glutamate

<400> SEQUENCE: 107

Glu Gln Trp Ala Val Gly His Phe Met
1               5

<210> SEQ ID NO 108
```

```
<211> LENGTH: 10
<212> TYPE: PRT
<213> ORGANISM: Homo sapiens

<400> SEQUENCE: 108

Gly Asn His Trp Ala Val Gly His Leu Met
1               5                   10

<210> SEQ ID NO 109
<211> LENGTH: 23
<212> TYPE: PRT
<213> ORGANISM: Influenza virus

<400> SEQUENCE: 109

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 110
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Val Arg Gly Ile Ile Pro Phe Lys Thr Lys Ser Leu Asp Glu Gly Tyr
1               5                   10                  15

Asn Lys Ala Leu Asn Asp Leu
            20

<210> SEQ ID NO 111
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Val Asp Gly Ile Ile Thr Ser Lys Thr Lys Ser Leu Ile Glu Gly Arg
1               5                   10                  15

Asn Lys Ala Leu Asn Leu Gln
            20

<210> SEQ ID NO 112
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Val Asp Gly Ile Ile Thr Ser Lys Thr Lys Ser Asp Asp Asp Asp Lys
1               5                   10                  15

Asn Lys Ala Leu Asn Leu Gln
            20

<210> SEQ ID NO 113
```

```
<211> LENGTH: 44
<212> TYPE: PRT
<213> ORGANISM: Artificial Sequence
<220> FEATURE:
<223> OTHER INFORMATION: GHRH Peptide Analogue

<400> SEQUENCE: 113

Tyr Ala Asp Ala Ile Phe Thr Asn Ser Tyr Arg Lys Val Leu
1               5                   10
Gly Gln Leu Ser Ala Arg Lys Leu Leu Gln Asp Ile Met Ser
15                  20                  25
Arg Gln Gln Gly Glu Ser Asn Gln Glu Arg Gly Ala Arg Ala
        30                  35                  40
Arg Leu

<210> SEQ ID NO 114
<211> LENGTH: 29
<212> TYPE: PRT
<213> ORGANISM: Artificial Sequence
<220> FEATURE:
<223> OTHER INFORMATION: GHRH Peptide Analogue

<400> SEQUENCE: 114

Tyr Ala Asp Ala Ile Phe Thr Asn Ser Tyr Arg Lys Val Leu
1               5                   10
Gly Gln Leu Ser Ala Arg Lys Leu Leu Gln Asp Ile Met Ser
15                  20                  25
Arg

<210> SEQ ID NO 115
<211> LENGTH: 29
<212> TYPE: PRT
<213> ORGANISM: Artificial Sequence
<220> FEATURE:
<223> OTHER INFORMATION: GHRH Peptide Analogue

<400> SEQUENCE: 115

Tyr Ala Asp Ala Ile Phe Thr Asn Ser Tyr Arg Lys Val Leu
1               5                   10
Gly Gln Leu Ser Ala Arg Lys Leu Leu Gln Asp Ile Met Ser
15                  20                  25
Arg

<210> SEQ ID NO 116
<211> LENGTH: 44
<212> TYPE: PRT
<213> ORGANISM: Artificial Sequence
<220> FEATURE:
<223> OTHER INFORMATION: GHRH Peptide Analogue

<400> SEQUENCE: 116

Tyr Ala Asp Ala Ile Phe Thr Asn Ser Tyr Arg Lys Ile Leu
1               5                   10
Gly Gln Leu Ser Ala Arg Lys Leu Leu Gln Asp Ile Met Asn
15                  20                  25
Arg Gln Gln Gly Glu Arg Asn Gln Glu Gln Gly Ala Lys Val
        30                  35                  40
Arg Leu

<210> SEQ ID NO 117
<211> LENGTH: 44
```

```
<212> TYPE: PRT
<213> ORGANISM: Artificial Sequence
<220> FEATURE:
<223> OTHER INFORMATION: GHRH Peptide Analogue

<400> SEQUENCE: 117

Tyr Ala Asp Ala Ile Phe Thr Asn Ser Tyr Arg Lys Val Leu
1               5                   10

Gly Gln Leu Ser Ala Arg Lys Leu Leu Gln Asp Ile Met Asn
        15                  20                  25

Arg Gln Gln Gly Glu Arg Asn Gln Glu Gln Gly Ala Lys Val
            30                  35                  40

Arg Leu

<210> SEQ ID NO 118
<211> LENGTH: 29
<212> TYPE: PRT
<213> ORGANISM: Artificial Sequence
<220> FEATURE:
<223> OTHER INFORMATION: GHRH Peptide Analogue

<400> SEQUENCE: 118

His Val Asp Ala Ile Phe Thr Gln Ser Tyr Arg Lys Val Leu
1               5                   10

Ala Gln Leu Ser Ala Arg Lys Leu Leu Gln Asp Ile Leu Asn
        15                  20                  25

Arg

<210> SEQ ID NO 119
<211> LENGTH: 40
<212> TYPE: PRT
<213> ORGANISM: Artificial Sequence
<220> FEATURE:
<223> OTHER INFORMATION: GHRH Peptide Analogue

<400> SEQUENCE: 119

His Val Asp Ala Ile Phe Thr Gln Ser Tyr Arg Lys Val Leu
1               5                   10

Ala Gln Leu Ser Ala Arg Lys Leu Leu Gln Asp Ile Leu Asn
        15                  20                  25

Arg Gln Gln Gly Glu Arg Asn Gln Glu Gln Gly Ala
            30                  35                  40

<210> SEQ ID NO 120
<211> LENGTH: 14
<212> TYPE: PRT
<213> ORGANISM: Artificial Sequence
<220> FEATURE:
<223> OTHER INFORMATION: Bombesin

<400> SEQUENCE: 120

Glu Gln Arg Leu Gly Asn Gln Trp Ala Val Gly His Leu Met
1               5                   10

<210> SEQ ID NO 121
<211> LENGTH: 27
<212> TYPE: PRT
<213> ORGANISM: Artificial Sequence
<220> FEATURE:
<223> OTHER INFORMATION: Porcine GRP

<400> SEQUENCE: 121

Ala Pro Val Ser Val Gly Gly Gly Thr Val Leu Ala Lys Met
```

```
1               5                   10
Tyr Pro Arg Gly Asn His Trp Ala Val Gly His Leu Met
15                  20                  25

<210> SEQ ID NO 122
<211> LENGTH: 27
<212> TYPE: PRT
<213> ORGANISM: Artificial Sequence
<220> FEATURE:
<223> OTHER INFORMATION: Human GRP

<400> SEQUENCE: 122

Val Pro Leu Pro Ala Gly Gly Gly Thr Val Leu Thr Lys Met
1               5                   10

Tyr Pro Arg Gly Asn His Trp Ala Val Gly His Leu Met
15                  20                  25

<210> SEQ ID NO 123
<211> LENGTH: 5
<212> TYPE: PRT
<213> ORGANISM: Artificial Sequence
<220> FEATURE:
<223> OTHER INFORMATION: Enterokinase protease cleavage sequence

<400> SEQUENCE: 123

Asp Asp Asp Asp Lys
1               5

<210> SEQ ID NO 124
<211> LENGTH: 4
<212> TYPE: PRT
<213> ORGANISM: Artificial Sequence
<220> FEATURE:
<223> OTHER INFORMATION: Factor Xa protease cleavage sequence

<400> SEQUENCE: 124

Ile Glu Gly Arg
1

<210> SEQ ID NO 125
<211> LENGTH: 4
<212> TYPE: PRT
<213> ORGANISM: Artificial Sequence
<220> FEATURE:
<223> OTHER INFORMATION: Factor Xa protease cleavage sequence

<400> SEQUENCE: 125

Ile Asp Gly Arg
1

<210> SEQ ID NO 126
<211> LENGTH: 7
<212> TYPE: PRT
<213> ORGANISM: Artificial Sequence
<220> FEATURE:
<223> OTHER INFORMATION: TEV protease cleavage sequence

<400> SEQUENCE: 126

Glu Asn Leu Tyr Phe Gln Gly
1               5

<210> SEQ ID NO 127
<211> LENGTH: 6
<212> TYPE: PRT
<213> ORGANISM: Artificial Sequence
<220> FEATURE:
```

<223> OTHER INFORMATION: Thrombin protease cleavage sequence

<400> SEQUENCE: 127

Leu Val Pro Arg Gly Ser
1               5

<210> SEQ ID NO 128
<211> LENGTH: 8
<212> TYPE: PRT
<213> ORGANISM: Artificial Sequence
<220> FEATURE:
<223> OTHER INFORMATION: PreScission protease cleavage sequence

<400> SEQUENCE: 128

Leu Glu Val Leu Phe Gln Gly Pro
1               5

<210> SEQ ID NO 129
<211> LENGTH: 4
<212> TYPE: PRT
<213> ORGANISM: Artificial Sequence
<220> FEATURE:
<223> OTHER INFORMATION: Caspase 3 destructive cleavage site recognition
      sequence

<400> SEQUENCE: 129

Asp Met Gln Asp
1

<210> SEQ ID NO 130
<211> LENGTH: 10
<212> TYPE: PRT
<213> ORGANISM: Artificial Sequence
<220> FEATURE:
<223> OTHER INFORMATION: ADAM17 destructive cleavage site recognition
      sequence

<400> SEQUENCE: 130

Pro Leu Ala Gln Ala Val Arg Ser Ser Ser
1               5                   10

<210> SEQ ID NO 131
<211> LENGTH: 10
<212> TYPE: PRT
<213> ORGANISM: Artificial Sequence
<220> FEATURE:
<223> OTHER INFORMATION: HAT destructive cleavage site recognition
      sequence

<400> SEQUENCE: 131

Ser Lys Gly Arg Ser Leu Ile Gly Arg Val
1               5                   10

<210> SEQ ID NO 132
<211> LENGTH: 6
<212> TYPE: PRT
<213> ORGANISM: Artificial Sequence
<220> FEATURE:
<223> OTHER INFORMATION: Elastase (leukocyte) destructive cleavage
      site recognition sequence

<400> SEQUENCE: 132

Met Glu Ala Val Thr Tyr
1               5

<210> SEQ ID NO 133
<211> LENGTH: 4

```
<212> TYPE: PRT
<213> ORGANISM: Artificial Sequence
<220> FEATURE:
<223> OTHER INFORMATION: Furin destructive cleavage site recognition
      sequence
<220> FEATURE:
<221> NAME/KEY: MISC_FEATURE
<222> LOCATION: (2)..(2)
<223> OTHER INFORMATION: Xaa is any amino acid residue
<220> FEATURE:
<221> NAME/KEY: MISC_FEATURE
<222> LOCATION: (3)..(3)
<223> OTHER INFORMATION: Xaa is Arg or Lys

<400> SEQUENCE: 133

Arg Xaa Xaa Arg
1

<210> SEQ ID NO 134
<211> LENGTH: 4
<212> TYPE: PRT
<213> ORGANISM: Artificial Sequence
<220> FEATURE:
<223> OTHER INFORMATION: Granzyme destructive cleavage site recognition
      sequence

<400> SEQUENCE: 134

Ile Glu Pro Asp
1

<210> SEQ ID NO 135
<211> LENGTH: 4
<212> TYPE: PRT
<213> ORGANISM: Artificial Sequence
<220> FEATURE:
<223> OTHER INFORMATION: Caspase 2 destructive cleavage site
      recognition sequence

<400> SEQUENCE: 135

Asp Val Ala Asp
1

<210> SEQ ID NO 136
<211> LENGTH: 4
<212> TYPE: PRT
<213> ORGANISM: Artificial Sequence
<220> FEATURE:
<223> OTHER INFORMATION: Caspase 3 destructive cleavage site recognition
      sequence

<400> SEQUENCE: 136

Asp Met Gln Asp
1

<210> SEQ ID NO 137
<211> LENGTH: 4
<212> TYPE: PRT
<213> ORGANISM: Artificial Sequence
<220> FEATURE:
<223> OTHER INFORMATION: Caspase 4 destructive cleavage site recognition
      sequence

<400> SEQUENCE: 137

Leu Glu Val Asp
1

<210> SEQ ID NO 138
<211> LENGTH: 4
<212> TYPE: PRT
```

```
<213> ORGANISM: Artificial Sequence
<220> FEATURE:
<223> OTHER INFORMATION: Caspase 7 destructive cleavage site recognition
      sequence

<400> SEQUENCE: 138

Asp Glu Val Asp
1

<210> SEQ ID NO 139
<211> LENGTH: 4
<212> TYPE: PRT
<213> ORGANISM: Artificial Sequence
<220> FEATURE:
<223> OTHER INFORMATION: Caspase 9 destructive cleavage site recognition
      sequence

<400> SEQUENCE: 139

Leu Glu His Asp
1

<210> SEQ ID NO 140
<211> LENGTH: 4
<212> TYPE: PRT
<213> ORGANISM: Artificial Sequence
<220> FEATURE:
<223> OTHER INFORMATION: Caspase 10 destructive cleavage site
      recognition sequence

<400> SEQUENCE: 140

Ile Glu His Asp
1

<210> SEQ ID NO 141
<211> LENGTH: 9
<212> TYPE: PRT
<213> ORGANISM: Artificial Sequence
<220> FEATURE:
<223> OTHER INFORMATION: Fragment of TGF-alpha
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: METHYLATION
<222> LOCATION: (9)..(9)
<223> OTHER INFORMATION: C-terminal methylation

<400> SEQUENCE: 141

Cys His Ser Gly Tyr Val Gly Ala Arg
1               5

<210> SEQ ID NO 142
<211> LENGTH: 12
<212> TYPE: PRT
<213> ORGANISM: Artificial Sequence
<220> FEATURE:
<223> OTHER INFORMATION: Modified ErbB targeting moiety

<400> SEQUENCE: 142

Tyr His Trp Tyr Gly Tyr Thr Pro Gln Asn Val Ile
1               5                   10

<210> SEQ ID NO 143
<211> LENGTH: 116
<212> TYPE: PRT
<213> ORGANISM: Artificial Sequence
<220> FEATURE:
<223> OTHER INFORMATION: Somatostatin
```

```
<400> SEQUENCE: 143

Met Leu Ser Cys Arg Leu Gln Cys Ala Leu Ala Ala Leu Ser
1               5                   10
Ile Val Leu Ala Leu Gly Cys Val Thr Gly Ala Pro Ser Asp
15                  20                  25
Pro Arg Leu Arg Gln Phe Leu Gln Lys Ser Leu Ala Ala Ala
        30                  35                  40
Ala Gly Lys Gln Glu Leu Ala Lys Tyr Phe Leu Ala Glu Leu
            45                  50                  55
Leu Ser Glu Pro Asn Gln Thr Glu Asn Asp Ala Leu Glu Pro
                60                  65                  70
Glu Asp Leu Ser Gln Ala Ala Glu Gln Asp Glu Met Arg Leu
                    75                  80
Glu Leu Gln Arg Ser Ala Asn Ser Asn Pro Ala Met Ala Pro
85                  90                  95
Arg Glu Arg Lys Ala Gly Cys Lys Asn Phe Phe Trp Lys Thr
        100                 105                 110
Phe Thr Ser Cys
        115

<210> SEQ ID NO 144
<211> LENGTH: 155
<212> TYPE: PRT
<213> ORGANISM: Artificial Sequence
<220> FEATURE:
<223> OTHER INFORMATION: Cortistatin

<400> SEQUENCE: 144

Met Tyr Arg His Lys Asn Ser Trp Arg Leu Gly Leu Lys Tyr
1               5                   10
Pro Pro Ser Ser Lys Glu Glu Thr Gln Val Pro Lys Thr Leu
15                  20                  25
Ile Ser Gly Leu Pro Gly Arg Lys Ser Ser Arg Val Gly
        30                  35                  40
Glu Lys Leu Gln Ser Ala His Lys Met Pro Leu Ser Pro Gly
            45                  50                  55
Leu Leu Leu Leu Leu Leu Ser Gly Ala Thr Ala Thr Ala Ala
                60                  65                  70
Leu Pro Leu Glu Gly Gly Pro Thr Gly Arg Asp Ser Glu His
                    75                  80
Met Gln Glu Ala Ala Gly Ile Arg Lys Ser Ser Leu Leu Thr
85                  90                  95
Phe Leu Ala Trp Trp Phe Glu Trp Thr Ser Gln Ala Ser Ala
        100                 105                 110
Gly Pro Leu Ile Gly Glu Glu Ala Arg Glu Val Ala Arg Arg
            115                 120                 125
Gln Glu Gly Ala Pro Pro Gln Ser Ala Arg Arg Asp Arg
                130                 135                 140
Met Pro Cys Arg Asn Phe Phe Trp Lys Thr Phe Ser Ser Cys
                    145                 150
Lys
155

<210> SEQ ID NO 145
<211> LENGTH: 7
```

```
<212> TYPE: PRT
<213> ORGANISM: Artificial Sequence
<220> FEATURE:
<223> OTHER INFORMATION: Targeting moiety for somatostatin receptor

<400> SEQUENCE: 145

Asn Phe Phe Trp Lys Thr Phe
1               5

<210> SEQ ID NO 146
<211> LENGTH: 8
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Arg or Lys

<400> SEQUENCE: 146

Xaa Asn Phe Phe Trp Lys Thr Phe
1               5

<210> SEQ ID NO 147
<211> LENGTH: 9
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (2)..(2)
<223> OTHER INFORMATION: Xaa is Arg or Lys

<400> SEQUENCE: 147

Cys Xaa Asn Phe Phe Trp Lys Thr Phe
1               5

<210> SEQ ID NO 148
<211> LENGTH: 10
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Pro or Gly
<220> FEATURE:
<221> NAME/KEY: MISC_FEATURE
<222> LOCATION: (3)..(3)
<223> OTHER INFORMATION: Xaa is Arg or Lys

<400> SEQUENCE: 148

Xaa Cys Xaa Asn Phe Phe Trp Lys Thr Phe
1               5                   10

<210> SEQ ID NO 149
<211> LENGTH: 8
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (8)..(8)
<223> OTHER INFORMATION: Xaa is Ser or Thr

<400> SEQUENCE: 149
```

Asn Phe Phe Trp Lys Thr Phe Xaa
1               5

<210> SEQ ID NO 150
<211> LENGTH: 9
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (8)..(8)
<223> OTHER INFORMATION: Xaa is Ser or Thr

<400> SEQUENCE: 150

Asn Phe Phe Trp Lys Thr Phe Xaa Ser
1               5

<210> SEQ ID NO 151
<211> LENGTH: 10
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (8)..(8)
<223> OTHER INFORMATION: Xaa is Ser or Thr

<400> SEQUENCE: 151

Asn Phe Phe Trp Lys Thr Phe Xaa Ser Cys
1               5                   10

<210> SEQ ID NO 152
<211> LENGTH: 9
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Ser or Thr

<400> SEQUENCE: 152

Xaa Asn Phe Phe Trp Lys Thr Phe Xaa
1               5

<210> SEQ ID NO 153
<211> LENGTH: 10
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Ser or Thr

<400> SEQUENCE: 153

Xaa Asn Phe Phe Trp Lys Thr Phe Xaa Ser
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Ser or Thr

<400> SEQUENCE: 154

Xaa Asn Phe Phe Trp Lys Thr Phe Xaa Ser Cys
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Ser or Thr

<400> SEQUENCE: 155

Cys Xaa Asn Phe Phe Trp Lys Thr Phe Xaa
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Ser or Thr

<400> SEQUENCE: 156

Cys Xaa Asn Phe Phe Trp Lys Thr Phe Xaa Ser
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Ser or Thr

```
<400> SEQUENCE: 157

Cys Xaa Asn Phe Phe Trp Lys Thr Phe Xaa Ser Cys
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Pro or Gly
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (11)..(11)
<223> OTHER INFORMATION: Xaa is Ser or Thr

<400> SEQUENCE: 158

Xaa Cys Xaa Asn Phe Phe Trp Lys Thr Phe Xaa
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Pro or Gly
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (11)..(11)
<223> OTHER INFORMATION: Xaa is Ser or Thr

<400> SEQUENCE: 159

Xaa Cys Xaa Asn Phe Phe Trp Lys Thr Phe Xaa Ser
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Targeting moiety for somatostatin receptor
<220> FEATURE:
<221> NAME/KEY: MISC_FEATURE
<222> LOCATION: (1)..(1)
<223> OTHER INFORMATION: Xaa is Pro or Gly
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (11)..(11)
<223> OTHER INFORMATION: Xaa is Ser or Thr

<400> SEQUENCE: 160

Xaa Cys Xaa Asn Phe Phe Trp Lys Thr Phe Xaa Cys
1               5                   10
```

<210> SEQ ID NO 161
<211> LENGTH: 28
<212> TYPE: PRT
<213> ORGANISM: Artificial Sequence
<220> FEATURE:
<223> OTHER INFORMATION: Somatostatin Targeting Moiety

<400> SEQUENCE: 161

Ser Ala Asn Ser Asn Pro Ala Met Ala Pro Arg Glu Arg Lys
1               5                   10

Ala Gly Cys Lys Asn Phe Phe Trp Lys Thr Phe Thr Ser Cys
15                  20                  25

<210> SEQ ID NO 162
<211> LENGTH: 14
<212> TYPE: PRT
<213> ORGANISM: Artificial Sequence
<220> FEATURE:
<223> OTHER INFORMATION: Somatostatin Targeting Moiety

<400> SEQUENCE: 162

Ala Gly Cys Lys Asn Phe Phe Trp Lys Thr Phe Thr Ser Cys
1               5                   10

<210> SEQ ID NO 163
<211> LENGTH: 29
<212> TYPE: PRT
<213> ORGANISM: Artificial Sequence
<220> FEATURE:
<223> OTHER INFORMATION: Cortistatin Targeting Moiety

<400> SEQUENCE: 163

Gln Glu Gly Ala Pro Pro Gln Gln Ser Ala Arg Arg Asp Arg
1               5                   10

Met Pro Cys Arg Asn Phe Phe Trp Lys Thr Phe Ser Ser Cys
15                  20                  25

Lys

<210> SEQ ID NO 164
<211> LENGTH: 29
<212> TYPE: PRT
<213> ORGANISM: Artificial Sequence
<220> FEATURE:
<223> OTHER INFORMATION: Cortistatin Targeting Moiety

<400> SEQUENCE: 164

Gln Glu Arg Pro Pro Leu Gln Gln Pro Pro His Arg Asp Lys
1               5                   10

Lys Pro Cys Lys Asn Phe Phe Trp Lys Thr Phe Ser Ser Cys
15                  20                  25

Lys

<210> SEQ ID NO 165
<211> LENGTH: 29
<212> TYPE: PRT
<213> ORGANISM: Artificial Sequence
<220> FEATURE:
<223> OTHER INFORMATION: Cortistatin Targeting Moiety

<400> SEQUENCE: 165

Gln Glu Arg Pro Pro Pro Gln Gln Pro Pro His Leu Asp Lys
1               5                   10

```
Lys Pro Cys Lys Asn Phe Phe Trp Lys Thr Phe Ser Ser Cys
 15                  20                  25

Lys

<210> SEQ ID NO 166
<211> LENGTH: 17
<212> TYPE: PRT
<213> ORGANISM: Artificial Sequence
<220> FEATURE:
<223> OTHER INFORMATION: Cortistatin Targeting Moiety

<400> SEQUENCE: 166

Asp Arg Met Pro Cys Arg Asn Phe Phe Trp Lys Thr Phe Ser
 1               5                  10

Ser Cys Lys
 15

<210> SEQ ID NO 167
<211> LENGTH: 14
<212> TYPE: PRT
<213> ORGANISM: Artificial Sequence
<220> FEATURE:
<223> OTHER INFORMATION: Cortistatin Targeting Moiety

<400> SEQUENCE: 167

Pro Cys Arg Asn Phe Phe Trp Lys Thr Phe Ser Ser Cys Lys
 1               5                  10

<210> SEQ ID NO 168
<211> LENGTH: 14
<212> TYPE: PRT
<213> ORGANISM: Artificial Sequence
<220> FEATURE:
<223> OTHER INFORMATION: Cortistatin Targeting Moiety

<400> SEQUENCE: 168

Pro Cys Lys Asn Phe Phe Trp Lys Thr Phe Ser Ser Cys Lys
 1               5                  10

<210> SEQ ID NO 169
<211> LENGTH: 10
<212> TYPE: PRT
<213> ORGANISM: Artificial Sequence
<220> FEATURE:
<223> OTHER INFORMATION: Last 10 Amino Acids of Bombesin

<400> SEQUENCE: 169

Gly Asn Gln Trp Ala Val Gly His Leu Met
 1               5                  10

<210> SEQ ID NO 170
<211> LENGTH: 10
<212> TYPE: PRT
<213> ORGANISM: Artificial Sequence
<220> FEATURE:
<223> OTHER INFORMATION: Neuromedin B

<400> SEQUENCE: 170

Gly Asn Leu Trp Ala Thr Gly His Phe Met
 1               5                  10

<210> SEQ ID NO 171
<211> LENGTH: 10
<212> TYPE: PRT
<213> ORGANISM: Artificial Sequence
<220> FEATURE:
```

```
<223> OTHER INFORMATION: Neuromedin C

<400> SEQUENCE: 171

Gly Asn His Trp Ala Val Gly His Leu Met
1               5                   10

<210> SEQ ID NO 172
<211> LENGTH: 9
<212> TYPE: PRT
<213> ORGANISM: Artificial Sequence
<220> FEATURE:
<223> OTHER INFORMATION: Litorin

<400> SEQUENCE: 172

Glu Gln Trp Ala Val Gly His Phe Met
1               5

<210> SEQ ID NO 173
<211> LENGTH: 10
<212> TYPE: PRT
<213> ORGANISM: Artificial Sequence
<220> FEATURE:
<223> OTHER INFORMATION: Last 10 Amino Acids of Human GRP

<400> SEQUENCE: 173

Gly Asn His Trp Ala Val Gly His Leu Met
1               5                   10

<210> SEQ ID NO 174
<211> LENGTH: 23
<212> TYPE: PRT
<213> ORGANISM: Artificial Sequence
<220> FEATURE:
<223> OTHER INFORMATION: Influenza virus haemagglutinin

<400> SEQUENCE: 174

Gly Leu Phe Gly Ala Ile Ala Gly Phe Ile Glu Asn Gly Trp
1               5                   10

Glu Gly Met Ile Asp Gly Trp Tyr Gly
15                  20

<210> SEQ ID NO 175
<211> LENGTH: 23
<212> TYPE: PRT
<213> ORGANISM: Artificial Sequence
<220> FEATURE:
<223> OTHER INFORMATION: Serotype A Linker

<400> SEQUENCE: 175

Val Arg Gly Ile Ile Pro Phe Lys Thr Lys Ser Leu Asp Glu
1               5                   10

Gly Tyr Asn Lys Ala Leu Asn Asp Leu
15                  20

<210> SEQ ID NO 176
<211> LENGTH: 23
<212> TYPE: PRT
<213> ORGANISM: Artificial Sequence
<220> FEATURE:
<223> OTHER INFORMATION: Linker with Factor Xa Sequence

<400> SEQUENCE: 176

Val Asp Gly Ile Ile Thr Ser Lys Thr Lys Ser Leu Ile Glu
1               5                   10

Gly Arg Asn Lys Ala Leu Asn Leu Gln
```

```
<210> SEQ ID NO 177
<211> LENGTH: 23
<212> TYPE: PRT
<213> ORGANISM: Artificial Sequence
<220> FEATURE:
<223> OTHER INFORMATION: Linker with Enterokinase Sequence

<400> SEQUENCE: 177

Val Asp Gly Ile Ile Thr Ser Lys Thr Lys Ser Asp Asp Asp
1               5                  10

Asp Lys Asn Lys Ala Leu Asn Leu Gln
15                  20
```

What is claimed is:

1. A polypeptide comprising:
   (i) a non-cytotoxic protease capable of cleaving a SNARE protein expressed in a cancer cell;
   (ii) a targeting moiety capable of binding to a somatostatin receptor or a cortistatin receptor on the cancer cell;
   (iii) a translocation domain capable of translocating the protease from within an endosome, across the endosomal membrane and into the cytosol of the cancer cell; and
   (iv) an intein, a destructive cleavage site, or a non-clostridial cleavage site;
   wherein the polypeptide lacks the natural binding function of a clostridial neurotoxin $H_{CC}$ domain, which domain enables the clostridial neurotoxin to bind to one or more nerve terminals at the neuromuscular junction.

2. The polypeptide of claim 1, wherein the cancer cell is a prostate cancer cell.

3. The polypeptide of claim 1, wherein the cancer cell is selected from the group consisting of: a lung cancer cell, a renal cancer cell, a brain cancer cell, a breast cancer cell, a pancreatic cancer cell, a colorectal cancer cell, an adrenal cancer cell, an oesophageal cancer cell, a lymphoma cancer cell, a B-cell lymphoma cancer cell, a Mantle cell lymphoma cancer cell, a leukaemia cancer cell, a multiple myeloma cell, an acute leukaemia cancer cell, a bladder cancer cell, a bone cancer cell, a bowel cancer cell, a cervical cancer cell, a chronic lymphocytic leukaemia cell, a Hodgkin's lymphoma cell, a liver cancer cell, a melanoma skin cancer cell, an oropharyngeal cancer cell, a myeloma cell, a prostate cancer cell, a soft tissue sarcoma cell, a gastric cancer cell, a testicular cancer cell, a uterine cancer cell and a Kaposi sarcoma cancer cell.

4. The polypeptide of claim 1, wherein the non-cytotoxic protease is a clostridial neurotoxin L-chain or an IgA protease.

5. The polypeptide of claim 1, wherein the translocation domain is a clostridial neurotoxin translocation domain.

6. The polypeptide of claim 1, wherein the targeting moiety consists of the amino acid sequence of SEQ ID NO: 145.

7. The polypeptide of claim 1, wherein the targeting moiety consists of an amino acid sequence selected from the group consisting of: SEQ ID NO: 161; SEQ ID NO: 162; SEQ ID NO: 163; SEQ ID NO: 164; SEQ ID NO: 165; SEQ ID NO: 166; SEQ ID NO: 167; and SEQ ID NO: 168.

8. The polypeptide of claim 1, comprising an intein.

9. The polypeptide of claim 1, comprising a destructive cleavage site.

10. The polypeptide of claim 1, wherein the polypeptide consists of an amino acid sequence selected from the group consisting of: SEQ ID NO: 7; SEQ ID NO: 16; SEQ ID NO: 17; SEQ ID NO: 33; SEQ ID NO: 34; and SEQ ID NO: 35.

11. The polypeptide of claim 1, wherein the targeting moiety is fused to the non-cytotoxic protease, the translocation domain, or both by way of a direct covalent bond.

12. The polypeptide of claim 11, wherein the targeting moiety is fused to the non-cytotoxic protease by way of a direct covalent bond.

13. The polypeptide of claim 1, wherein the targeting moiety is located at the C-terminal end of the polypeptide.

14. The polypeptide of claim 1, wherein the targeting moiety is located between the non-cytotoxic protease and the translocation domain of the polypeptide.

15. A method of suppressing a cancer in a patient, the method comprising administering to the patient an effective amount of the polypeptide of claim 1.

16. The method of claim 15, wherein the non-cytotoxic protease comprises a clostridial neurotoxin protease or an IgA protease.

17. The method of claim 15, wherein the translocation domain comprises a clostridial neurotoxin translocation domain.

18. The method of claim 15, wherein the polypeptide consists of an amino acid sequence selected from the group consisting of: SEQ ID NO: 7; SEQ ID NO: 16; SEQ ID NO: 17; SEQ ID NO: 33; SEQ ID NO: 34; and SEQ ID NO: 35.

19. The method of claim 15, wherein the cancer is selected from the group consisting of: lung cancer, renal cancer, brain cancer, breast cancer, pancreatic cancer, colorectal cancer, colon cancer, rectal cancer, adrenal cancer, oesophageal cancer, lymphoma, B-celllymphoma, mantle cell lymphoma, leukaemia, multiple myeloma, acute leukaemia, bladder cancer, bone cancer, bowel cancer, cervical cancer, chronic lymphocytic leukaemia, Hodgkin's lymphoma, liver cancer, skin cancer, oropharyngeal cancer, myeloma, prostate cancer, prostate soft tissue sarcoma, gastric cancer, testicular cancer, uterine cancer and Kaposi sarcoma.

20. The method of claim 15, wherein the cancer is prostate cancer.

21. A method of suppressing a cancer in a patient, the method comprising administering to the patient an effective amount of the polypeptide of claim 6.

22. A method of suppressing a cancer in a patient, the method comprising administering to the patient an effective amount of the polypeptide of claim 7.

* * * * *